(12) United States Patent
Yeh et al.

(10) Patent No.: US 12,303,686 B2
(45) Date of Patent: May 20, 2025

(54) MIDFIELD POWER SOURCE FOR WIRELESS IMPLANTED DEVICES

(71) Applicant: NeuSpera Medical Inc., San Jose, CA (US)

(72) Inventors: Alexander Yeh, Los Altos Hills, CA (US); Hui Zhang, Newark, CA (US); Thomas Burpee Ellsworth, III, San Jose, CA (US); Elia Junco, Palo Alto, CA (US); Stephen James Schellenberg, Aptos, CA (US); Carl Lance Boling, San Jose, CA (US)

(73) Assignee: NEUSPERA MEDICAL INC., San Jose, CA (US)

( * ) Notice: Subject to any disclaimer, the term of this patent is extended or adjusted under 35 U.S.C. 154(b) by 106 days.

(21) Appl. No.: 17/046,687

(22) PCT Filed: Apr. 12, 2019

(86) PCT No.: PCT/US2019/027270
§ 371 (c)(1),
(2) Date: Oct. 9, 2020

(87) PCT Pub. No.: WO2019/200285
PCT Pub. Date: Oct. 17, 2019

(65) Prior Publication Data
US 2021/0361940 A1    Nov. 25, 2021

Related U.S. Application Data

(63) Continuation of application No. 16/220,815, filed on Dec. 14, 2018, now Pat. No. 10,561,842.
(Continued)

(51) Int. Cl.
*A61N 1/08*    (2006.01)
*A61N 1/372*    (2006.01)
(Continued)

(52) U.S. Cl.
CPC .......... *A61N 1/08* (2013.01); *A61N 1/37229* (2013.01); *A61N 1/37252* (2013.01);
(Continued)

(58) Field of Classification Search
CPC .............. A61N 1/3605; A61N 1/37229; A61N 1/37252; A61N 1/375; A61N 1/3787; A61N 1/08; H02J 50/20; H01Q 1/38
See application file for complete search history.

(56) References Cited

U.S. PATENT DOCUMENTS

| | | |
|---|---|---|
| 5,086,773 A | 2/1992 | Ware |
| 7,191,013 B1 | 3/2007 | Miranda et al. |

(Continued)

FOREIGN PATENT DOCUMENTS

| | | |
|---|---|---|
| AU | 2019252904 B2 | 9/2022 |
| AU | 2022221472 | 3/2024 |

(Continued)

OTHER PUBLICATIONS

"Chinese Application Serial No. 201980039503.0, Office Action mailed Jan. 13, 2021", with English translation, 2 pages.
(Continued)

*Primary Examiner* — Pamela M. Bays
(74) *Attorney, Agent, or Firm* — SCHWEGMAN LUNDBERG & WOESSNER, P.A.

(57) ABSTRACT

Systems, devices, and methods discussed herein include wireless midfield transmitters and implantable receiver devices. A midfield transmitter can be configured to provide signals outside of tissue that give rise to propagating signals inside of tissue. The present subject matter includes a protection circuit for a transmitter device, a layered transmitter device, an implantable receiver device, implantation and extraction methods, test and assembly methods, and the like. In an example, a protection circuit includes a first
(Continued)

control circuit to receive an RF drive signal and conditionally provide an output signal to an antenna. A second control circuit can generate a control signal based on the antenna output signal and/or information about the RF drive signal. A gain circuit can provide the RF drive signal to the first control circuit. The gain circuit can change an amplitude of the RF drive signal based on the control signal from the second control circuit.

21 Claims, 78 Drawing Sheets

Related U.S. Application Data

(60) Provisional application No. 62/756,648, filed on Nov. 7, 2018, provisional application No. 62/701,062, filed on Jul. 20, 2018, provisional application No. 62/656,637, filed on Apr. 12, 2018, provisional application No. 62/656,675, filed on Apr. 12, 2018.

(51) Int. Cl.
*A61N 1/375* (2006.01)
*A61N 1/378* (2006.01)
*H01Q 1/38* (2006.01)
*H02J 50/20* (2016.01)
*A61N 1/02* (2006.01)
*A61N 1/05* (2006.01)
*A61N 1/36* (2006.01)
*H01G 4/35* (2006.01)

(52) U.S. Cl.
CPC .......... *A61N 1/375* (2013.01); *A61N 1/3787* (2013.01); *H01Q 1/38* (2013.01); *H02J 50/20* (2016.02); *A61N 1/025* (2013.01); *A61N 1/05* (2013.01); *A61N 1/3605* (2013.01); *A61N 1/37205* (2013.01); *H01G 4/35* (2013.01)

(56) References Cited

U.S. PATENT DOCUMENTS

| | | | |
|---|---|---|---|
| 7,202,790 | B2 | 4/2007 | Copeland et al. |
| 8,634,928 | B1 | 1/2014 | O'Driscoll et al. |
| 9,461,648 | B1 | 10/2016 | Lee et al. |
| 10,485,980 | B2 | 11/2019 | Yeh et al. |
| 10,561,842 | B2 | 2/2020 | Yeh et al. |
| 11,596,794 | B2 | 3/2023 | Yeh et al. |
| 2004/0250820 | A1 | 12/2004 | Forsell |
| 2005/0105917 | A1 | 5/2005 | Narusawa et al. |
| 2006/0038597 | A1 | 2/2006 | Becker et al. |
| 2006/0253107 | A1 | 11/2006 | Hashimshony et al. |
| 2008/0269740 | A1 | 10/2008 | Bonde et al. |
| 2009/0284220 | A1 | 11/2009 | Toncich et al. |
| 2010/0109966 | A1* | 5/2010 | Mateychuk ............. H01Q 9/42 427/2.24 |
| 2011/0148519 | A1 | 6/2011 | Drogi et al. |
| 2011/0166629 | A1 | 7/2011 | Dion et al. |
| 2012/0119698 | A1 | 5/2012 | Karalis et al. |
| 2014/0031837 | A1 | 1/2014 | Perryman et al. |
| 2014/0031903 | A1* | 1/2014 | Mashiach ........... A61N 1/37229 307/104 |
| 2014/0036409 | A1 | 2/2014 | Stevenson et al. |
| 2014/0203823 | A1* | 7/2014 | Joshi ................. G01R 19/0092 324/654 |
| 2015/0066155 | A1* | 3/2015 | Haque ..................... A61F 2/38 623/24 |
| 2016/0344238 | A1 | 11/2016 | Yeh et al. |
| 2017/0001003 | A1 | 1/2017 | Pivonka et al. |
| 2017/0095667 | A1 | 4/2017 | Yakovlev et al. |
| 2017/0125897 | A1* | 5/2017 | Rubin ..................... C23C 4/12 |
| 2017/0214127 | A1 | 7/2017 | Newham et al. |
| 2017/0271919 | A1 | 9/2017 | Von Novak, III et al. |
| 2018/0050208 | A1 | 2/2018 | Shuros et al. |
| 2018/0071540 | A1 | 3/2018 | Poon et al. |
| 2018/0085593 | A1 | 3/2018 | Fayram et al. |
| 2018/0289971 | A1 | 10/2018 | Yeh et al. |
| 2018/0294676 | A1 | 10/2018 | Davlantes |
| 2019/0184159 | A1 | 6/2019 | Yeh et al. |
| 2019/0290923 | A1 | 9/2019 | Yeh et al. |
| 2020/0155843 | A1 | 5/2020 | Yeh et al. |

FOREIGN PATENT DOCUMENTS

| | | |
|---|---|---|
| CN | 102769440 A | 11/2012 |
| CN | 110461218 A | 11/2019 |
| CN | 112673567 | 11/2024 |
| JP | 2009518116 | 5/2009 |
| JP | 2013521676 A | 6/2013 |
| JP | 2016518219 | 6/2016 |
| JP | 2016149783 A | 8/2016 |
| JP | 2016538090 A | 12/2016 |
| JP | 2018514366 A | 6/2018 |
| JP | 2018532501 A | 11/2018 |
| JP | 7261814 B2 | 4/2023 |
| WO | WO-2011024355 A1 | 3/2011 |
| WO | WO-2011089676 A1 | 7/2011 |
| WO | WO-2015039108 A2 | 3/2015 |
| WO | WO-2015179225 A1 | 11/2015 |
| WO | 2017070372 | 4/2017 |
| WO | WO-2018140983 A1 | 8/2018 |
| WO | WO-2019200285 A1 | 10/2019 |

OTHER PUBLICATIONS

"U.S. Appl. No. 16/722,593, Restriction Requirement mailed Apr. 9, 2021", 8 pgs.
U.S. Appl. No. 16/220,815 U.S. Pat. No. 10,561,842, filed Dec. 14, 2018, Layered Midfield Transmitter With Dielectric Tuning.
U.S. Appl. No. 16/722,593, filed Dec. 20, 2019, Enhanced Wireless Comniunication and Power Transfer Between External and Implanted Devices.
"Canadian Application Serial No. 3,096,463, Office Action mailed Oct. 20, 2021", 5 pages.
"Australian Application Serial No. 2019252904, First Examination Report mailed Nov. 5, 2021", 5 pages.
"European Application Serial No. 19785104.1, Partial Supplementary European Search Report mailed Dec. 10, 2021", 12 pages.
"U.S. Appl. No. 16/722,593, Non Final Office Action mailed May 12, 2022", 5 pgs.
"Australian Application Serial No. 2019252904, Response Filed Apr. 6, 2022 to First Examination Report mailed Nov. 5, 2021", 10 pgs.
"Canadian Application Serial No. 3,096,463, Response filed Feb. 17, 2022 to Office Action mailed Oct. 20, 2021", 17 pgs.
"European Application Serial No. 19785104.1, Extended European Search Report mailed Apr. 5, 2022", 13 pgs.
"Japanese Application Serial No. 2020-554854, Response Filed Apr. 4, 2022 to Notification of Reasons for Refusal mailed Feb. 1, 2022", W/ English Claims, 11 pgs.
"U.S. Appl. No. 16/004,894,312 Amendment filed Jul. 17, 2019", 4 pgs.
"U.S. Appl. No. 16/004,894, Notice of Allowance mailed Jun. 12, 2019", 11 pgs.
"U.S. Appl. No. 16/004,894, Response filed May 6, 2019 to Restriction Requirement mailed Apr. 3, 2019", 10 pgs.
"U.S. Appl. No. 16/004,894, Restriction Requirement mailed Apr. 3, 2019", 10 pgs.
"U.S. Appl. No. 16/220,815, Non Final Office Action mailed Sep. 10, 2019", 7 pgs.
"U.S. Appl. No. 16/220,815, Notice of Allowance mailed Dec. 11, 2019", 5 pgs.
"U.S. Appl. No. 16/220,815, Response filed Jun. 24, 2019 to Restriction Requirement—Prioritized Examination mailed May 21, 2019", 10 pgs.

(56) References Cited

OTHER PUBLICATIONS

"U.S. Appl. No. 16/220,815, Response filed Sep. 27, 2019 to Non-Final Office Action mailed Sep. 10, 2019", 10 pgs.
"U.S. Appl. No. 16/722,593, Preliminary Amendment filed Feb. 7, 2020", 7 pgs.
"Australian Application Serial No. 2018213427, First Examination Report mailed Oct. 25, 2019", 3 pgs.
"Australian Application Serial No. 2018213427, Response filed Dec. 18, 2019 to First Examination Report mailed Oct. 25, 2019", 9 pgs.
"European Applicatioin Serial No. 18745034.1, Response filed Mar. 27, 2020 to Communication Pursuant to Rules 161(1) and 162 EPC mailed Oct. 11, 2019", 31 pgs.
"International Application Serial No. PCT/US2018/016051, International Preliminary Report on Patentability mailed Aug. 8, 2019", 9 pgs.
"International Application Serial No. PCT/US2018/016051, International Search Report mailed May 10, 2018", 5 pgs.
"International Application Serial No. PCT/US2018/016051, Invitation to Pay Add'l Fees and Partial Search Rpt mailed Mar. 23, 2018", 2 pgs.
"International Application Serial No. PCT/US2018/016051, Written Opinion mailed May 10, 2018", 7 pgs.
"International Application Serial No. PCT/US2019/027270, International Preliminary Report on Patentability mailed Jul. 27, 2020", 10 pgs.
"International Application Serial No. PCT/US2019/027270, International Search Report mailed Aug. 19, 2019", 5 pgs.
"International Application Serial No. PCT/US2019/027270, Invitation to Pay Additional Fees mailed Jun. 19, 2019", 3 pgs.
"International Application Serial No. PCT/US2019/027270, Response to Written Opinion filed Feb. 12, 2020 to Written Opinion mailed Aug. 19, 2019", 41 pgs.
"International Application Serial No. PCT/US2019/027270, Written Opinion mailed Aug. 19, 2019", 9 pgs.
"Near and far field", Wikipedia contributors, The Free Encyclopedia, Retrieved from the Internet: <URL: https://en.wikipedia.org/wiki/Near_and_far_field>, (Accessed Sep. 4, 2019), 11 pages.
"Stripline", Wikipedia contributors, Wikipedia, The Free Encyclopedia, [Online]. Retrieved from the Internet: <URL: https://en.wikipedia.org/wiki/Stripline>, (Accessed Sep. 4, 2019), 3 pages.
"Japanese Application Serial No. 2020-554854, Notification of Reasons for Refusal mailed Feb. 1, 2022", with English translation, 13 pages.
"European Application Serial No. 19785104.1, Response to Communication pursuant to Rules 161(2) and 162 EPC filed May 26, 2021", 38 pages.
"U.S. Appl. No. 16 722,593, Response filed Jun. 9, 2021 to Restriction Requirement mailed Apr. 9, 2021", 9 pages.
"U.S. Appl. No. 16/722,593, Corrected Notice of Allowability mailed Feb. 1, 2023", 2 pgs.
"U.S. Appl. No. 16/722,593, Notice of Allowability mailed Nov. 10, 2022", 2 pgs.
"U.S. Appl. No. 16/722,593, Notice of Allowance mailed Nov. 1, 2022", 5 pgs.
"Canadian Application Serial No. 3096483, Examiner's Rule 86 2 Requisition mailed Nov. 4, 2022", 4 pgs.
"Japanese Application Serial No. 2020-554854, Examiners Decision of Final Refusal mailed Sep. 27, 2022", w/ English Translation, 15 pgs.
"Japanese Application Serial No. 2020-554854, Response Filed Jan. 20, 2023 to Examiners Decision of Final Refusal mailed Sep. 27, 2022", W/ English Claims, 17 pgs.
"Australian Application Serial No. 2022221472, First Examination Report mailed Jun. 30, 2023", 4 pgs.
"Canadian Application Serial No. 3096483, Response Filed Feb. 15, 2023 to Examiner's Rule 86 2 Requisition mailed Nov. 4, 2022", 5 pgs.
"European Application Serial No. 19785104.1, Response Filed Nov. 7, 2022 Extended European Search Report mailed Apr. 5, 2022", 9 pgs.
"Canadian Application Serial No. 3,096,463, Examiners Rule 86(2) Requisition mailed Oct. 5, 2023", 3 pgs.
"Australian Application Serial No. 2022221472, Response Filed Nov. 16, 2023 First Examination Report mailed Jun. 30, 2023", 14 pgs.
"Canadian Application Serial No. 3,096,463, Response filed Jan. 30, 2024 to Examiners Rule 86(2) Requisition mailed Oct. 5, 2023", 6 pgs.
"Japanese Application Serial No. 2023-007138, Notification of Reasons for Refusal mailed Feb. 27, 2024", w English translation, 9 pgs.
"Chinese Application Serial No. 201980039503.0, Office Action mailed Apr. 8, 2024", w English translation, 21 pgs.
"Chinese Application Serial No. 201980039503.0, Response filed Jun. 26, 2024 to Office Action mailed Apr. 8, 2024", w current English claims, 126 pgs.
"Japanese Application Serial No. 2023-007138, Response filed Jul. 16, 2024 to Notification of Reasons for Refusal mailed Feb. 27, 2024", w current English claims, 12 pgs.
"Chinese Application Serial No. 201980039503.0 , Response to Examiner Telephone Interview Filed Aug. 2, 2024", w English Claims, 10 pgs.
"Japanese Application Serial No. 2023-007138, Final Notification of Reasons for Refusal mailed Oct. 8, 2024", w English Translation, 10 pgs.
"Japanese Application Serial No. 2023-007138, Response filed Nov. 26, 2024 to Final Notification of Reasons for Refusal mailed Oct. 8, 2024", w current English claims, 12 pgs.
"European Application Serial No. 19785104.1, Communication Pursuant to Article 94(3) EPC mailed Mar. 6, 2025", 5 pgs.

\* cited by examiner

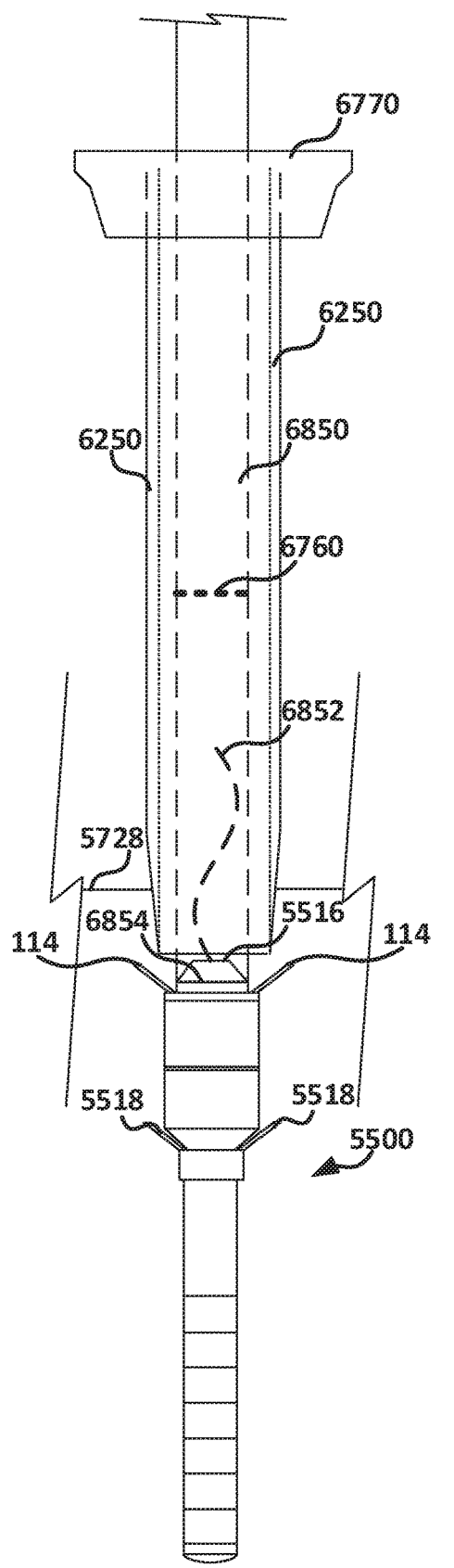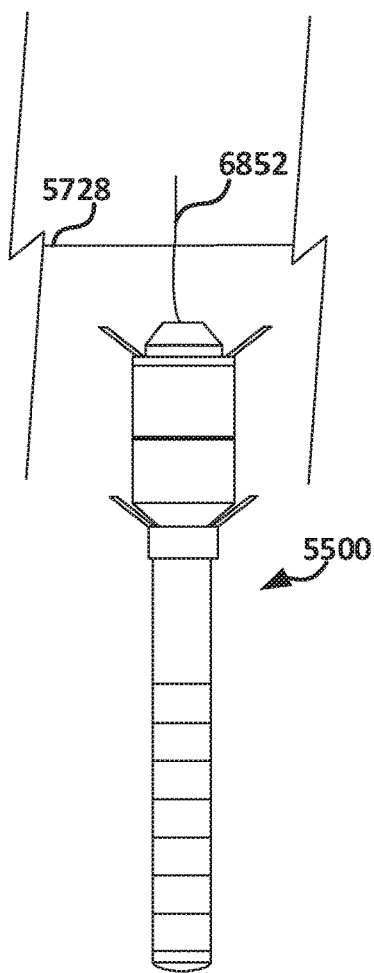
FIG. 67
FIG. 68

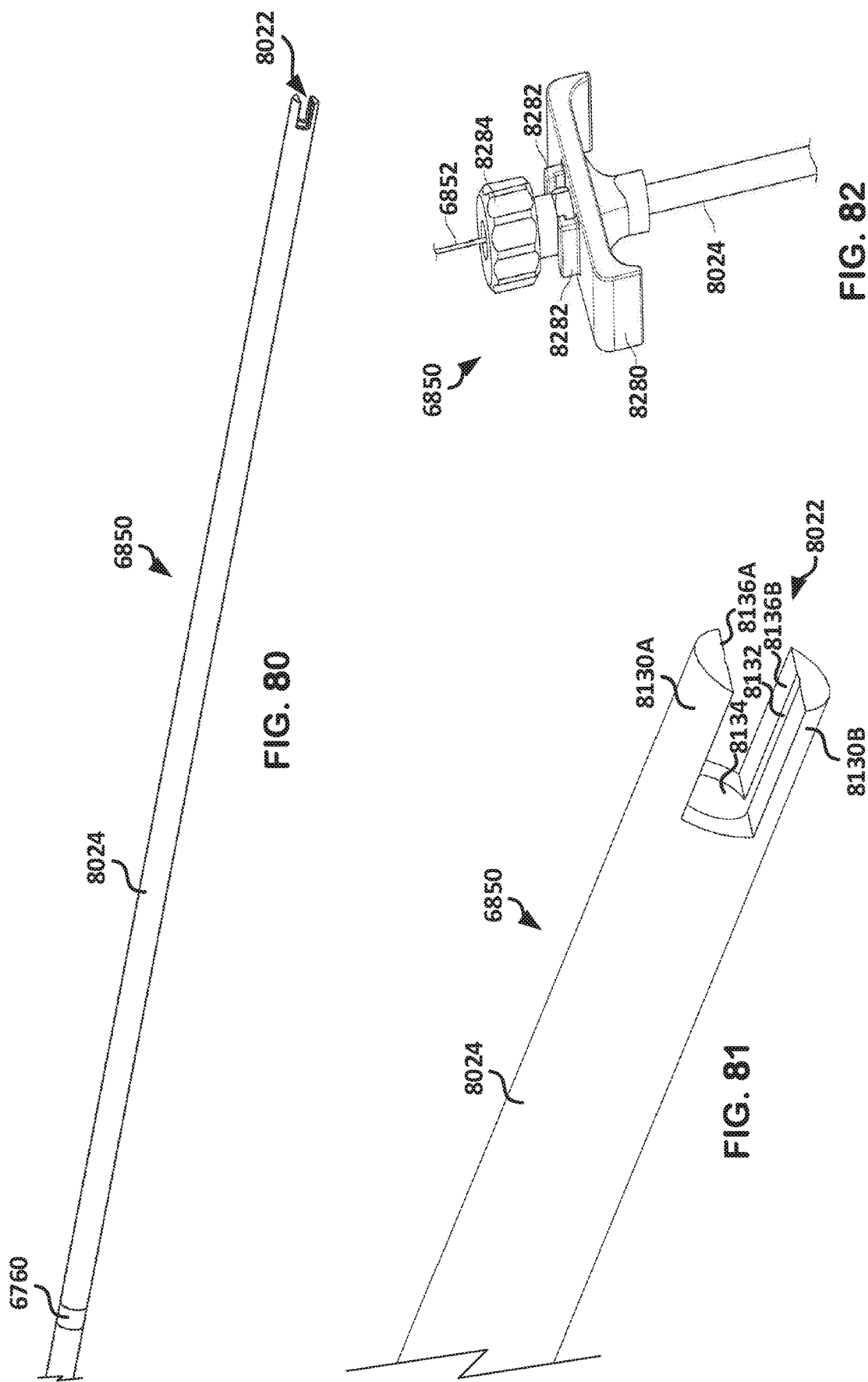

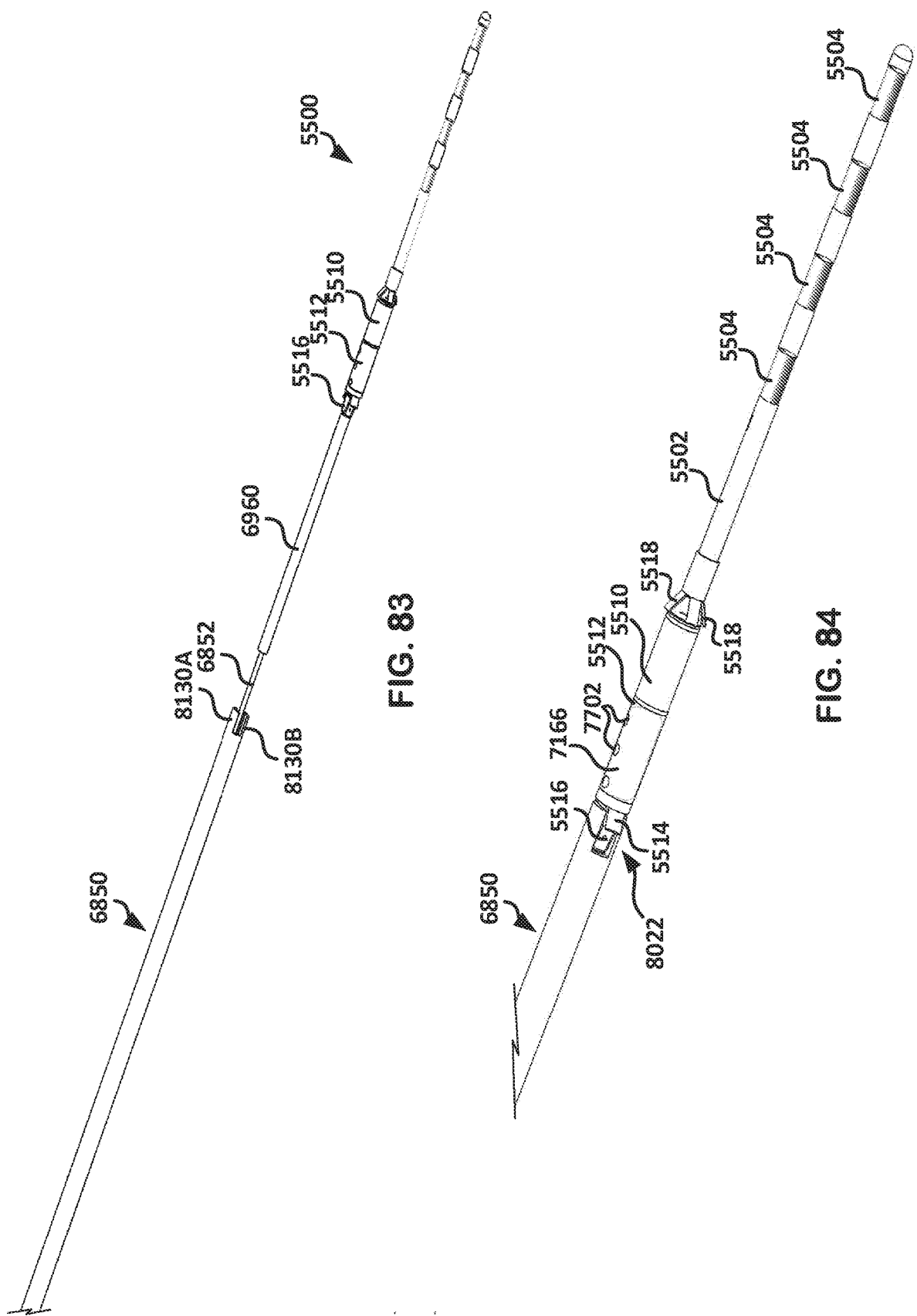

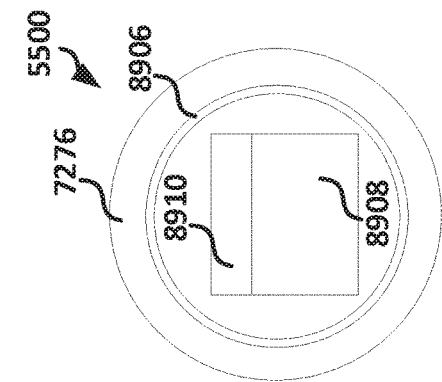
FIG. 89
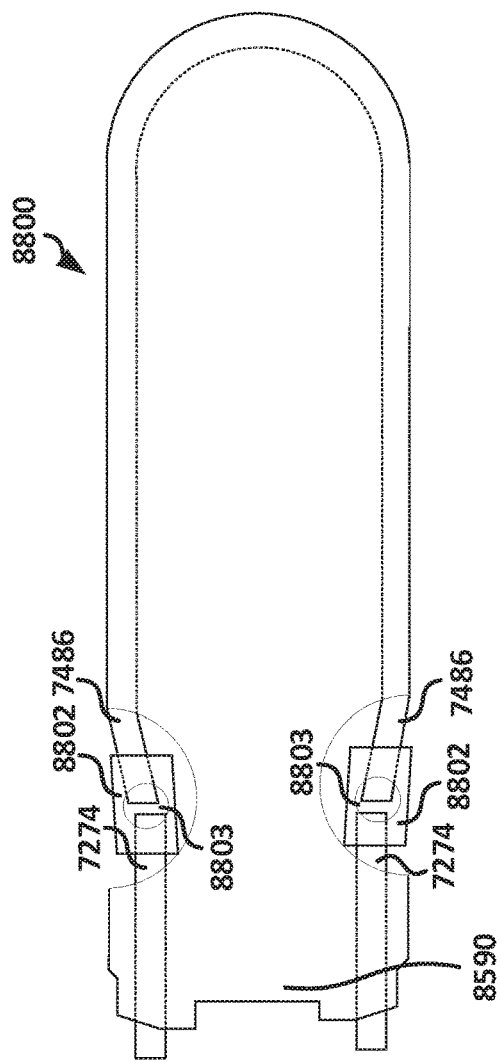
FIG. 88
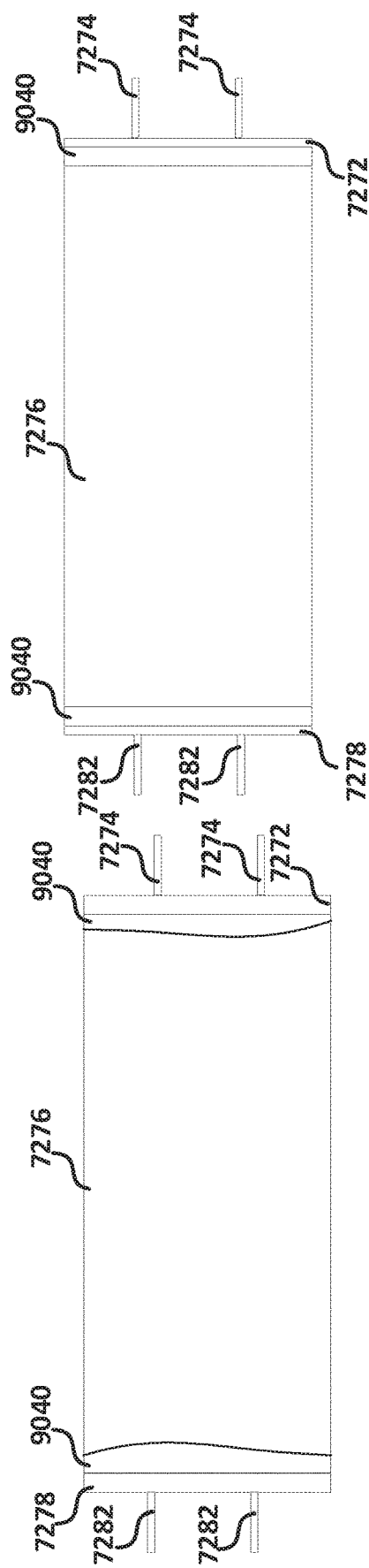
FIG. 91
FIG. 90

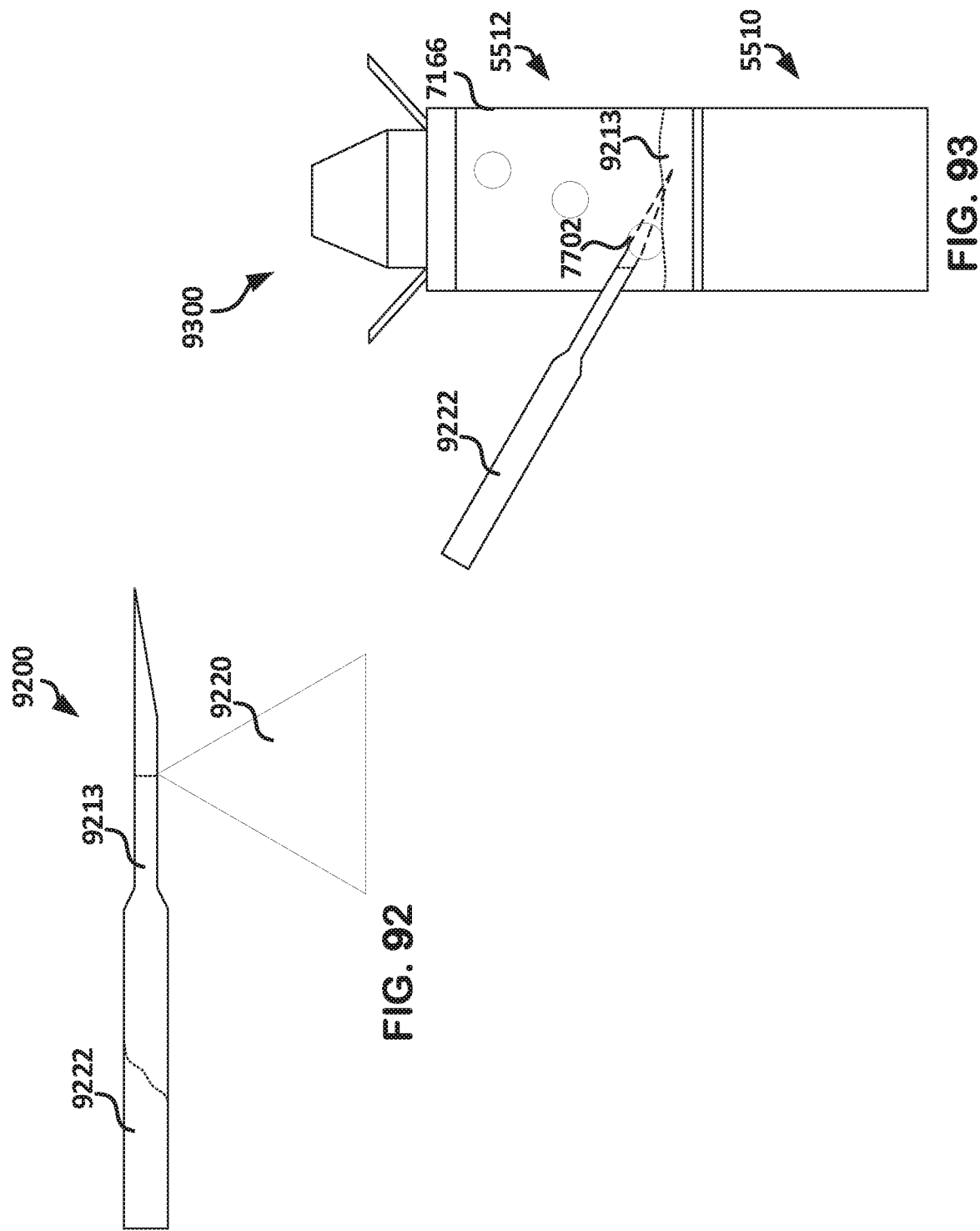

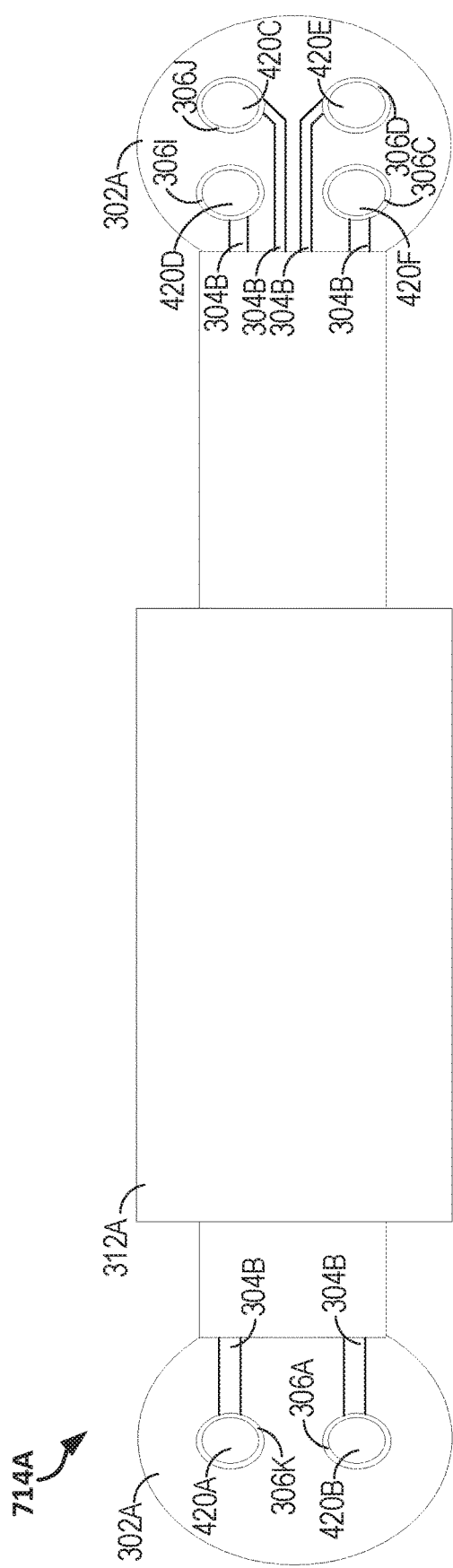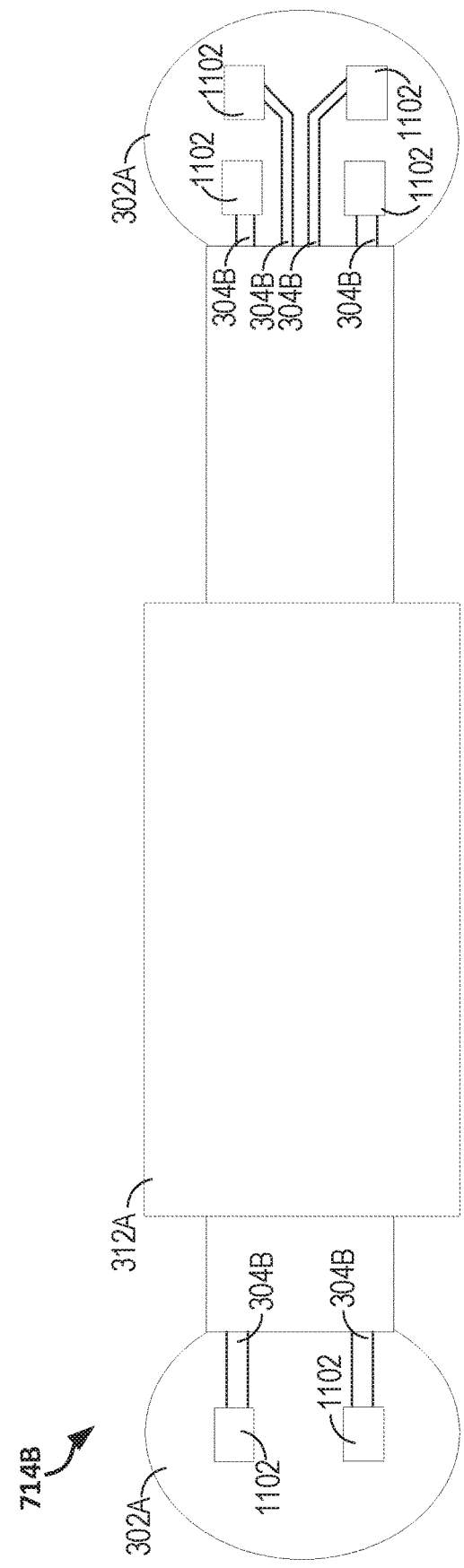

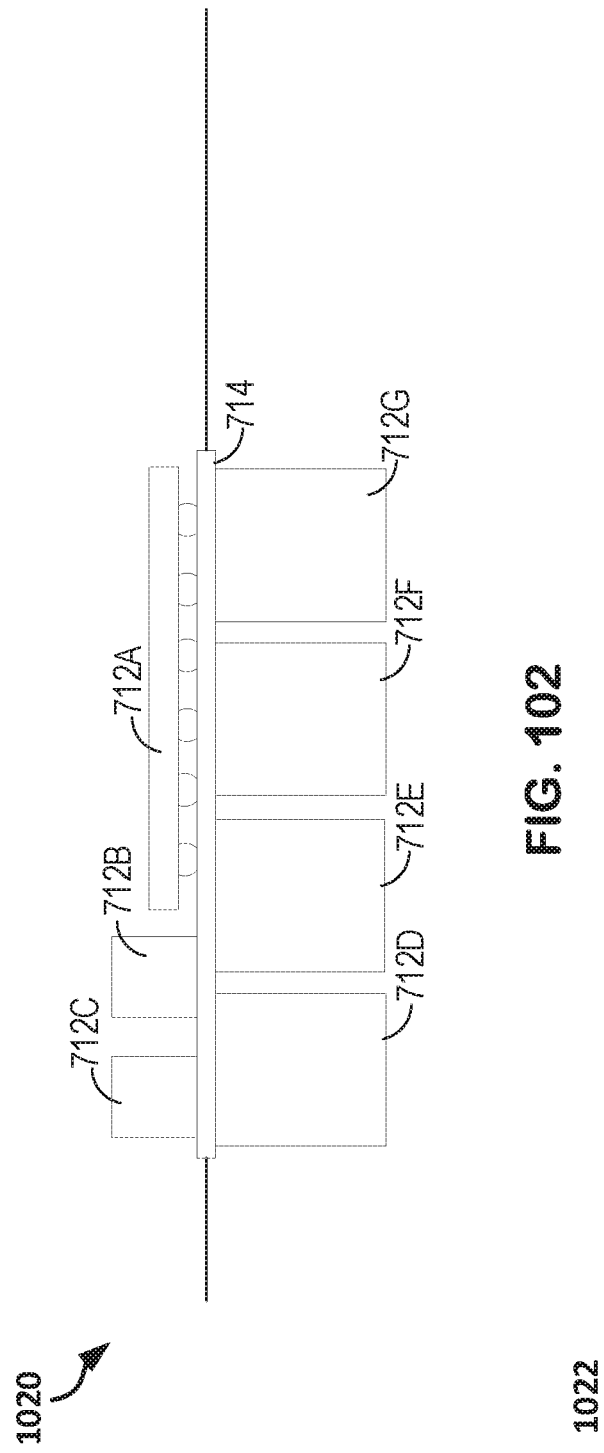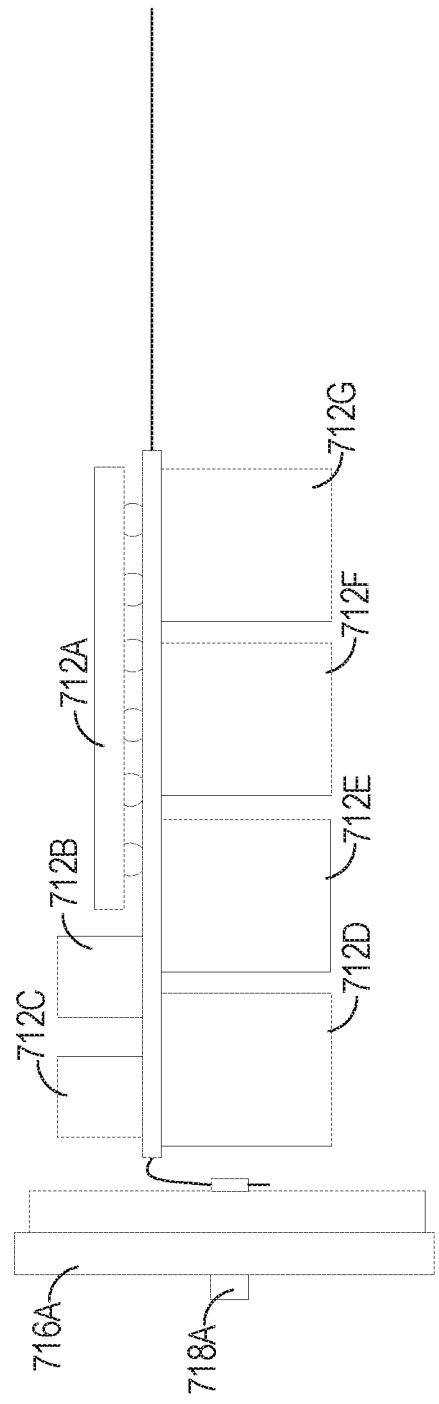

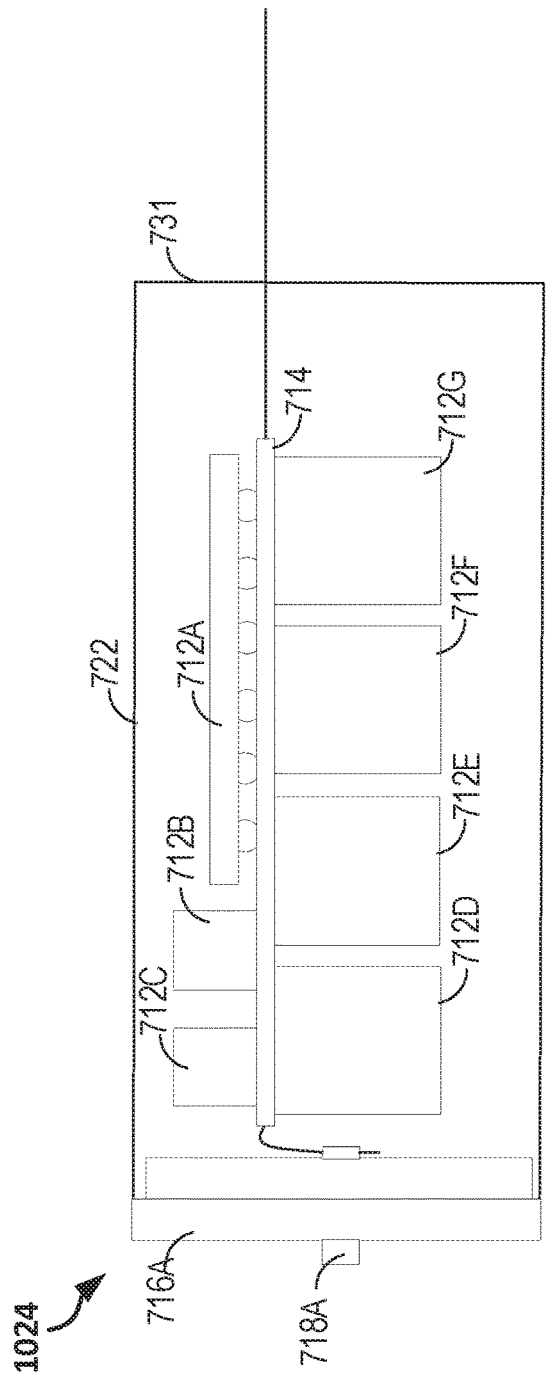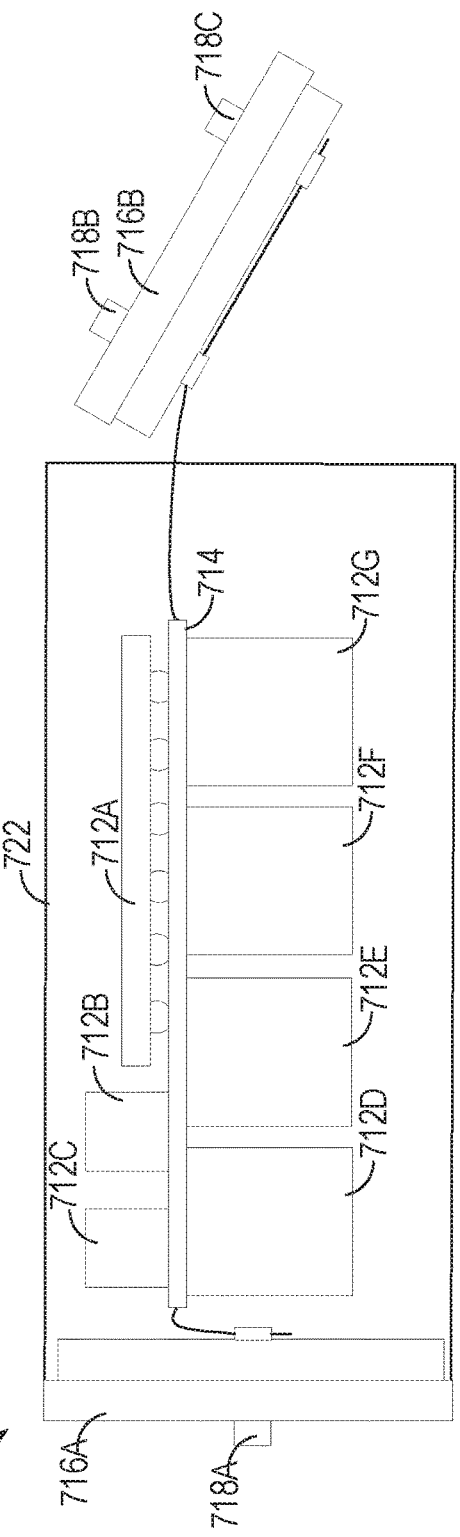
FIG. 104
FIG. 105

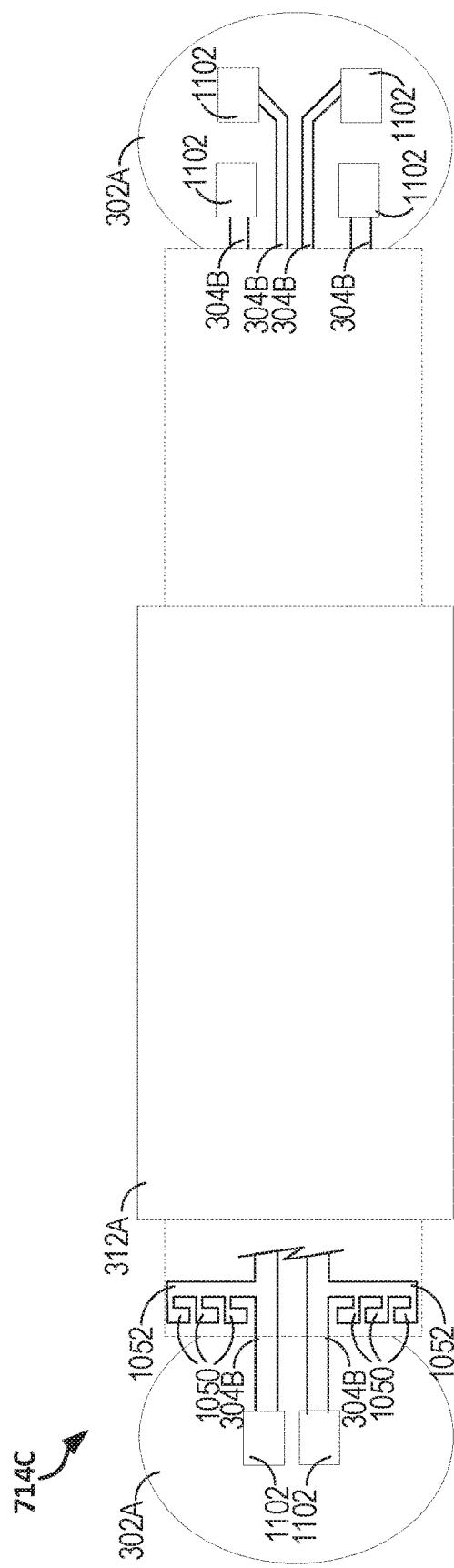
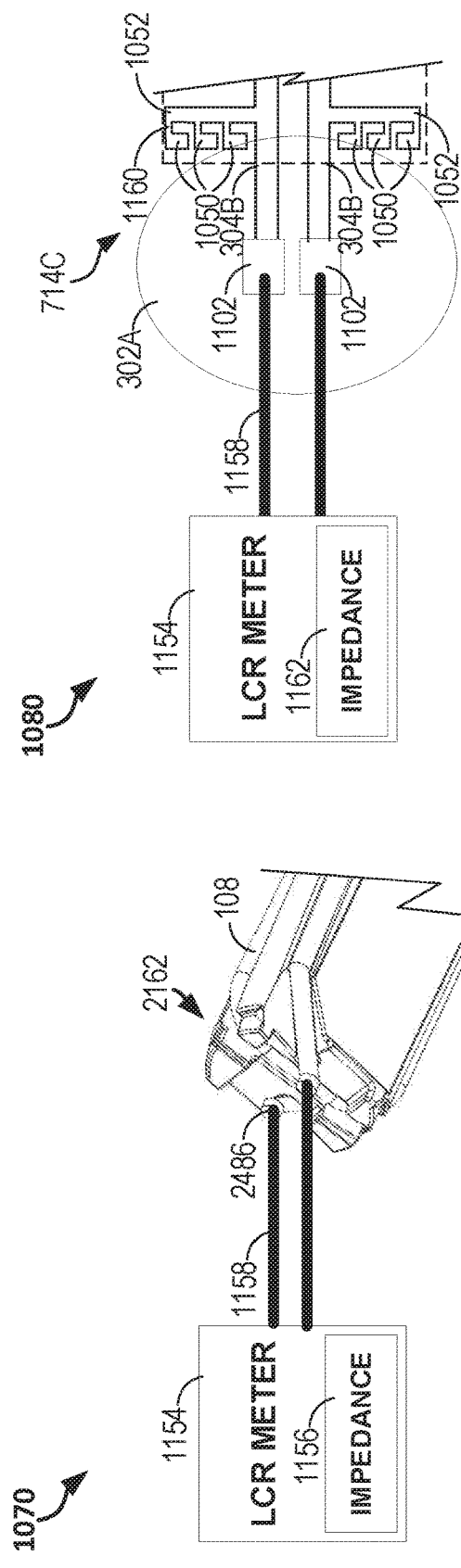
FIG. 106
FIG. 107
FIG. 108

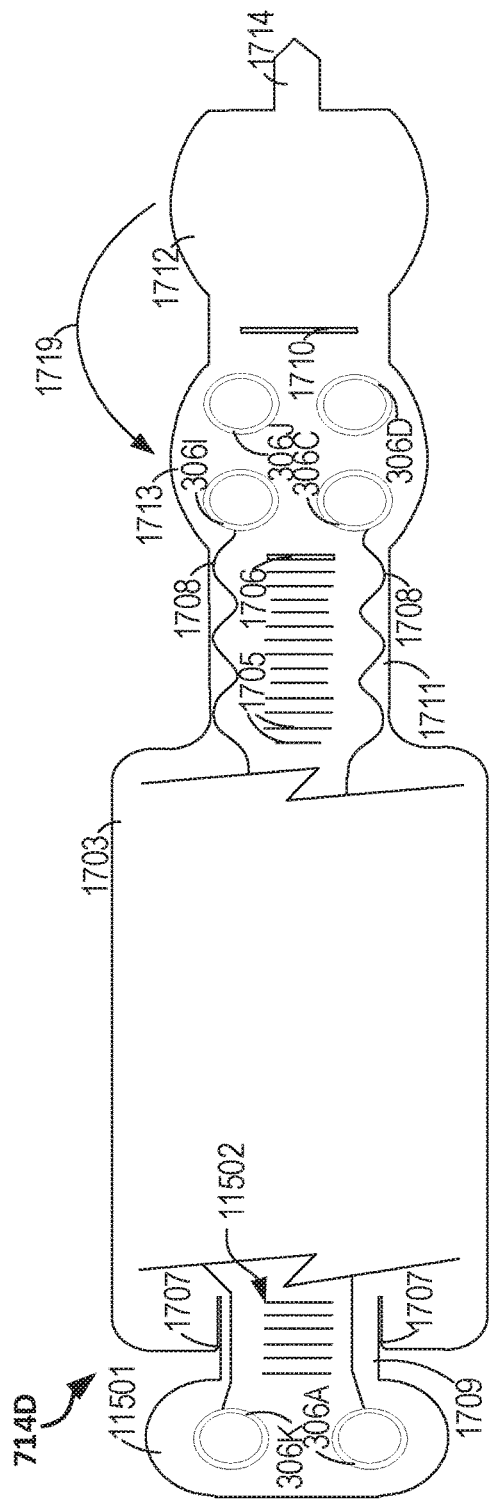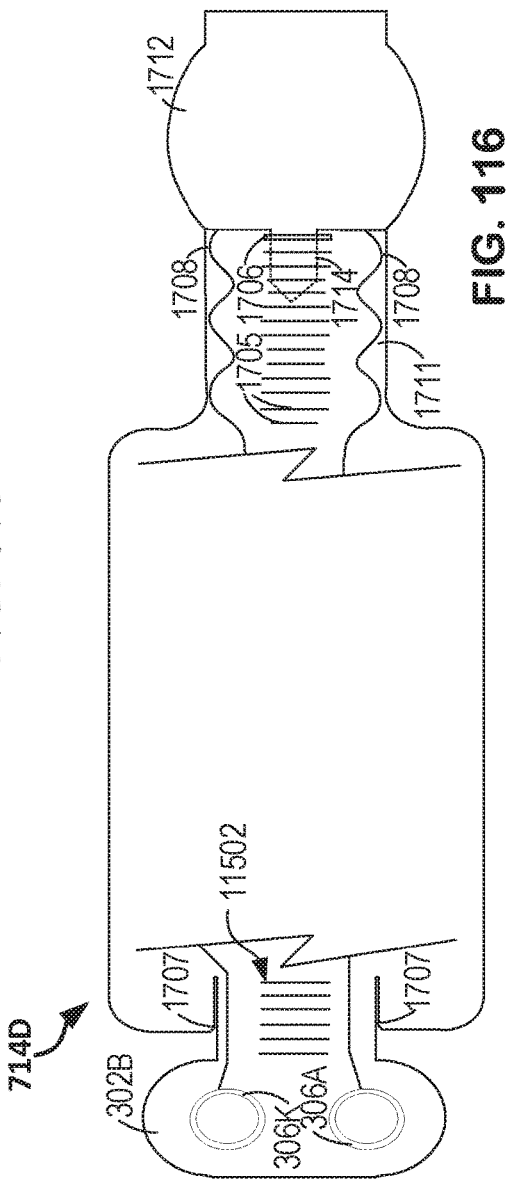

MIDFIELD POWER SOURCE FOR WIRELESS IMPLANTED DEVICES

CLAIM OF PRIORITY

This patent application is a U.S. National Stage filing of PCT International Application No. PCT/US2019/027270, filed Apr. 12, 2019, which is hereby incorporated herein by reference in its entirety; which claims the benefit of priority to U.S. Provisional Patent Application No. 62/656,637, filed Apr. 12, 2018, which is hereby incorporated herein by reference in its entirety; and is a continuation of, and claims the benefit of priority to U.S. patent application Ser. No. 16/220,815, filed Dec. 14, 2018, which is hereby incorporated herein by reference in its entirety; and claims the benefit of priority to U.S. Provisional Patent Application No. 62/656,675, filed Apr. 12, 2018, which is hereby incorporated herein by reference in its entirety; and claims the benefit of priority to U.S. Provisional Patent Application No. 62/701,062, filed Jul. 20, 2018, which is hereby incorporated herein by reference in its entirety; and claims the benefit of priority to U.S. Provisional Patent Application No. 62/756,648, filed Nov. 7, 2018, which is hereby incorporated herein by reference in its entirety.

BACKGROUND

Various wireless powering methods for implantable electronics are based on nearfield or farfield coupling. These and other methods suffer from several disadvantages. For example, using nearfield or farfield techniques, a power harvesting structure in an implanted device can typically be large (e.g., typically on the order of a centimeter or larger). In nearfield communications, coils external to the body can similarly be large, bulky and oftentimes inflexible. Such constraints present difficulties in incorporation of an external device into a patient's daily life. Furthermore, the intrinsic exponential decay of nearfield signals limits miniaturization of an implanted device beyond superficial depths, for example, at depths greater than 1 centimeter. On the other hand, the radiative nature of farfield signals can limit energy transfer efficiency.

Wireless midfield technology can be used to provide signals from an external source to an implanted sensor or therapy-delivery device. Midfield-based devices can have various advantages over conventional nearfield or farfield devices. For example, a midfield device may not require a relatively large implanted pulse generator and one or more leads that electrically connect the pulse generator to stimulation electrodes. A midfield device can have a relatively small receiver antenna and can therefore provide a simpler implant procedure relative to larger devices. Simpler implant procedures can correspond to lower cost and a lower risk of infection or other complications related to implant or explant.

Another advantage of using midfield powering technology includes a battery or power source that can be provided externally to a patient, and thus circuit requirements for battery-powered implantable devices, such as low power consumption and high efficiency, can be relaxed. Another advantage of using midfield powering technology can include an implanted device that can be physically smaller than a battery-powered device. Thus, midfield powering technology can help enable better patient tolerance and comfort along with potentially lower manufacturing and implantation costs.

SUMMARY

Although considerable progress has been made in the realm of medical device therapy, a need exists for a therapy device that provides stimulation or other therapy to targeted locations within a body. A need further exists for efficient, wireless power and data communication with an implanted therapy delivery device and/or an implanted diagnostic (e.g., sensor) device. The present inventors have recognized that a problem to be solved can include providing one or more of an external midfield transmitter, control and protection circuitry for an external midfield transmitter, a miniaturized implantable device that can receive midfield signals from an external transmitter, and drive and control circuitry for delivering electrostimulation using the implantable device. The problem to be solved can include providing a minimally-invasive implantation procedure for the implantable device. In an example, the problem to be solved can include manufacturing the implantable device and tuning various circuit and behavior characteristics of the implantable device. The present subject matter provides solutions to these and other problems.

In an example, a midfield transmitter can include a layered structure, such as can include at least a first conductive plane provided on a first layer of the transmitter, one or more striplines provided on a second layer of the transmitter, and a third conductive plane provided on a third layer of the transmitter, the third conductive plane electrically coupled to the first conductive plane using one or more vias that extend through the second layer. In an example, the midfield transmitter can include a first dielectric member interposed between the first and second conductive planes, and a different second dielectric member interposed between the second and third conductive planes.

In an example, a midfield transmitter can include a first conductive portion provided on a first layer of the transmitter, a second conductive portion including one or more striplines provided on a second layer of the transmitter, a third conductive portion provided on a third layer of the transmitter, and the third conductive portion can be electrically coupled to the first conductive portion using one or more vias that extend through the second layer. Respective dielectric members can be interposed between the first and second layers and between the second and third layers to influence resonance characteristics of the transmitter. In an example, the first conductive portion includes an inner disc region and an outer annular region spaced apart by a dielectric member, air gap, or slot. The outer annular region of the first conductive portion can be electrically coupled to the third conductive portion on the third layer using the one or more vias. In an example, the transmitter can optionally include or use a tuning device, such as a variable capacitor having a first capacitor node coupled to the first region of the first conductive portion and a second capacitor node coupled to the second region of the first conductive portion.

Driver and protection circuitry can be included with or coupled to a midfield transmitter. In an example, a signal processor for use in a wireless transmitter device includes a first control circuit configured to receive an RF drive signal and conditionally provide an output signal to an antenna or to another device. The signal processor can further include a second control circuit configured to generate a control signal based on information about the antenna output signal and/or information about the RF drive signal. In an example, the signal processor can further include a gain circuit configured to provide the RF drive signal to the first control circuit, wherein the gain circuit is configured to change an amplitude of the RF drive signal based on the control signal from the second control circuit. In an example, the first control circuit is configured to receive a reflected voltage signal that indicates a loading condition of the antenna, and then change a phase or amplitude of the antenna output signal based on the reflected voltage signal. In an example, the first control circuit is configured to attenuate the antenna output signal when the reflected voltage signal exceeds a specified reflection signal magnitude or threshold value.

In an example, the present subject matter can include a method for configuring a wireless power transmitter, the wireless power transmitter including a signal generator coupled to an antenna, and a tuner circuit configured to influence a resonant frequency of the antenna. The method can include energizing an antenna with a first drive signal having a first frequency, the first drive signal provided by the signal generator, sweeping parameter values of the tuner circuit to tune the antenna to multiple different resonant frequencies at respective multiple instances, and for each of the multiple different resonant frequencies, detecting respective amounts of power reflected by the antenna when the antenna is energized by the first drive signal. In an example, the method can include identifying a particular parameter value of the tuner circuit corresponding to a detected minimum amount of power reflected to the antenna, and programming the wireless power transmitter to use the particular parameter value of the tuner circuit to communicate power and/or data to an implanted device using a wireless propagating wave inside body tissue.

In an example, the present subject matter can include a midfield receiver device that can include a first antenna configured to receive a propagating wireless power signal originated at a remote midfield transmitter, a rectifier circuit coupled to the first antenna and configured to provide at least first and second harvested power signals having respective first and second voltage levels, and a multiplexer circuit coupled to the rectifier circuit and configured to route a selected one of the first and second harvested power signals to an electrostimulation output circuit.

In an example, the present subject matter can include a method for implanting a wireless implantable device. The method for implanting can include, for example, piercing tissue with a foramen needle that includes a guidewire therein, removing the foramen needle, leaving the guidewire at least partially in the tissue, situating a dilator and catheter over an exposed portion of the guidewire to at least partially situate the guidewire in the dilator, pushing the dilator and catheter along the guidewire and into the tissue, removing the guidewire and dilator from the tissue, inserting an implantable device into a lumen in the catheter, pushing, using a push rod, the implantable device into the tissue through the catheter, and removing the catheter, leaving the implantable device in the tissue.

In an example, the present subject matter can include an implantable device that includes an elongated body portion with a plurality of electrodes exposed thereon, and a circuitry housing including circuitry electrically coupled to provide electrical signals to the electrodes. The implantable device can include a frustoconical connector between the circuitry housing and the elongated body portion, the frustoconical connector attached to the body portion at a distal end thereof and the circuitry housing at a proximal end thereof, and an antenna housing including an antenna therein and connected to the circuitry housing at a proximal end of the circuitry housing. The implantable device can further include a push rod interface connected to the antenna housing at a proximal end of the antenna housing.

In an example, the present subject matter can include a method for dispensing a dielectric material into a portion of an implantable device. The method for dispensing can include cooling a portion of a hollow needle below a free flow temperature of a dielectric material by situating the needle on or near a cooling device, flowing the dielectric material into the needle to the cooled portion of the hollow needle, situating the hollow needle in a hole in a core housing of an implantable device, warming the hollow needle to the free flow temperature of the dielectric material or a greater temperature, and retaining the hollow needle in the hole to allow the dielectric material to free flow through the needle.

In an example, the present subject matter can include a first method for tuning an impedance characteristic of an implantable receiver device. The first method for tuning can include determining an impedance of a circuit board of an implantable device from the perspective of conductive contact pads to which an antenna assembly is to be attached, and in response to determining the impedance is not within a target range of impedance values, removing conductive material from other circuitry of the circuit board. In an example, the method for tuning can include, in response to determining the impedance is within the target range of impedance values, electrically connecting the antenna assembly to the contact pads to create a circuit board assembly, and sealing the circuit board in a hermetic enclosure. The method can further include providing or situating the circuit board assembly near or at least partially in a material such that transmissions from an external power unit travel through the material to be incident on an antenna of the antenna assembly, wherein the material includes a dielectric constant about that of tissue in which the implantable device is to be implanted, receiving the transmissions from the external power unit, and producing a response indicative of a power of the received transmissions.

In an example, the present subject matter can include a second method for tuning an impedance of an implantable device. The second method for tuning can include removing conductive material from a circuit board of an implantable device to adjust an impedance of the circuit board, and hermetically sealing the circuit board in a circuitry housing of the implantable device after verifying an impedance of the circuit board is within a specified range of frequencies and after removing the conductive material, and attaching an antenna to a feedthrough of the circuitry housing after hermetically sealing the circuit board in the circuitry housing.

This Summary is intended to provide an overview of subject matter of the present application. It is not intended to provide an exclusive or exhaustive explanation of the invention or inventions discussed herein. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 56-68 illustrate generally side view diagrams of portions of a process for implanting a device in tissue.

FIG. 80 illustrates, by way of example, a perspective view diagram of an embodiment of a push rod.

FIG. 81 illustrates, by way of example, an exploded view diagram of an embodiment of an implantable device interface of a push rod.

FIG. 82 illustrates, by way of example, a diagram of an embodiment of a proximal portion of a push rod.

FIG. 83 illustrates, by way of example, a perspective view diagram of an embodiment of a push rod with a suture situated partially in a lumen.

FIG. 84 illustrates, by way of example, a perspective view diagram of an embodiment of a push rod interface engaged with an implantable device interface.

FIG. 88 illustrates, by way of example, a side view diagram of an embodiment of a portion of an implantable device with a sleeve.

FIG. 89 illustrates, by way of example, a cross-section view diagram of an embodiment of a circuitry housing.

FIGS. 90-91 illustrate, by way of example, respective views of an embodiment of hermetically sealing a circuitry housing.

FIGS. 92-93 illustrate, by way of example, respective perspective view diagrams of an embodiment of situating the dielectric material into the antenna housing.

FIGS. 101A-101B illustrate embodiments of circuit boards for an implantable device.

FIG. 102 illustrates an embodiment of a device that includes electrical and/or electronic components soldered or otherwise electrically connected to the circuit board.

FIG. 103 illustrates an embodiment of a device after a second conductive material is soldered or otherwise electrically connected to respective feedthroughs of a cap.

FIG. 104 illustrates an embodiment of a device that includes the device of FIG. 103 after the circuit board and the electric and/or electronic components are situated in an enclosure.

FIG. 105 illustrates an embodiment of a device that includes the device of FIG. 7 after a second conductive material is soldered or otherwise electrically connected to respective feedthroughs of the cap.

FIG. 106 illustrates, by way of example, a diagram of a circuit board for an implantable device.

FIG. 107 illustrates, by way of example, a diagram of an embodiment of a system for measuring an impedance.

FIG. 108 illustrates, by way of example, a diagram of an embodiment of a system for measuring an impedance of a circuit board.

FIG. 115 illustrates, by way of example, a diagram of an embodiment of a circuit board.

FIG. 116 illustrates, by way of example, a diagram of an embodiment of the circuit board of FIG. 115 with a cover portion folded over connection circuitry.

DETAILED DESCRIPTION

Figure 1:
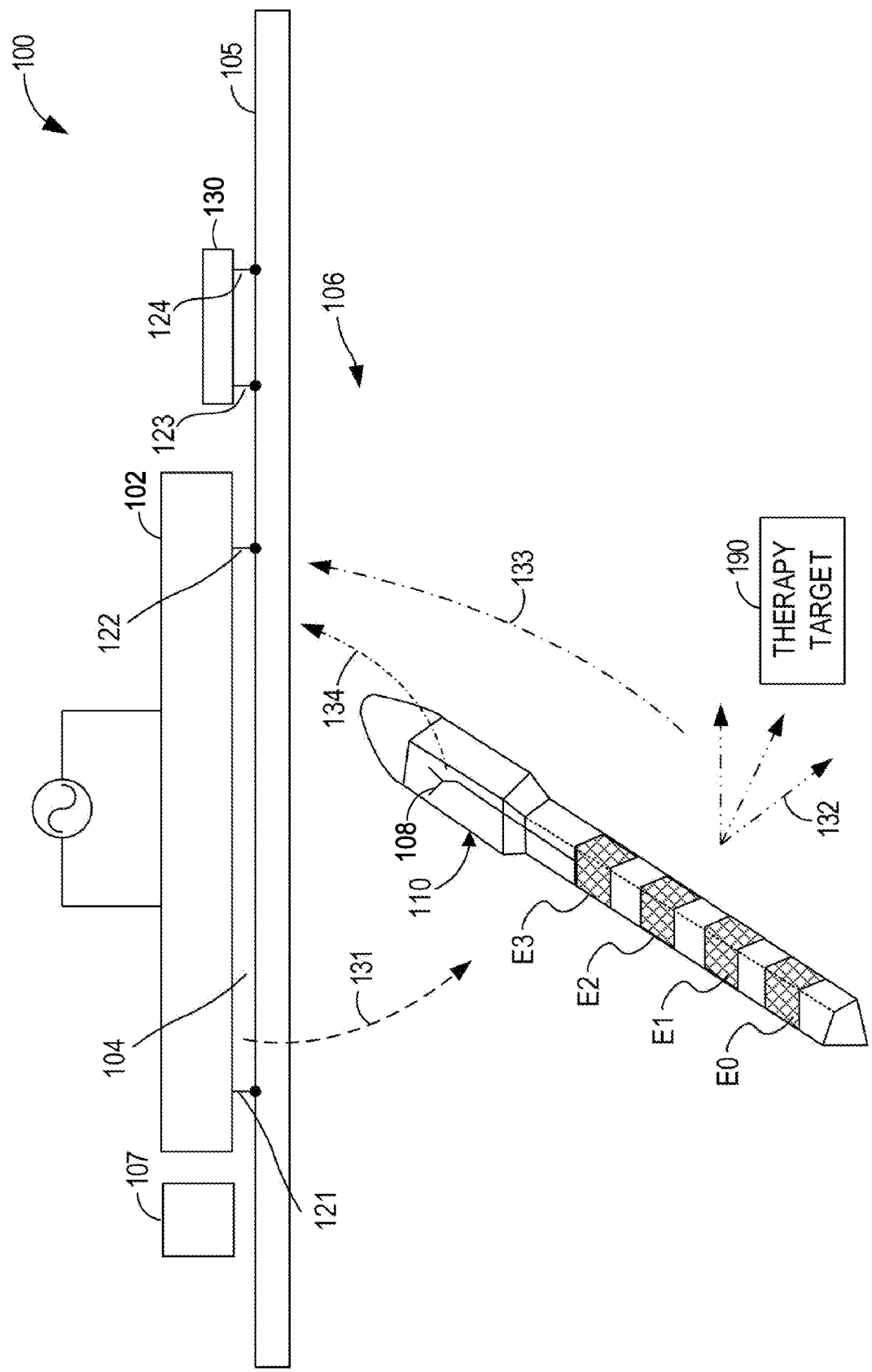
FIG. 1 illustrates generally a schematic of an embodiment of a system using wireless communication paths.

In the following description that includes examples of different nerve-electrode interfaces, reference is made to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. The present inventors contemplate examples using any combination or permutation of those elements shown or described (or one or more aspects thereof), either with respect to a particular example (or one or more aspects thereof), or with respect to other examples (or one or more aspects thereof) shown or described herein. Generally discussed herein are implantable devices and methods of assembling the implantable devices.

Implantable Systems and Devices

Section headings herein, like the one above ("IMPLANTABLE SYSTEMS AND DEVICES"), are provided to guide a reader generally to material corresponding to the topic indicated by the heading. However, discussions under a particular heading are not to be construed as applying only to configurations of a single type; instead, the various features discussed in the various sections or subsections herein can be combined in various ways and permutations. For example, some discussion of features and benefits of implantable systems and devices may be found in the text and corresponding figures under the present section heading "IMPLANTABLE SYSTEMS AND DEVICES".

Midfield powering technology can provide power to a deeply implanted electrostimulation device from an external power source located on or near a tissue surface, such as at an external surface of a user's skin. The user can be a clinical patient or other user. The midfield powering technology can have one or more advantages over implantable pulse generators. For example, a pulse generator can have one or more relatively large, implanted batteries and/or one or more lead systems. Midfield devices, in contrast, can include relatively small battery cells that can be configured to receive and store relatively small amounts of power. A midfield device can include one or more electrodes integrated in a unitary implantable package. Thus, in some examples, a midfield-powered device can provide a simpler implant procedure over other conventional devices, which can lead to a lower cost and a lower risk of infection or other implant complications. One or more of the advantages can be from an amount of power transferred to the implanted device. The ability to focus the energy from the midfield device can allow for an increase in the amount of power transferred to the implanted device.

An advantage of using midfield powering technology can include a main battery or power source being provided externally to the patient, and thus low power consumption and high efficiency circuitry requirements of conventional battery-powered implantable devices can be relaxed. Another advantage of using midfield powering technology can include an implanted device that can be physically smaller than a battery-powered device. Midfield powering technology can thus help enable better patient tolerance and comfort along with potentially lower costs to manufacture and/or to implant in patient tissue.

There is a current unmet need that includes communicating power and/or data using midfield transmitters and receivers, such as to communicate power and/or data from an external midfield coupler or source device to one or more implanted neural stimulation devices and/or one or more implanted sensor devices. The unmet need can further include communicating data from the one or more implanted neural stimulation devices and implanted sensor devices to the external midfield coupler or source device.

In one or more examples, multiple devices can be implanted in patient tissue and can be configured to deliver a therapy and/or sense physiologic information about a patient and/or about the therapy. The multiple implanted devices can be configured to communicate with one or more external devices. In one or more examples, the one or more external devices are configured to provide power and/or data signals to the multiple implanted devices, such as concurrently or in a time-multiplexed (e.g., "round-robin") fashion. The provided power and/or data signals can be steered or directed by an external device to transfer the signals to an implant efficiently. Although the present disclosure may refer to a power signal or data signal specifically, such references are to be generally understood as optionally including one or both of power and data signals.

Several embodiments described herein can be advantageous because they include one, several, or all of the following benefits: (i) a system configured to (a) communicate power and/or data signals from a midfield coupler device to an implantable device via midfield radiofrequency (RF) signals, (b) generate and provide a therapy signal via one or more electrodes coupled to the implantable device, the therapy signal including an information component, and producing a signal incident to providing the therapy signal, (c) receive a signal, based on the therapy signal, using electrodes coupled to the midfield coupler device, and (d) at the midfield coupler device or another device, decode and react to the information component from the received signal; (ii) a dynamically configurable, active midfield transceiver that is configured to provide RF signals to modulate an evanescent field at a tissue surface and thereby generate a propagating field within tissue, such as to transmit power and/or data signals to an implanted target device (see, e.g., the example of FIG. 16 that shows signal penetration inside tissue); (iii) an implantable device including an antenna configured to receive a midfield power signal from the midfield transceiver and including a therapy delivery circuitry configured to provide signal pulses to electrostimulation electrodes using a portion of the received midfield power signal, wherein the signal pulses include therapy pulses and data pulses, and the data pulses can be interleaved with or embedded in the therapy pulses; (iv) an implantable device configured to encode information, in a therapy signal, about the device itself, such as including information about the device's operating status, or about a previously-provided, concurrent, or planned future therapy provided by the device; (v) a midfield transceiver including electrodes that are configured to sense electrical signals at a tissue surface; (vi) adjustable wireless signal sources and receivers that are configured together to enable a communication loop or feedback loop; (vii) an external unit configured to detect or determine a presence at or near a tissue surface; and/or (ix) an external unit with protection circuitry to inhibit operation when the external unit determines it is not in communication with an implanted device, or when the external unit determines it is unlikely to be in proximity to tissue and/or to an implanted device.

In one or more examples, one or more of these benefits and others can be realized using a system for manipulating an evanescent field at or near an external tissue surface to transmit power and/or data wirelessly to one or more target devices implanted in the tissue. In one or more examples, one or more of these benefits can be realized using a device or devices implanted in a body or capable of being implanted in a body and as described herein. In one or more examples, one or more of these benefits can be realized using a midfield powering and/or communication device (e.g., a transmitter device and/or a receiver device or a transceiver device).

A system can include a signal generator system adapted to provide multiple different sets of signals (e.g., RF signals).

Each set can include two or more separate signals in some embodiments. The system can also include a midfield transmitter including multiple excitation ports, the midfield transmitter coupled to the RF signal generator system, and the midfield transmitter being adapted to transmit the multiple different sets of RF signals at respective different times via the excitation ports. The excitation ports can be adapted to receive respective ones of the separate signals from each set of RF signals. Each of the transmitted sets of RF signals can include a non-negligible magnetic field (H-field) component that is substantially parallel to the external tissue surface. In one or more examples, each set of transmitted RF signals is adapted or selected to differently manipulate an evanescent field at or near the tissue surface to transmit a power and/or data signal to one or more target devices implanted in the tissue via a midfield signal instead of via inductive nearfield coupling or radiative far-field transmission.

In one or more examples, one or more of the above-mentioned benefits, among others, can be realized, at least in part, using an implantable therapy delivery device (e.g., a device configured to provide neural stimulation) that includes receiver circuitry including an antenna (e.g., an electric-field or magnetic field based antenna) configured to receive a midfield power signal from an external source device, such as when the receiver circuitry is implanted within tissue. The implantable therapy delivery device can include therapy delivery circuitry. The therapy delivery circuitry can be coupled to the receiver circuitry. The therapy delivery circuitry can be configured to provide signal pulses to one or more energy delivery members (e.g., electrostimulation electrodes), which may be integrally coupled to a body of the therapy delivery device or positioned separately from (e.g., not located on) the body of the therapy delivery device), such as by using a portion of the received midfield power signal from the external source device (e.g., sometimes referred to herein as an external device, an external source, an external midfield device, a midfield transmitter device, a midfield coupler, a midfield powering device, a powering device, or the like, depending on the configuration and/or usage context of the device). The signal pulses can include one or more electrostimulation therapy pulses and/or data pulses. In one or more examples, one or more of the above-mentioned benefits, among others, can be realized, at least in part, using an external transmitter and/or receiver (e.g., transceiver) device that includes an electrode pair configured to be disposed at an external tissue surface, and the electrode pair is configured to receive an electrical signal via the tissue. The electrical signal can correspond to an electrostimulation therapy delivered to the tissue by the therapy delivery device. A demodulator circuitry can be coupled to the electrode pair and can be configured to demodulate a portion of the received electrical signal, such as to recover a data signal originated by the therapy delivery device.

In one or more examples that include using a midfield wireless coupler, tissue can act as a dielectric to tunnel energy. Coherent interference of propagating modes can confine a field at a focal plane to less than a corresponding vacuum wavelength, for example, with a spot size subject to a diffraction limit in a high-index material. In one or more examples, a receiver (e.g., implanted in tissue) positioned at such a high energy density region, can be one or more orders of magnitude smaller than a conventional nearfield implantable receiver, or can be implanted more deeply in tissue (e.g., greater than 1 cm in depth). In one or more examples, a transmitter source described herein can be configured to provide electromagnetic energy to various target locations, including for example to one or more deeply implanted devices. In an example, the energy can be provided to a location with greater than about a few millimeters of positioning accuracy. That is, a transmitted power or energy signal can be directed or focused to a target location that is within about one wavelength of the signal in tissue. Such energy focusing is substantially more accurate than the focusing available via traditional inductive means and is sufficient to provide adequate power to a receiver. In other wireless powering approaches using nearfield coupling (inductive coupling and its resonant enhanced derivatives), evanescent components outside tissue (e.g., near the source) remain evanescent inside tissue, which does not allow for effective depth penetration. Unlike nearfield coupling, energy from a midfield source is primarily carried in propagating modes and, as a result, an energy transport depth is limited by environmental losses rather than by intrinsic decay of the nearfield. Energy transfer implemented with these characteristics can be at least two to three orders of magnitude more efficient than nearfield systems.

One or more of the systems, apparatuses, and methods discussed herein can be used to help treat a patient disorder. Disorders such as fecal or urinary incontinence (e.g., overactive bladder) can be treated for example by stimulating the tibial nerve or any branch of the tibial nerve, such as but not limited to the posterior tibial nerve, one or more nerves or nerve branches originating from the sacral plexus, including but not limited to S1-S4, the tibial nerve, and/or the pudendal nerve. Urinary incontinence may be treated by stimulating one or more of muscles of the pelvic floor, nerves innervating the muscles of the pelvic floor, internal urethral sphincter, external urethral sphincter, and the pudendal nerve or branches of the pudendal nerve.

One or more of the systems, apparatuses, and methods discussed herein can be used to help treat sleep apnea and/or snoring by stimulating one or more of a nerve or nerve branches of the hypoglossal nerve, the base of the tongue (muscle), phrenic nerve(s), intercostal nerve(s), accessory nerve(s), and cervical nerves C3-C6. Treating sleep apnea and/or snoring can include providing energy to an implant to sense a decrease, impairment, or cessation of breathing (such as by measuring oxygen saturation).

One or more of the systems, apparatuses, and methods discussed herein can be used to help treat vaginal dryness, such as by stimulating one or more of Bartholin gland(s), Skene's gland(s), and inner wall of vagina. One or more of the systems, apparatuses, and methods discussed herein can be used to help treat migraines or other headaches, such as by stimulating one or more of the occipital nerve, supraorbital nerve, C2 cervical nerve, or branches thereof, and the frontal nerve, or branches thereof. One or more of the systems, apparatuses, and methods discussed herein can be used to help treat post-traumatic stress disorder, hot flashes, and/or complex regional pain syndrome such as by stimulating one or more of the stellate ganglion and the C4-C7 of the sympathetic chain.

One or more of the systems, apparatuses, and methods discussed herein can be used to help treat neuralgia (e.g., trigeminal neuralgia), such as by stimulating one or more of the sphenopalatine ganglion nerve block, the trigeminal nerve, or branches of the trigeminal nerve. One or more of the systems, apparatuses, and methods discussed herein can be used to help treat dry mouth (e.g., caused by side effects from medications, chemotherapy or radiation therapy cancer treatments, Sjogren's disease, or by other cause of dry mouth), such as by stimulating one or more of Parotid glands, submandibular glands, sublingual glands, submucosa of the oral mucosa in the oral cavity within the tissue of the buccal, labial, and/or lingual mucosa, the soft palate, the lateral parts of the hard palate, and/or the floor of the mouth and/or between muscle fibers of the tongue, Von Ebner glands, glossopharyngeal nerve (CN IX), including branches of CN IX, including otic ganglion, a facial nerve (CN VII), including branches of CN VII, such as the submandibular ganglion, and branches of T1-T3, such as the superior cervical ganglion.

One or more of the systems, apparatuses, and methods discussed herein can be used to help treat a transected nerve, such as by sensing electrical output from the proximal portion of a transected nerve and delivering electrical input into the distal portion of a transected nerve, and/or sensing electrical output from the distal portion of a transected nerve and delivering electrical input into the proximal portion of a transected nerve. One or more of the systems, apparatuses, and methods discussed herein can be used to help treat cerebral palsy, such as by stimulating one or more muscles or one or more nerves innervation one or more muscles affected in a patient with cerebral palsy. One or more of the systems, apparatuses, and methods discussed herein can be used to help treat erectile dysfunction, such as by stimulating one or more of pelvic splanchnic nerves (S2-S4) or any branches thereof, the pudendal nerve, cavernous nerve(s), and inferior hypogastric plexus.

One or more of the systems, apparatuses, and methods discussed herein can be used to help treat menstrual pain, such as by stimulating one or more of the uterus and the vagina. One or more of the systems, apparatuses, and methods discussed herein can be used as an intrauterine device, such as by sensing one or more PH and blood flow or delivering current or drugs to aid in contraception, fertility, bleeding, or pain. One or more of the systems, apparatuses, and methods discussed herein can be used to incite human arousal, such as by stimulating female genitalia, including external and internal, including clitoris or other sensory active parts of the female, or by stimulating male genitalia.

One or more of the systems, apparatuses, and methods discussed herein can be used to help treat hypertension, such as by stimulating one or more of a carotid sinus, left or right cervical vagus nerve, or a branch of the vagus nerve. One or more of the systems, apparatuses, and methods discussed herein can be used to help treat paroxysmal supraventricular tachycardia, such as by stimulating one or more of trigeminal nerve or branches thereof, anterior ethmoidal nerve, and the vagus nerve. One or more of the systems, apparatuses, and methods discussed herein can be used to help treat vocal cord dysfunction, such as by sensing the activity of a vocal cord and the opposite vocal cord or just stimulating one or more of the vocal cords by stimulating nerves innervating the vocal cord, the left and/or Right recurrent laryngeal nerve, and the vagus nerve.

One or more of the systems, apparatuses, and methods discussed herein can be used to help repair tissue, such as by stimulating tissue to do one or more of enhancing microcirculation and protein synthesis to heal wounds and restoring integrity of connective and/or dermal tissues. One or more of the systems, apparatuses, and methods discussed herein can be used to help asthma or chronic obstructive pulmonary disease, such as by one or more of stimulating the vagus nerve or a branch thereof, blocking the release of norepinephrine and/or acetylcholine and/or interfering with receptors for norepinephrine and/or acetylcholine.

One or more of the systems, apparatuses, and methods discussed herein can be used to help treat cancer, such as by stimulating, to modulate one or more nerves near or in a tumor, such as to decrease the sympathetic innervation, such as epinephrine/NE release, and/or parasympathetic innervation. One or more of the systems, apparatuses, and methods discussed herein can be used to help treat diabetes, such as by powering a sensor inside the human body that detects parameters of diabetes, such as a glucose level or ketone level and using such sensor data to adjust delivery of exogenous insulin from an insulin pump. One or more of the systems, apparatuses, and methods discussed herein can be used to help treat diabetes, such as by powering a sensor inside the human body that detects parameters of diabetes, such as a glucose level or ketone level, and using a midfield coupler to stimulate the release of insulin from islet beta cells.

One or more of the systems, apparatuses, and methods discussed herein can be used to help treat neurological conditions, disorders or diseases (such as Parkinson's disease (e.g., by stimulating an internus or nucleus of the brain), Alzheimer's disease, Huntington's disease, dementia, Creutzfeldt-Jakob disease, epilepsy (e.g., by stimulating a left cervical vagus nerve or a trigeminal nerve), posttraumatic stress disorder (PTSD) (e.g., by stimulating a left cervical vagus nerve), or essential tremor, such as by stimulating a thalamus), neuralgia, depression, dystonia (e.g., by stimulating an internus or nucleus of the brain), phantom limb (e.g., by stimulating an amputated nerve, such an ending of an amputated nerve), dry eyes (e.g., by stimulating a lacrimal gland), arrhythmia (e.g., by stimulating the heart), a gastrointestinal disorder, such as obesity, gastroesophageal reflux, and/or gastroparesis, such as by stimulating a C1-C2 occipital nerve or deep brain stimulation (DBS) of the hypothalamus, an esophagus, a muscle near sphincter leading to the stomach, and/or a lower stomach, and/or stroke (e.g., by subdural stimulation of a motor cortex). Using one or more examples discussed herein, stimulation can be provided continuously, on demand (e.g., as demanded by a physician, patient, or other user), or periodically.

In providing the stimulation, an implantable device can be situated five centimeters or more below a tissue interface, that is, below a surface of the skin. In one or more examples, an implantable device can be situated between about 2 centimeters and 4 centimeters, about 3 centimeters, between about 1 centimeter and five centimeters, less than 1 centimeter, about two centimeters, or other distance below the surface of the skin. The depth of implantation can depend on the use of the implanted device. For example, to treat depression, hypertension, epilepsy, and/or PTSD the implantable device can situated between about 2 centimeters and about four centimeters below the surface of the skin. In another example, to treat sleep apnea, arrhythmia (e.g., bradycardia), obesity, gastroesophageal reflux, and/or gastroparesis the implantable device can be situated at greater than about 3 centimeters below the surface of the skin. In yet another example, to treat Parkinson's, essential tremors, and/or dystonia the implantable device can be situated between about 1 centimeter and about 5 centimeters below the surface of the skin. Yet other examples include situating the implantable device between about 1 centimeter and about 2 centimeters below the surface of the skin, such as to treat fibromyalgia, stroke, and/or migraine, at about 2 centimeters to treat asthma, and at about one centimeter or less to treat dry eyes.

Although many embodiments included herein describe devices or methods for providing stimulation (e.g., electrostimulation), the embodiments may be adapted to provide other forms of modulation (e.g., denervation) in addition to or instead of stimulation. In addition, although many embodiments included herein refer to the use of electrodes to deliver therapy, other energy delivery members (e.g., ultrasound transducers or other ultrasound energy delivery members) or other therapeutic members or substances (e.g., fluid delivery devices or members to deliver chemicals, drugs, cryogenic fluid, hot fluid or steam, or other fluids) may be used or delivered in other embodiments.

FIG. 1 illustrates generally a schematic of an embodiment of a system 100 using wireless communication paths. The system 100 includes an example of an external source 102, such as a midfield transmitter source, sometimes referred to as a midfield coupler or external unit or external power unit, and the external source 102 can be located at or above an interface 105 between air 104 and a higher-index material 106, such as body tissue. The external source 102 can produce a source current (e.g., an in-plane source current). The source current can generate an electric field and a magnetic field. The magnetic field can include a non-negligible component that is parallel to the surface of the source 102 and/or to a surface of the higher-index material 106 (e.g., a surface of the higher-index material 106 that faces the external source 102). In accordance with several embodiments, the external source 102 may comprise structural features and functions described in connection with the midfield couplers and external sources included in WIPO Publication No. WO/2015/179225 published on Nov. 26, 2015 and titled "MIDFIELD COUPLER", which is incorporated herein by reference in its entirety.

In an example, the external source 102 can include at least a pair of outwardly facing electrodes 121 and 122. The electrodes 121 and 122 can be configured to contact a tissue surface, for example, at the interface 105. In one or more examples, the external source 102 is configured for use with a sleeve, pocket, or other garment or accessory that maintains the external source 102 adjacent to the higher-index material 106, and that optionally maintains the electrodes 121 and 122 in physical contact with a tissue surface. In one or more examples, the sleeve, pocket, or other garment or accessory can include or use a conductive fiber or fabric, and the electrodes 121 and 122 can be in physical contact with the tissue surface via the conductive fiber or fabric.

In one or more examples, more than two outwardly facing electrodes can be used and processor circuitry on-board or auxiliary to the source 102 can be configured to select an optimal pair or group of electrodes to use to sense farfield signal information (e.g., signal information corresponding to a delivered therapy signal or to a nearfield signal). In such embodiments, the electrodes can operate as antennas. In one or more examples, the source 102 includes three outwardly facing electrodes arranged as a triangle, or four outwardly facing electrodes arranged as a rectangle, and any two or more of the electrodes can be selected for sensing and/or can be electrically grouped or coupled together for sensing or diagnostics. In one or more examples, the processor circuitry can be configured to test multiple different electrode combination selections to identify an optimal configuration for sensing a farfield signal (an example of the processor circuitry is presented in FIG. 2A, among others).

FIG. 1 illustrates an embodiment of an implantable device 110, such as can include a multi-polar therapy delivery device configured to be implanted in the higher-index material 106 or in a blood vessel. In one or more examples, the implantable device 110 includes all or a portion of the circuitry 500 from FIG. 5, discussed in further detail below. In one or more examples, the implantable device 110 is implanted in tissue below the tissue-air interface 105. In FIG. 1, the implantable device 110 includes an elongate body and multiple electrodes E0, E1, E2, and E3 that are axially spaced apart along a portion of the elongate body. The implantable device 110 includes receiver and/or transmitter circuitry (not shown in FIG. 1, see e.g., FIGS. 2A, 2B, and 4, among others) that can enable communication between the implantable device 110 and the external source 102.

The various electrodes E0-E3 can be configured to deliver electrostimulation therapy to patient tissue, such as at or near a neural or muscle target. In one or more examples, at least one electrode can be selected for use as an anode and at least one other electrode can be selected for use as a cathode to define an electrostimulation vector. In one or more examples, electrode E1 is selected for use as an anode and electrode E2 is selected for use as a cathode. Together, the E1-E2 combination defines an electrostimulation vector V12. Various vectors can be configured independently to provide a neural electrostimulation therapy to the same or different tissue target, such as concurrently or at different times.

In one or more examples, the source 102 includes an antenna (see, e.g., FIG. 3) and the implantable device 110 includes an antenna 108 (e.g., and electric field-based or magnetic field-based antenna). The antennas can be configured (e.g., in length, width, shape, material, etc.) to transmit and receive signals at substantially the same frequency. The implantable device 110 can be configured to transmit power and/or data signals through the antenna 108 to the external source 102 and can receive power and/or data signals transmitted by the external source 102. The external source 102 and implantable device 110 can be used for transmission and/or reception of RF signals. A transmit/receive (T/R) switch can be used to switch each RF port of the external source 102 from a transmit (transmit data or power) mode to a receive (receive data) mode. A T/R switch can similarly be used to switch the implantable device 110 between transmit and receive modes. See FIG. 4, among others, for examples of T/R switches.

Figure 3:
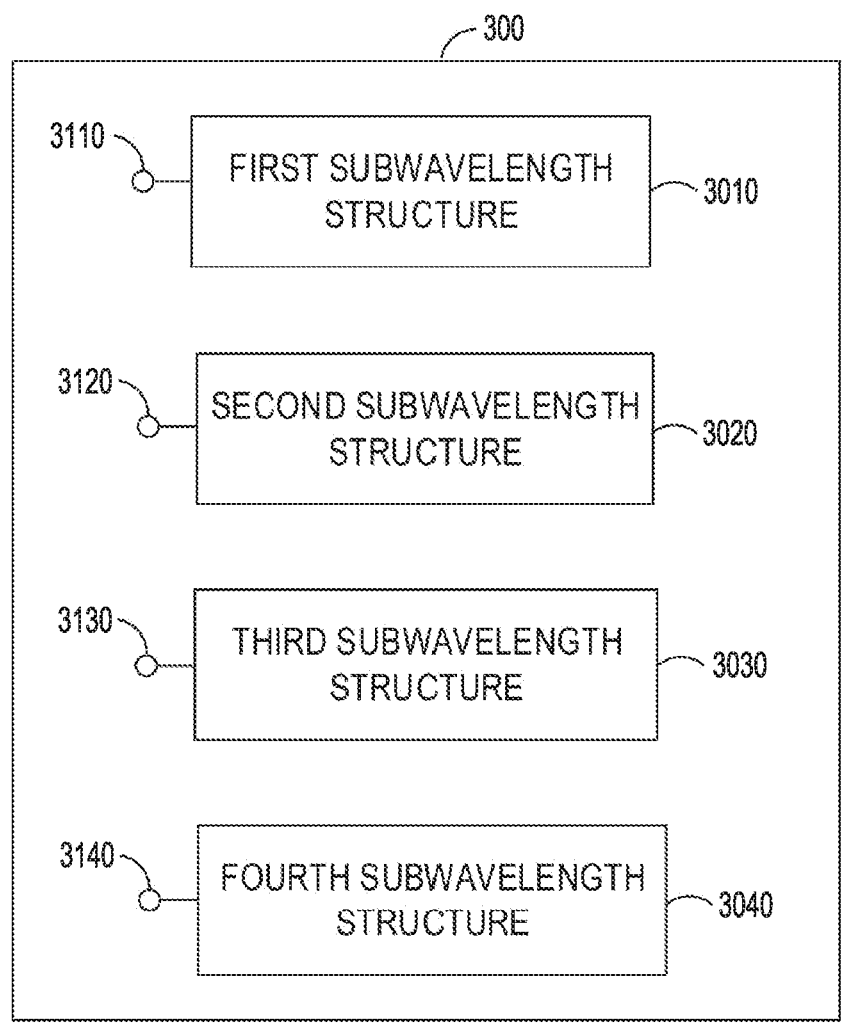
FIG. 3 illustrates generally a schematic view of an embodiment of a midfield antenna with multiple subwavelength structures.
Figure 4:
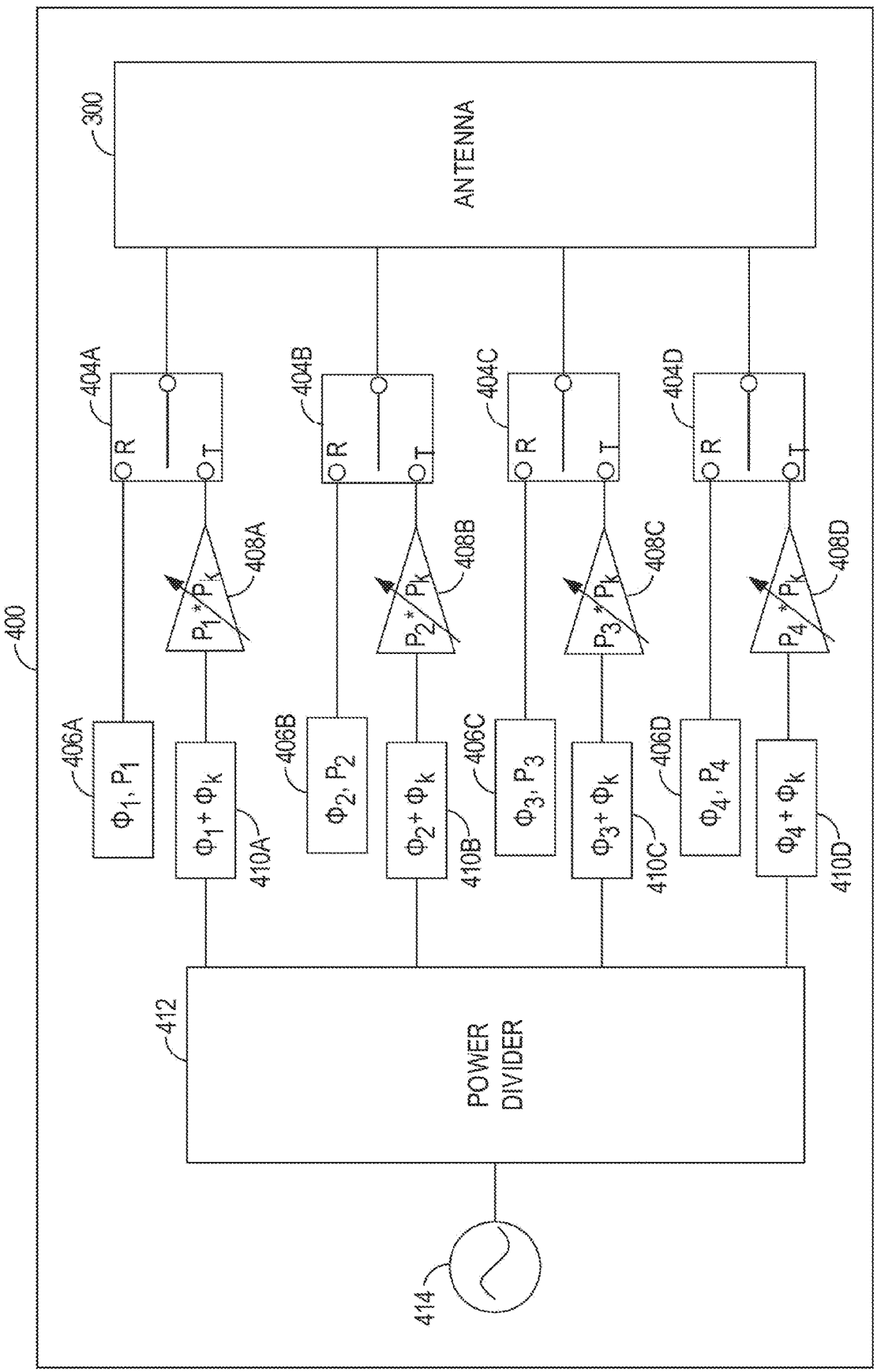
FIG. 4 illustrates generally a diagram of an embodiment of circuitry of an external midfield source device.

In one or more examples, a receive terminal on the external source 102 can be connected to one or more components that detect a phase and/or amplitude of a received signal from the implantable device 110. The phase and amplitude information can be used to program a phase of the transmit signal, such as to be substantially the same relative phase as a signal received from the implantable device 110. To help achieve this, the external source 102 can include or use a phase-matching and/or amplitude-matching network, such as shown in the embodiment of FIG. 4. The phase-matching and/or amplitude matching network can be configured for use with a midfield antenna that includes multiple ports, such as shown in the embodiment of FIG. 3.

Referring again to FIG. 1, in one or more examples, the implantable device 110 can be configured to receive a midfield signal 131 from the external source 102. The midfield signal 131 can include power and/or data signal components. In some embodiments, a power signal component can include one or more data components embedded therein. In one or more examples, the midfield signal 131 includes configuration data for use by the implantable device 110. The configuration data can define, among other things, therapy signal parameters, such as a therapy signal frequency, pulse width, amplitude, or other signal waveform parameters. In one or more examples, the implantable device 110 can be configured to deliver an electrostimulation therapy to a therapy target 190, such as can include a neural target (e.g., a nerve, or other tissue such as a vein, connective tissue, or other tissue that includes one or more neurons within or near the tissue), a muscle target, or other tissue target. An electrostimulation therapy delivered to the therapy target 190 can be provided using a portion of a power signal received from the external source 102. Examples of the therapy target 190 can include nerve tissue or neural targets, for example including nerve tissue or neural targets at or near cervical, thoracic, lumbar, or sacral regions of the spine, brain tissue, muscle tissue, abnormal tissue (e.g., tumor or cancerous tissue), targets corresponding to sympathetic or parasympathetic nerve systems, targets at or near peripheral nerve bundles or fibers, at or near other targets selected to treat incontinence, urinary urge, overactive bladder, fecal incontinence, constipation, pain, neuralgia, pelvic pain, movement disorders or other diseases or disorders, deep brain stimulation (DBS) therapy targets or any other condition, disease or disorder (such as those other conditions, diseases, or disorders identified herein).

Delivering the electrostimulation therapy can include using a portion of a power signal received via the midfield signal 131, and providing a current signal to an electrode or an electrode pair (e.g., two or more of E0-E3), coupled to the implantable device 110, to stimulate the therapy target 190. As a result of the current signal provided to the electrode(s), a nearfield signal 132 can be generated. An electric potential difference resulting from the nearfield signal 132 can be detected remotely from the therapy delivery location. Various factors can influence where and whether the potential difference can be detected, including, among other things, characteristics of the therapy signal, a type or arrangement of the therapy delivery electrodes, and characteristics of any surrounding biologic tissue. Such a remotely detected electric potential difference can be considered a farfield signal 133. The farfield signal 133 can represent an attenuated portion of the nearfield signal 132. That is, the nearfield signal 132 and the farfield signal 133 can originate from the same signal or field, such as with the nearfield signal 132 considered to be associated with a region at or near the implantable device 110 and the therapy target 190, and with the farfield signal 133 considered to be associated with other regions more distal from the implantable device 110 and the therapy target 190. In one or more examples, information about the implantable device 110, or about a previously-provided or future planned therapy provided by the implantable device 110, can be encoded in a therapy signal and detected and decoded by the external source 102 by way of the farfield signal 133.

In one or more examples, the device 110 can be configured to provide a series of electrostimulation pulses to a tissue target (e.g., neural target). For example, the device 110 can provide multiple electrostimulation pulses separated in time, such as using the same or different electrostimulation vectors, to provide a therapy. In one or more examples, a therapy comprising multiple signals can be provided to multiple different vectors in parallel, or can be provided in sequence such as to provide a series or sequence of electrostimulation pulses to the same neural target. Thus, even if one vector is more optimal than the others for eliciting a patient response, the therapy as a whole can be more effective than stimulating only the known-optimal vector because (1) the target may experience a rest period during periods of non-stimulation, and/or (2) stimulating the areas nearby and/or adjacent to the optimal target can elicit some patient benefit.

The system 100 can include a sensor 107 at or near the interface 105 between air 104 and the higher-index material 106. The sensor 107 can include, among other things, one or more electrodes, an optical sensor, an accelerometer, a temperature sensor, a force sensor, a pressure sensor, or a surface electromyography (EMG) device. The sensor 107 may comprise multiple sensors (e.g., two, three, four or more than four sensors). Depending on the type of sensor(s) used, the sensor 107 can be configured to monitor electrical, muscle, or other activity near the device 110 and/or near the source 102. For example, the sensor 107 can be configured to monitor muscle activity at a tissue surface. If muscle activity greater than a specified threshold activity level is detected, then a power level of the source 102 and/or of the device 110 can be adjusted. In one or more examples, the sensor 107 can be coupled to or integrated with the source 102, and in other examples, the sensor 107 can be separate from, and in data communication with (e.g., using a wired or wireless electrical coupling or connection), the source 102 and/or the device 110.

The system 100 can include a farfield sensor device 130 that can be separate from, or communicatively coupled with, one or more of the source 102 and the sensor 107. The farfield sensor device 130 can include two or more electrodes and can be configured to sense a farfield signal, such as the farfield signal 133 corresponding to a therapy delivered by the device 110. The farfield sensor device 130 can include at least one pair of outwardly facing electrodes 123 and 124 configured to contact a tissue surface, for example, at the interface 105. In one or more examples, three or more electrodes can be used, and processor circuitry on-board or auxiliary to the farfield sensor device 130 can select various combinations of two or more of the electrodes for use in sensing the farfield signal 133. In one or more examples, the farfield sensor device 130 can be configured for use with a sleeve, pocket, or other garment or accessory that maintains the farfield sensor device 130 adjacent to the higher-index material 106, and that optionally maintains the electrodes 123 and 124 in physical contact with a tissue surface. In one or more examples, the sleeve, pocket, or other garment or accessory can include or use a conductive fiber or fabric, and the electrodes 123 and 124 can be in physical contact with the tissue surface via the conductive fiber or fabric. An example of at least a portion of a farfield sensor device 130 is further described herein in connection with FIG. 2B.

In one or more examples, the external source 102 provides a midfield signal 131 including power and/or data signals to the implantable device 110. The midfield signal 131 includes a signal (e.g., an RF signal) having various or adjustable amplitude, frequency, phase, and/or other signal characteristics. The implantable device 110 can include an antenna, such as described below, that can receive the midfield signal 131 and, based on characteristics of receiver circuitry in the implantable device 110, can modulate the received signal at the antenna to thereby generate a backscatter signal or backscatter communication signal. In one or more examples, the implantable device 110 can encode information in the backscatter signal 112, such as information about a characteristic of the implantable device 110 itself, about a received portion of the midfield signal 131, about a therapy provided by the implantable device 110, and/or other information. The backscatter signal 112 can be received by an antenna at the external source 102 and/or the farfield sensor device 130, or can be received by another device. In one or more examples, a biological signal can be sensed by a sensor of the implantable device 110, such as a glucose sensor, an electropotential (e.g., an electromyography sensor, electrocardiograph (ECG) sensor, resistance, or other electrical sensor), a light sensor, a temperature, a pressure sensor, an oxygen sensor, a motion sensor, or the like. A signal representative of the detected biological signal can be modulated onto the backscatter signal 112. Other sensors are discussed elsewhere herein, such as with regard to FIG. 47, among others. In such embodiments, the sensor 107 can include a corresponding monitor device, such as a glucose, temperature, ECG, EMG, oxygen, or other monitor, such as to receive, demodulate, interpret, and/or store data modulated onto the backscatter signal. In one or more examples, the external source 102 and/or the implantable device 110 can include an optical transceiver configured to facilitate communication between the external source 102 and the implantable device 110. The external source 102 can include a light source, such as a photo laser diode or LED, or can include a photo detector, or can include both of a light source and a photo detector. The implantable device 110 can include a light source, such as a photo laser diode or LED, or can include a photo detector, or can include both of a light source and a photo detector. In an example, the external source 102 and/or implantable device 110 can include a window, such as made of quartz, glass, or other translucent material, adjacent to its light source or photo detector.

In an example, optical communications can be separate from or supplemental to an electromagnetic coupling between the external source 102 and the implantable device 110. Optical communication can be provided using light pulses modulated according to various protocols, such as using pulse position modulation (PPM). In an example, a light source and/or photo detector on-board the implantable device 110 can be powered by a power signal received at least in part via midfield coupling with the external source 102.

In an example, a light source at the external source 102 can send a communication signal through skin, into subcutaneous tissue, and through an optical window (e.g., quartz window) in the implantable device 110. The communication signal can be received at a photo detector on-board the implantable device 110. Various measurement information, therapy information, or other information from or about the implantable device can be encoded and transmitted from the implantable device 110 using a light source provided at the implantable device 110. The light signal emitted from the implantable device 110 can travel through the same optical window, subcutaneous tissue, and skin tissue, and can be received at photo detector on-board the external source 102. In an example, the light sources and/or photo detectors can be configured to emit and/or receive, respectively, electromagnetic waves in the visible or infrared ranges, such as in a range of about 670-910 nm wavelength (e.g., 670 nm-800 nm, 700 nm-760 nm, 670 nm-870 nm, 740 nm-850 nm, 800 nm-910 nm, overlapping ranges thereof, or any value within the recited ranges).

In an example, the external source 102 can include various circuitry to facilitate device reset, storage, user access, and other features. For example, the external source 102 can include a latching switch to provide a device-level power switch, such as can be used to remove power from drive or sense circuitry provided in the external source 102. In an example, the external source 102 can include a reed switch (e.g., a magnetic reed switch) that can be activated to perform a manual reset or to enter a device configuration mode or learning mode. In an example, the external source 102 can include an environmental sensor (e.g., a thermistor, humidity or moisture sensor, etc.) to detect device conditions and change device operating behavior accordingly. For example, information from a thermistor can be used to indicate a fault condition to prevent device overheating.

Figure 2A:
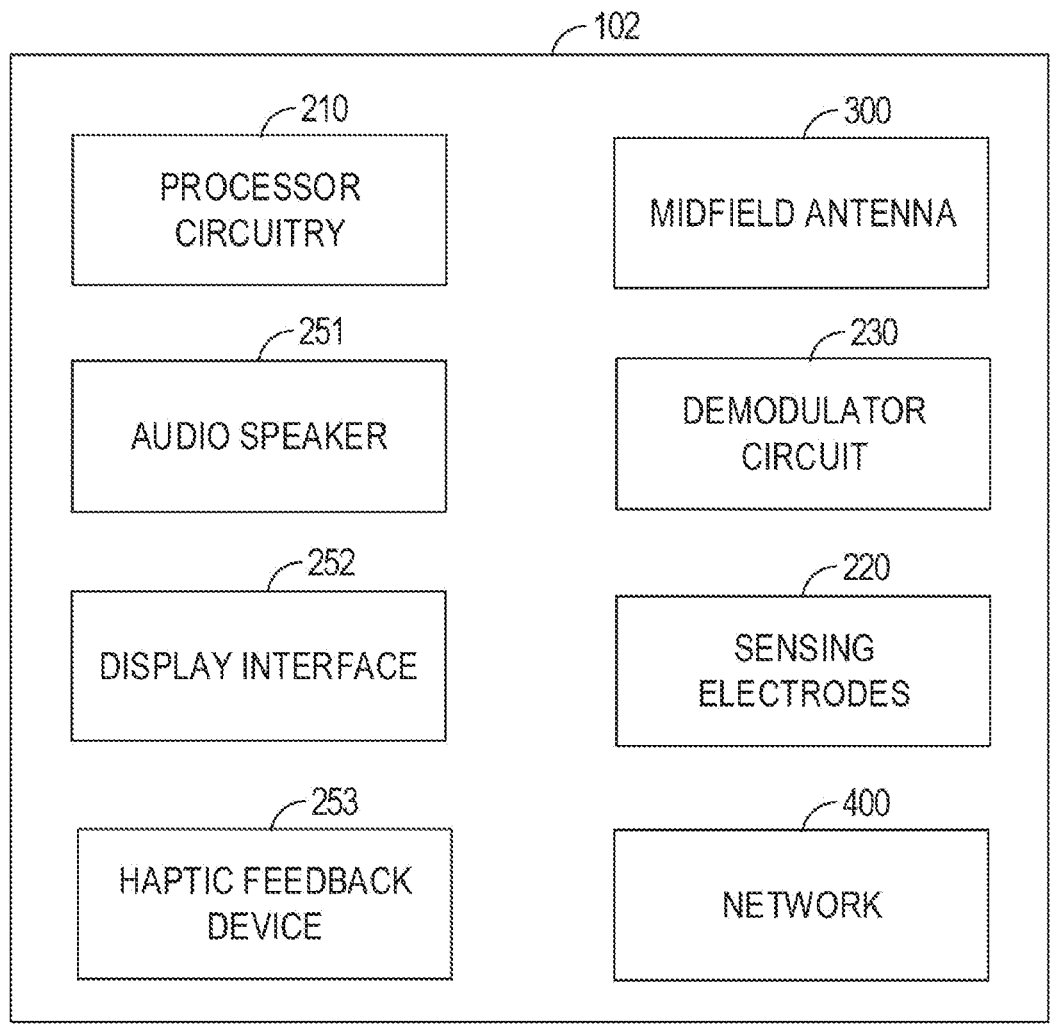
FIG. 2A illustrates generally a block diagram of an embodiment of a midfield source device.

FIG. 2A illustrates, by way of example, a block diagram of and embodiment of a midfield source device, such as the external source 102. The external source 102 can include various components, circuitry, or functional elements that are in data communication with one another. In the example of FIG. 2A, the external source 102 includes components, such as processor circuitry 210, one or more sensing electrodes 220 (e.g., including the electrodes 121 and 122), a demodulator circuitry 230, a phase-matching or amplitude-matching network 400, a midfield antenna 300, and/or one or more feedback devices, such as can include or use an audio speaker 251, a display interface 252, and/or a haptic feedback device 253. The midfield antenna 300 is further described below in the embodiment of FIG. 3, and the network 400 is further described below in the embodiment of FIG. 4. The processor circuitry 210 can be configured to coordinate the various functions and activities of the components, circuitry, and/or functional elements of the external source 102.

The midfield antenna 300 can be configured to provide a midfield excitation signal, such as can include RF signals having a non-negligible H-field component that is substantially parallel to an external tissue surface. In one or more examples, the RF signals can be adapted or selected to manipulate an evanescent field at or near a tissue surface, such as to transmit a power and/or data signal to respective different target devices (e.g., the implantable device 110, or any one or more other implantable devices discussed herein) implanted in tissue. The midfield antenna 300 can be further configured to receive backscatter or other wireless signal information that can be demodulated by the demodulator circuitry 230. The demodulated signals can be interpreted by the processor circuitry 210.

The midfield antenna 300 can include a dipole antenna, a loop antenna, a coil antenna, a slot or strip antenna, or other antenna. The antenna 300 can be shaped and sized to receive signals in a range of between about 400 MHz and about 4 GHz (e.g., between 400 MHz and 1 GHz, between 400 MHz and 3 GHz, between 500 MHz and 2 GHz, between 1 GHz and 3 GHz, between 500 MHz and 1.5 GHz, between 1 GHz and 2 GHz, between 2 GHz and 3 GHz, overlapping ranges thereof, or any value within the recited ranges). For embodiments incorporating a dipole antenna, the midfield antenna 300 may comprise a straight dipole with two substantially straight conductors, a folded dipole, a short dipole, a cage dipole, a bow-tie dipole or batwing dipole.

The demodulator circuitry 230 can be coupled to the sensing electrodes 220. In one or more examples, the sensing electrodes 220 can be configured to receive the farfield signal 133, such as based on a therapy provided by the implantable device 110, such as can be delivered to the therapy target 190. The therapy can include an embedded or intermittent data signal component that can be extracted from the farfield signal 133 by the demodulator circuitry 230. For example, the data signal component can include an amplitude-modulated or phase-modulated signal component that can be discerned from background noise or other signals and processed by the demodulator circuitry 230 to yield an information signal that can be interpreted by the processor circuitry 210. Based on the content of the information signal, the processor circuitry 210 can instruct one of the feedback devices to alert a patient, caregiver, or other system or individual. For example, in response to the information signal indicating successful delivery of a specified therapy, the processor circuitry 210 can instruct the audio speaker 251 to provide audible feedback to a patient, can instruct the display interface 252 to provide visual or graphical information to a patient, and/or can instruct the haptic feedback device 253 to provide a haptic stimulus to a patient. In one or more examples, the haptic feedback device 253 includes a transducer configured to vibrate or to provide another mechanical signal.

Figure 2B:
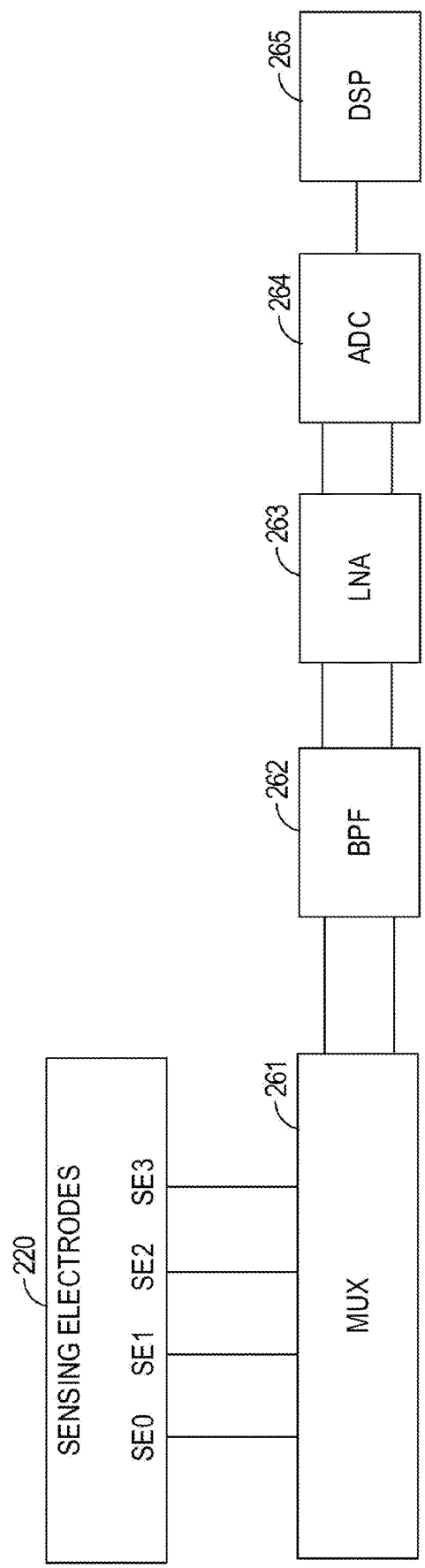
FIG. 2B illustrates generally a block diagram of an embodiment of a portion of a system configured to receive a signal.

FIG. 2B illustrates generally a block diagram of a portion of a system configured to receive a farfield signal. The system can include the sensing electrodes 220, such as can include the electrodes 121 and 122 of the source 102, or the electrodes 123 and 124 of the farfield sensor device 130. In the example of FIG. 2B, there are four sensing electrodes represented collectively as the sensing electrodes 220, and individually as SE0, SE1, SE2, and SE3; however, other numbers of sensing electrodes 220 may be used. The sensing electrodes can be communicatively coupled to multiplexer circuitry 261. The multiplexer circuitry 261 can select pairs of the electrodes, or electrode groups, for use in sensing farfield signal information. In one or more examples, the multiplexer circuitry 261 selects an electrode pair or grouping based on a detected highest signal to noise ratio of a received signal, or based on another relative indicator of signal quality, such as amplitude, frequency content, and/or other signal characteristic.

Sensed electrical signals from the multiplexer circuitry 261 can undergo various processing to extract information from the signals. For example, analog signals from the multiplexer circuitry 261 can be filtered by a band pass filter 262. The band pass filter 262 can be centered on a known or expected modulation frequency of a sensed signal of interest. A band pass filtered signal can then be amplified by a low-noise amplifier 263. The amplified signal can be converted to a digital signal by an analog-to-digital converter circuit (ADC) 264. The digital signal can be further processed by various digital signal processors 265, as further described herein, such as to retrieve or extract an information signal communicated by the implantable device 110.

FIG. 3 illustrates generally a schematic view of an embodiment of a midfield antenna 300 with multiple excitable structures, including subwavelength structures 3010, 3020, 3030, and 3040. The midfield antenna 300 can include a midfield plate structure with a substantially planar surface. The one or more subwavelength structures 3010-3040 can be formed in the plate structure. In the example of FIG. 3, the antenna 300 includes a first subwavelength structure 3010, a second subwavelength structure 3020, a third subwavelength structure 3030, and a fourth subwavelength structure 3040. Fewer or additional subwavelength structures can be used. The subwavelength structures can be excited individually or selectively by one or more RF ports (e.g., first through fourth RF ports 3110, 3120, 3130, and 3140) respectively coupled thereto.

A "subwavelength structure" can include a hardware structure with dimensions defined relative to a wavelength of a field that is rendered and/or received by the external source 102. For example, for a given $\lambda_0$ corresponding to a signal wavelength in air, a source structure that includes one or more dimensions less than $\lambda_0$ can be considered to be a subwavelength structure. Various designs or configurations of subwavelength structures can be used. Some examples of a subwavelength structure can include a slot in a planar structure, or a strip or patch of a conductive sheet of substantially planar material. Various examples of midfield antenna and excitable structures are discussed elsewhere herein. In some examples, the excitable structures include or use striplines or microstrips.

In an example, the midfield antenna 300 and its associated drive circuitry (discussed elsewhere herein) are configured to provide signals to manipulate or influence an evanescent field at or adjacent to tissue, where tissue serves as a medium with a relatively high dielectric constant (e.g., tissue is a high-K medium). That is, energy from the antenna 300 can be directed through the tissue or other high-K medium rather than through air. An efficiency of transmission from the midfield antenna 300 can be greatest when the antenna 300 is properly loaded by tissue, and the efficiency can be intentionally low when unloaded by tissue.

FIG. 4 illustrates generally the phase-matching or amplitude-matching network 400. In an example, the network 400 can include the antenna 300, and the antenna 300 can be electrically coupled to a plurality of switches 404A, 404B, 404C, and 404D, for example, via the first through fourth RF ports 311, 312, 313, and 314 illustrated in FIG. 3. The switches 404A-D are each electrically coupled to a respective phase and/or amplitude detector 406A, 406B, 406C, and 406D, and a respective variable gain amplifier 408A, 408B, 408C, and 408D. Each amplifier 408A-D is electrically coupled to a respective phase shifter 410A, 410B, 410C, and 410D, and each phase shifter 410A-D is electrically coupled to a common power divider 412 that receives an RF input signal 414 to be transmitted using the external source 102.

In one or more examples, the switches 404A-D can be configured to select either a receive line ("R") or a transmit line ("T"). A number of switches 404A-D of the network 400 can be equal to a number of ports of the midfield source 402. In the example of the network 400, the midfield source 402 includes four ports (e.g., corresponding to the four subwavelength structures in the antenna 300 of the example of FIG. 3), however any number of ports (and switches), such as one, two, three, four, five, six, seven, eight or more, can be used.

The phase and/or amplitude detectors 406A-D are configured to detect a phase ($\Phi1$, $\Phi2$, $\Phi3$, $\Phi4$) and/or power (P1, P2, P3, P4) of a signal received at each respective port of the midfield source 402. In one or more examples, the phase and/or amplitude detectors 406A-D can be implemented in one or more modules (hardware modules that can include electric or electronic components arranged to perform an operation, such as determining a phase or amplitude of a signal), such as including a phase detector module and/or an amplitude detector module. The detectors 406A-D can include analog and/or digital components arranged to produce one or more signals representative of a phase and/or amplitude of a signal received at the external source 102.

The amplifiers 408A-D can receive respective inputs from the phase shifters 410A-D (e.g., Pk phase shifted by $\Phi k$, $\Phi1+\Phi k$, $\Phi2+\Phi k$, $\Phi3+\Phi k$, or $\Phi4+\Phi k$). The output of the amplifier, O, is generally the output of the power divider, M when the RF input signal 414 has an amplitude of 4*M (in the embodiment of FIG. 4), multiplied by the gain of the amplifier Pi*Pk. Pk can be set dynamically as the values for P1, P2, P3, and/or P4 change. $\Phi k$ can be a constant. In one or more examples, the phase shifters 410A-D can dynamically or responsively configure the relative phases of the ports based on phase information received from the detectors 406A-D.

In one or more examples, a transmit power requirement from the midfield source 402 is Ptt. The RF signal provided to the power divider 412 has a power of 4*M. The output of the amplifier 408A is about M*P1*Pk. Thus, the power transmitted from the midfield coupler is M*(P1*Pk+P2*Pk+P3*Pk+P4*Pk)=Ptt. Solving for Pk yields Pk=Ptt (M*(P1+P2+P3+P4)).

The amplitude of a signal at each RF port can be transmitted with the same relative (scaled) amplitude as the signal received at the respective port of the midfield coupler coupled thereto. The gain of the amplifiers 408A-D can be further refined to account for any losses between the transmission and reception of the signal from the midfield coupler. Consider a reception efficiency of $\eta=Pir/Ptt$, where Pir is the power received at the implanted receiver. An efficiency (e.g., a maximum efficiency), given a specified phase and amplitude tuning, can be estimated from an amplitude received at the external midfield source from the implantable source. This estimation can be given as $\eta \approx (P1+P2+P3+P4)/Pit$, where Pit is an original power of a signal from the implanted source. Information about a magnitude of the power transmitted from the implantable device 110 can be communicated as a data signal to the external source 102. In one or more examples, an amplitude of a signal received at an amplifier 408A-D can be scaled according to the determined efficiency, such as to ensure that the implantable device receives power to perform one or more programmed operation(s). Given the estimated link efficiency, $\eta$, and an implant power (e.g., amplitude) requirement of Pir', Pk can be scaled as $Pk=Pir'/[\eta(P1+P2+P3+P4)]$, such as to help ensure that the implant receives adequate power to perform the programmed functions.

Control signals for the phase shifters 410A-D and the amplifiers 408A-D, such as the phase input and gain input, respectively, can be provided by processing circuitry that is not shown in FIG. 4. The circuitry is omitted to not overly complicate or obscure the view provided in FIG. 4. The same or different processing circuitry can be used to update a status of one or more of the switches 404A-D between receive and transmit configurations. See the processor circuitry 210 of FIG. 2A and its associated description for an example of processing circuitry.

Various initialization circuitry and protection circuitry can be added to or used with the network 400. For example, the example of FIG. 37, including transmitter circuitry 3700, includes a first protection circuit 3720 and a second protection circuit 3760 that can be used to identify and compensate for poor antenna loading or antenna mismatch conditions.

Figure 5:
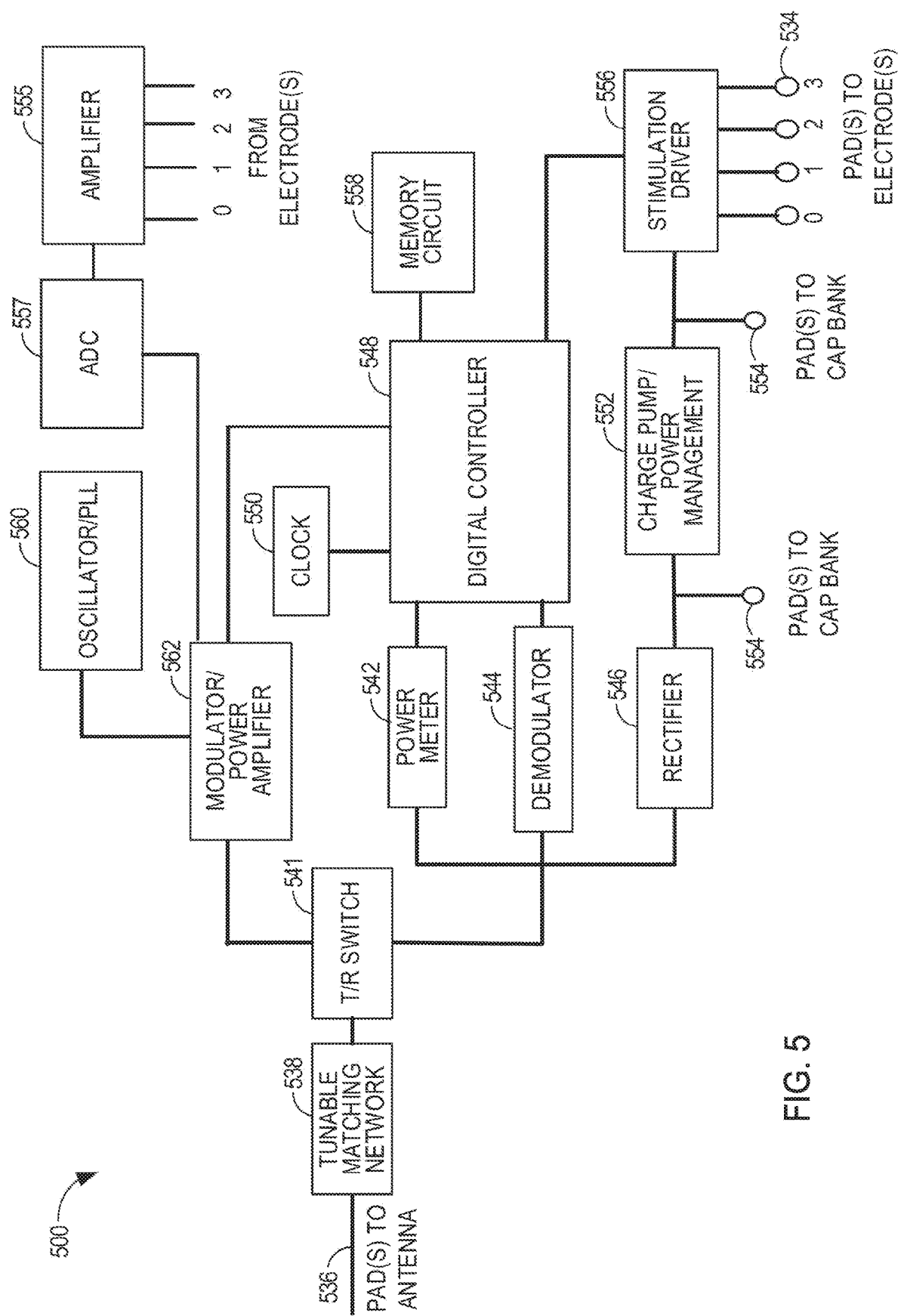
FIG. 5 illustrates generally a diagram of an embodiment of circuitry of an implantable midfield receiver device.

FIG. 5 illustrates generally a diagram of an embodiment of circuitry 500 of the implantable device 110, or target device, such as can include an elongate device and such as can optionally be deployed inside a blood vessel, according to one or more of the embodiments discussed herein. The circuitry 500 includes one or more pad(s) 536, such as can be electrically connected to the antenna 108. The circuitry 500 can include a tunable matching network 538 to set an impedance of the antenna 108 based on an input impedance of the circuitry 500. The impedance of the antenna 108 can change, for example, due to environmental changes. The tunable matching network 538 can adjust the input impedance of the circuitry 500 based on the varying impedance of the antenna 108. In one or more examples, the impedance of the tunable matching network 538 can be matched to the impedance of the antenna 108. In one or more examples, the impedance of the tunable matching network 538 can be set to cause a portion of a signal incident on the antenna 108 reflect back from the antenna 108, thus creating a backscatter signal.

A transmit-receive (T/R) switch 541 can be used to switch the circuitry 500 from a receive mode (e.g., in which power and/or data signals can be received) to a transmit mode (e.g., in which signals can be transmitted to another device, implanted or external). An active transmitter can operate at an Industrial, Scientific, and Medical (ISM) band of 2.45 GHZ or 915 MHz, or the 402 MHz Medical Implant Communication Service (MICS) band for transferring data from the implant. Alternatively, data can be transmitted using a Surface Acoustic Wave (SAW) device that backscatters incident radio frequency (RF) energy to the external device.

The circuitry 500 can include a power meter 542 for detecting an amount of received power at the implanted device. A signal that indicates power from the power meter 542 can be used by a digital controller 548 to determine whether received power is adequate (e.g., above a specified threshold) for the circuitry to perform some specified function. A relative value of a signal produced by the power meter 542 can be used to indicate to a user or machine whether an external device (e.g., the source 102) used to power the circuitry 500 is in a suitable location for transferring power and/or data to the target device.

In one or more examples, the circuitry 500 can include a demodulator 544 for demodulating received data signals. Demodulation can include extracting an original information-bearing signal from a modulated carrier signal. In one or more examples, the circuitry 500 can include a rectifier 546 for rectifying a received AC power signal.

Circuitry (e.g., state logic, Boolean logic, or the like) can be integrated into the digital controller 548. The digital controller 548 can be configured to control various functions of the receiver device, such as based on the input(s) from one or more of the power meter 542, demodulator 544, and/or the clock 550. In one or more examples, the digital controller 548 can control which electrode(s) (e.g., E0-E3) are configured as a current sink (anode) and which electrode(s) are configured as a current source (cathode). In one or more examples, the digital controller 548 can control a magnitude of a stimulation pulse produced through the electrode(s).

A charge pump 552 can be used to increase the rectified voltage to a higher voltage level, such as can be suitable for stimulation of the nervous system. The charge pump 552 can use one or more discrete components to store charge for increasing the rectified voltage. In one or more examples, the discrete components include one or more capacitors, such as can be coupled to pad(s) 554. In one or more examples, these capacitors can be used for charge balancing during stimulation, such as to help avoid tissue damage.

A stimulation driver circuit 556 can provide programmable stimulation through various outputs 534, such as to an electrode array. The stimulation driver circuit 556 can include an impedance measurement circuitry, such as can be used to test for correct positioning of the electrode(s) of the array. The stimulation driver circuit 556 can be programmed by the digital controller to make an electrode a current source, a current sink, or a shorted signal path. The stimulation driver circuit 556 can be a voltage or a current driver. The stimulation driver circuit 556 can include or use a therapy delivery circuitry that is configured to provide electrostimulation signal pulses to one or more electrodes, such as using at least a portion of a received midfield power signal from the external source 102. In one or more examples, the stimulation driver circuit 556 can provide pulses at frequencies up to about 100 kHz. Pulses at frequencies around 100 kHz can be useful for nerve blocking.

The circuitry 500 can further include a memory circuitry 558, such as can include a non-volatile memory circuitry. The memory circuitry 558 can include storage of a device identification, neural recordings, and/or programming parameters, among other implant related data.

The circuitry 500 can include an amplifier 555 and analog digital converter (ADC) 557 to receive signals from the electrode(s). The electrode(s) can sense electricity from nerve signals within the body. The nerve signals can be amplified by the amplifier 555. These amplified signals can be converted to digital signals by the ADC 557. These digital signals can be communicated to an external device. The amplifier 555, in one or more examples, can be a transimpedance amplifier.

The digital controller 548 can provide data to a modulator/power amplifier 562. The modulator/power amplifier 562 modulates the data onto a carrier wave. The power amplifier 562 increases the magnitude of the modulated waveform to be transmitted.

The modulator/power amplifier 562 can be driven by an oscillator/phase locked loop (PLL) 560. The PLL disciplines the oscillator so that it remains more precise. The oscillator can optionally use a different clock from the clock 550. The oscillator can be configured to generate an RF signal used to transmit data to an external device. A typical frequency range for the oscillator is about 10 kHz to about 2600 MHz (e.g., from 10 kHz to 1000 MHz, from 500 kHz to 1500 kHz, from 10 kHz to 100 kHz, from 50 kHz to 200 kHz, from 100 kHz to 500 kHz, from 100 kHz to 1000 kHz, from 500 kHz to 2 MHz, from 1 MHz to 2 MHz, from 1 MHz to 10 MHz, from 100 MHz to 1000 MHz, from 500 MHz to 800 MHz, overlapping ranges thereof, or any value within the recited ranges). Other frequencies can be used, such as can be dependent on the application. The clock 550 is used for timing of the digital controller 548. A typical frequency of the clock 550 is between about one kilohertz and about one megahertz (e.g., between 1 kHz and 100 kHz, between 10 kHz and 150 kHz, between 100 kHz and 500 kHz, between 400 kHz and 800 kHz, between 500 kHz and 1 MHz, between 750 kHz and 1 MHz, overlapping ranges thereof, or any value within the recited ranges). Other frequencies can be used depending on the application. A faster clock generally uses more power than a slower clock.

A return path for a signal sensed from a nerve is optional. Such a path can include the amplifier 555, the ADC 557, the oscillator/PLL 560, and the modulator/power amplifier 562. Each of these items and connections thereto can optionally be removed.

In one or more examples, the digital controller 548, the amplifier 555, and/or the stimulation driver circuit 556, among other components of the circuitry 500, can comprise portions of a state machine device. The state machine device can be configured to wirelessly receive power and data signals via the pad(s) 536 and, in response, release or provide an electrostimulation signal via one or more of the outputs 534. In one or more examples, such a state machine device needs not retain information about available electrostimulation settings or vectors, and instead the state machine device can carry out or provide electrostimulation events after, and/or in response to, receipt of instructions from the source 102.

For example, the state machine device can be configured to receive an instruction to deliver a neural electrostimulation therapy signal, such as at a specified time or having some specified signal characteristic (e.g., amplitude, duration, etc.), and the state machine device can respond by initiating or delivering the therapy signal at the specified time and/or with the specified signal characteristic(s). At a subsequent time, the device can receive a subsequent instruction to terminate the therapy, to change a signal characteristic, or to perform some other task. Thus, the device can optionally be configured to be substantially passive, or can be configured to be responsive to received instructions (e.g., contemporaneously received instructions).

Circuitry Housing Assemblies

This section describes embodiments and/or features of therapy devices, guiding mechanisms for situating an implantable device (e.g., the therapy device) within tissue, and/or affixing mechanisms for helping ensure the implantable device does not appreciably move when situated within the tissue. One or more examples regard therapy devices for treatment of various disorders.

In accordance with several embodiments, a system includes an implantable device comprising an elongated member having a distal portion and a proximal portion. The device includes a plurality of electrodes, a circuitry housing, circuitry within the circuitry housing adapted to provide electrical energy to the plurality of electrodes, an antenna housing, and an antenna (e.g., a helical antenna) in the antenna housing. The plurality of electrodes is situated or located along the distal portion of the elongated member. The circuitry housing is attached to the proximal portion of the elongated member. The circuitry is hermetically sealed or encased within the circuitry housing. The antenna housing is attached to the circuitry housing at a proximal end of the circuitry housing opposite to an end of the circuitry housing attached to the elongated member.

The system may optionally comprise an external midfield power source adapted to provide a power or electrical signal or energy to the implantable device. The implantable device may be adapted to communicate information (e.g., data signals) to an antenna of the external source via the antenna. One, more than one or all the electrodes may optionally be located at a proximal portion or central portion of the elongated member instead of the distal portion. The circuitry housing may optionally be attached to a distal portion or central portion of the elongated member. The antenna housing may not be attached to the circuitry housing or may not be attached to the proximal end of the circuitry housing. The antenna housing may optionally include a dielectric material with a dielectric constant between that of human tissue and air, such as a ceramic material. The ceramic material may optionally cover the antenna. The elongated member may optionally be flexible and/or cylindrical. The electrodes may optionally be cylindrically-shaped and positioned around a circumference of the elongated member.

The elongated member may optionally include a channel extending through the elongated member from a proximal end of the member to the distal portion of the elongated member and a memory metal wire situated in the channel, the memory metal wire pre-shaped in an orientation to provide curvature to the elongated member. The memory metal may optionally be shaped to conform to a shape of an S3 foramen and generally match a curve of a sacral nerve. The antenna may be a primary antenna and the device may further include a secondary antenna in a housing attached to the antenna housing, the secondary antenna shaped and positioned to provide a near field coupling with the primary antenna. The device may optionally include one or more sutures attached at one or more of: (1) a proximal portion of the antenna housing; (2) a proximal portion of the circuitry housing; and (3) an attachment structure attached to a proximal end of the antenna housing. The antenna may optionally be coupled to a conductive loop of the circuitry situated in a proximal portion of the circuitry housing. There may be a ceramic material between the antenna and the conductive loop.

There is an ongoing desire to reduce a displacement volume of implantable sensor and/or stimulator devices, such as including neurostimulation devices. Additional miniaturization can allow for an easier less invasive implant procedure, reduce a surface area of the implantable device which can in turn reduce a probability of post-implant infection, and provide patient comfort in a chronic ambulatory patient setting. In some examples, a miniaturized device can be injected using a catheter or cannula, further reducing invasiveness of an implant procedure.

In an example, a configuration of an implantable neurostimulation device is different from a conventional lead implanted with a pulse generator. The implantable stimulation device can include a lead-less design and can be powered from a remote source (e.g., a midfield source located distal to the implantable device).

In an example, a method of making an implantable stimulation device can include forming electrical connections at both ends of a circuitry housing, such as can be a hermetically sealed circuitry housing. The method can include forming electrical connections between a feedthrough assembly and pads of a circuit board. In an example, the feedthrough assembly includes a cap-like structure inside of which electrical and/or electronic components can be provided. A surface of the pads of the circuit board can be generally perpendicular to a surface of an end of feedthroughs of the feedthrough assembly. The method can be useful in, for example, forming a hermetic circuitry housing, such as can be part of an implantable stimulation device or other device that can be exposed to liquid or other environmental elements that can adversely affect electrical and/or electronic components.

Figure 6:
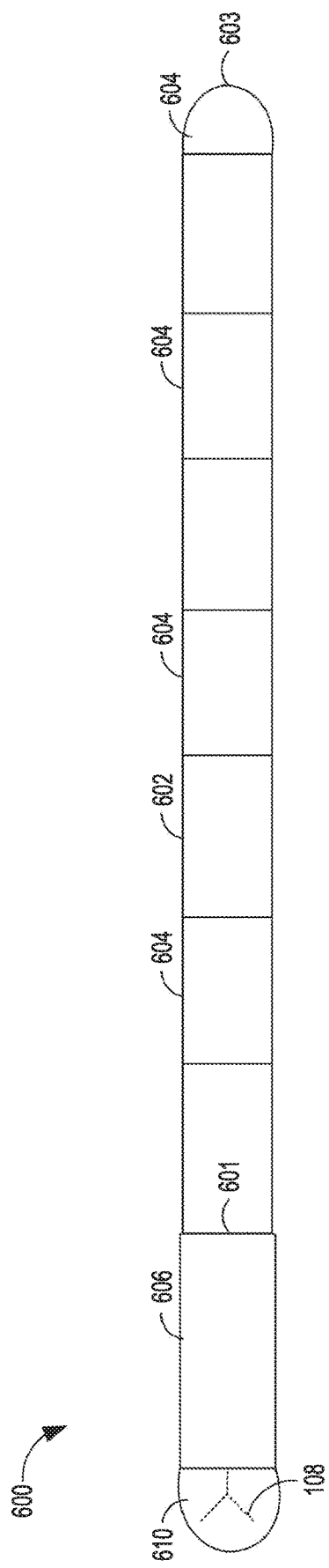
FIG. 6 illustrates generally a diagram of an embodiment of a first implantable device.

FIG. 6 illustrates generally a diagram of an embodiment of a first implantable device 600. In an example, the first implantable device 600 includes or comprises components or an assembly that can be the same or similar to those in the example of the implantable device 110 from FIG. 1. For example, the device 600 can include a body portion 602, multiple electrodes 604, a circuitry housing 606, and an antenna housing 610. In an example, the body portion 602 includes or comprises a body portion of the implantable device 110. The antenna housing 610 can enclose or encapsulate the antenna 108. The implantable device 600 can be configured to sense electrical (or other) activity information from a patient, or to deliver an electrostimulation therapy to the patient such as using one or more of the electrodes 604.

The body portion 602 can be made of a flexible or rigid material. In one or more examples, the body portion 602 can include a bio-compatible material. The body portion 602 can include, among other materials, platinum, iridium, titanium, ceramic, zirconia, alumina, glass, polyurethane, silicone, epoxy, and/or a combination thereof. The body portion 602 includes one or more electrodes 604 thereon or at least partially therein. The electrodes 604, as illustrated in the example of FIG. 6, are ring electrodes. In the example of FIG. 6, the electrodes 604 are substantially evenly distributed along the body portion, that is, a substantially equal space is provided between adjacent electrodes. Other electrode configurations can additionally or alternatively be used.

The body portion 602 can include, or can be coupled to, a circuitry housing 606. In an example, the circuitry housing 606 is coupled to the body portion 602 at a first end 601 of the body portion 602. In the example of FIG. 6, the first end 601 of the body portion 602 is opposite a second end 603 of the body portion 602.

The circuitry housing 606 can provide a hermetic seal for electric and/or electronic components 712 (see, e.g., FIG. 7) and/or interconnects housed therein. The electrodes 604 can be respectively electrically connected to circuitry in the circuitry housing 606 using one or more feedthroughs and one or more conductors, such as is illustrated and described herein. That is, the circuitry housing 606 can provide a hermetic enclosure for the electronic components 712 (e.g., electric and/or electronic components provided inside or encapsulated by the circuitry housing 606).

In an example, the antenna housing 610 is attached to the circuitry housing 606 at a first side end 711 (see, e.g., FIG. 7) of the circuitry housing 606. The antenna 108 can be provided inside the antenna housing 610. In an example, the antenna 108 is used for receiving at and/or transmitting from the device 600 power and/or data signals. The first side end 711 is opposite a second side end 713 of the circuitry housing 606. In an example, the second side end 713 is an end to which an electrode assembly, such as including the electrodes 604, or other assembly, can be electrically connected.

The antenna housing 610 can be coupled to the circuitry housing 606 in various ways or using various connective means. For example, the antenna housing 610 can be brazed (e.g., using gold or other conductive or non-conductive material) to the circuitry housing 606. The antenna housing 610 can include an epoxy, tecothane, or other substantially radio frequency (RF) transparent (e.g., at a frequency used to communicate to/from the device 600) and protective material.

In one or more examples, the antenna housing 610 can include a ceramic material such as zirconia or alumina. The dielectric constant of zirconia is similar to a dielectric constant of typical body muscle tissue. Using a material with a dielectric constant similar to that of muscle tissue can help stabilize the circuit impedance of the antenna 108 and can decrease a change in impedance when the antenna 108 is surrounded by different tissue types.

A power transfer efficiency such as from an external transmitter to the device 600 can be influenced by the selection of antenna or housing materials. For example, a power transfer efficiency of the device 600 can be increased when the antenna 108 is surrounded or encapsulated by a lower permittivity tissue, such as when the antenna housing 610 comprises a ceramic material. In an example, the antenna 108 can be composed as a single ceramic structure with the feedthrough.

Figure 7:
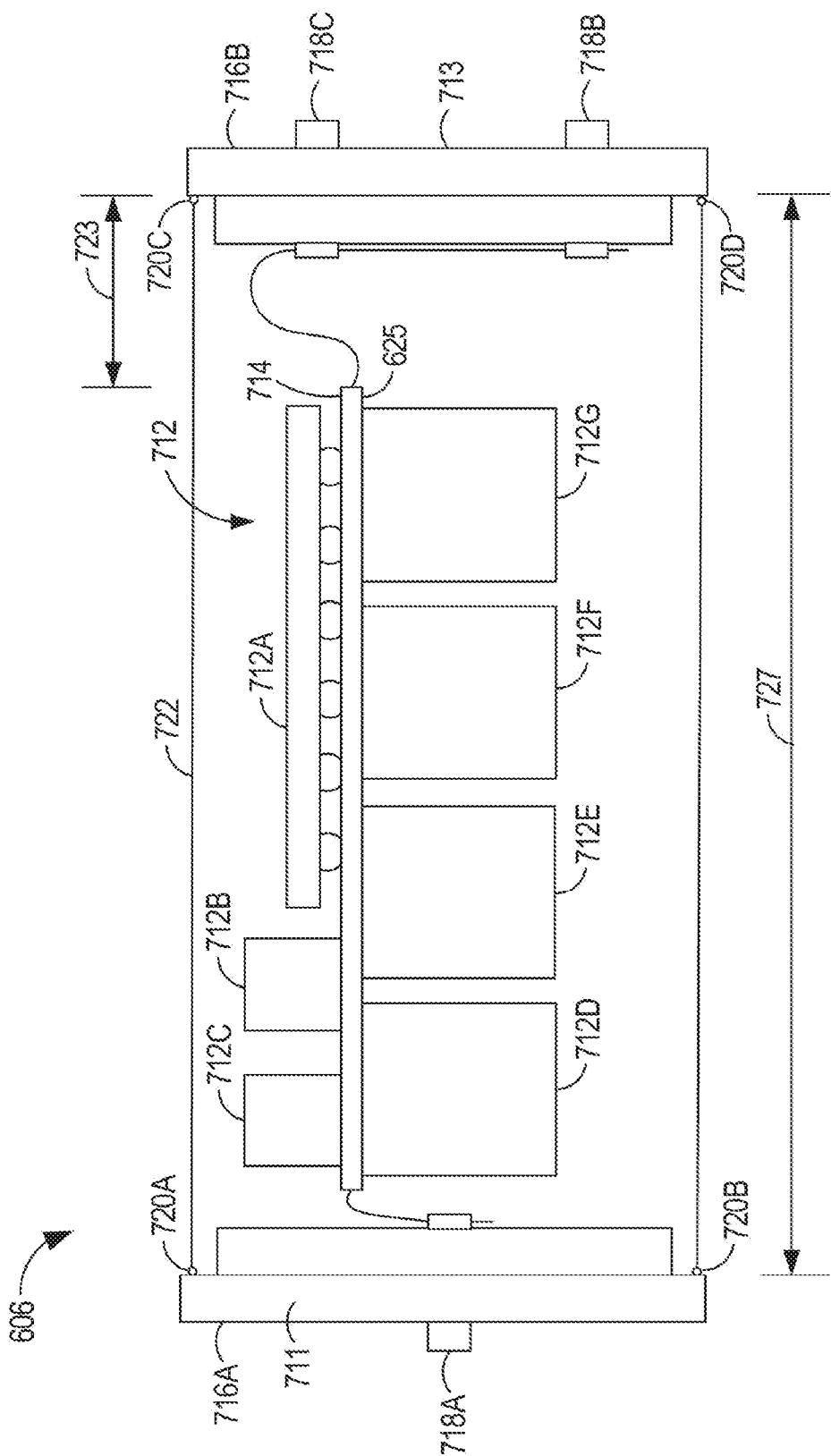
FIG. 7 illustrates generally a schematic view of an embodiment of a circuitry housing.

FIG. 7 illustrates generally a schematic view of an embodiment of the circuitry housing 606. The circuitry housing 606 as illustrated includes various electric and/or electronic components 712A, 712B, 712C, 712D, 712E, 712F, and 712G, such as can be electrically connected to a circuit board 714. The components 712A-G and the circuit board 714 are situated within an enclosure 722. In an example, the enclosure 722 comprises a portion of the circuitry housing 606.

One or more of the components 712A-G can include one or more transistors, resistors, capacitors, inductors, diodes, central processing units (CPUs), field programmable gate arrays (FPGAs), Boolean logic gates, multiplexers, switches, regulators, amplifiers, power sources, charge pumps, oscillators, phase locked loops (PLLs), modulators, demodulators, radios (receive and/or transmit radios), and/or antennas (e.g., a helical shaped antenna, a coil antenna, a loop antenna, or a patch antenna, among others), or the like. The components 712A-G in the circuitry housing 606 can be arranged or configured to form, among other things, stimulation therapy generation circuitry configured to provide stimulation therapy signals, such as can be delivered to a body using the electrodes 604, receiver circuitry configured to receive power and/or data from a remote device, transmitter circuitry configured to provide data to a remote device, and/or electrode selection circuitry such as configured to select which of the electrodes 604 is configured as one or more anodes or cathodes.

The enclosure 722 can include a platinum and iridium alloy (e.g., 90/10, 80/20, 95/15, or the like), pure platinum, titanium (e.g., commercially pure, 6Al/4V or another alloy), stainless steel, or a ceramic material (such as zirconia or alumina, for example), or other hermetic, biocompatible material. The circuitry housing 606 and/or the enclosure 722 can provide an airtight space for the circuitry therein. A thickness of a sidewall of the enclosure 722 can be about tens of micrometers, such as can be about ten, twenty, thirty, forty, fifty, sixty, seventy, eighty, ninety, one hundred, one hundred ten, etc. micrometers, or some thickness in between. An outer diameter of the enclosure 722 can be on the order of less than ten millimeters, such as can be about one, one and a half, two, two and a half, three, three and a half, etc. millimeters or some outer diameter in between. A length of the enclosure can be on the order of millimeters, such as can include two, three, four, five, six, seven, eight, nine, ten, eleven, twelve, thirteen, etc. millimeters, or some length in between. If a metallic material is used for the enclosure 722, the enclosure 722 can be used as part of the electrode array, effectively increasing the number of selectable electrodes 604 for stimulation.

Rather than being hermetic, the enclosure 722 can be backfilled to prevent ingress of moisture therein. The backfill material can include a non-conductive, waterproof material, such as epoxy, parylene, tecothane, or other material or combination of materials.

In the example of FIG. 7, the circuitry housing 606 can include a first end cap 716A and a second end cap 716B. In an example, the caps 716A and 716B are situated on or at least partially in the enclosure 722. The caps 716A and 716B can be provided to cover openings such as on substantially opposite sides of the enclosure 722. The cap 716A forms a portion of the first side end 711 of the circuitry housing 606 and the cap 716B forms a portion of the second side end 713 of the circuitry housing 606. Each of the caps 716A-B includes one or more conductive feedthroughs. In the example of FIG. 7, the first end cap 716A includes a first feedthrough 718A, and the second end cap 716B includes second and third feedthroughs 718B, and 718C. The conductive feedthroughs 718A-C provide an electrical path to a conductor connected thereto.

Elongated Implantable Assemblies

As similarly discussed elsewhere herein, using an external wireless power transmitter to power an implantable device can be difficult, especially when the implantable device is deeply implanted. Embodiments discussed herein can help overcome such a difficulty, for example using an implantable device with an extended length characteristic. In some embodiments, a distance between a wireless power transmitter (e.g., external to the patient body) and an antenna of an implanted device is less than an implantation depth of electrodes on the implantable device. Some embodiments can include an elongated portion, such as between circuitry housings, that can extend a length of an implantable device.

The present inventors have recognized a need to increase an operating depth for devices that provide neuro stimulation pulses to tissue. Embodiments can allow an implantable device (e.g., an implantable neuro stimulation device) to: (a) deliver therapy pulses to deep nerves (e.g., nerves at the center of a torso or deep within a head, e.g., at a depth greater than ten centimeters); and/or (b) deliver therapy pulses deep within vascular structures requiring stimulation originating from locations deeper than currently available using other wireless technologies. In an example, some structures internal to the body may be within about 10 cm of a surface of the skin, but may nonetheless not be reachable using earlier techniques. This can be because an implant path may not be linear or electrodes of the device may not be able to reach the structure due to bends or other obstacles in the implant path.

The present inventors have recognized that a solution to this implantation depth problem, among other problems, can include an implantable device that is configured to function at various depths by separating proximal circuitry (e.g., circuitry situated in a proximal circuitry housing and generally including communication and/or power transceiver circuitry) into at least two portions, and providing an elongated (e.g., flexible, rigid, or semi-rigid) portion between the two circuitry portions. A more proximal portion of the circuitry (e.g., relative to the other circuitry portion) can include power reception and/or signal conditioning circuitry. A more distal portion of the circuitry (e.g., more distal relative to another circuitry portion) can include stimulation wave production circuitry. The more proximal housing is designated in the following discussion as the first circuitry housing, and the more distal housing is designated as the second circuitry housing.

Electrically sensitive radio frequency (RF) receiving and/or backscatter transmitting circuitry components can be provided or packaged in the proximal first circuitry housing. In an example, a received RF power signal may be rectified to direct current (DC) in the first circuitry housing, such as for use by circuitry disposed in the same or other portions of the assembly. Backscatter transmitting circuitry can optionally be provided. In an example, the first circuitry housing can be maintained within a sufficiently minimal distance to be powered by an external power transmitter, such as a midfield powering device, near field communication, or the like, such as including a midfield powering device described hereinabove.

Figure 8:
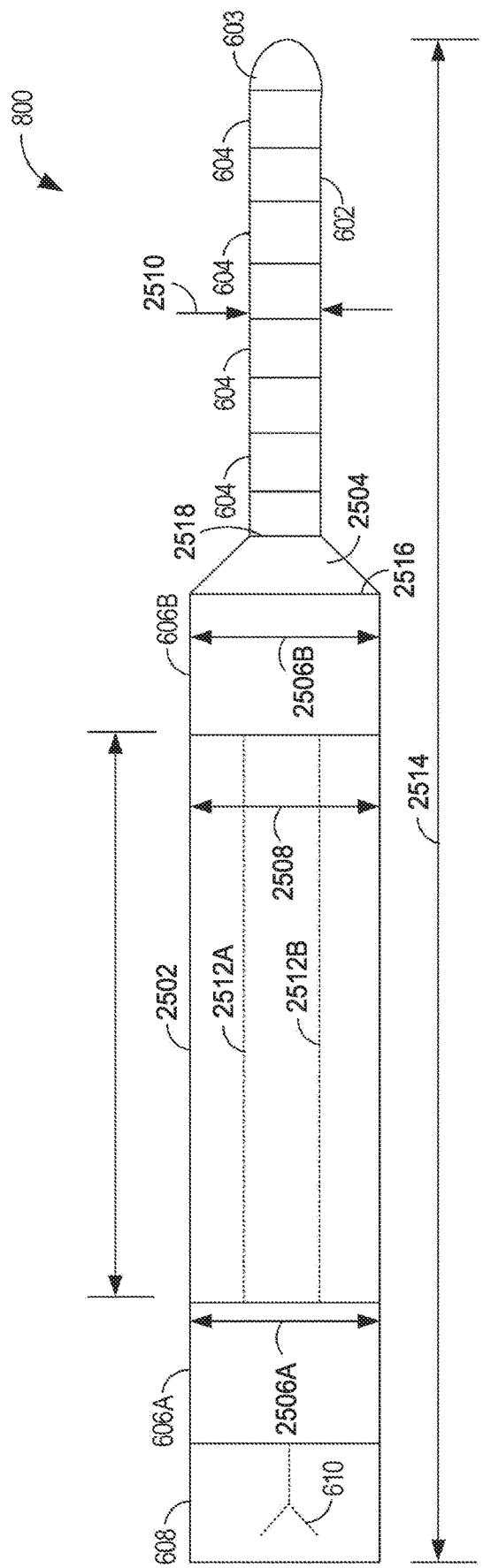
FIG. 8 illustrates generally an example of an elongated implantable device.

FIG. 8 illustrates generally an example of an elongated implantable device 800. In an example, the elongated implantable device 800 includes or comprises components or an assembly that can be the same or similar to those in the examples of the implantable device 110 from FIG. 1 or the first implantable device 600 from FIG. 6. The implantable device 800 can include an elongated portion 2502, a first circuitry housing 606A, a second circuitry housing 606B, and a connector 2504. In the example of FIG. 8, the connector 2504 is frustoconical, however, other shapes or configurations can similarly be used. The second circuitry housing 606B is optional and the elongated portion 2502 can connect directly to the frustoconical connector 2504. In an example, the first circuitry housing 606A includes communication circuitry, such as for receiving wireless power signals and/or communicating data to or from an external device. Various circuitry in the second circuitry housing 606B can include an application specific integrated circuit (ASIC), large-footprint capacitors, resistors, and/or other components configured to generate therapy signals or pulses, and can electrically connect to the electrodes 604.

The elongated portion 2502 separates the first and second circuitry housings 606A and 606B. The elongated portion 2502 can optionally include conductive material 2512A and 2512B (e.g., one or more conductors) extending therethrough or thereon. In an example, the conductive material 2512A and 2512B can electrically connect a conductive feedthrough of the first circuitry housing 606A to a conductive feedthrough of the circuitry housing 606B. In an example, the conductive material 2512A and 2512B is configured to carry various output signals.

The conductive material 2512A and 2512B can include copper, gold, platinum, iridium, nickel, aluminum, silver, a combination or alloy thereof, or the like. The elongated portion 2502 and/or a coating on the conductive material 2512A and 2512B can electrically insulate the conductive material 2512A and 2512B from a surrounding environment, such as can include body tissue when the device is implanted in a patient body. The coating can include a dielectric, such as an epoxy and/or other dielectric material. The elongated portion 2502 can include a dielectric material, such as a biocompatible material. The dielectric material can include Tecothane, Med 4719, or the like.

In an example, the elongated portion 2502 can be formed from or coated with a material that enhances or increases friction with respect to an expected material within which the device is configured to be implanted (e.g., body tissue). In an example, the materials include silicone. Additionally, or alternatively, a rough surface finish can be applied to a surface, or a portion of the surface, of the elongated portion 2502. A friction-increasing material and/or surface finish can increase friction of the implant relative to the biological tissue in which the implantable device can be implanted. Increasing friction can help the implantable device maintain its position within the tissue. In one or more examples, other small-scale features, such as protrusions (e.g., bumps, fins, barbs, or the like) can be added to increase friction in one direction. Increasing friction can help improve chronic fixation so that the implantable device is less likely to move (e.g., in an axial or other direction) while implanted.

A dimension 2506A (e.g., a width, cross-sectional area, or diameter) of the first circuitry housing 606A can be about the same as a corresponding dimension 2506B (e.g., a width) of the circuitry housing 606B. The elongated portion 2502 can include a first dimension 2508 (e.g., a width) that is about the same as the dimensions 2506A and 2506B of the first and second circuitry housings 606A and 606B, respectively. A second dimension 2510 (e.g., width) of a distal portion of the implantable device 800 can be less than the dimensions 2506A and 2506B and 2508.

In an example, the distal portion of the implantable device 800 includes the body portion 602, one or more electrodes 604, and other components coupled to a distal side of a frustoconical connector 2504. A proximal portion of the implantable device 800 includes the first and second circuitry housings 606A and 606B, the elongated portion 2502, the antenna 108, and other components on a proximal side of the frustoconical connector 2504. The dimensions 2506A and 2506B, 2508, and 2510 as illustrated are generally perpendicular to a length 2514 of the components of the device 800.

The frustoconical connector 2504 includes a proximal side 2516 coupled to the proximal portion of the implantable device 800. The frustoconical connector 2504 includes a distal side 2518 coupled to the distal portion of the implantable device 800. The distal side 2518 is opposite the proximal side 2516. A width or diameter dimension of the distal side 2518 can be about the same as the corresponding dimension 2510 for the body portion 602. A width or diameter dimension of the proximal side 2516 can be about the same as the corresponding dimension 2506A and/or 2506B.

In one or more examples, a length 2514 of the device 800 can be between about fifty millimeters to about hundreds of millimeters. In one or more examples, the elongated portion 2502 can be between about ten millimeters to about hundreds of millimeters. For example, the elongated portion 2502 can be between about ten millimeters and about one hundred millimeters. In one or more examples, the dimension 2510 can be about one millimeter (mm) to about one and one third mm. In one or more examples, the dimensions 2506A and 2506B can be between about one and a half millimeters and about two and a half millimeters. In one or more examples, the dimensions 2506A and 2506B can be between about one and two-thirds millimeters and about two and one-third millimeters. In one or more examples, the dimension 2508 can be between about one millimeter and about two and a half millimeters. In one or more examples, the dimension 2508 can be between about one millimeter and about two and one-third millimeters.

Figure 9:
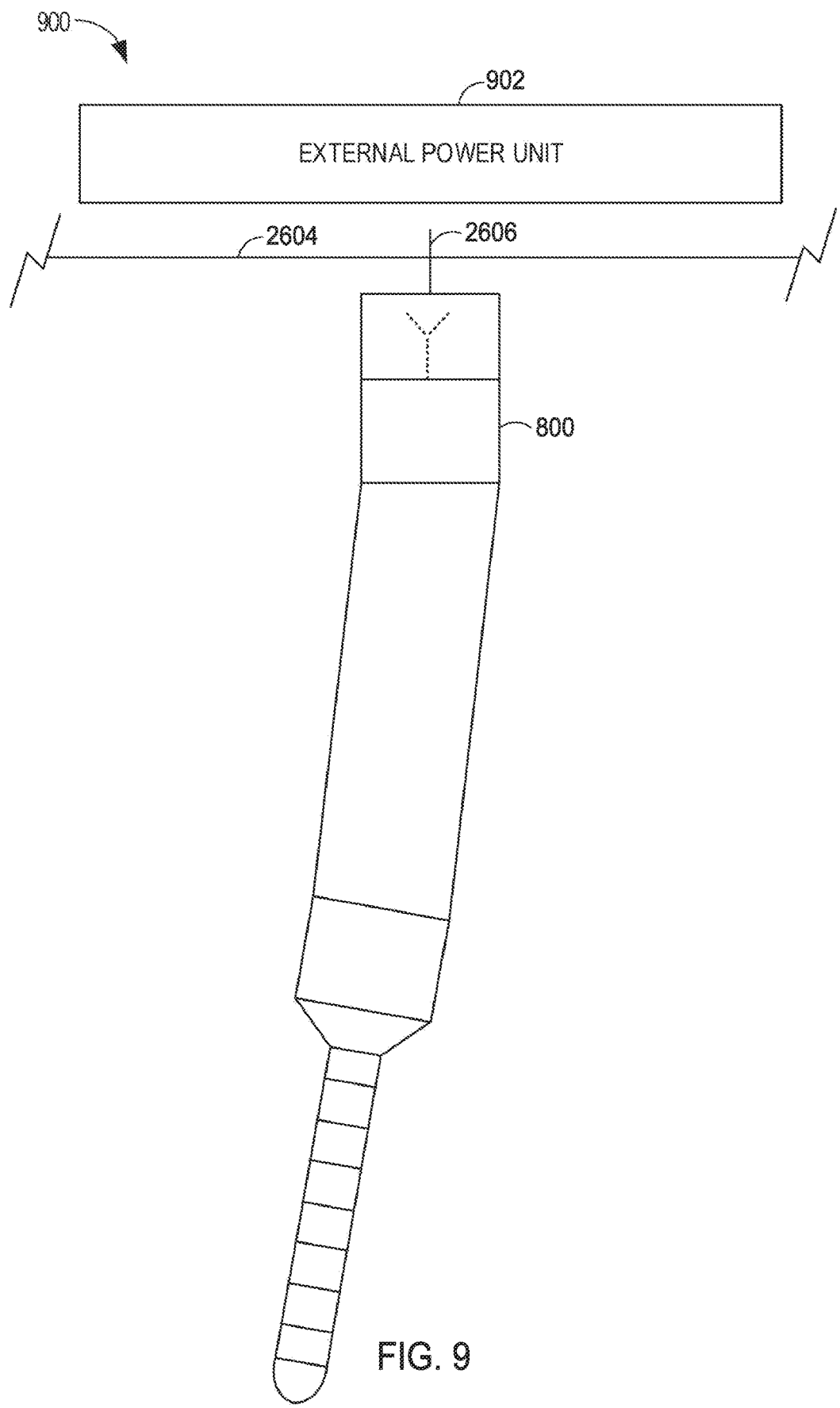
FIG. 9 illustrates generally an example of a system that includes the implantable device from FIG. 8 implanted within tissue.

FIG. 9 illustrates generally an example of a system 900 that includes the implantable device 800 implanted within tissue 2604. The system 900 as illustrated includes the implantable device 800, tissue 2604, an external power unit 902, and a wire 2606 (e.g., a push rod, suture, or other component to implant or remove the implantable device 800). In an example, the external power unit 902 includes the external source 102.

The elongated portion 2502 of the device 800 allows the electrodes 604 of the implantable device 800 to reach deep within the tissue 2604 and allows the antenna to be sufficiently close to the tissue surface and the external power unit 902. The device 800 is illustrated with the elongated portion bent, such as to illustrate that the elongated portion can stretch (e.g., a portion is stretchable and/or can be elongated) and/or flex (e.g., can be rotated about one or more axes along the device's length).

In one or more examples, the external power unit 902 can include a midfield power device, such as the external source 102 described herein. Other configurations of an elongated implantable device can similarly be used to receive or provide signals to the external power unit 902. In an example, the elongated portion 2502 from the example of FIG. 8 can be omitted and the various implantable device circuitry can be included in a single circuitry housing.

Layered Midfield Transmitter Systems and Devices

In an example, a midfield transmitter device, such as corresponding to the external source 102 of the example of FIG. 1, can include a layered structure with one or multiple tuning elements. The midfield transmitter can be a dynamically configurable, active transceiver that is configured to provide RF signals to modulate an evanescent field at a tissue surface and thereby generate a propagating field within tissue, such as to transmit power and/or data signals to an implanted target device.

In an example, a midfield transmitter device includes a combination of transmitter and antenna features. The device can include a slot or patch antenna with a back plane or ground plane, and can include one or more striplines or microstrips or other features that can be excited by an electrical signal. In an example, the device includes one or more conductive plates that can be excited and thereby caused to generate a signal, such as in response to excitation of one or more corresponding striplines or microstrips. In an example, the external source 102 includes a layered structure with excitable features that comprise the antenna 300, and the antenna is coupled to the network 400 illustrated in FIG. 4. In an example, one or more layers of the various transmitters discussed herein can include one or more flexible substrates or flexible layers to provide a flexible transmitter device.

Figure 10:
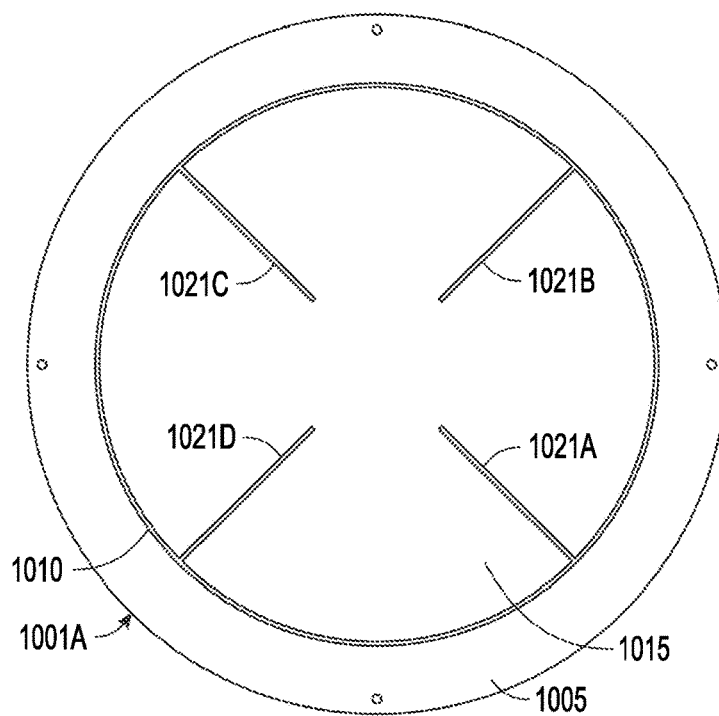
FIG. 10 illustrates generally a top view of an example of a first layer of a first transmitter.

FIG. 10 illustrates generally a top view of an example of a layered first transmitter 1000, including a first layer 1001A. Various features of the first transmitter 1000 are illustrated as being circular, however other shapes or profiles for the transmitter and its various elements or layers can be similarly used. The first layer 1001A includes a conductive plate that can be etched or cut to provide various layer features as shown in the drawing and/or as described herein.

In the example of FIG. 10, the first layer 1001A includes a copper substrate that is etched with a circular slot 1010 to separate a conductive outer region 1005 from a conductive inner region 1015. In this example, the outer region 1005 includes a ring or annular feature that is separated by the circular slot 1010 from a substantially disc-shaped feature comprising the inner region 1015. That is, in the example of FIG. 10, the conductive inner region 1015 is electrically isolated from the conductive annulus comprising the outer region 1005. When the first transmitter 1000 is excited using one or more stripline features, such as can be provided on a different device layer than is illustrated in FIG. 10, the conductive inner region 1015 produces a tuned field, and the outer annulus or outer region 1005 can be coupled to a reference voltage or ground. That is, the conductive inner region 1015 comprises at least a portion of an emitter provided on a surface of the first layer 1001A or substrate.

The example of FIG. 10 includes tuning features with various physical dimensions and locations with respect to the first layer 1001A to influence a field transmitted by the first transmitter 1000. In addition to the etched circular slot 1010, the example includes four radial slots, or arms 1021A, 1021B, 1021C, and 1021D, that extend from the circular slot 1010 toward the center of the first layer 1001A. Fewer or additional tuning features, such as having the same shape as illustrated or another shape, can similarly be used to influence a resonant frequency of the device. That is, although linear radial slots are shown, one or more differently shaped slots can be used.

A diameter of the first layer 1001A and the slot 1010 dimensions can be adjusted to tune or select a resonant frequency of the device. In the example of FIG. 10, as the length of one or more of the arms 1021A-1021D increases, a resonance or center operating frequency correspondingly decreases. Dielectric characteristics of one or more layers adjacent or near to the first layer 1001A can also be used to tune or influence a resonance or transmission characteristic.

In the example of FIG. 10, the arms 1021A-1021D are substantially the same length. In an example, the arms can have different lengths. Orthogonal pairs of the arms can have substantially the same or different length characteristics. In an example, the first and third arms 1021A and 1021C have a first length characteristic, and the second and fourth arms 1021B and 1021D can have a different second length characteristic. Designers can adjust the arm lengths to tune a device resonance. Changing an arm length, a slot width, or other characteristic of the first layer 1001A can also lead to corresponding changes in a current distribution pattern about the layer when the layer is excited.

In an example, one or more capacitive elements can be provided to bridge the slot 1010 in one or more places, such as to further tune an operating frequency of the transmitter. That is, respective plates of a capacitor can be electrically coupled to the outer region 1005 and the inner region 1015 to tune the first transmitter 1000, as further discussed below.

Dimensions of the first layer 1001A can vary. In an example, an optimal radius is determined by a desired operating frequency, characteristics of nearby or adjacent dielectric materials, and excitation signal characteristics. In an example, a nominal radius of the first layer 1001A is about 25 to 45 mm, and a nominal radius of the slot 1010 is about 20 to 40 mm. In an example, a transmitter device comprising the first layer 1001A can be made smaller at a cost of device efficiency, such as by decreasing the slot radius and/or increasing the length of the arms.

Figure 11:
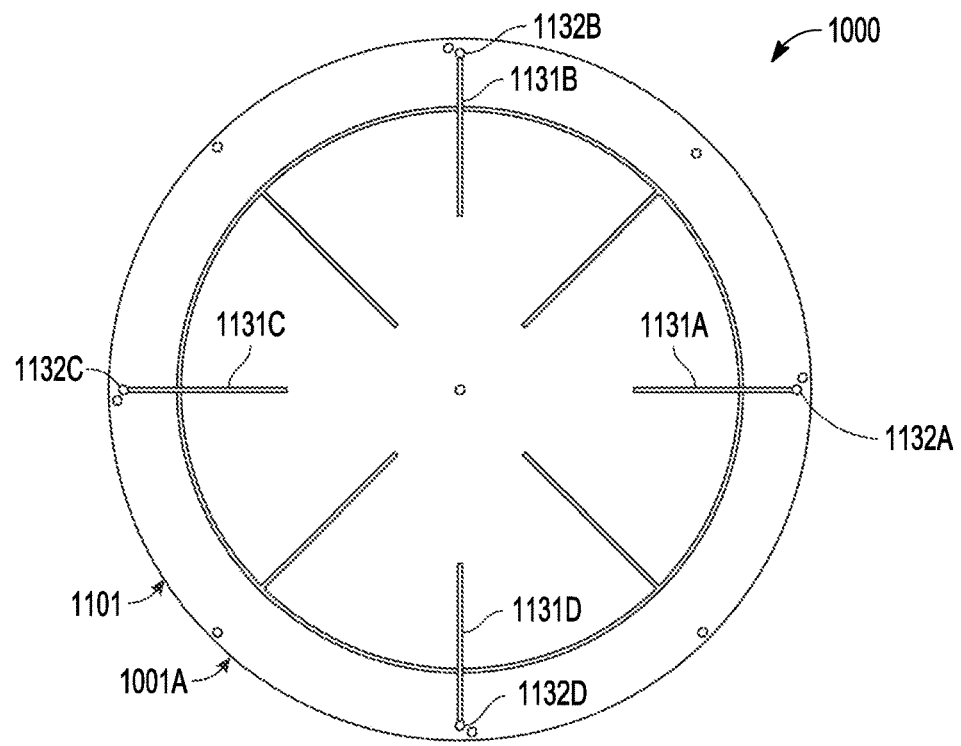
FIG. 11 illustrates generally a top view of a second layer superimposed over a first layer of a layered first transmitter.

FIG. 11 illustrates generally a top view of a second layer 1101 superimposed over the first layer 1001A of the layered first transmitter 1000. The second layer 1101 is spaced apart from the first layer 1001A, such as using a dielectric material interposed therebetween. In an example, the second layer 1101 includes multiple striplines configured to excite the first transmitter 1000. The example of FIG. 11 includes first through fourth striplines 1131A, 1131B, 1131C, and 1131D, corresponding respectively to the four regions of the conductive inner region 1015 of the first layer 1001A. In the example of FIG. 11, the striplines 1131A-1131D are oriented at about 45 degrees relative to respective ones of the arms 1021A-1021D. Different orientations or offset angles can be used. Although the example of FIG. 11 shows the striplines 1131A-1131D spaced at equal intervals about the circular device, other non-equal spacings can be used. In an example, the device can include additional striplines or as few as one stripline.

The first through fourth striplines 1131A-1131D provided on the second layer 1101 can be electrically isolated from the first layer 1001A. That is, the striplines can be physically spaced apart from the conductive annular outer region 1005 and from the disc-shaped conductive inner region 1015, and a dielectric material can be interposed between the first and second layers 1001A and 1101 of the first transmitter 1000.

In the example of FIG. 11, the first through fourth striplines 1131A-1131D are coupled to respective first through fourth vias 1132A-1132D. The first through fourth vias 1132A-1132D can be electrically isolated from the first layer 1001A, however, in some examples the first through fourth vias 1132A-1132D can extend through the first layer 1001A. In an example, the vias can include or can be coupled to respective ones of the RF ports 311, 312, 313, and 314 illustrated in the examples of FIG. 3.

In an example, one or more of the first through fourth striplines 1131A-1131D can be electrically coupled to the conductive inner region 1015 of the first layer 1001A, such as using respective other vias that are not illustrated in the example of FIG. 11. Such electrical connections are unnecessary to generate midfield signals using the device, however, the connections may be useful for further tuning or performance enhancement of the device.

Various benefits are conferred by providing excitation microstrips and/or striplines, such as the first through fourth striplines 1131A-1131D, on a layer that is adjacent to and extends over the conductive inner region 1015 of the first layer 1001A. For example, an overall size of the first transmitter 1000 can be reduced. Various different dielectric materials can be used between the first and second layers 1001A and 1101 to additionally reduce a size or thickness of the first transmitter 1000.

Figure 12:
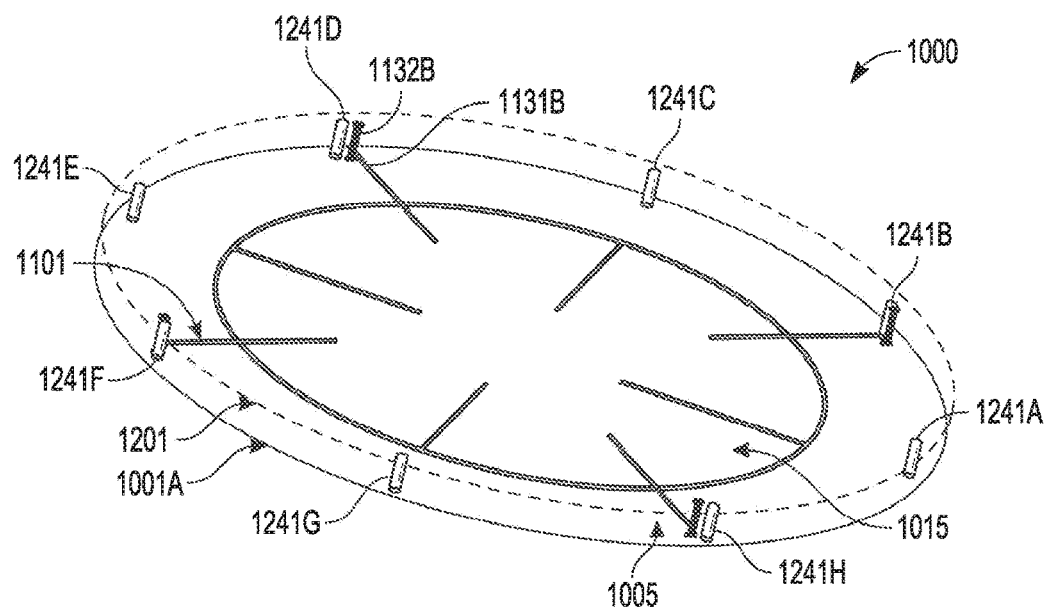
FIG. 12 illustrates generally a perspective view of an example of a layered first transmitter.
Figure 13:
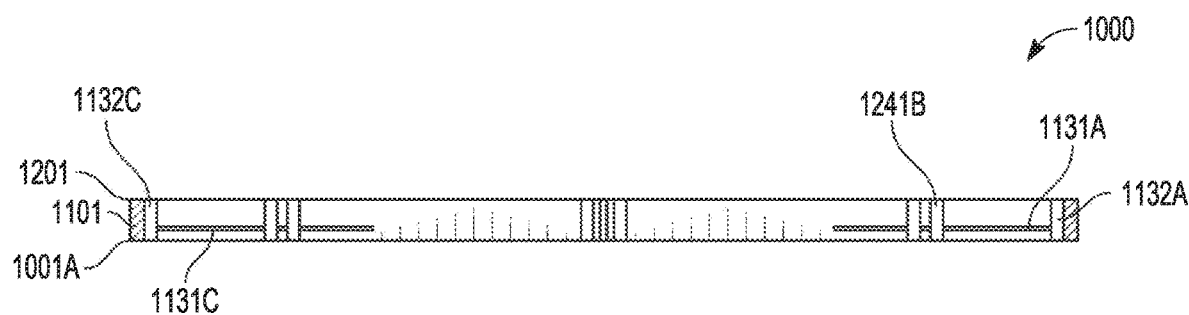
FIG. 13 illustrates generally a side, cross-section view of the layered first transmitter from FIG. 12.

FIG. 12 illustrates generally a perspective view of an example of the layered first transmitter 1000. FIG. 13 illustrates generally a side, cross-section view of the layered first transmitter 1000. The examples include, at the bottom side of each of FIGS. 12 and 13, the first layer 1001A of the first transmitter 1000. At the top of the figures, the first transmitter 1000 includes a third layer 1201. The third layer 1201 can be a conductive layer that provides a shield or backplane for the first transmitter 1000. The second layer 1101, such as comprising one or more striplines, can be interposed between the first and third layers 1001A and 1201. One or more dielectric layers (not illustrated) can be interposed between the first and second layers 1001A and 1101, and one or more other dielectric layers can be interposed between the second and third layers 1101 and 1201.

The examples of FIG. 12 and FIG. 13 include vias that electrically couple the outer region 1005 on the first layer 1001A with the third layer 1201. That is, ground vias 1241A-1241H can be provided to couple a ground plane (e.g., the third layer 1201) with one or more features or regions on the first layer 1001A. In the example, and as described above, each of the first through fourth striplines 1131A-1131D is coupled to a respective signal excitation source via 1132A-1132D. The signal excitation source vias 1132A-1132D can be electrically isolated from the first and third layers 1001A and 1201.

In the examples of FIG. 12 and FIG. 13, the transmitting side of the illustrated device is downward. That is, when the first transmitter 1000 is used and positioned against or adjacent to a tissue surface, the tissue-facing side of the device is the downward direction in the figures as illustrated.

Providing the third layer 1201 as a ground plane confers various benefits. For example, other electronic devices or circuitry can be provided on top of the third layer 1201 and can be operated substantially without interfering with the transmitter. In an example, other radio circuitry (e.g., operating outside of the range of the midfield transmitter) can be provided over the third layer 1201, such as for radio communication with an implanted or other device (e.g., the implantable device 110, or other implantable device as described herein). In an example, a second transmitter can be provided, such as in a back-to-back relationship with the first transmitter 1000, and can be separated from the first transmitter 1000 using the ground plane of the third layer 1201.

Figure 14A:
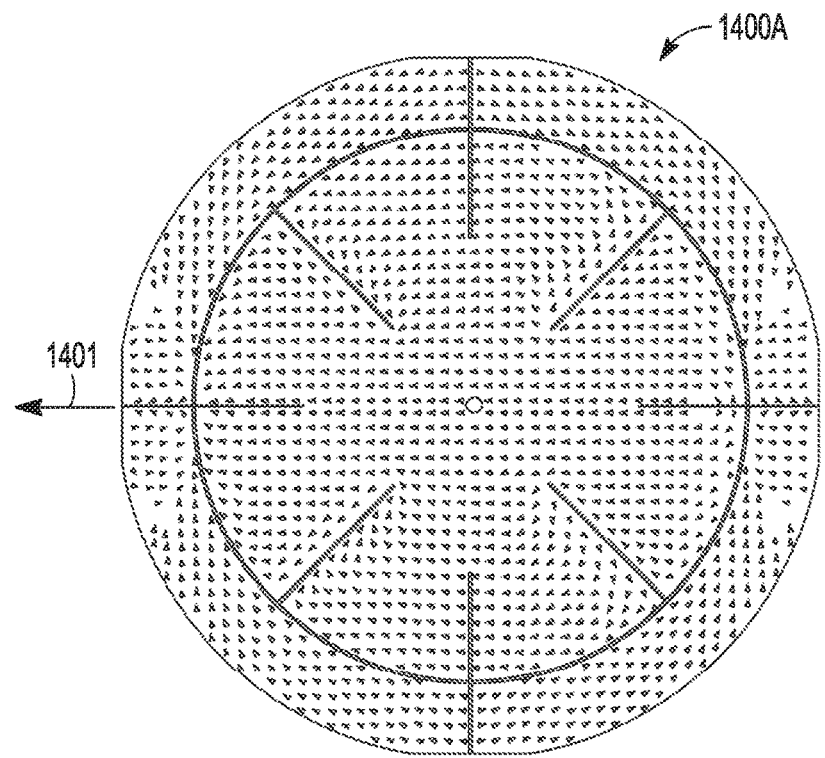
FIG. 14A illustrates generally an example that shows a surface current pattern on an example transmitter when the example transmitter is excited by a drive signal.

FIG. 14A illustrates generally an example that shows a surface current pattern 1400A that results when the first transmitter 1000 is excited by a drive signal, or by a plurality of drive signals provided respectively to the first through fourth striplines 1131A-1131D. The various drive signals can be adjusted in phase and/or amplitude relative to one another to produce various surface currents at the first transmitter 1000. In the example of FIG. 14A, the surface current pattern closely mimics an oscillatory, optimal distribution that, when provided using the transmitter placed near a tissue interface, influences an evanescent field that will give rise to propagating or non-stationary fields inside of tissue.

Figure 14B:
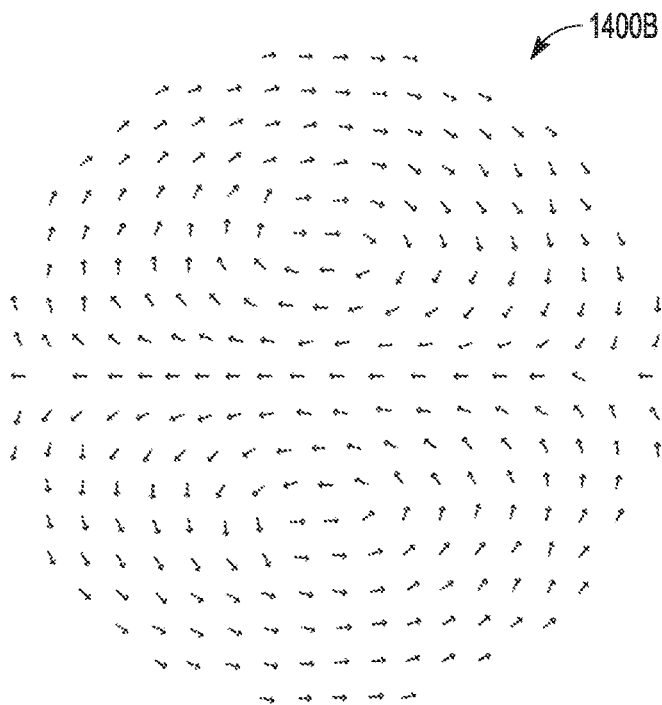
FIG. 14B illustrates generally an example of an optimal current distribution for a transmitter.

An example of an optimal current distribution for a transmitter is illustrated generally by the pattern 1400B in FIG. 14B. That is, when the first transmitter 1000 is excited with signals that induce or provide a particular current pattern that corresponds to the pattern 1400B, one representative instance of which is illustrated in the surface current pattern 1400A, then a corresponding optimal evanescent field can be provided, such as at or near a tissue interface.

In an example, the excitation signals (e.g., provided to the first through fourth striplines 1131A-1131D) that provide an optimal or target current pattern include oscillating signals provided to oppositely-oriented striplines (e.g., second and fourth striplines 1131B and 1131D in the example of FIG. 11). In an example, the excitation signals further include signals provided to one or more other pairs of striplines (e.g., first and third striplines 1131A and 1131C in the example of FIG. 11). This type or mode of excitation can be used to generate the optimal current pattern and efficiently transfer signals to a deeply implanted receiver. In an example, an implanted receiver such as the implantable device 110 includes a loop receiver oriented in parallel with the current signal direction 1401. That is, the loop receiver can be installed in tissue in parallel with a prominent direction of the oscillating current distribution, as illustrated by the arrow indicating the signal direction 1401. Stated differently, a normal of the loop receiver can be oriented orthogonally to the current signal direction 1401.

Figure 15A:
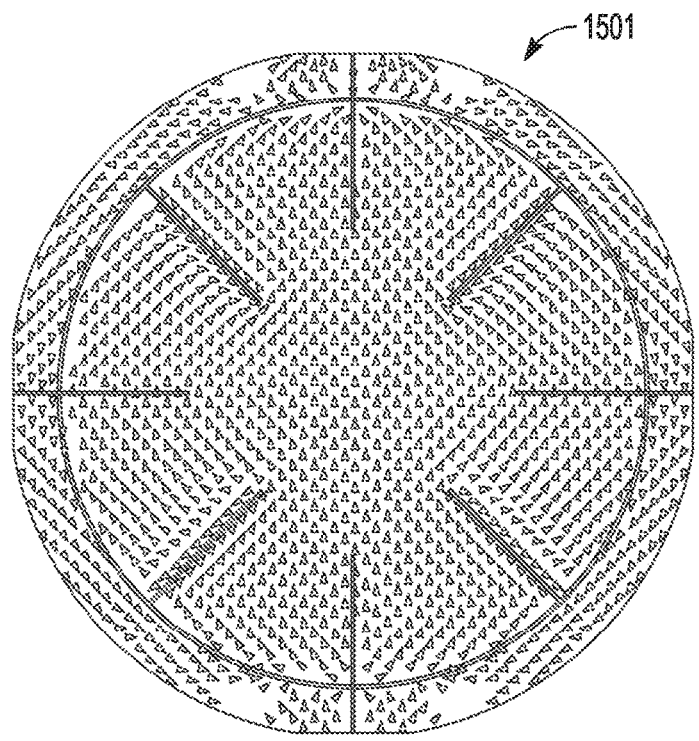
FIGS. 15A, 15B, and 15C illustrate generally examples of different polarizations of a midfield transmitter in response to different excitation signals.
Figure 15B:
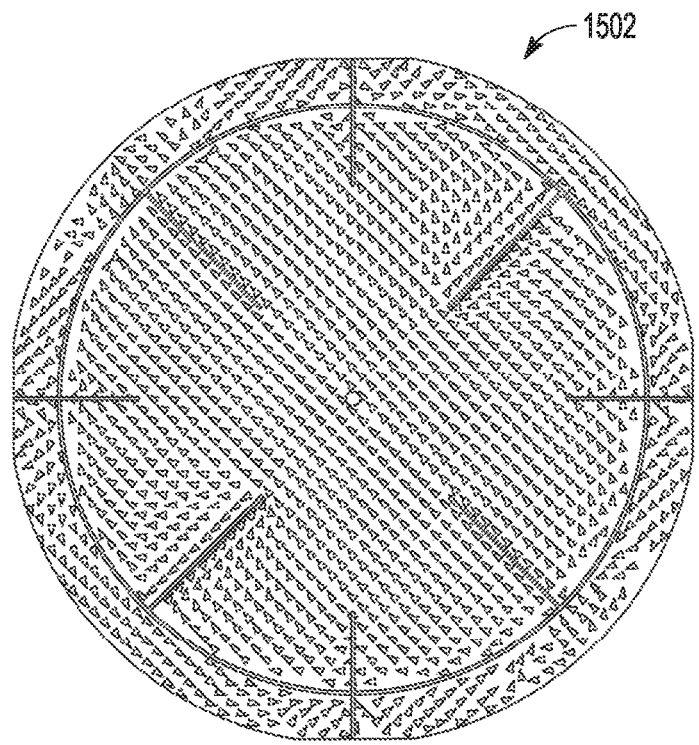
Figure 15C:
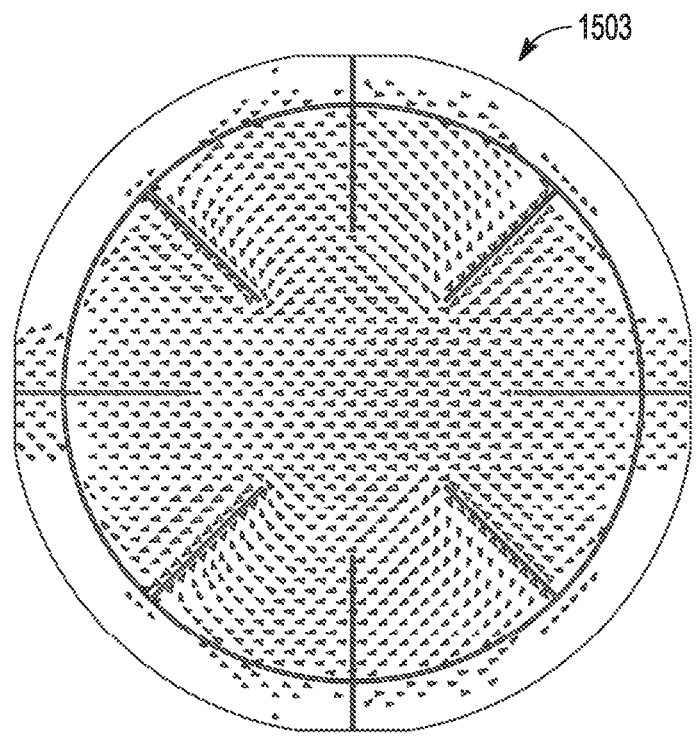

FIGS. 15A, 15B, and 15C illustrate generally examples of different polarizations of a midfield transmitter, such as the first transmitter 1000, in response to different excitation signals or excitation signal patterns. In an example, a polarization direction of the transmitter can be changed by adjusting a phase and/or magnitude of an excitation signal provided to one or more of the striplines or to other excitation features of a transmitter. Adjusting the excitation signals changes the current distribution over the conductive portions of the transmitter, and can be used to polarize the transmitter into or toward alignment with a receiver, such as to optimize a signal transfer efficiency.

In an example, an optimal excitation signal configuration can be determined using information from the implantable device 110. For example, the external source 102 can change a signal phase and/or weighting of one or more transmission signals provided to the excitable features of the first transmitter 1000, or other transmitter. In an example, the implantable device 110 can use an integrated power meter to measure a strength of a received signal and communicate information about the strength to the external source 102, such as to determine an effect of the signal phase change. In an example, the external source 102 can monitor a reflected power characteristic to determine an effect of the signal phase change on coupling efficiency. The system can thus be configured to converge toward a maximum transfer efficiency over time, using adjustments in both positive and negative directions for phase and port weighting between orthogonal or other ports.

The example of FIG. 15A illustrates an example of a first current distribution 1501 in left and right quadrants of the transmitter. In this example, the top and bottom striplines receive a first pair of excitation signals and the orthogonal striplines at the left and right can be unused.

The example of FIG. 15B illustrates an example of a second current distribution 1502 that is rotated about 45 degrees relative to the example of the first current distribution 1501 in FIG. 15A. In FIG. 15B, all four of the first through fourth striplines 1131A-1131D can be excited by different excitation signals, such as with phase offsets relative to one another.

The example of FIG. 15C illustrates an example of a third current distribution 1503 that is rotated about 90 degrees relative to the example of the first current distribution 1501 in FIG. 15A. In FIG. 15C, the left and right striplines receive a second pair of excitation signals and the orthogonal striplines at the top and bottom can be unused.

FIGS. 15A through 15C thus show different current distribution patterns that can be used to change a direction or characteristic of an evanescent field which, in turn, can influence a direction or magnitude of a propagating field inside tissue in the direction of the implantable device 110. Thus changes in a current distribution pattern on an external transmitter can correspond to changes in coupling efficiency with the implantable device 110 or other device configured to receive a signal from the external source 102.

Figure 16:
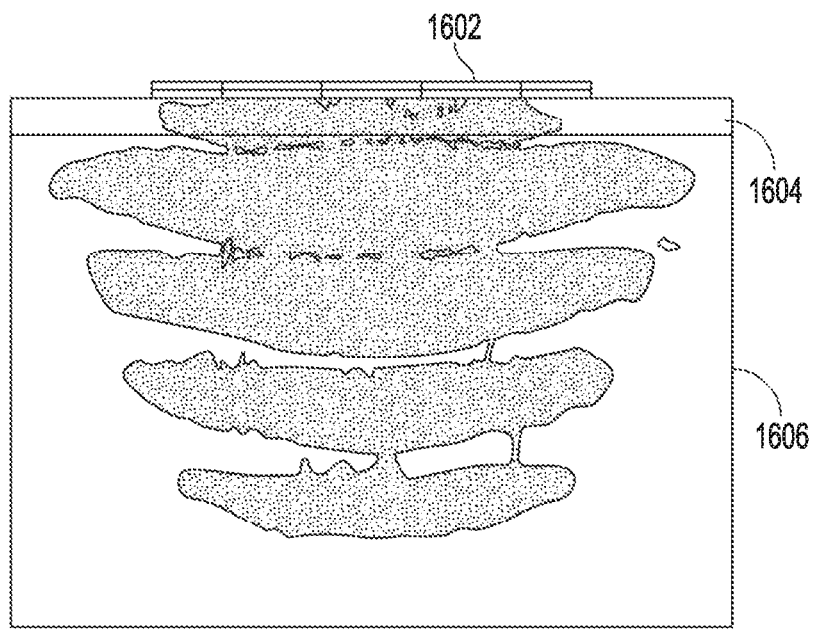
FIG. 16 illustrates generally an example that shows signal or field penetration within tissue.

FIG. 16 illustrates generally an example that shows signal or field penetration within tissue 1606. A transmitter, such as corresponding to the first transmitter 1000 or one or more of the other transmitter examples discussed herein, is designated 1602 in this example, and is provided at the top of the illustration. When the transmitter 1602 is activated to manipulate evanescent fields at an airgap 1604 between the transmitter 1602 and the tissue 1606, a propagating field (as illustrated by the progressive lobes in the figure) is produced that extends away from the transmitter 1602 and into the tissue 1606 toward the bottom of the illustration.

Figure 17:
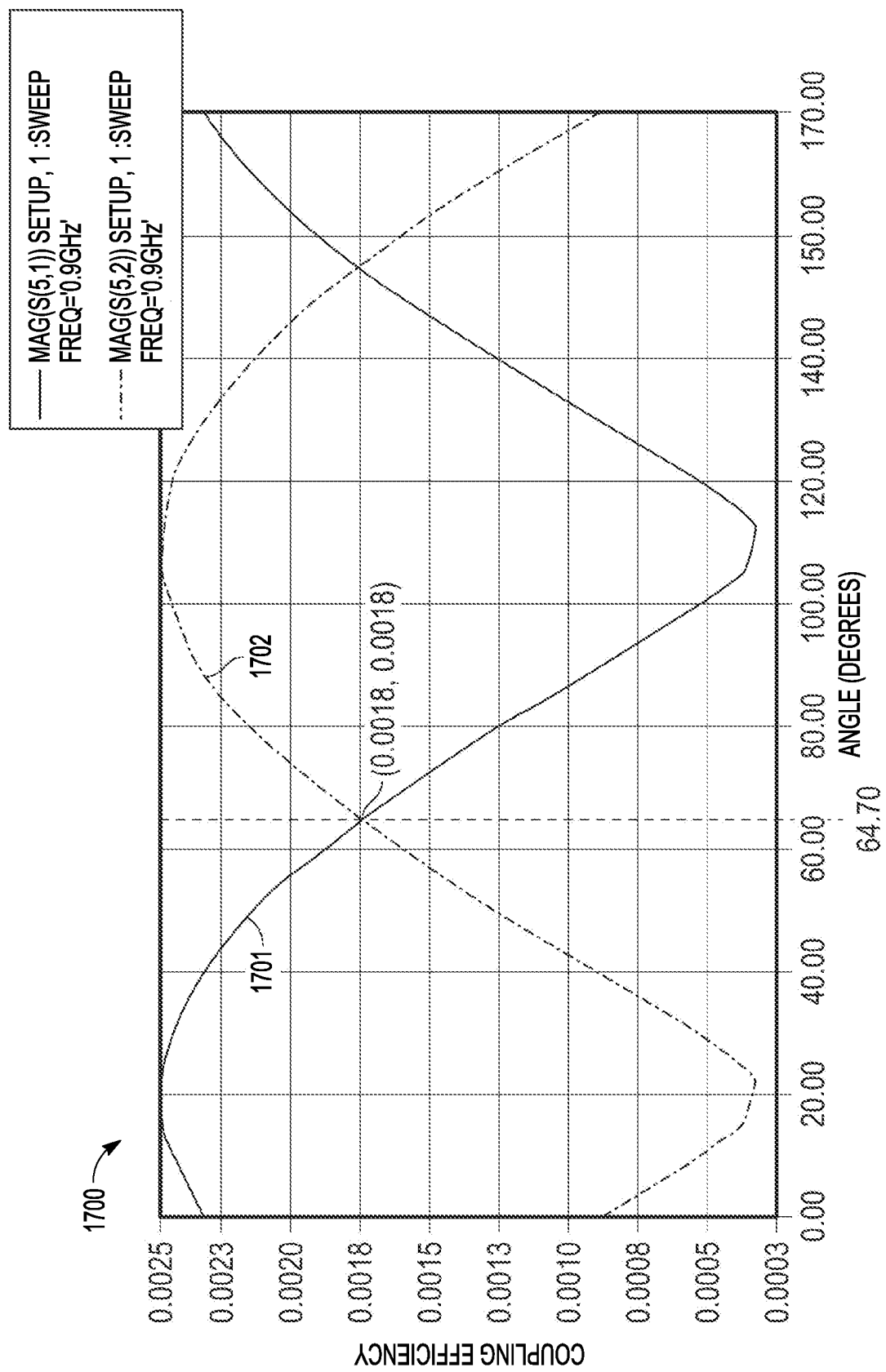
FIG. 17 illustrates generally an example of a chart that shows a relationship between coupling efficiency of orthogonal transmitter ports of a first transmitter to an implanted receiver with respect to a changing angle or rotation of the implanted receiver.

FIG. 17 illustrates generally an example of a chart 1700 that shows a relationship between coupling efficiency of orthogonal transmitter ports of the first transmitter to an implanted receiver with respect to a changing angle or rotation of the implanted receiver. The example illustrates that weighting the input or excitation signals provided to the orthogonal ports (e.g., to the first through fourth striplines 1131A-1131D) can be used to compensate for a changing location or rotation of the implanted receiver. When the transmitter can compensate for such variations in target device location, consistent power can be delivered to the target device even when the target device moves away from an initially-configured position.

In the example of FIG. 17, a first curve 1701 shows an S-parameter, or voltage ratio of signal at the transmitter and the receiver, when a first pair of oppositely-oriented (e.g., top/bottom, or left/right) striplines are excited by an oscillating signal. A second curve 1702 shows an S-parameter when a second pair of the oppositely-oriented striplines are excited by an oscillating signal. In the example of FIG. 17, the first and second pairs of striplines are orthogonal pairs. The example illustrates that signals provided to the orthogonal pairs can be optimally weighted to achieve consistent powering with different implant angles, such as through constructive interference.

The example of FIG. 17 further illustrates that the transmitters discussed herein and their equivalents can be used to effectively steer or orient a propagating field such as without moving the transmitter or external source 102 itself. For example, rotational changes in a position of the implantable device 110 can be compensated by weighting the signals provided to the various striplines with different phases, such as to ensure a consistent signal is delivered to the implantable device 110. In an example, the weighting can be adjusted based on a sensed or measured signal transfer efficiency, such as can be obtained using feedback from the implantable device 110 itself. Adjusting the excitation signal weighting can change a direction of the transmitter current distribution, which in turn can change characteristics of the evanescent field outside of the body tissue and thereby affect a propagation direction or magnitude of a field in tissue.

Figure 18:
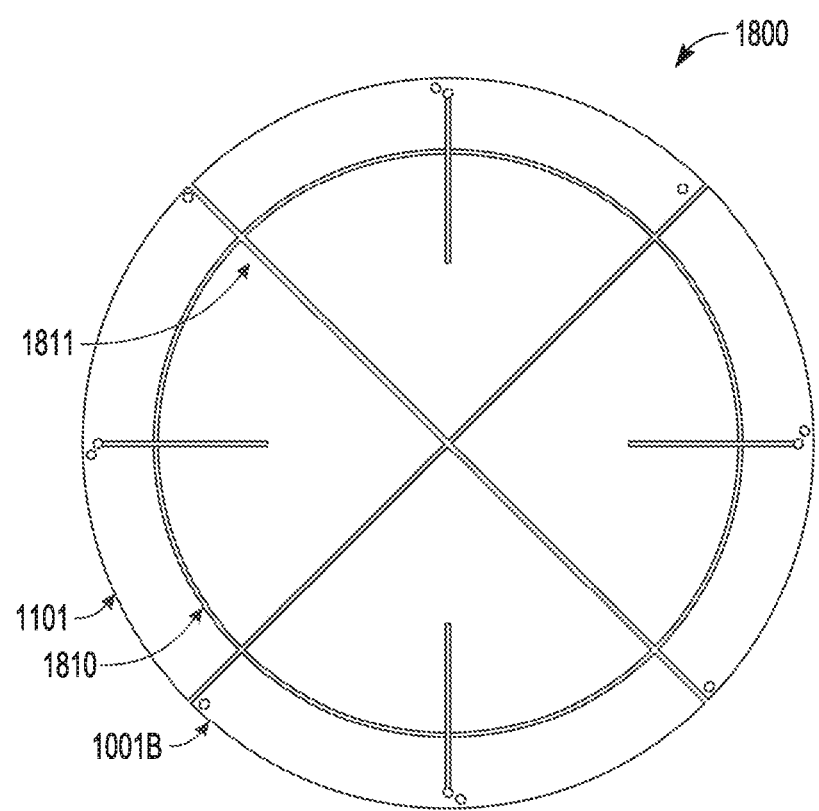
FIG. 18 illustrates generally a top view of the second layer from the example of FIG. 11 superimposed over a different first layer of a layered transmitter.

FIG. 18 illustrates generally a top view of the second layer 1101 from the example of FIG. 11 superimposed over a different first layer 1001B of a layered transmitter. That is, relative to FIG. 11, the example of FIG. 18 includes the different first layer 1001B instead of the first layer 1001A that includes the arms 1021A-1021D. The different first layer 1001B includes a substrate that is etched with a circular slot 1810 to separate a conductive outer region from a conductive inner region. In addition to the etched circular slot 1810, the example includes a pair of linear slots 1811 arranged in an "X" pattern and configured to cross at a central axis of the device. In the example of FIG. 18, the pair of linear slots 1811 extends to opposite side edges of the substrate or layer. The example thus includes, on the different first layer 1001B, eight regions that are electrically decoupled, including four equally-sized sectors, or pie-piece shaped regions, and four equally-sized regions of an annulus. Differently-sized, rather than equally-sized, regions can similarly be used, such as when the linear slots 1811 are not arranged exactly orthogonally to each other.

Figure 19B:
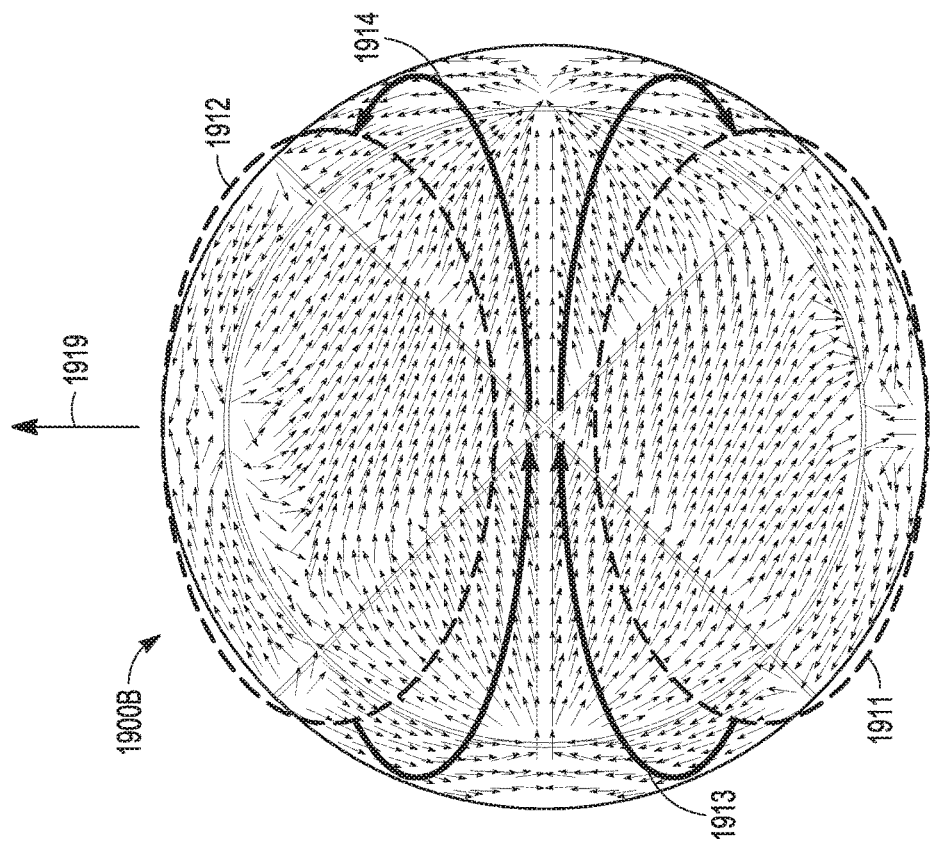
FIGS. 19A and 19B illustrate generally examples showing different surface current patterns for an excited device.
Figure 19A:
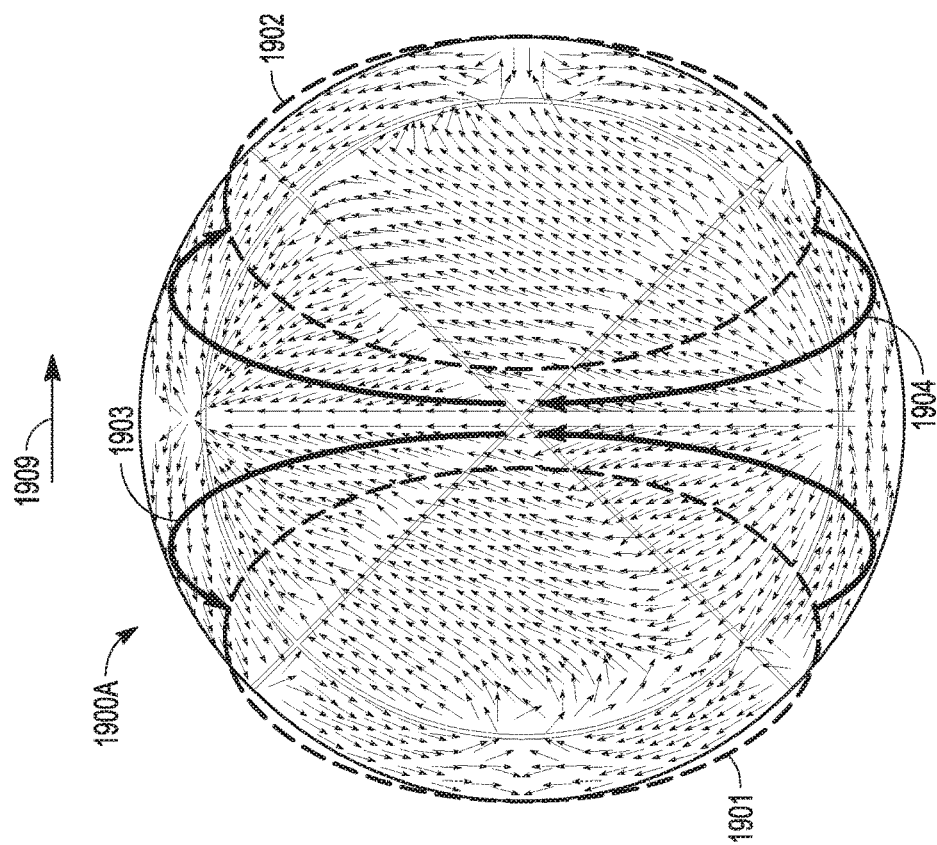

When a device with the different first layer 1001B is excited (e.g., using the striplines on the second layer 1101), a resulting current density across or over the different first layer 1001B can be relatively more concentrated at the outer annulus portions of the layer than at the inner sector portions of the layer. FIGS. 19A and 19B illustrate generally examples showing different surface current patterns 1900A and 1900B, respectively, for an excited device that includes or uses the different first layer 1001B. Drive signals providing excitation of the device can be tuned or adjusted in phase and/or amplitude relative to each other to produce the different surface currents.

In the example of FIG. 19A, the surface current pattern closely mimics an oscillatory, optimal distribution to adjust an evanescent field that will give rise to propagating fields inside of tissue. As indicated by the illustrated arrow density, a current density can be more concentrated at the outer annulus portion than at the inner sector portion of the different first layer 1001B. When the device in the example of FIG. 19A is excited by a first excitation signal or signal pattern, the device can have an oscillatory current distribution that approximates a pair of adjacent, vertically-oriented lobes, indicated by dashed line segments 1901 and 1902 and corresponding to the directions indicated by the bolded arrows 1903 and 1904, at the different first layer 1001B. A receiver, such as the implantable device 110, can be most strongly coupled with the transmitter comprising the different first layer 1001B excited in the manner illustrated in FIG. 19A when the implantable device 110 includes a receiver antenna normal that is oriented orthogonally to a direction of the lobes as illustrated by a first receiver orientation arrow 1909.

A direction or orientation of the current paths induced on the different first layer 1001B can change in correspondence with changes in excitation signals. In the example of FIG. 19B, a second surface current pattern closely mimics an oscillatory, optimal distribution to adjust an evanescent field that will give rise to propagating fields inside of tissue. As indicated by the illustrated arrow density, a current density can be more concentrated at the outer annulus portion than at the inner sector portion of the different first layer 1001B. When the device in the example of FIG. 19B is excited by a second excitation signal or signal pattern, the device can have an oscillatory current distribution that approximates a pair of adjacent, horizontally-oriented lobes, indicated by dashed line segments 1911 and 1912 and corresponding to the directions indicated by the bolded arrows 1913 and 1914, at the different first layer 1001B. A receiver, such as the implantable device 110, can be most strongly coupled with the transmitter comprising the different first layer 1001B excited in the manner illustrated in FIG. 19B when the implantable device 110 includes a receiver antenna normal that is oriented orthogonally to a direction of the lobes as illustrated by a first receiver orientation arrow 1919.

A device that includes or uses the different first layer 1001B can have its operating frequency or resonance determined based in part on an area characteristic of the outer annulus, such as rather than being based on the length of the arms 1021A-1021D from the example of FIG. 11. Total signal transfer efficiency from a transmitter using the embodiment of FIG. 18 to an implanted midfield receiver is similar to the efficiency from a transmitter using the embodiment of FIG. 11, however, greater current density at the outer annulus portion of the embodiment of FIG. 18 can allow for greater steerability (that is, transmitted field steering) and thus potentially better access and transmission characteristics for communication with the implantable device 110, including when the receiver is off-axis relative to the transmitter. Furthermore, the specific absorption rate (SAR) can be reduced when the embodiment of FIG. 18 is used, and unwanted coupling between ports can be reduced. Other transmitter configurations and geometries for an external source 102 can similarly be used to achieve the same current distribution and steerable fields contemplated herein for the illustrated embodiments.

Figure 20:
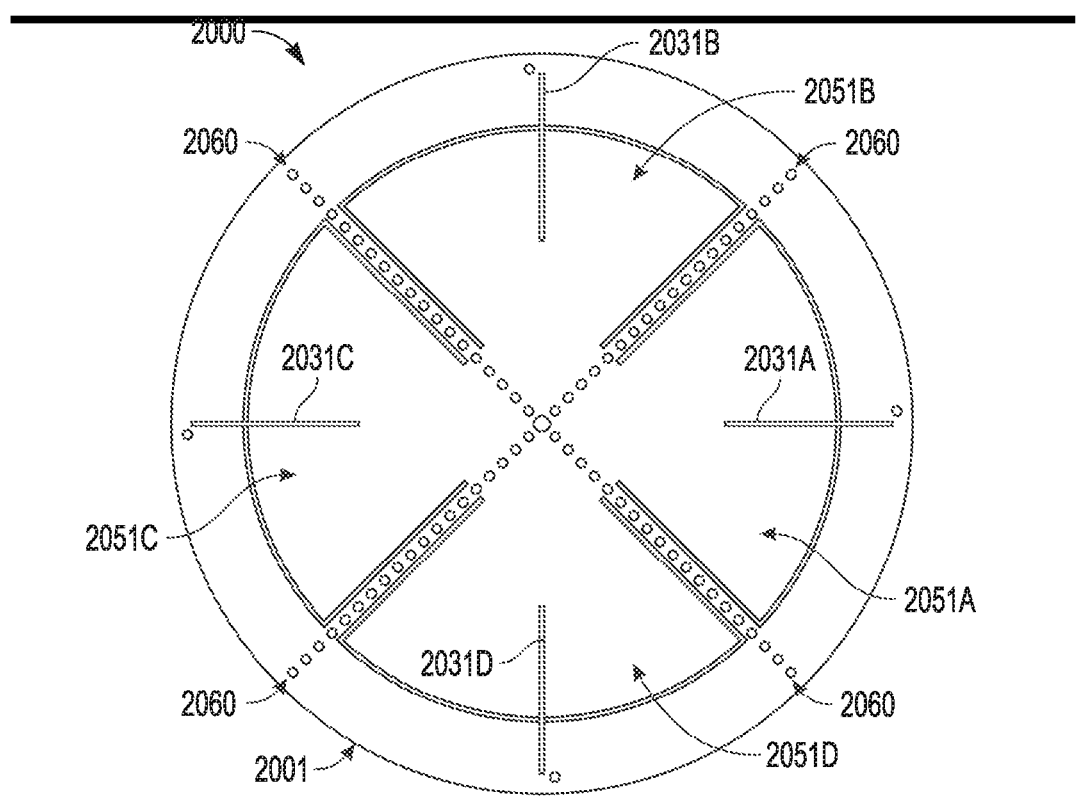
FIG. 20 illustrates generally a top view of an example of a layered second transmitter.
Figure 21:
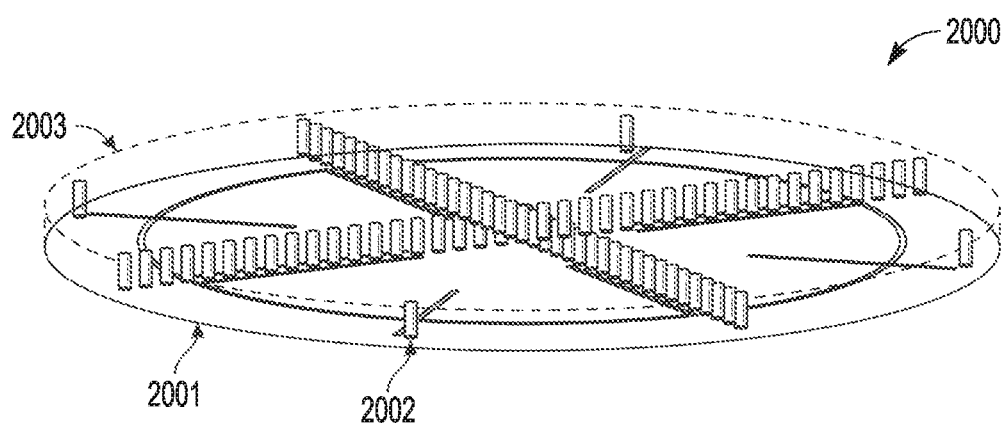
FIG. 21 illustrates generally a perspective view of the layered second transmitter from FIG. 20.

Other transmitter configurations can additionally or alternatively be used. FIG. 20, for example, illustrates generally a top view of an example of a layered second transmitter 2000. The second transmitter 2000 is similar to the first transmitter 1000 in profile and in its layered structure. The second transmitter 2000 includes stripline excitation elements 2031A-2031D on a second layer that is offset from a first layer 2001 that includes first through fourth patch-like features 2051A-2051D. FIG. 21 illustrates generally a perspective view of the layered second transmitter 2000.

In the example of FIG. 20, the first layer 2001 includes a conductive plate that can be etched or cut to provide various layer features. The first layer 2001 includes a copper substrate that is etched to form several discrete regions. In the example of FIG. 20, the etchings partially separate the layer into quadrants. Unlike several other examples discussed herein, the etched portion does not create a physically isolated inner region. Instead, the example of FIG. 20 includes a pattern of vias 2060 that are used to partially electrically separate the discrete regions. The vias 2060 are coupled to another layer that serves as a ground plane. In the illustrated example, the vias 2060 are arranged in an "X" pattern corresponding to and defining the quadrants. In an example, the vias 2060 extend between the first layer 2001 and a second layer 2003, and the vias 2060 can be electrically isolated from another layer that comprises one or more striplines. The arrangement of the vias 2060 divides the first layer 2001 into quadrants that can be substantially independently excitable, such as by respective striplines or other excitation means.

The etched portions of the first layer 2001 include various linear slots, or arms, that extend from the outer portion of the first layer toward the center of the device. In an example, a diameter of the second transmitter 2000 and its slot or arm dimensions can be adjusted to tune or select a resonant frequency of the device. Dielectric characteristics of one or more layers adjacent or near to the first layer 2001 can also be used to tune or influence a transmission characteristic of the second transmitter 2000.

In the example of FIG. 20, the vias 2060 and via walls provided in the "X" pattern can be used to isolate the different excitation regions, and can facilitate steering of propagating fields, such as to target an implantable device that is imprecisely aligned with the transmitter. Signal steering can be provided by adjusting various characteristics of the excitation signals that are respectively provided to the striplines, such as the first through fourth stripline excitation elements 2031A-2031D. For example, excitation signal amplitude and phase characteristics can be selected to achieve a particular transmission localization.

The present inventors have recognized that the vias, such as the vias 2060, provide other benefits. For example, the via walls can cause some signal reflections to and from the excitation elements, which in turn can provide more surface current and thereby increase an efficiency of signals transmitted to tissue.

Figure 22:
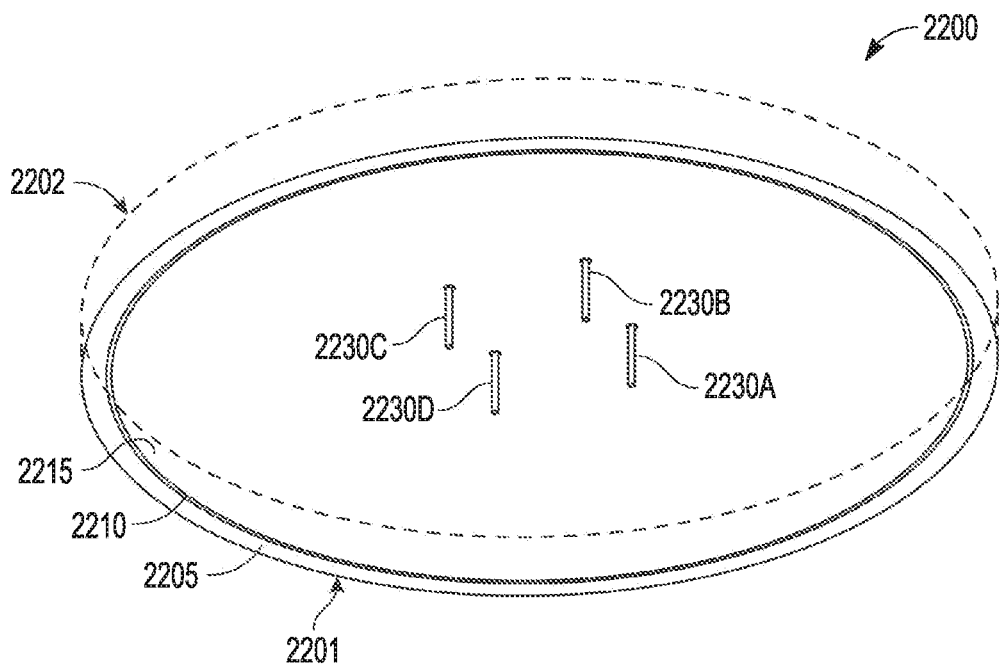
FIG. 22 illustrates generally a perspective view of an example of a layered third transmitter.

FIG. 22 illustrates generally a perspective view of an example of a layered third transmitter 2200. The example includes, at the bottom side of the illustration, a first layer 2201 of the third transmitter 2200. At the top of the figure, the third transmitter 2200 includes a second layer 2202. The first and second layers 2201 and 2202 can be separated using a dielectric layer. The first layer 2201 can include a slot 2210 that separates, or electrically isolates, an outer region 2205 of the first layer 2201 from an inner region 2215 of the first layer 2201. The slot 2210 separates the annular outer region 2205 (e.g., an outer annular region) from a disc-shaped inner region 2215 (e.g., an inner disc region). In an example, the second layer 2202 can be a conductive layer that provides a shield or backplane for the third transmitter 2200. In an example, a circumference of the slot 2210 and/or of the disc-shaped inner region 2215 is less than a wavelength of a signal to be transmitted using the third transmitter 2200.

The example of FIG. 22 includes vias 2230A-2230D that electrically couple the inner region 2215 on the first layer 2201 with drive circuitry, such as can be disposed on the second layer 2202. Ground vias (not shown) can be used to electrically couple the outer region 2205 with the second layer 2202. That is, the example of FIG. 22 can include a transmitter with an inner region 2215 of the first layer 2201 that is excitable without the use of additional layers and striplines. In an example, the first layer 2201 can be tuned or modified, such as by adding one or more arms that extend from the slot 2210 toward a center of the device. However, the circular slot 2210 can generally be made large enough that a suitable operating resonance or frequency can be achieved without using such additional features.

Figure 23:
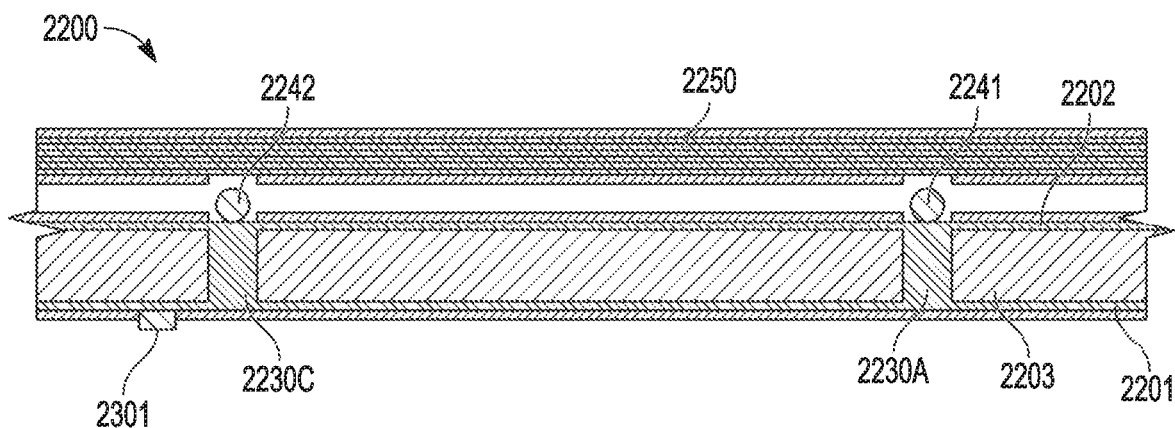
FIG. 23 illustrates generally a side, cross-section view of the layered third transmitter from FIG. 22.

FIG. 23 illustrates generally a side, cross-section view of the layered third transmitter 2200. The example of FIG. 23 illustrates generally that a dielectric layer 2203 can be provided between the first and second layers 2201 and 2202 of the third transmitter 2200. In an example, a circuit assembly 2250 can be provided adjacent to the third transmitter 2200, and can be coupled with the third transmitter 2200 such as using solder bumps 2241, 2242.

Using solder bumps can be convenient to facilitate assembly by using established solder reflow processes. Other electrical connections can similarly be used. For example, the top and bottom layers can include an edge plating and/or pads to facilitate interconnection of the layers. In such an example, the top layer can optionally be smaller than the bottom layer (e.g., the top layer can have a smaller diameter than the bottom layer) to facilitate optical verification of the assembly. In an example, the third transmitter 2200 can include one or more capacitive tuning elements 2301 coupled with the first layer 2201, such as at or adjacent to the slot 2210. In an example, a capacitive tuning element 2301 can be coupled to conductive surfaces on opposite sides of the slot 2210. The capacitive tuning element 2301 can provide a fixed or variable capacitance to adjust a tuning characteristic of the transmitter.

Figure 24:
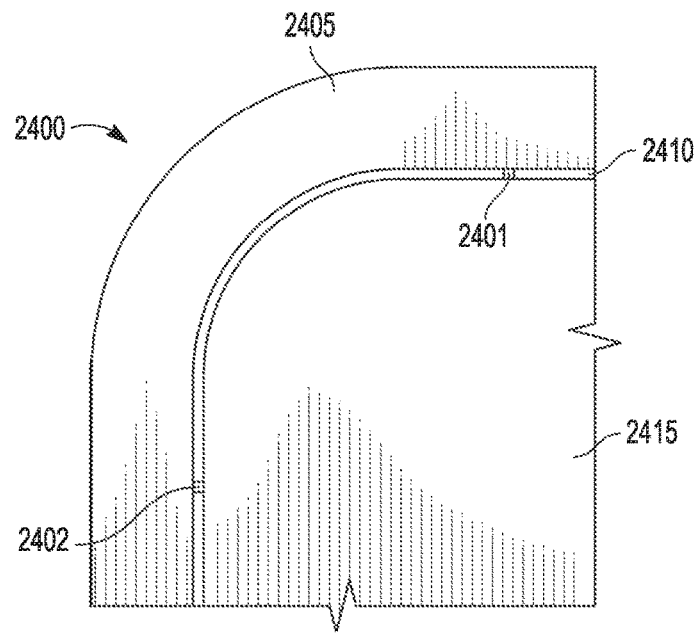
FIG. 24 illustrates generally an example of a portion of a layered midfield transmitter showing a first layer with a slot and a capacitive element.

FIG. 24 illustrates generally an example of a portion of a layered midfield transmitter 2400 showing a first layer with a slot 2410. In an example, the slot separates a first conductive region 2405 (e.g., corresponding to an outer conductive region) from a second conductive region 2415 (e.g., corresponding to an inner conductive region) of a transmitter layer. Additionally or alternatively to adding arms or radial slots to tune an operating frequency of the transmitter 2400, capacitive elements can be coupled across opposing conductive sides of the slot 2410, such as to bridge the first and second conductive regions 2405 and 2415. In the example of FIG. 24, first and second capacitive elements 2401 and 2402 bridge the first and second conductive regions 2405 and 2415 at different locations along the slot 2410.

The capacitive elements for such bridging and tuning can generally be in the picofarad range, but other values can be used depending on a desired operating frequency. In an example, one or more of the first and second capacitive elements 2401 and 2402 includes a tunable or variable capacitor, such as having a capacitance value that can be set by a control signal. The control signal can be updated or adjusted based on a desired tuning frequency for the midfield transmitter.

Tunable or variable capacitor elements, or other fixed capacitors, can be applied to or implemented in various embodiments of the external source 102, such as including one or more of the several different embodiments illustrated herein at FIGS. 10-24. Referring to FIG. 10, for example, variable capacitor elements can be provided at multiple locations around the transmitter, such as at several locations about the slot 1010, or at one or more locations along one or more of the four radial slots or arms 1021A, 1021B, 1021C, and 1021D, that extend from the circular slot 1010 toward the center of the first layer 1001A. In an example, variable capacitor elements are provided at different locations about the slot 1010, such as including one variable capacitor element in each of the four quadrants divided by the arms 1021A-1021D.

Figure 25:
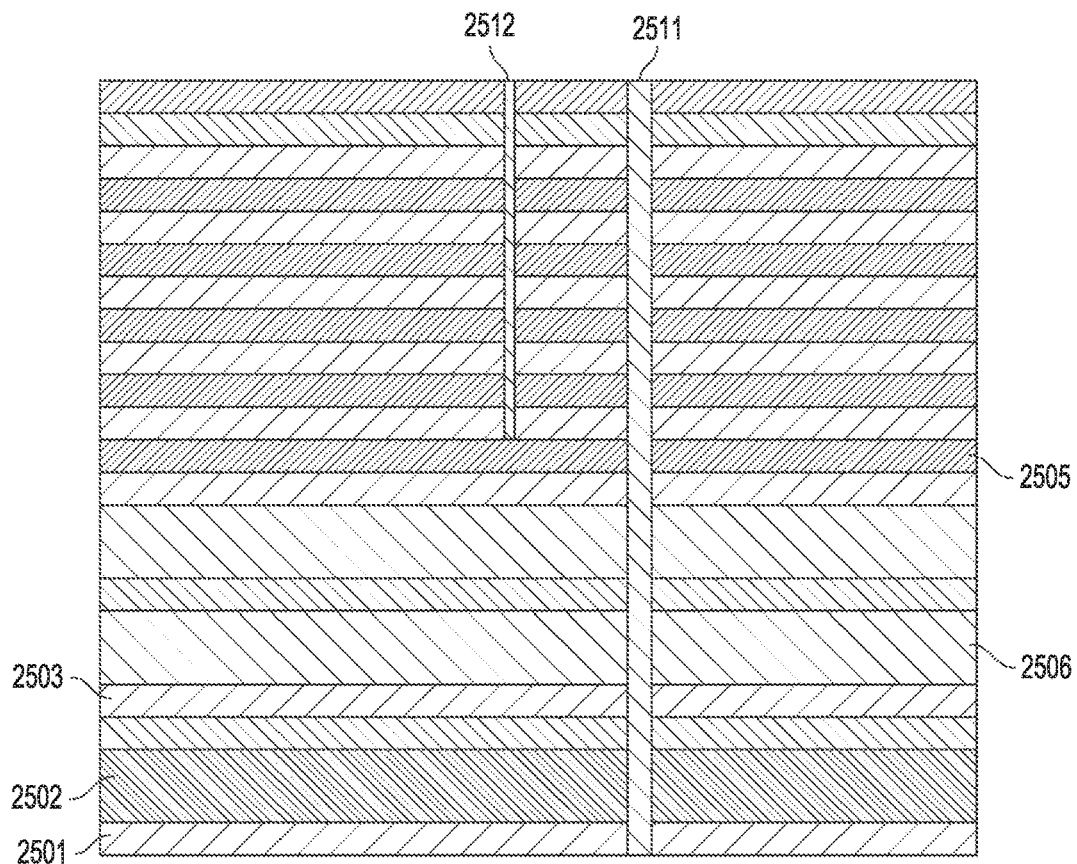
FIG. 25 illustrates generally an example of a cross-section schematic for a layered transmitter.

FIG. 25 illustrates generally an example of a cross-section schematic for a layered transmitter. The schematic can correspond generally to a portion of any one or more of the transmitter examples illustrated herein. In the example of FIG. 25, a bottom layer 2501 is a conductive first layer, such as copper, and can correspond to, e.g., the first layer 1001A of the example of FIG. 10. That is, the bottom layer 2501 in FIG. 25 can be the etched first layer 1001A in the example of FIG. 10.

Moving upward from the bottom layer 2501, FIG. 25 includes a first dielectric layer 2502. This first dielectric layer 2502 can include a low-loss dielectric material, preferably with Dk~3-13. A conductive second layer 2503 can be provided above the first dielectric layer 2502. The conductive second layer 2503 can include the one or more of the striplines or other excitation features discussed herein.

A second dielectric layer 2506 can be provided above the conductive second layer 2503. The first and second dielectric layers 2502 and 2506 can include the same or different materials and can have the same or different dielectric properties or characteristics. In an example, the first and second dielectric layers 2502 and 2506 can have different dielectric characteristics and such characteristics are selected to achieve a particular device resonance characteristic when the device is excited using a signal generator.

In the example of FIG. 25, the second dielectric layer 2506 can include multiple layers of dielectric material. As the second dielectric layer becomes thicker, a distance increases between the conductive second layer 2503 and a conductive third layer 2505. The conductive third layer 2505 can include backplane or ground. As the distance between the conductive second and third layers 2503 and 2505 increases, the bandwidth of the transmitter can correspondingly increase. The greater bandwidth can allow for greater data throughput, wider operating frequency range for frequency hopping, and can also improve manufacturability by increasing acceptable tolerances.

One or more vias can extend vertically through the layered assembly as illustrated in FIG. 25. For example, a first via 2511 can extend entirely through a vertical height of the device, while a second via 2512 can extend partially through the device. The vias can terminate at the various conductive layers, such as to provide electrical communication between the different layers and various drive circuitry or ground.

Various other layers can be provided above the conductive third layer 2505. For example, multiple layers of copper and/or dielectrics can be provided, such as can be used to integrate various electronic devices with the transmitter. Such devices can include one or more of a signal amplifier, sensor, transceiver, radio, or other device, or components of such devices, such as including resistors, capacitors, transistors, and the like. Such other components or circuitry for the external source 102 are discussed elsewhere herein.

Transmitter Tuning

The external source 102, such as including a midfield transmitter, can be tuned or adjusted to enhance signal transfer efficiency to the implantable device 110 or other midfield receiver. Signal transfer characteristics can be monitored, such as using a bidirectional coupler or circulator, and transmitter power or drive signal characteristics can be intermittently or periodically updated to enhance transfer efficiency. In an example, midfield transmitter tuning includes adjusting a value of a capacitive tuning element based on a reflected power measurement, such as can be used to determine a coupling efficiency between a transmitter and a receiver antenna. In an example, midfield transmitter tuning includes adjusting a value of a capacitive tuning element based on a data signal received from the implanted or other midfield receiver, and the data signal includes information about a quality or quantity of signal received at the receiver.

Figure 26A:
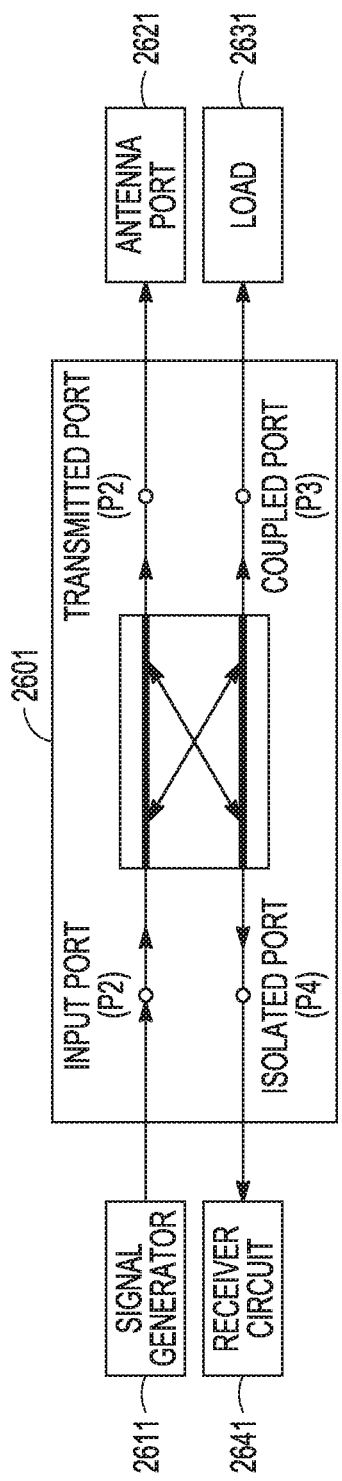
FIG. 26A illustrates a diagram that includes a bidirectional coupler that can comprise a portion of a midfield transmitter.

FIG. 26A illustrates a diagram that includes a bidirectional coupler 2601 that can comprise a portion of a midfield transmitter. The bidirectional coupler 2601 includes multiple ports, including an input port P1, a transmitted port P2, a coupled port P3, and an isolated port P4. The input port P1 receives a signal, such as a test signal or power signal, from a signal generator 2611 (e.g., a signal generator component of a midfield transmitter device or external source 102). In an example, the signal generator 2611 is configured to provide an AC signal having a frequency between about 300 MHz and 3 GHz.

The coupled port P3 receives a portion of the signal that is received by the input port P1 from the signal generator 2611. In the example of FIG. 26A, the coupled port P3 is terminated with a load 2631. In an example, the load 2631 includes a reference load with a specified matching impedance, such as a fixed-value resistor (e.g., a 50 ohm resistor). The transmitted port P2 transmits another portion of the signal that is received by the input port P1 from the signal generator 2611. In other words, the transmitted port P2 transmits a signal that corresponds to the signal received at the input port P1 less any signal provided at the coupled port P3 and less any other losses. In an example, the transmitted port P2 is coupled with an antenna port 2621 or other excitation port of a midfield transmitter, such as one of the first through fourth RF ports 311, 312, 313, and 314 from the example of FIG. 3.

The isolated port P4 can be coupled to a receiver circuit 2641. The receiver circuit 2641 can include monitoring or analysis circuitry. In an example, the receiver circuit 2641 is configured to monitor signals received from the isolated port P4 and provide information about a reflected power, such as can be used to determine an efficiency of a transmitted power signal from the transmitted port P2. In an example, the isolated port P4 is coupled to an RF diode detector circuit or a switch. The switch can be configured to switch between the RF diode detector and a mixer circuit, such as for receiving backscatter communications from the implantable device 110.

In the example of FIG. 26A, the input port P1 receives an amplified test signal from the signal generator 2611 or other transceiver circuit portion of a midfield transmitter device. When signal characteristics on the transmitter side are well-matched to a receiver device, then a relatively large portion of the energy from the test signal is provided through the bidirectional coupler 2601 to the transmitted port P2, and a relatively small portion of the energy from the test signal is provided at the isolated port P4. If, however, the transmitter and receiver devices are not well-matched, then a relatively larger portion of the energy from the test signal is provided at the isolated port P4. Therefore, signal characteristics at the isolated port P4 can be monitored and used to assess a transmission quality or a power transfer efficiency, or to detect a fault condition. In an example, characteristics of a test signal provided to the input port P1, such as a signal frequency, can be changed to enhance the signal transmission efficiency.

Figure 26B:
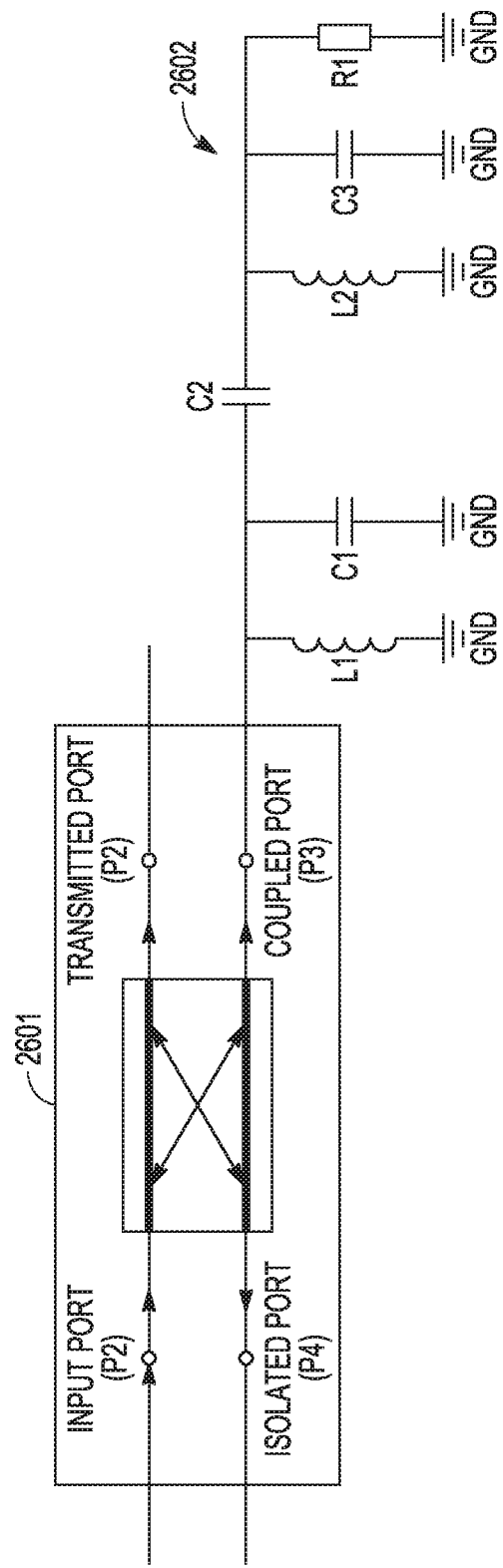
FIG. 26B illustrates a diagram that includes an example of a bidirectional coupler with an adjustable load.

FIG. 26B illustrates a diagram that includes an example of the bidirectional coupler 2601 with an adjustable load 2602. The example of FIG. 26B can comprise a portion of a midfield transmitter that is configured to receive or use a backscatter signal such as for communication with an implanted midfield receiver device. Due at least in part to a changing position of an external transmitter relative to its target receiver, there can be interference, or changes in interference, between an external transmitter source and a receiver. Such interference can compromise an effectiveness of backscatter communications. In an example, a cancelation signal can be introduced to help mitigate or process such interference. For example, an external transmitter can be configured to generate a tuned, self-interference cancellation signal to help separate a carrier signal from self-interference or leakage signals from the transmitter to receiver sides of the bidirectional coupler 2601.

In the example of FIG. 26B, the bidirectional coupler 2601 can receive an RF source signal at the input port P1 (e.g., from the signal generator 2611), and can provide a corresponding signal to the transmitted port P2 (e.g., to be provided to an output port of a midfield transmitter or to the antenna port 2621) and to the coupled port P3. The coupled port P3 can feed the adjustable load 2602, and the adjustable load 2602 can be tuned to a specified nominal impedance.

In the example of FIG. 26B, the adjustable load 2602 is nominally tuned to about 50 ohms at various different frequencies, and a particular operating frequency can be selected by adjusting a capacitance of one or more of the capacitors C1, C2, and C3. Other nominal impedance set points can similarly be used. In an example, the capacitors can be adjusted such that the adjustable load 2602 is mismatched to the coupled port P3, and a reflection can be generated and added to a received signal (e.g., a backscatter signal) from the transmitted port P2.

In an example, a leakage signal can be present at the isolated port P4 (e.g., based on an input signal provided at the input port P1). An iterative algorithm can be used to minimize a power of a signal received at the receiver circuit 2641 (e.g., an IQ receiver circuit) via the isolated port P4 to mitigate the leakage signal and improve an efficacy of backscatter communication. For example, capacitances provided by the capacitors C1, C2, and/or C3, can be adjusted during use to provide a cancellation signal that is substantially opposite in phase and equal in magnitude to the leakage signal. The adjustable load 2602 and the bidirectional coupler 2601 can thus be used by the external source 102 to generate a dynamic, controlled reflection or cancellation signal that can be used to help minimize noise and extract information from a backscatter signal, such as under changing use or interference conditions.

The examples of FIGS. 26A and 26B include the bidirectional coupler 2601, however, other examples can similarly include or use other elements to determine information about a coupling efficiency between a midfield transmitter and midfield receiver. For example, a circulator can be used to couple an RF port of a midfield transmitter to both an excitation source and to a receiver circuit, such as can be configured to receive a backscatter or other signal that can include information about a received power signal at a midfield receiver. A circulator device and backscatter processing, such as including encoding or decoding information about a power signal or signal transfer efficiency in a backscatter signal or other data signal, is discussed in PCT Patent Application PCT/US2016/057952, filed Oct. 20, 2016 (for example, at FIG. 105 and at corresponding portions of the '952 application), and in U.S. Provisional Application 62/397,620, filed Sep. 21, 2016 (for example at FIG. 9 and at corresponding portions of the '620 application), each of which is herein incorporated by reference in its entirety.

Figure 27:
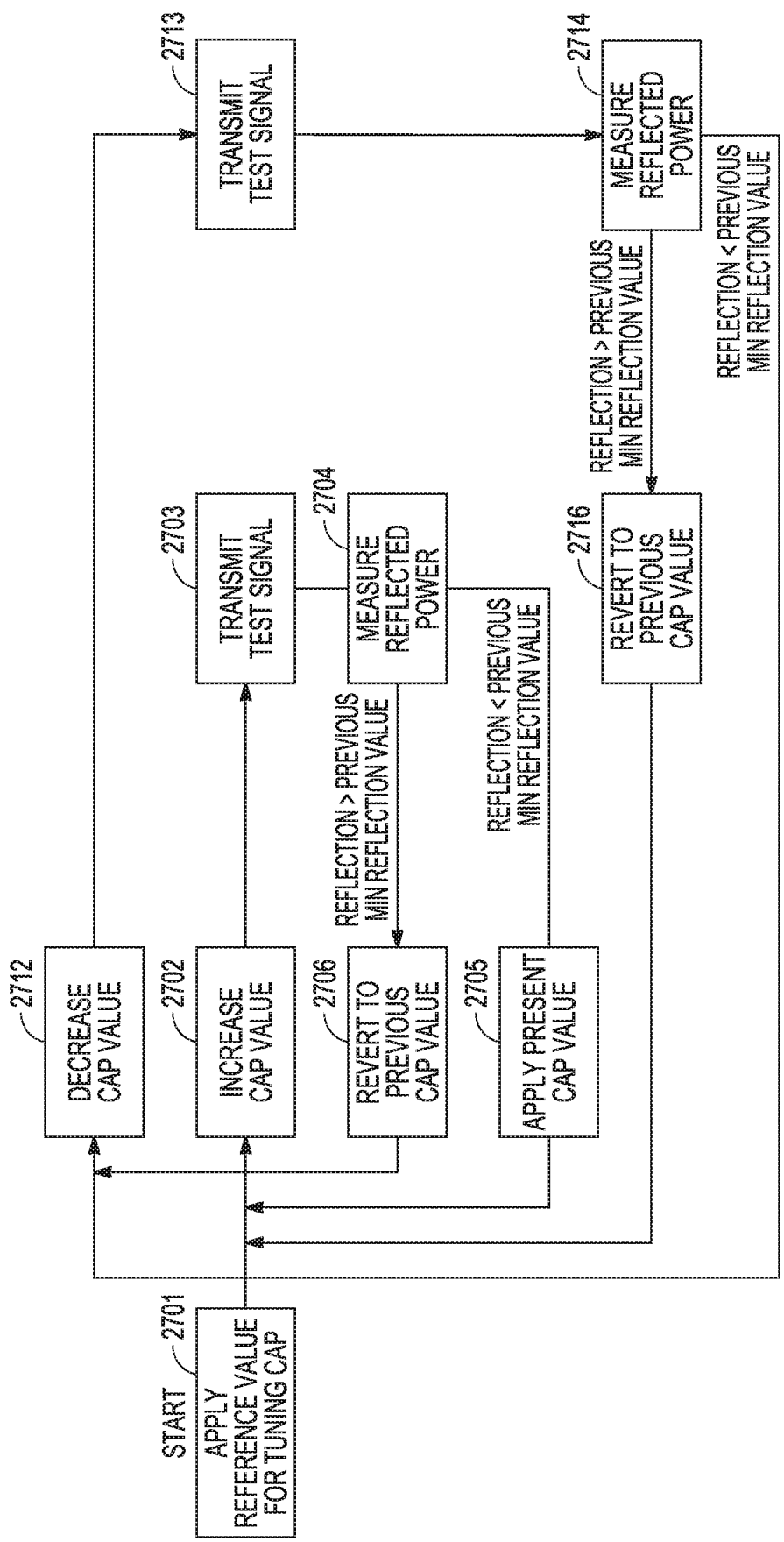
FIG. 27 illustrates a first flow chart showing a process for updating a value of a tuning capacitor for a midfield transmitter.

FIG. 27 illustrates, by way of example, a first flow chart showing a process for updating a value of a tuning capacitor for a midfield transmitter. In an example, the process is similar to a level detection algorithm or level finding algorithm, however the "level" to be found is a capacitance value for a variable or tunable capacitor in a midfield transmitter. In the examples discussed herein, the tunable capacitor corresponds to a capacitive tuning element as discussed elsewhere herein, for example, one or more of the capacitive tuning elements 2301 from the example of FIG. 23, and/or to the first or second capacitive elements 2401 and 2402 from the example of FIG. 24. Capacitive tuning elements can be similarly applied to the others of the illustrated transmitters or to other unillustrated embodiments.

The example of FIG. 27 includes using information about a reflected power signal to adjust a capacitance value of a tuning capacitor. In an example, the information about the reflected power signal is included in a signal monitored at the isolated port P4 in the example of the bidirectional coupler 2601 or the information about the reflected power signal is determined using a feedback signal from a circulator.

The capacitance value-finding example of FIG. 27 can begin at step 2701 with applying a reference value for a first tuning capacitor (sometimes referred to herein as a "tunable capacitor", a "capacitive element", a "capacitive tuning element", or similar device) in a midfield transmitter, such as comprising a portion of the external source 102. That is, at step 2701, a control signal can be provided to a tunable capacitor circuit to cause the tunable capacitor to provide a capacitance corresponding to the reference value. The reference value can be a stored capacitance value, a specified initial or starting capacitance value, a previously-used capacitance value, or other capacitance value. In an example, the capacitance value is between about 0.1 pF and 10 pF. At step 2702, the example includes increasing a capacitance of the tunable capacitor. The magnitude of the increment can be fixed or variable and can be different depending on circumstances of a particular use case. In an example, the magnitude of the increment is about 0.1 pF. Increments (or decrements) in capacitance can be linear or non-linear.

Following the capacitance increase at step 2702, step 2703 includes transmitting a test signal using the updated transmitter configuration with the tunable capacitor. Transmitting the test signal at step 2703 can include, for example, providing the test signal to an RF port on a midfield transmitter, such as using the transmitted port P2 from the bidirectional coupler 2601.

At step 2704, the example can include measuring a reflected power characteristic. Measuring the reflected power characteristic can include, for example, measuring a power level at the isolated port P4 of the bidirectional coupler 2601. Based on a result of the measurement at step 2704, the increased capacitance of the tunable capacitor can be applied or the capacitance can revert to a previous (or other) capacitance value. For example, if the reflected power is less than a previously measured or specified minimum reflected power value, then the example can proceed to step 2705 and the increased capacitance of the tunable capacitor can be applied and used for further transmissions from the transmitter to the receiver. In other words, if the measurement or determination at step 2704 indicates that a lesser amount of power is being reflected, then a greater amount of power is assumed to be received at the receiver device. Following step 2705, the example can use the increased capacitance value for a specified duration or until an interrupt or other indication is received that triggers a further update to, or check of, the capacitance value. The further update can begin, for example, by returning to step 2702 and increasing the capacitance value. In other examples, the further update can proceed to step 2712 and trigger a decrease in the capacitance value.

Returning to step 2704, if the measured reflected power is greater than a previously measured or specified minimum reflected power value, then the example proceeds to step 2706. In this case, the increased capacitance corresponds to a greater amount of power being reflected, and the transmission efficiency is determined to be less than that prior to the capacitance change at step 2702. Accordingly, a value of the tunable capacitor can revert to a previous capacitance value (or other default value) for further tuning or for use in other signal transfers.

At step 2712, the capacitance value of the tunable capacitor can be decreased and, at step 2713, a test signal can be transmitted using the updated transmitter configuration with the decreased capacitance value. Transmitting the test signal at step 2713 can include, for example, providing the test signal to an RF port on a midfield transmitter, such as using the transmitted port P2 from the bidirectional coupler 2601.

From step 2713, the example can continue at step 2714 with measuring a reflected power characteristic. Measuring the reflected power characteristic can include, for example, measuring a power level at the isolated port P4 of the bidirectional coupler 2601. Based on a result of the measurement at step 2714, the decreased capacitance of the tunable capacitor can be used or the capacitance can revert to a previous capacitance value (or other default value). For example, if the reflected power is less than a previously measured or minimum reflected power value, then the example can use the present, decreased capacitance value for a signal transmission and/or the example can proceed to step 2712. In other words, if the measurement or determination at step 2714 indicates that a lesser amount of power is being reflected, then a greater amount of power is assumed to be received at the receiver device and the decreased capacitance value can be applied for a specified duration or until an interrupt or other indication is received to trigger a further update. The further update can begin, for example, by returning to step 2712 and further decreasing the capacitance value. In other examples, the further update can proceed to step 2702 and trigger an increase in the capacitance value.

Returning to step 2714, if the measured reflected power is greater than a previously measured or specified minimum reflected power value, then the example proceeds to step 2716. In this case, the decreased capacitance corresponds to a greater amount of power reflected, and the transmission efficiency is determined to be less than an efficiency prior to the capacitance change. Accordingly, a value of the tunable capacitor can revert to a previous capacitance value (or other default value) for further tuning or for use in other signal transfers.

Figure 28:
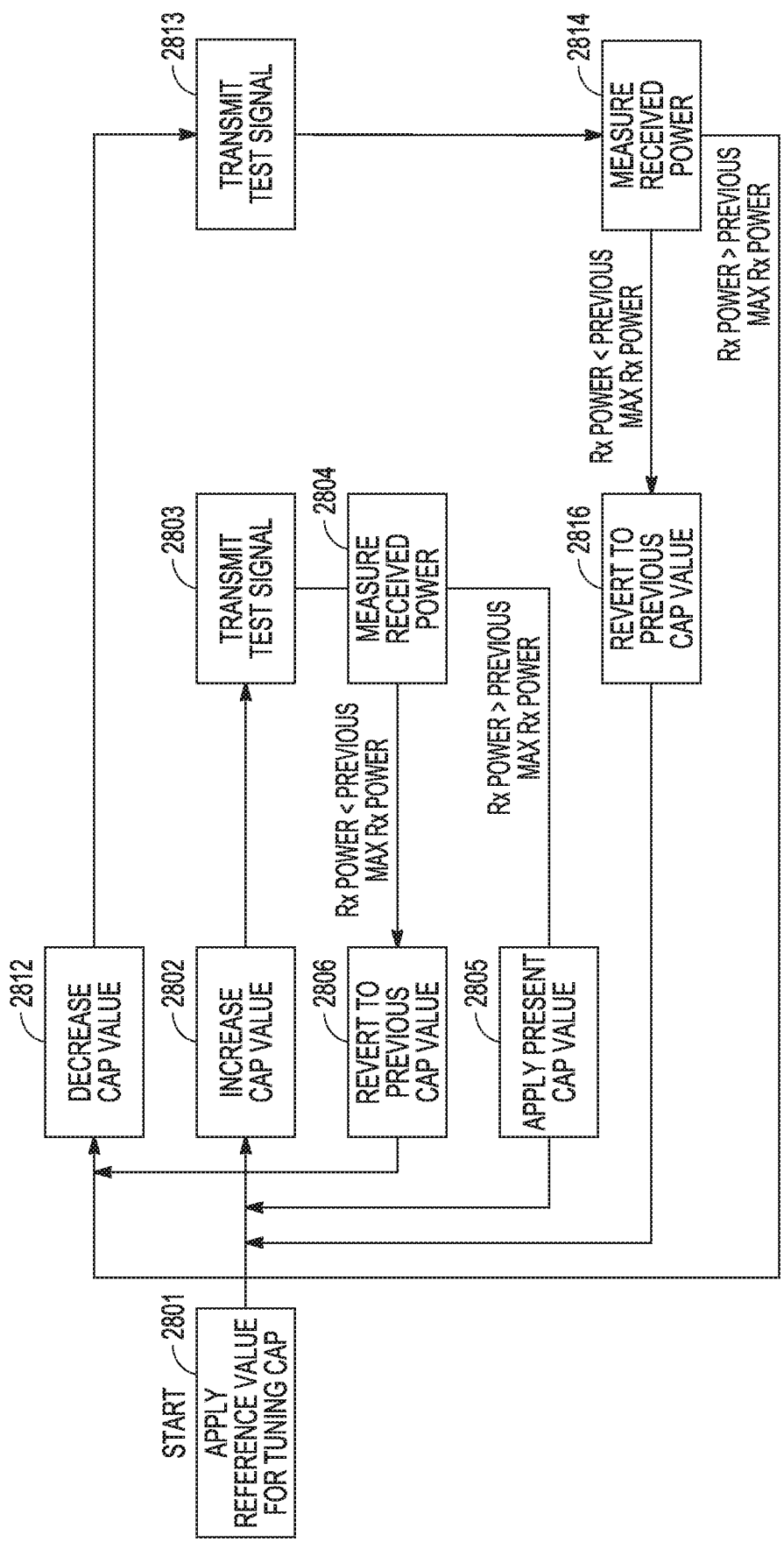
FIG. 28 illustrates a second flow chart showing a process for updating a value of a tuning capacitor for a midfield transmitter.

FIG. 28 illustrates, by way of example, a second flow chart showing a process for updating a value of a tuning capacitor for a midfield transmitter. The example of FIG. 28 includes using information about a power signal, such as received at or by an implanted midfield receiver device, to adjust a capacitance value of a tuning capacitor. In an example, the information about the power signal comprises a portion of a data signal received from an implanted or other midfield receiver device, such as can be received using a receiver circuit coupled to the midfield transmitter. In other words, the example of FIG. 28 can include using circuitry on-board an implanted midfield device to measure a value of a power signal received at the implanted midfield device, and then sending information about the measured value back to the transmitter, such as using a modulated and encoded backscatter signal or using another channel for data communication. The information received by the transmitter can be used, for example, to update or adjust a transmission signal characteristic, such as to enhance a power signal transmission and reception efficiency.

The example of FIG. 28 includes a level detection or value-finding algorithm for a variable capacitance of a tuning capacitor that is similar to the example discussed above in FIG. 27. The capacitance value-finding example of FIG. 28 can begin at step 2801 with applying a reference value for a first tuning capacitor in a midfield transmitter. That is, at step 2801, a tunable capacitor can be updated to provide a capacitance corresponding to the reference value. The reference value can be a stored capacitance value, a specified initial or starting capacitance value, a previously-used capacitance value, or other capacitance value. In an example, the capacitance value is between about 0.1 pF and 10 pF. At step 2802, the example includes increasing a capacitance of the tunable capacitor. The magnitude of the increment can be fixed or variable and can be different depending on circumstances of a particular use case. In an example, the magnitude of the increment is about 0.1 pF.

Following the capacitance increase at step 2802, the example can proceed to step 2803 that includes transmitting a test signal using the updated transmitter configuration with the tunable capacitor. Transmitting the test signal at step 2803 can include, for example, providing the test signal to an RF port on a midfield transmitter, such as using the transmitted port P2 from the bidirectional coupler 2601.

At step 2804, the example can include measuring a received power characteristic at a receiver device. Measuring the received power characteristic can include, for example, measuring a magnitude of a power signal received at an implanted device. Based on a value of the measurement at step 2804, the increased capacitance of the tunable capacitor can be applied or the capacitance can revert to a previous capacitance value (or other default value). For example, if the received power is less than a previously measured or minimum received power value, then the example can proceed to step 2806. In this case, the increased capacitance corresponds to a greater amount of power being reflected or lost, and the transmission efficiency is less than the efficiency prior to the capacitance increase at step 2802. Accordingly, a value of the tunable capacitor can revert to a previous capacitance value (or other default value) at step 2806, such as for further tuning or for use in other signal transfers. The example can continue at step 2812, discussed below.

Returning to step 2804, if the measured received power is greater than a previously measured or specified minimum received power value, then the example proceeds to step 2805 and the increased capacitance of the tunable capacitor can be applied and used for further transmissions from the transmitter to the receiver. Following step 2805, the example can use the increased capacitance value for a specified duration or until an interrupt or other indication is received to trigger a further update. The further update can begin, for example, by returning to step 2802 and further increasing the capacitance value. In other examples, the further update can proceed to step 2812 and trigger a decrease in the capacitance value.

At step 2812, the capacitance value of the tunable capacitor can be decreased and, at step 2813, a test signal can be transmitted using the updated transmitter configuration with the decreased capacitance value. Transmitting the test signal at step 2813 can include, for example, providing the test signal to an RF port on a midfield transmitter, such as using the transmitted port P2 from the bidirectional coupler 2601.

From step 2813, the example can continue at step 2814 with measuring a received power characteristic. Based on a result of the measurement at step 2814, the decreased capacitance of the tunable capacitor can be applied or the capacitance can revert to a previous capacitance value (or other default value). For example, if the received power is less than a previously measured or minimum reflected power value, then the example proceeds to step 2816. In this case, the decreased capacitance corresponds to a lesser amount of power being received at the implant, such as due to a decrease in transmission efficiency. Accordingly, a value of the tunable capacitor can revert to a previous (or other) capacitance value for further tuning or for use in other signal transfers.

Returning to step 2814, if the measured received power is greater than a previously measured or specified minimum reflected power value, then the example can include using the decreased capacitance of the tunable capacitor for further transmissions from the transmitter to the receiver, such as before tuning or adjusting at step 2812. That is, following step 2814, the example can use or apply the decreased capacitance value for a specified duration or until an interrupt or other indication is received to trigger a further update. The further update can begin, for example, by returning to step 2812 and further decreasing the capacitance value. In other examples, the further update can proceed to step 2802 and trigger an increase in the capacitance value.

The capacitance value-finding algorithms or processes described in FIGS. 27 and 28 can be performed when a device is first used, or can be performed periodically or intermittently. Known-good capacitance values can be specified, programmed, and/or stored in a memory circuit on-board the transmitter, and can be used as a starting point (e.g., at steps 2701 and/or 2801) when a particular device is first turned on or after an adjustment or other period of non-use.

Figure 29:
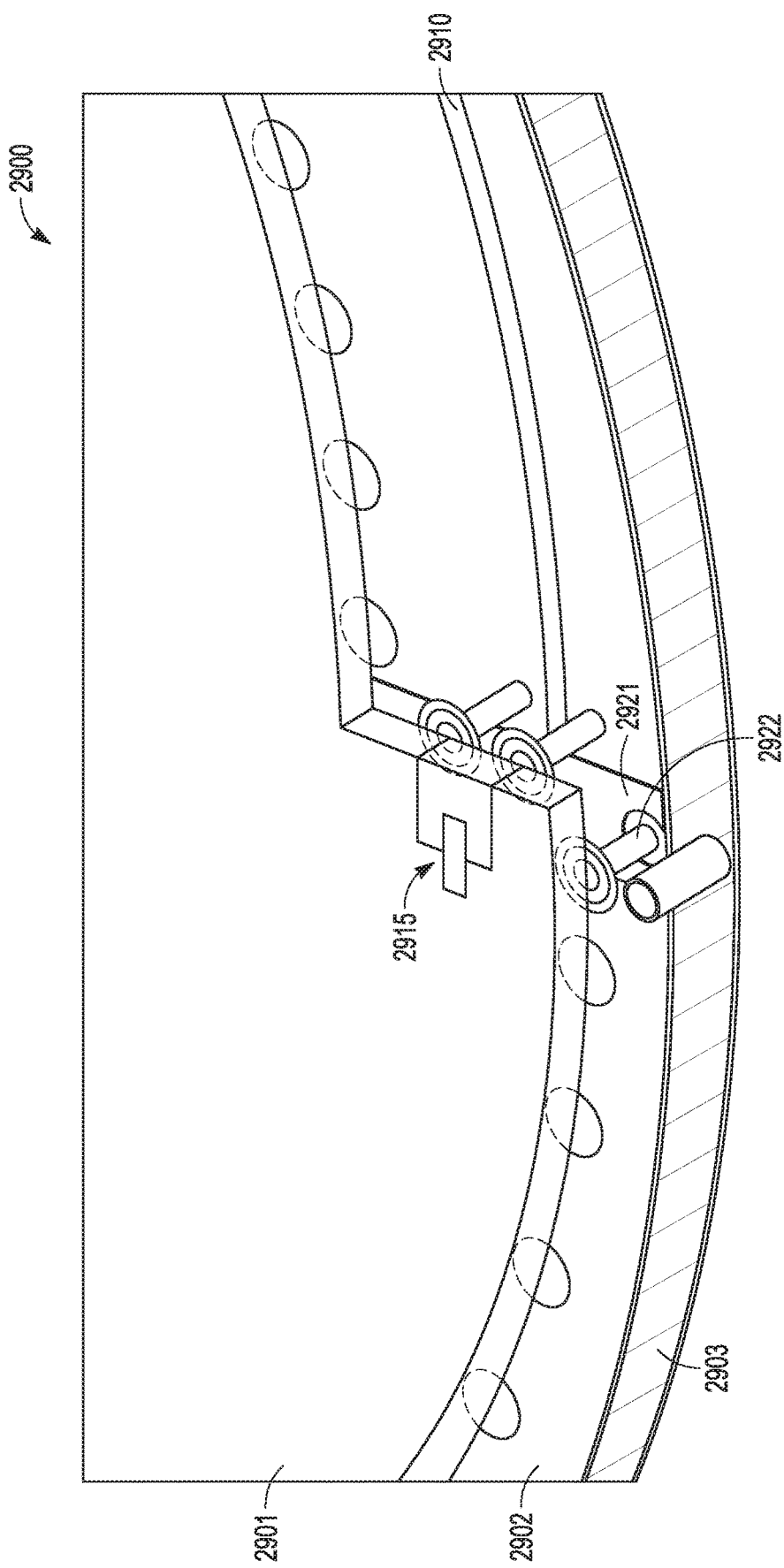
FIG. 29 illustrates a portion of a transmitter with a tuning capacitor.

FIG. 29 illustrates, by way of example, a portion of a transmitter 2900 with a tuning capacitor or variable capacitor circuit 2915. The illustrated portion can include one or more features that can be similarly applied to any one or more of the transmitter examples discussed herein or illustrated herein.

The example transmitter 2900 can include several layers, including (in the perspective illustrated) a top layer 2901, a middle layer 2902, and a bottom layer 2903, with one or more other layers (not illustrated) interposed between the top, middle, and bottom layers 2901, 2902, and 2903. In the example, various circuitry can be disposed on the top layer 2901. For example, drive circuitry, processing circuitry, and a variable capacitor circuit 2915 can be provided on the top layer 2901.

The top layer 2901 can include castellation features, vias, through holes, or other conductive portions that electrically connect traces or components from the top layer 2901 to one or more of the other layers in the transmitter 2900. In an example, the top layer 2901 includes castellation features (not illustrated) provided about its perimeter and that coincide with vias or other conductors that are coupled to one or more of the other layers. For example, the variable capacitor circuit 2915 can be coupled to a pair of castellation features that are coupled with vias that extend through the middle layer 2902, and that further couple with different conductive portions of the bottom layer 2903.

In an example, the bottom layer 2903 includes a slot 2910, and respective terminals of the variable capacitor circuit 2915 can be coupled to conductive portions on respective sides of the slot 2910 using the vias. Other castellation features on the top layer 2901 can be coupled to striplines on the middle layer 2902, to a grounding plane, or to other features, layers, or devices. In the example of FIG. 29, a stripline 2921, such as provided on the middle layer 2902 or on another interposing layer, can be coupled to drive circuitry on the top layer using a first via 2922.

In an example, an efficiency of a power signal transfer from a midfield transmitter to an implanted receiver can be monitored over multiple frequencies, such as at each of multiple different transmitter tuning settings. The monitored information can be used to identify or determine a transmitter tuning that provides a greatest signal transfer efficiency at a particular frequency. In an example, different transmitter tunings can be tested using circuitry that is on-board the transmitter, such as can include circuitry for testing multiple different capacitance values for a tunable capacitor that comprises a portion of the transmitter.

Figure 30:
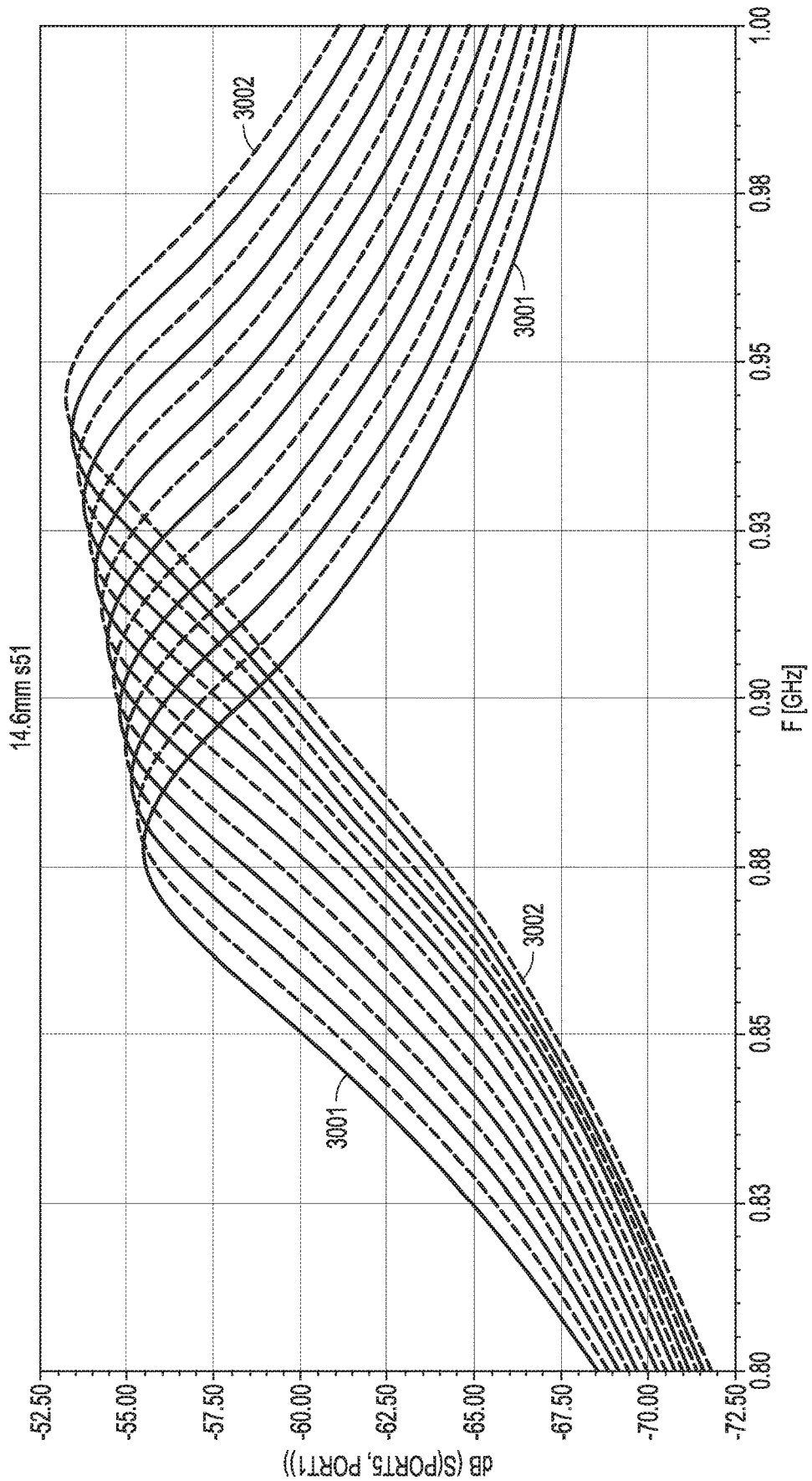
FIG. 30 illustrates a first chart showing signal transfer efficiency information over a range of frequencies and for different capacitance values of a tunable capacitor that is coupled to a transmitter.

FIG. 30 illustrates, by way of example, a first chart showing signal transfer efficiency information over a range of frequencies and for different capacitance values of a tunable capacitor that is coupled to the transmitter. In the example, a midfield transmitter is separated from tissue by about 14.6 millimeters, and the transmitter is thus weakly loaded by the tissue. In other words, the tissue has a negligible effect on the tuning of the transmitter. The y-axis represents a relative energy or voltage transfer ratio from the midfield transmitter to a receiver, and the x-axis represents operating or drive frequency. Generally, a transmission frequency to be used is specified or known, and the transmitter performs a capacitance value-finding algorithm (see, e.g., the examples of FIGS. 27 and 28, however other techniques can be used) to identify a capacitance value to use to tune the transmitter to be best matched with a receiver, such as to maximize a power transfer efficiency between the transmitter and receiver.

In the example of FIG. 30, the different traces correspond to different values of a variable or tunable capacitor used in the midfield transmitter. A first trace 3001 corresponds to a maximum capacitance value (e.g., 5 pF) for the tunable capacitor, and a second trace 3002 corresponds to a minimum capacitance value (e.g., 0.5 pF) for the tunable capacitor. In the example of FIG. 30, a target or desired operating frequency can be 890 MHz Accordingly, the transmitter or other circuitry can perform a value-finding process to identify a value for the tunable capacitor that maximizes the response or efficiency of the midfield transmitter system. In this example, the maximum efficiency at 890 MHz is closer to the first trace 3001 than it is to the second trace 3002. In an example, the maximum efficiency corresponds to the third curve in the illustration, such as corresponding to a capacitance value of about 4 pF.

Figure 31:
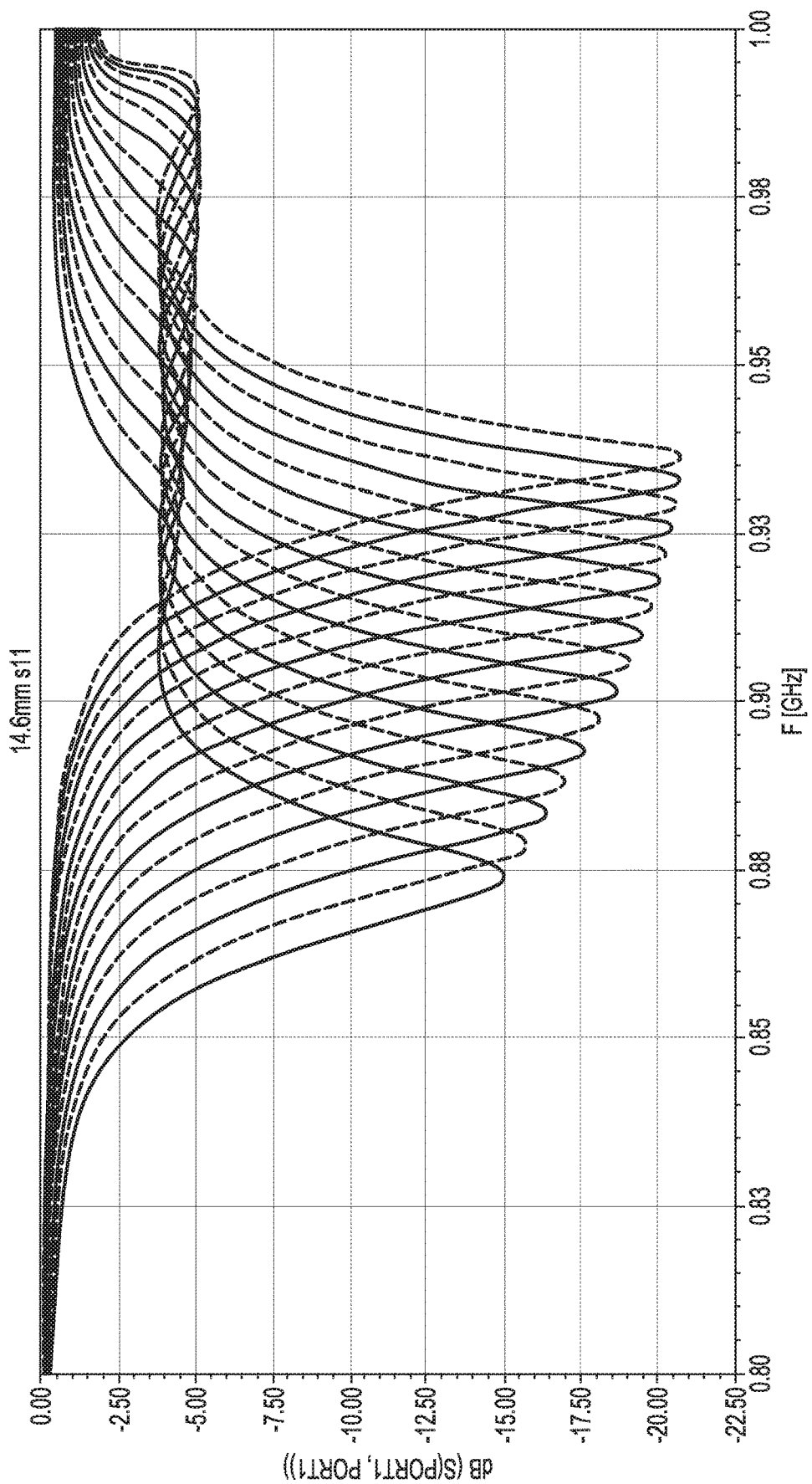
FIG. 31 illustrates a second chart showing reflection information over a range of frequencies and for different capacitance values of a tunable capacitor that is coupled to a transmitter.

FIG. 31 illustrates, by way of example, a second chart showing reflection information over a range of frequencies and for different capacitance values of a tunable capacitor that is coupled to a transmitter. In the example, a midfield transmitter is separated from tissue by about 14.6 millimeters, and the transmitter is weakly loaded by the tissue. The example of FIG. 31 can represent or use a value-finding process that analyzes or uses a reflection ratio at the transmitter to tune the transmitter for maximum efficiency. In this example, lower values in the chart represent better matching between the transmitter and receiver at a given frequency. In other words, the trace valleys represent frequencies at which energy is best able to leave the transmitter, such as at each of multiple different capacitive tuning values.

In the example of FIG. 31, a target or desired operating frequency can be 900 MHz. The transmitter or other circuitry can perform a value-finding process to identify a value for the tunable capacitor that minimizes a reflection characteristic of the system, that is, by identifying a minimum in the response curves at the desired frequency. In this example, a maximum efficiency can correspond to about the seventh curve from the left of the chart, such as corresponding to a capacitance value of about 3 pF.

In an example, if the transmitter from the example of FIG. 31 were to approach tissue and be separated from tissue by less than 14.6 millimeters, then the illustrated curves would shift to the left indicating higher efficiency at lower frequencies. Accordingly as the distance from the transmitter to tissue changes, loading conditions correspondingly change and the transmitter can be tuned or adjusted to maintain maximum efficiency.

Figure 32:
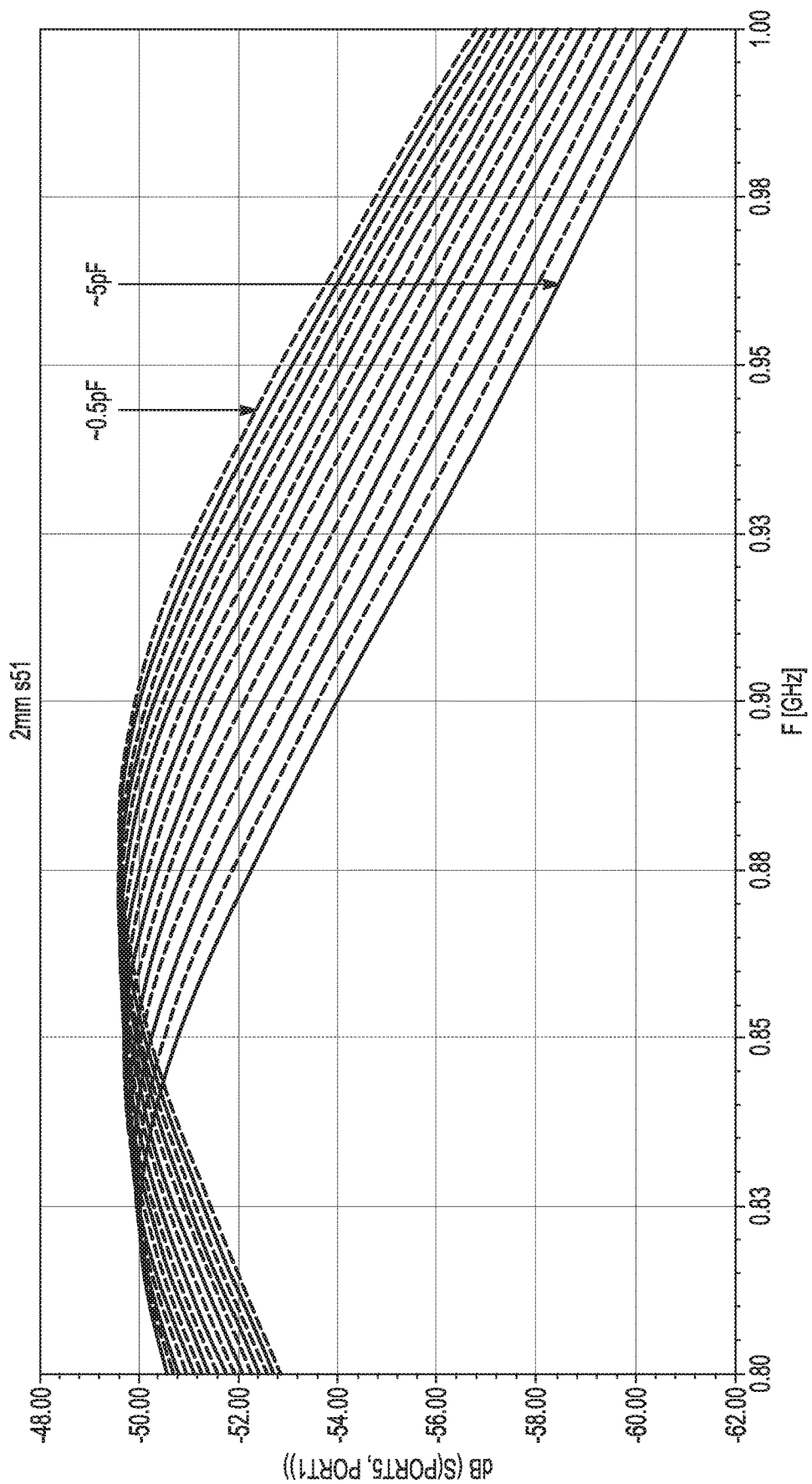
FIG. 32 illustrates a third chart showing signal transfer efficiency information over a range of frequencies and for different capacitance values of a tunable capacitor that is coupled to a transmitter.

FIG. 32 illustrates, by way of example, a third chart showing signal transfer efficiency information over a range of frequencies and for different capacitance values of a tunable capacitor that is coupled to the transmitter. In the example, a midfield transmitter is separated from tissue by about 2 millimeters, and the transmitter is loaded relatively strongly by the tissue. In this example, a minimum capacitance value for the tunable capacitor is selected to maximize a transfer efficiency at 900 MHz.

In the example of FIG. 32, such as compared to the example of FIG. 30, the efficiency curves shift to the left, to relatively lower frequencies, such as due to the loading effect of the tissue. In this example, a least amount of capacitance is used (e.g., 0.5 pF) for the tunable capacitor to maximize a wireless signal transfer efficiency of the transmitter and receiver system.

Figure 33:
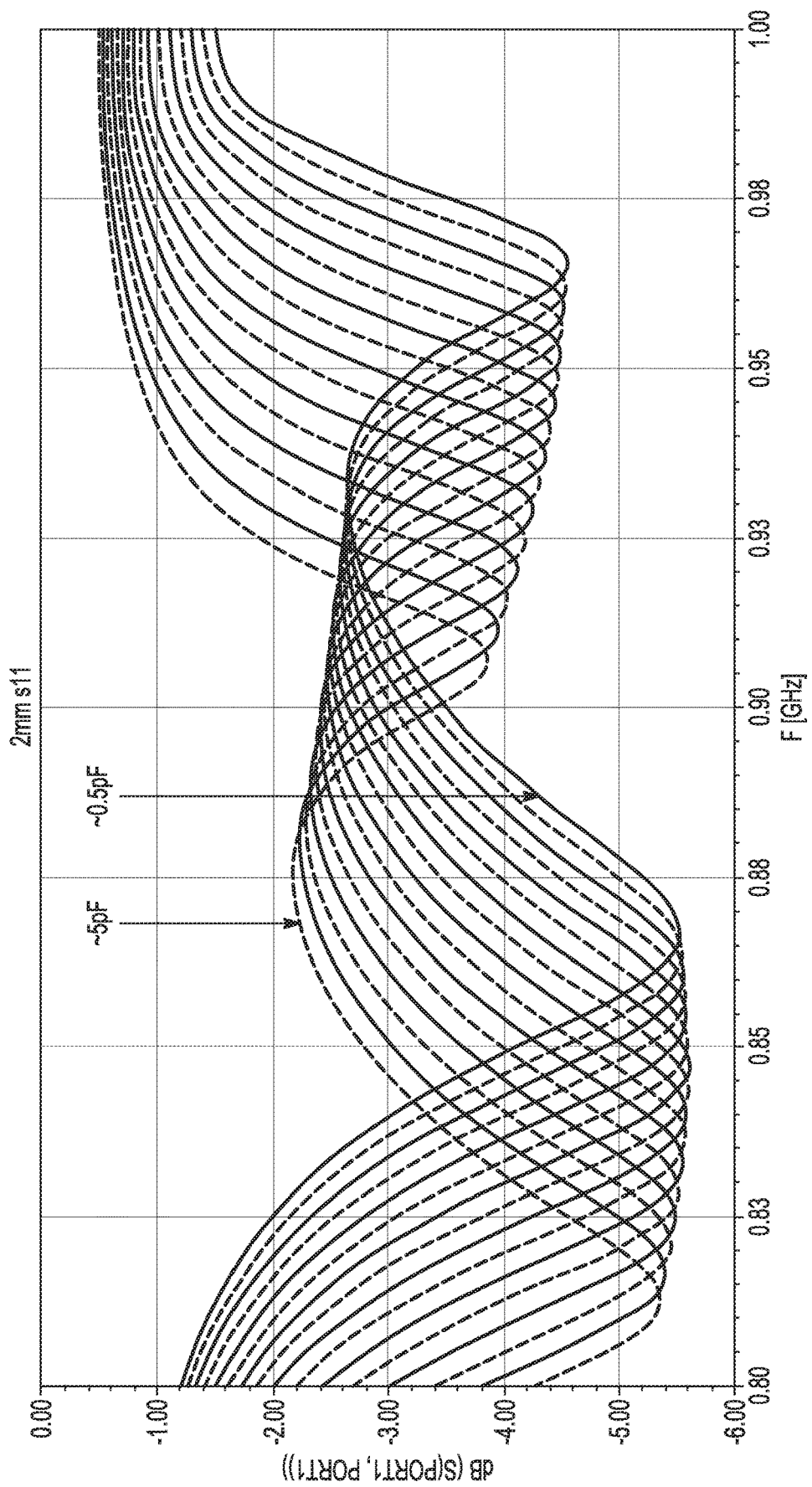
FIG. 33 illustrates a fourth chart showing reflection coefficient information, such as determined using voltage standing wave ratio (VSWR) information, over a range of frequencies and for different capacitance values of a tunable capacitor that is coupled to a transmitter.

FIG. 33 illustrates, by way of example, a fourth chart showing reflection coefficient information, such as determined using voltage standing wave ratio (VSWR) information, over a range of frequencies and for different capacitance values of a tunable capacitor that is coupled to a transmitter. In the example, a midfield transmitter is separated from tissue by about 2 millimeters, and the transmitter is loaded relatively strongly by the tissue. In this example, a maximum capacitance value (e.g., 5 pF) for the tunable capacitor is selected to maximize a transfer efficiency at 900 MHz.

The example of FIG. 33 can represent or use a value-finding process that analyzes or uses a reflection ratio at the transmitter. In this example, lower values in the chart represent better matching between the transmitter and receiver at a given frequency. In other words, the trace valleys represent frequencies at which energy is best able to leave the transmitter, at each of multiple different capacitive tuning values. Since the curve corresponding to the maximum capacitance value includes a valley nearest the target operating frequency of 900 MHz, that maximum capacitance value can be selected for use.

FIG. 33 illustrates, however, that using reflection coefficient information to make a determination about transfer efficiency can be misleading unless a sufficient amount of data is collected. For example, the various traces in FIG. 33 exhibit a "double dip" behavior, showing a first valley in the frequency range of about 810 MHz to 880 MHz, and another valley in the frequency range of about 905 MHz to 970 MHz. In examples that include a transmitter that is loaded by nearby tissue, a value-finding algorithm should be configured to ascertain whether a particular valley represents a true minimum or whether a different, lesser minimum exists for the system for particular use conditions. Alternatively, the value-finding algorithm can be configured to perform a more comprehensive search throughout a full range of available capacitance (or other) tuning values, which can be time consuming and energy intensive.

In an example, information from a frequency sweep, such as with or without a corresponding sweep of capacitive tuning element values, can be used to determine a likelihood that the external source 102 is near or adjacent to tissue. In an example, determining a likelihood that the external source 102 is near tissue precedes a search for the implantable device 110.

Figure 34:
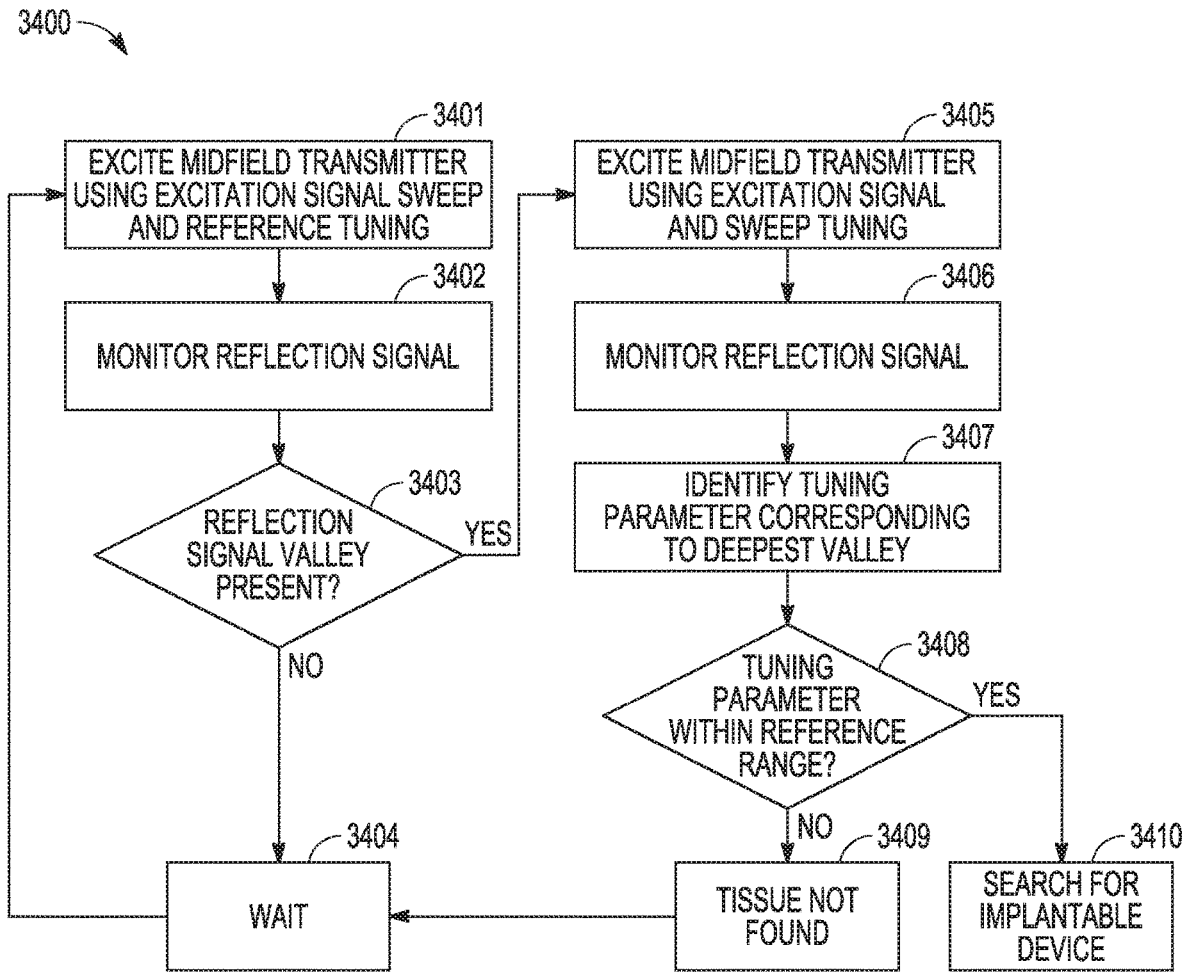
FIG. 34 illustrates generally an example that includes identifying whether an external source is near tissue and, when it is near tissue, then identifying whether to search for an implantable device.

FIG. 34 illustrates generally an example that includes identifying whether the external source 102 is near tissue and, when it is near tissue, then identifying whether to search for the implantable device 110. At step 3401, the external source 102 can use an excitation signal to excite a midfield transmitter, such as by providing the excitation signal to one or more midfield transmitter elements at one or more excitation signal frequencies or using a frequency sweep. In an example, the excitation at step 3401 includes using a default or reference tuning configuration for the external source 102. At step 3402, the external source 102 can monitor a VWSR or reflection coefficient to identify a transmission efficiency from the external source 102. At step 3403, processing circuitry from the external source 102 can analyze the reflection signal from step 3402 to determine whether the reflection signal includes a valley or other characteristic that can indicate loading of the external source 102, such as due to the presence of tissue near the external source 102. Based on information about the reflection, such as a presence or characteristic of a valley in the reflection signal such as indicated in the examples of FIGS. 31 and 33, the external source 102 can be determined to be near tissue. If no valley or other characteristic exists in the reflection signal, then at step 3404 the example can include initiating a wait or standby mode for the external source 102. If, however, a valley or other characteristic is identified in the reflection signal, then the example can continue at step 3405.

At step 3405, the example includes exciting the external source 102 using an excitation signal and sweeping available tuning parameters for the external source 102. In an example, sweeping the tuning parameters includes sweeping values of a tunable capacitor as discussed elsewhere herein. At step 3406, a VWSR or reflection signal can be monitored for each of the different tuning parameters used at step 3405. At step 3407, a processor of the external source 102 can identify a tuning parameter that corresponds to a greatest transmission efficiency or least reflection. In the examples of FIGS. 31 and 33, the tuning parameter that corresponds to a greatest transmission efficiency corresponds to a deepest valley in a particular frequency range.

At step 3408, a value of the tuning parameter identified at step 3407 can be analyzed to determine whether it falls within a specified tuning parameter range. For example, if a highest-available capacitance value is identified for use, and that highest value falls outside of the specified tuning parameter range, then the external source 102 may not be sufficiently near tissue, and the example can continue at step 3409 by indicating tissue was not found. Similarly, if no dip or valley in the VWSR or reflection coefficient is observed over a frequency sweep of, e.g., 880 MHz to 940 MHz, then the external source 102 can consider no tissue found and the external source 102 can enter the wait mode at step 3404. If, however, the capacitance value corresponding to a dip or valley in the VWSR is within the specified tuning parameter range, then the external source 102 can consider tissue found and can proceed at step 3410 with an attempt to communicate with the implantable device 110.

The example of FIG. 34 can thus be used to identify a tuning parameter that corresponds to a least amount of power reflected back to the transmitter or external source 102. Consequently, a processor on-board the external source 102 can be used to determine whether or not the external source 102 should expend further processing resources and enter a search mode for the implantable device 110. Operating in this manner can help the external source 102 to reduce battery drain and reduce unnecessary emissions.

Figure 35:
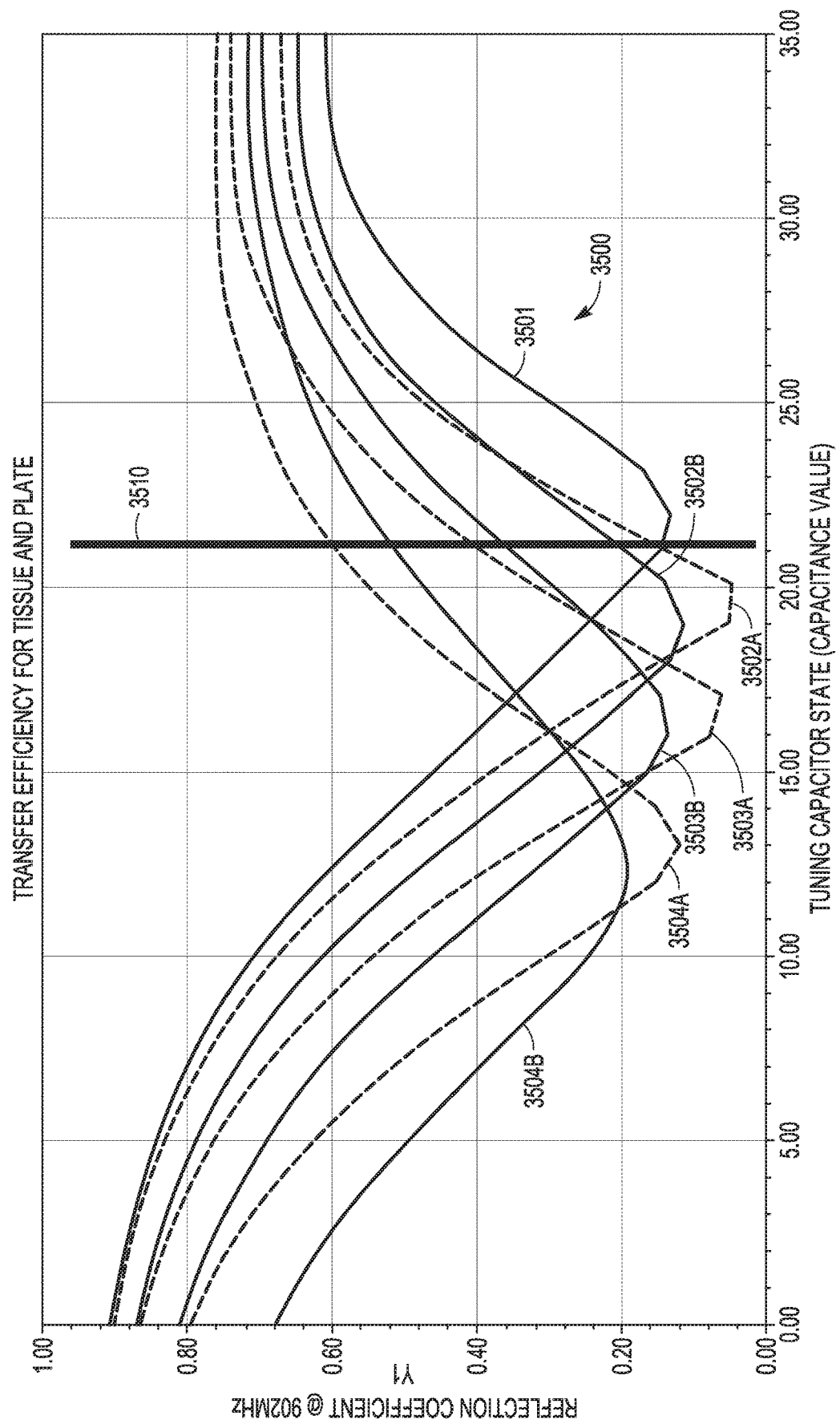
FIG. 35 illustrates generally an example of a chart that shows using information from a tuning capacitor sweep to determine a likelihood that an external source is near or adjacent to tissue.

FIG. 35 illustrates generally an example of a chart 3500 that shows using information from a tuning capacitor sweep to determine a likelihood that the external source 102 is near or adjacent to tissue. The chart includes a tuning capacitor state (corresponding to various capacitance values) on the x-axis and a reflection coefficient on the y-axis. The example of FIG. 35 corresponds to an excitation center frequency of about 902 MHz, however, other frequencies can similarly be used, with similar results expected. The example of FIG. 35 includes multiple traces or curves corresponding to different sweep instances, with the external source 102 positioned at different distances from simulated tissue and from a metal plate.

In an example, the chart 3500 includes a first curve 3501 showing a reference reflection characteristic for the external source 102 used in open air, that is, away from tissue and away from a metal plate. The first curve 3501 exhibits a minimum or valley at a capacitor state of 22 (corresponding to a particular capacitance value, e.g., around 5 pF). Using the open-air capacitor state as a reference, the external source 102 can set a threshold for the tuning capacitor state for use in test conditions. If, for example, the external source 102 is testing for tissue and the resulting capacitor state falls at or above the threshold, then the external source 102 can be configured to recognize that it is likely not near tissue and therefore no processing, battery, or other resources should be used to attempt to locate or communicate with the implantable device 110. If, on the other hand, the external source 102 tests for tissue and the resulting capacitor state falls below the threshold, then the external source 102 can be configured to recognize that there is a higher likelihood that the external source 102 is adjacent to tissue and further device resources can be made available to attempt communication with the implantable device 110.

In an example, second curves 3502A and 3502B can correspond to the external source 102 provided a first distance away from a metal plate and provided the same first distance away from tissue, respectively. A tuning capacitor state of about 19 can be identified for the external source 102 for such a loading configuration corresponding to the second curves 3502A and 3502B. That is, the external source 102 can have a maximum transfer efficiency when a tunable capacitor of the external source is tuned to a capacitance value corresponding to state 19 (e.g., corresponding to a capacitance value of about 3 pF).

In the example of FIG. 35, third curves 3503A and 3503B can correspond to the external source 102 provided a second lesser distance away from a metal plate and from tissue, respectively. A tuning capacitor state of about 17 can be identified for the external source 102 for such a loading configuration corresponding to the third curves 3503A and 3503B. That is, the external source 102 can have a maximum transfer efficiency when a tunable capacitor of the external source is tuned to a capacitance value corresponding to state 17 (e.g., corresponding to a capacitance value of about 2 pF). Similarly, fourth curves 3504A and 3504B can correspond to the external source 102 provided a third and least distance away from a metal plate and from tissue, respectively. A tuning capacitor state of about 13 can be identified for the external source 102 for such a loading configuration corresponding to the fourth curves 3504A and 3504B. That is, the external source 102 can have a maximum transfer efficiency when a tunable capacitor of the external source is tuned to a capacitance value corresponding to state 13 (e.g., corresponding to a capacitance value of about 1 pF).

The chart 3500 illustrates generally that a minimum reflection coefficient and minimum capacitor state (e.g., corresponding to a minimum capacitance value for a tunable capacitor of the external source 102) indicates maximum transfer efficiency. Additionally, a lower capacitor state and lower capacitance value at a particular minimum corresponds with the external source 102 being more closely located to tissue. However, as shown in the example of FIG. 35, the tissue-identification can be confounded or compromised if the external source 102 is used near or adjacent to other conductive materials, such as a metal plate. Various signal processing and device configuration techniques can be applied to address this problem. In an example, different transmission signal profiles can be observed when the external source 102 is used or excited and it is adjacent to tissue as compared to when the external source 102 is used or excited and it is not adjacent to tissue. In other words, an indication of a coupling between oppositely-oriented ports, or emission structures, of a transmitter can be used to determine whether the external source 102 is near tissue or near non-tissue.

In an example, compensation for the metal plate or other confounding effects of the tissue search can include or use transmitting from one port at a first location on the transmitter and receiving from an oppositely-oriented port with the same polarization on the same transmitter. In an example that includes the first transmitter 1000 from the example of FIG. 11, compensating for the metal plate or other confounding effects can include providing a first drive signal to the first stripline 1131A and receiving a response or reflection signal using a sensor or receiver circuit coupled to the third stripline 1131C. An example of such a technique is described with reference to FIG. 36.

Figure 36:
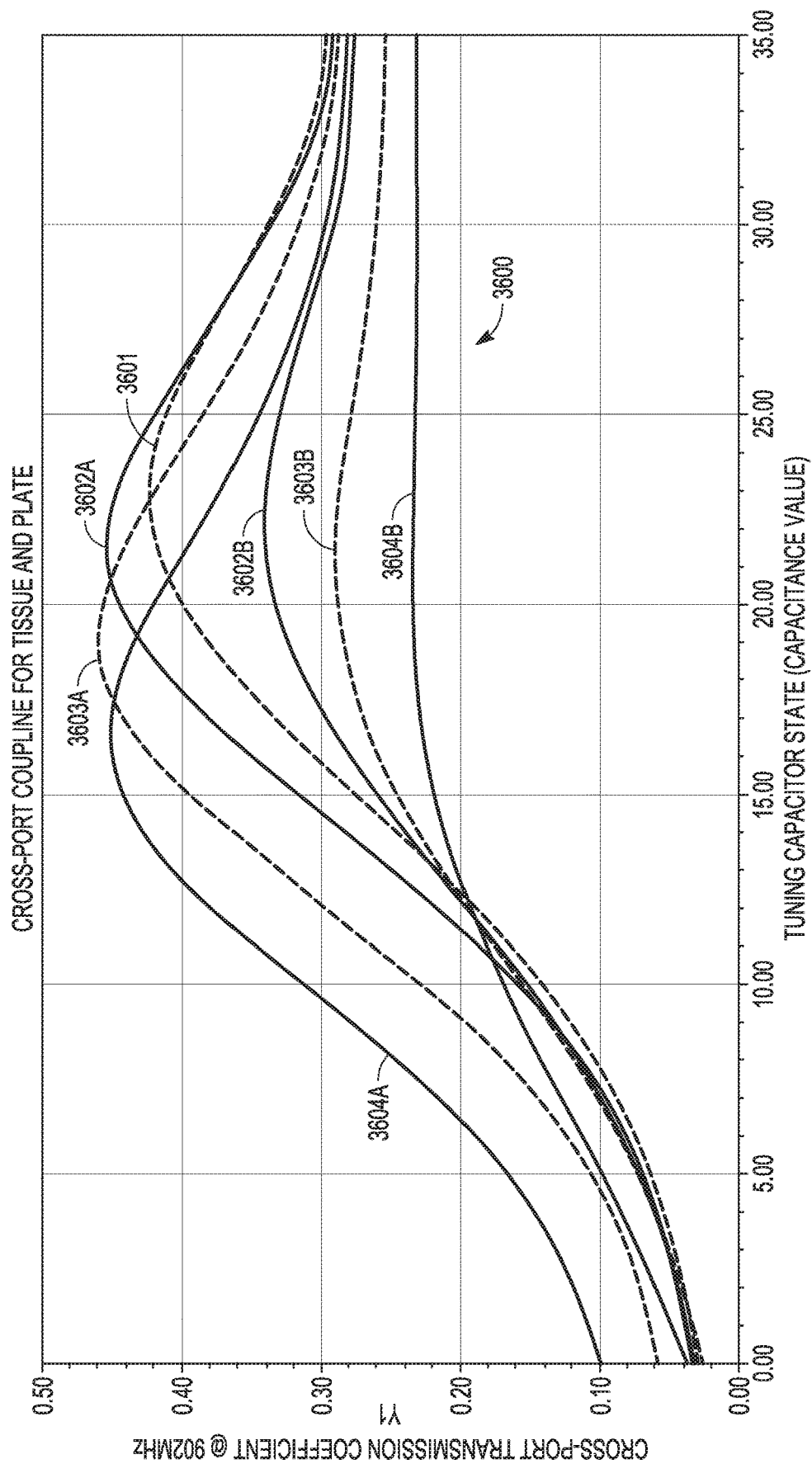
FIG. 36 illustrates generally an example of a chart that shows a cross-port transmission coefficient for multiple different use conditions of an external source.

FIG. 36 illustrates generally an example of a chart 3600 that shows a cross-port transmission coefficient for multiple different use conditions of the external source 102. The chart includes a tuning capacitor state (corresponding to various capacitance values) on the x-axis and a cross-port transmission coefficient on the y-axis. The example of FIG. 36 corresponds to an excitation center frequency of about 902 MHz, however, other frequencies can similarly be used, with similar results expected. The example of FIG. 36 includes multiple traces or curves corresponding to different sweep instances, with the external source 102 positioned at different spacings or distances away from simulated tissue and from a metal plate. When the external source 102 is positioned adjacent to a metal plate, there is a relatively high degree of coupling between the oppositely-oriented ports of the transmitter, as indicated by the various peaks in the second, third, and fourth curves 3602A, 3603A, and 3604A. However, when the external source 102 is positioned adjacent to tissue, there is a lesser amount of coupling between the oppositely-oriented ports of the transmitter, as indicated by the more muted or plateaued profiles of the second, third, and fourth curves 3602B, 3603B, and 3604B.

The chart 3600 includes a first curve 3601 showing a reference reflection characteristic for the external source 102 used in open air, that is, used away from tissue and away from a metal plate. The first curve 3601 exhibits a peak at a capacitor state of 23 (corresponding to a particular capacitance value, e.g., around 5 pF). In an example, the open-air capacitor state can be used as a reference to set a threshold for the tuning capacitor state for use in test conditions. If, for example, the external source 102 tests for tissue and the resulting capacitor state falls at or above the threshold, then the external source 102 can be configured to recognize that it is likely not near tissue and therefore no processing, battery, or other resources should be used to attempt to locate or communicate with the implantable device 110. If, on the other hand, the external source 102 tests for tissue and the resulting capacitor state falls below the threshold, then the external source 102 can be configured to recognize that there is a greater likelihood that the external source 102 is adjacent to tissue and further device resources can be enabled or made available to attempt to communicate with the implantable device 110.

In an example, a waveform shape or morphology characteristic of the first curve 3601 can be used as a reference condition. For example, characteristics of one or more of a slope, peak, width, magnitude, or other characteristic can be used. Data from measured responses can be compared against the reference condition, or reference characteristic, and adjusted for example to select a preferred capacitor state.

In an example, second curves 3602A and 3602B can correspond to the external source 102 provided a first distance away from a metal plate and tissue, respectively. A tuning capacitor state of about 22 can be identified for the external source 102 for such a loading configuration corresponding to the second curves 3602A and 3602B. That is, the external source 102 can have a maximum transfer efficiency when a tunable capacitor of the external source is tuned to a capacitance value corresponding to state 22. In the example of FIG. 35, a difference in reflection coefficient for the second curves 3502A and 3502B at the minimum valley is about 0.08 units. However, in the example of FIG. 36, a difference in the cross-port coupling coefficient is about 0.1 units.

In the example of FIG. 36, a morphology characteristic of peak behavior of the second curves 3602A and 3602B differs from a morphology characteristic of peak behavior of the first curve 3601. That is, the second curve 3602A corresponding to the metal plate has a narrower peak characteristic relative to the first curve 3601, whereas the second curve 3602B corresponding to tissue has a wider or less pronounced peak characteristic relative to the first curve 3601. This illustrates that a morphology characteristic of the capacitance sweep curve can be used to discern device placement and use near tissue from use under improper or fault conditions.

In the example of FIG. 36, third curves 3603A and 3603B can correspond to the external source 102 provided a second lesser distance away from a metal plate and tissue, respectively. A tuning capacitor state of about 19 can be identified for the external source 102 for such a loading configuration corresponding to the third curves 3603A and 3603B. In the example of FIG. 35, a difference in reflection coefficient for the third curves 3503A and 3503B at the minimum valley is about 0.08 units. However, in the example of FIG. 36, a difference in the cross-port coupling coefficient is about 0.15 units.

In the example of FIG. 36, a morphology characteristic of peak behavior of the third curves 3603A and 3603B differs from a morphology characteristic of peak behavior of the first curve 3601. That is, the third curve 3603A corresponding to the metal plate has a narrower peak characteristic relative to the first curve 3601, whereas the third curve 3603B corresponding to use of external source 102 adjacent to tissue has a wider or less pronounced peak characteristic relative to the first curve 3601.

Similarly, fourth curves 3604A and 3604B can correspond to the external source 102 provided a third and least distance away from a metal plate and tissue, respectively. A tuning capacitor state of about 16 can be identified for the external source 102 for such a loading configuration corresponding to the fourth curves 3604A and 3604B. In the example of FIG. 35, a difference in reflection coefficient for the fourth curves 3504A and 3504B at the minimum valley is about 0.08 units. However, in the example of FIG. 36, a difference in the cross-port coupling coefficient is about 0.2 units.

In the example of FIG. 36, a morphology characteristic of peak behavior of the fourth curves 3604A and 3604B differs from a morphology characteristic of peak behavior of the first curve 3601. That is, the fourth curve 3604A corresponding to the metal plate has a narrower peak characteristic relative to the first curve 3601, whereas the fourth curve 3604B corresponding to use of external source 102 adjacent to tissue has a wider or less pronounced peak characteristic relative to the first curve 3601.

In an example, information about the relative difference in cross-port coupling can be used to determine whether the external source 102 is near tissue, and to distinguish the presence of tissue from a presence of other materials near the external source 102. In another example, information about signal morphology or peak characteristics can be used to help determine whether the external source 102 is near tissue, and to distinguish the presence of tissue from a presence of other materials near the external source 102.

In an example, the external source 102 can be programmed to use a learning mode to establish a reference for one or more known-good capacitor states when the external source 102 is properly positioned near or adjacent to tissue.

In an example, the reference can include information about morphology characteristics of various excitation signals, reflection coefficients, and/or cross-port transmission coefficients such as for one or multiple excitation frequencies. The external source 102 can then be used in a test mode to determine whether actual loading conditions match or approximate the reference. If conditions during test do not conform to the reference within a specified margin of error, then the external source 102 can be inhibited from using its device resources to look for or attempt to communicate with the implantable device 110. If, however, conditions during test do conform to the reference, then the external source 102 can attempt to communicate power and/or data to the implantable device 110.

Transmitter Protection Circuitry

Figure 37:
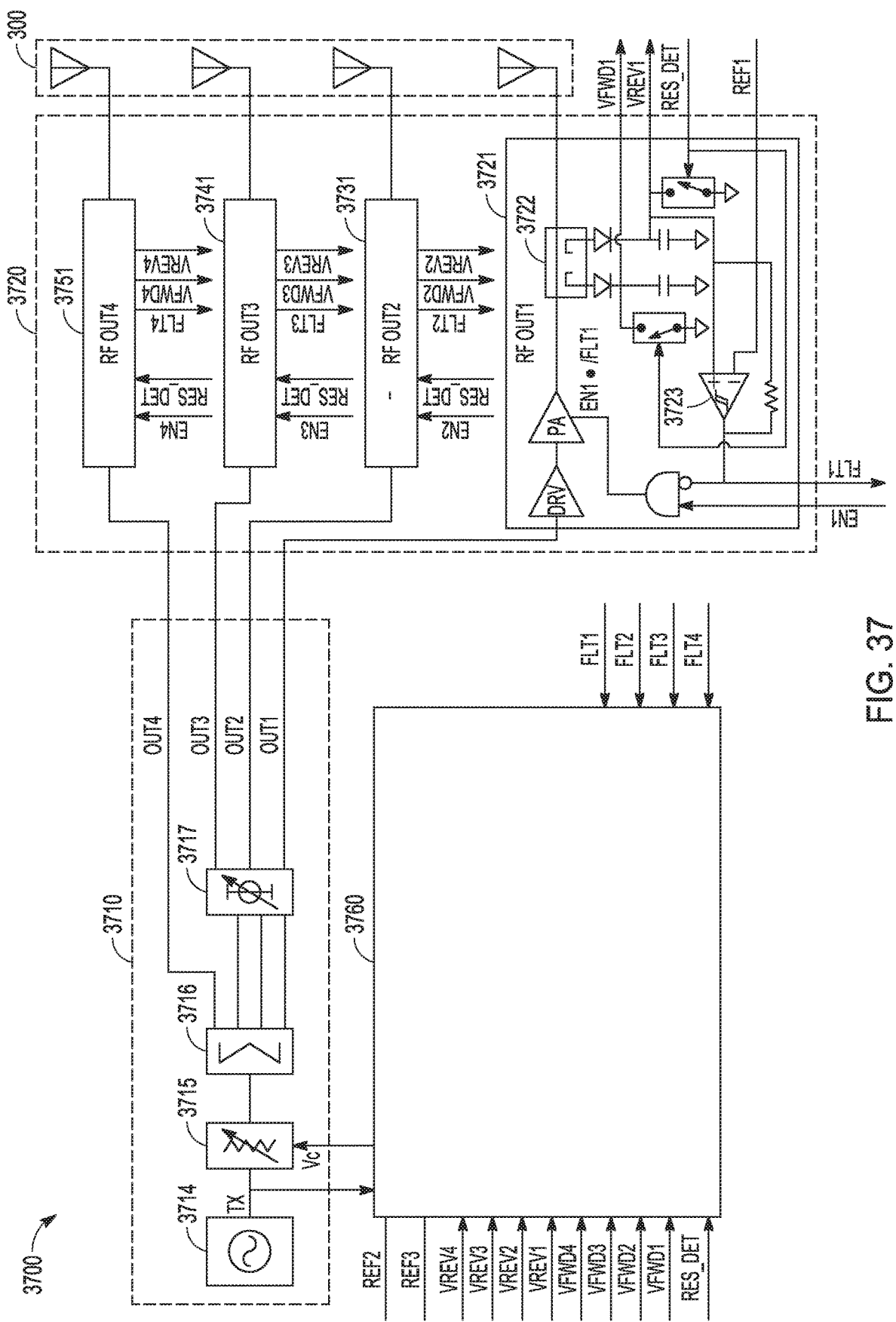
FIG. 37 illustrates generally a first example of transmitter circuitry that can be used or included in an external source.

FIG. 37 illustrates generally an example of transmitter circuitry 3700 that can be used or included in the external source 102. The transmitter circuitry 3700 can include a drive and splitter circuit 3710, a first protection circuit 3720, and a second protection circuit 3760. In the example of FIG. 37, the first protection circuit 3720 is coupled between the antenna 300 and the drive and splitter circuit 3710. In some examples and discussion herein, the first and second protection circuits 3720 and 3760 are referred to as first and second control circuits, respectively, because they can be used to control one or more aspects of a transmitter or of signals processed by the transmitter.

The transmitter circuitry 3700 and its various protection circuits include output power controls configured to protect the circuit's amplifiers against damage such as due to output load mismatches, while maintaining output power at a desired set point for output loads within the safe operating ranges of the amplifiers. Output load mismatches can occur if an antenna is in an environment substantially different from the intended, on-patient (e.g., adjacent to tissue or at a specified distance apart from a tissue interface) nominal environment, or if a fault exists in any of the RF output paths. In the example of FIG. 37, the first protection circuit 3720 includes four inner control loops (Fast Loops) or first, second, third, and fourth channel drivers 3721, 3731, 3741, and 3751, each of which is configured to shut down or attenuate any forward path amplifier therein when a high mismatch is detected. The second protection circuit 3760 includes an outer loop (Main Loop) that is configured to operate substantially continuously in an automatic level control (ALC) mode to deliver a target RF output power under varying amplifier drive, temperature, and load conditions, and is configured to reduce power output power for load mismatches that may occur outside of specified safe operating conditions. That is, for well-matched loads, the Main Loop can help maintain RF output power at a desired level, whereas for mismatched loads, the Main Loop can be used to reduce RF output power to a safe level for the amplifier circuitry as a function of a reverse power characteristic.

In an example, the transmitter circuitry 3700 can be configured to maintain operation at reduced RF output power when 1, 2, or 3 of the channel drivers are shut down (e.g., due to detected mismatch conditions). In this case, the remaining active channel driver(s) can drive the Main Loop and continue to deliver RF output at the target power level commensurate with load conditions.

The external source 102 is configured generally for optimal use and efficiency when the antenna 300 is positioned close to or adjacent to tissue. If the external source 102 is placed instead on a metal surface or in open air, then there can be an antenna mismatch and a strong reflection at the device's output. Such use cases can damage the external source 102 unless the mismatched conditions can be identified and mitigated. Thus the transmitter circuitry 3700 is configured to protect amplifier circuitry of the external source 102 for example when the external source 102 is positioned away from tissue. The transmitter circuitry 3700 is also configured to reduce incidental radiation (and therefore battery consumption) when the external source 102 is positioned away from tissue and therefore is not in use with an implanted device. In an example, the transmitter circuitry 3700 detects one or more reflected power characteristics, identifies whether a mismatch condition exists from the detected reflected power characteristics, and responds by changing gain or attenuation characteristics of one or more amplifiers used in the circuitry. In other words, the transmitter circuitry 3700 provides protection against damage due to output load mismatches.

Substantially concurrently with its damage prevention functions, the transmitter circuitry 3700 is configured to maintain a constant output power under nominal operating conditions. Output load mismatches can occur if an antenna, such as driven by the transmitter circuitry 3700, is used in an environment that is substantially different from its intended on-patient, nominal environment, or when a fault exists in any of the RF output or antenna excitation paths. In an example, the transmitter circuitry 3700 includes a relatively fast or quick-response inner control loop (see, e.g., the first protection circuit 3720) that can attenuate or shut down one or more forward path amplifiers when significant antenna mismatch conditions are detected. The transmitter circuitry 3700 further includes an outer loop (see, e.g., the second protection circuit 3760) that can operate substantially continuously in an automatic level-controlling mode to deliver a target RF output power under varying forward signal drive and loading conditions, and can be used to reduce output power when load mismatch conditions are detected.

The drive and splitter circuit 3710 can include an RF signal generator 3714 that generates an RF signal and provides the RF signal to a gain circuit 3715. The gain circuit 3715 has a control signal input that receives a control signal Vc from the second protection circuit 3760 as further described below. The gain circuit 3715 can pass the RF signal, with or without attenuation or gain, to a splitter 3716. The splitter 3716 can apportion the RF signal to one or more output channels. In the example of FIG. 37, the splitter 3716 provides the RF signal to four different output channels: OUT1, OUT2, OUT3, and OUT4. In an example, the gain circuit 3715 is configured to ramp its attenuation from maximum attenuation during startup of the external source 102 to a specified operating attenuation level or no attenuation. The ramp time or other ramp characteristics can be specified by ramp circuitry in the second protection circuit 3760 or elsewhere.

In an example, the drive and splitter circuit 3710 includes a phase adjust circuit 3717. The phase adjust circuit 3717 can be coupled to the splitter 3716 to receive information from one or more of the output channels. In the example of FIG. 37, the phase adjust circuit 3717 receives and processes information from three of the four output channels from the splitter 3716. In an example, the phase adjust circuit 3717 includes or uses the same or similar elements from the network 400 of FIG. 4, including one or more of an amplifier, phase shifter, power divider, and/or switch circuit as illustrated therein. Following the phase adjust circuit 3717 and the splitter 3716, the drive and splitter circuit 3710 provides different RF drive signals on respective different channels OUT1, OUT2, OUT3, and OUT4 to the first protection circuit 3720.

The first protection circuit 3720 is configured to receive RF drive signals on one or more different channels and, when an error condition is identified, prevent or inhibit the RF drive signals from being amplified and/or transmitted to ports of the antenna 300. The first protection circuit 3720 includes respective first, second, third, and fourth channel drivers 3721, 3731, 3741, and 3751 that are respectively coupled to the output channels OUT1, OUT2, OUT3, and OUT4 from the drive and splitter circuit 3710. The channel drivers can be separate instances of substantially identical circuitry. The example of FIG. 37 includes schematic details for the first channel driver 3721. The second, third, and fourth channel drivers 3731, 3741, and 3751 can be understood to include substantially the same or similar components as are illustrated for the first channel driver 3721, but the details of these other driver instances are omitted from the drawing for brevity. Outputs of the first, second, third, and fourth channel drivers 3721, 3731, 3741, and 3751 can be coupled to respective different ports to feed signals to the antenna 300.

In an example, each of the first, second, third, and fourth channel drivers 3721, 3731, 3741, and 3751 can be configured to receive the same or different channel-specific enable signal at respective enable nodes EN1, EN2, EN3, and EN4. In an example, each of the first, second, third, and fourth channel drivers 3721, 3731, 3741, and 3751 can be configured to provide a respective channel-specific fault signal at respective fault nodes FLT1, FLT2, FLT3, and FLT4. In an example, information from a channel's enable node can be used together information from the same channel's fault node to update an operating characteristic of the same or different channel driver.

In an example, each of the first, second, third, and fourth channel drivers 3721, 3731, 3741, and 3751 can be configured to receive a global input signal at node RES_DET. The global input signal can be configured to discharge the RF detector capacitors at the P3 and P4 ports of the bidirectional coupler 3722, thereby setting the detector output voltages to zero (or another reference). In an example, the global input is used as a fault reset.

In the example of FIG. 37, the first channel driver 3721 receives a first RF drive signal via a first channel OUT1. The first channel driver 3721 can include various amplifier, attenuator, or other processing circuitry that can be used to change a characteristic of the first RF drive signal, such as before the signal is provided to the antenna 300. In an example, the first channel driver 3721 includes, along a signal path from its input at the first channel OUT1 to its output at a port of the antenna 300, a first amplifier DRV, a second amplifier PA, and a bidirectional coupler 3722. In an example, the bidirectional coupler 3722 is the same as or is similar to the bidirectional coupler 2601 from the example of FIGS. 26A and 26B. In other examples, a component other than a bidirectional coupler can be used, such as a circulator circuit.

In an example, an input port (P1) of the bidirectional coupler 3722 can receive an amplified (or attenuated) version of the first RF drive signal from the second amplifier PA and a transmitted port (P2) of the bidirectional coupler 3722 can provide the drive signal to the antenna 300. A coupled port (P3) of the bidirectional coupler 3722 can be coupled to a forward node Vfwd1, and an isolated port (P4) of the bidirectional coupler 3722 can be coupled to a reverse node Vrev1. Each of the second, third, and fourth channel drivers 3731, 3741, and 3751 can include a respective bidirectional coupler that is coupled to respective other forward nodes Vfwd2, Vfwd3, and Vfwd4, and is coupled to respective other reverse nodes Vrev2, Vrev3, and Vrev4.

The node Vfwd1 can include information about a forward signal provided to the antenna 300 from the first channel driver 3721. The forward signal can be proportional to a power level of a signal provided to the antenna 300, and thus can be used as verification that one or more other portions or components of the transmitter circuitry 3700 are operational. The node Vrev1 can include information about a reverse signal sensed from the antenna 300. The reverse signal can be proportional to a reflected power at the antenna 300 and thus can be used to indicate whether the external source 102 is located properly against tissue (e.g., with a specified optimal standoff or spacing distance between the source and the tissue surface) and that the antenna 300 is properly loaded.

In an example, the reverse signal on Vrev1 can be used inside the first channel driver 3721 to update a gain characteristic of the second amplifier PA. A detected level of reflected power, such as indicated by the reverse signal at node Vrev1, can be compared with a specified threshold reflected power level REF1, such as using a comparator circuit 3723. If the reflected power is greater than the specified threshold reflected power level REF1, then the comparator circuit 3723 can indicate a fault condition by providing a fault signal at a fault node FLT1. The fault signal can be used to interrupt or inhibit operation of the second amplifier PA, for example by disabling the second amplifier PA. In the example of FIG. 37, the second amplifier PA is configured to operate conditionally depending on whether a fault condition is indicated at fault node FLT1 and whether an enable signal is present at the first channel enable node EN1. In other words, the first channel driver 3721 can be configured to cease amplification of the RF drive signal under a detected load mismatch condition, as indicated by the reverse signal at node Vrev1.

In an example, in the first channel driver 3721, the bidirectional coupler 3722 in conjunction with diode detectors D1 and D2 provide output voltages proportional to the PA forward and reverse output powers. The diode detectors can be fast attack/slow decay, with the decay time constants set by R1*C1 and R2*C2 for the reverse and forward detectors respectively. Longer detector decay time constants in conjunction with a longer integrator time constant can be used to support envelope modulated RF, in which case the second protection circuit 3760 can be configured to operate on peak values of the RF envelope. Switches S1 and S2 can set the detector output voltages to zero in accordance with the logic signal RES_DET to ensure optimal PA output power ramp up. In an example, if a PA load mismatch fault occurs, then the FLT1 output of U1 goes high and latches the reverse detector Vrev1 high via D3 and R3. This helps maintain a logic high state when a fault occurs, such as until a fault reset indication is received. The outputs FLT1-FLT4 from RF OUT1-RF OUT4 are processed as interrupts by the control logic, and the control logic ensures that faults may only be reset under specific conditions to prevent accidental loss of fault status.

The first channel driver 3721 further includes circuitry configured to protect the PA from rapidly occurring load mismatch conditions. Such circuitry can include, for example, a comparator U1, D3, R3, and logic gate U2. The output of U1 transitions to a high state if reverse detector Vrev exceeds a PA safe operating threshold as-determined by REF1, and can be configured to shut down the PA by pulling the PA EN line low via logic gate U2. Logic gate U2 is configured to ensure that the PA is only enabled if set by a control signal EN input and a fault condition (FLT) is not present. In the example of FIG. 37, if a fault is present and/or the EN input is not active, then the PA will be disabled. Diode D3 and R3 can be configured to provide a latching function to maintain the output of U1 in a high state and therefore disable the PA following a load fault condition. For example, this result can be provided by pulling high the non-inverting input of U1, which is connected to Vrev, where it remains until it is reset low via the RES_DET input. In an example, the output of U1 can be used as a PA fault (FLT) indicator.

In an example, the second protection circuit 3760 is coupled to forward nodes Vfwd1-Vfwd4 and reverse nodes Vrev1-Vrev4. That is, the second protection circuit 3760 is configured to receive information about respective forward signals and reverse signals from the first through fourth channel drivers 3721, 3731, 3741, and 3751. The second protection circuit 3760 can be coupled to fault nodes FLT1-FLT4 to receive information about fault conditions at any one or more of the channel drivers. In an example, the second protection circuit 3760 is configured to receive various reference signals, including an output power reference signal REF2 and an RF threshold reference REF3. In an example, the second protection circuit 3760 is configured to receive information about whether a signal is present at an output of the RF signal generator 3714.

In an example, the second protection circuit 3760 includes a processor circuit configured to provide the control signal Vc based on information received from the forward nodes Vfwd1-Vfwd4 and from the reverse nodes Vrev1-Vrev4. That is, the second protection circuit 3760 can include, or can comprise a portion of, one or more feedback circuits configured to receive information from the first protection circuit 3720 about the forward nodes and/or reverse nodes and, in response, provide a corresponding control signal Vc for use by the gain circuit 3715.

The feedback or processor circuit can monitor signals from the various nodes (e.g., the processor circuit can monitor the signals together, such as using an "active or" configuration to monitor the nodes concurrently) and determine whether an antenna mismatch or loading issue exists. In an example, the processor circuit compares the monitored signals with the output power reference signal REF2 to identify an error condition. The monitored signals can optionally be scaled to provide greater or lesser sensitivity to forward path and reverse path signal changes. In an example, the output power reference signal REF2 includes an analog reference voltage signal that can be used to set an output power level for the external source 102 under normal or nominal loading conditions, that is, under conditions when the antenna is sufficiently matched or loaded by tissue. Under mismatched or poor loading conditions, a signal on one or more of the forward nodes Vfwd1-Vfwd4 and the reverse nodes Vrev1-Vrev4 can deviate from the output power reference signal REF2 and the processor circuit 3760 can adjust the control signal Vc to a first value that indicates the gain circuit 3715 should attenuate an input signal from the RF signal generator 3714. If no error condition exists, then the second protection circuit 3760 provides the control signal Vc at a second value that indicates a lesser or zero attenuation to be applied by the gain circuit 3715.

In an example, the second protection circuit 3760 includes an RF monitor input. In the example of FIG. 37, the RF monitor input is coupled to an output of the RF signal generator 3714 to monitor whether the RF signal, TX, is present. The processor circuit of the second protection circuit 3760 can compare information from the RF monitor input to the RF threshold reference REF3 to determine whether to enable or disable a forward path of the drive and splitter circuit 3710, such as by modulating the gain circuit 3715 using the control signal Vc.

The transmitter circuitry 3700 is thus configured to respond to antenna mismatch or poor loading conditions in multiple different ways, and with different degrees or severity of response. For example, the second protection circuit 3760 is configured to adjust the control signal Vc to slowly or gradually roll-back the output power of the external source 102 as a function of antenna mismatch or deviation from a nominal level. A relative amount of mismatch to be tolerated by the system can be specified, for example, by selecting a particular value for the output power reference signal REF2, or by changing a sensitivity of the response circuitry. That is, the second protection circuit 3760 can be configured to provide real-time, continuous output power adjustment as a function of detected loading conditions. The first protection circuit 3720 is configured to quickly respond to antenna mismatches by shutting down amplifier circuitry inside of one or more of the channel driver circuits. A relative amount of mismatch to be tolerated by the system can similarly be specified for the first protection circuit 3720, such as by selecting a particular value for the threshold reflected power level REF1. It can be desirable to tolerate mismatch under certain use conditions, for example, when a user may be locating or shifting the external source 102 relative to the body during initial positioning or startup of the external source 102. In an example, a mismatch tolerance can be dynamic and can change in response to different use conditions.

In an example, the second protection circuit 3760 includes or uses RF input detection and control circuitry to ensure that the transmitter remains in a high attenuation, low RF output power state until an RF drive signal from an RF source is detected. This configuration helps minimize RF output overshoot by preventing the transmitter from attempting to deliver output power while the RF source output is low or non-existent. Without this feature, an ALC loop would "get ahead" of its input, increasing the RF gain to its upper limit and resulting in large and potentially damaging RF output overshoot upon application of RF input.

Figure 38:
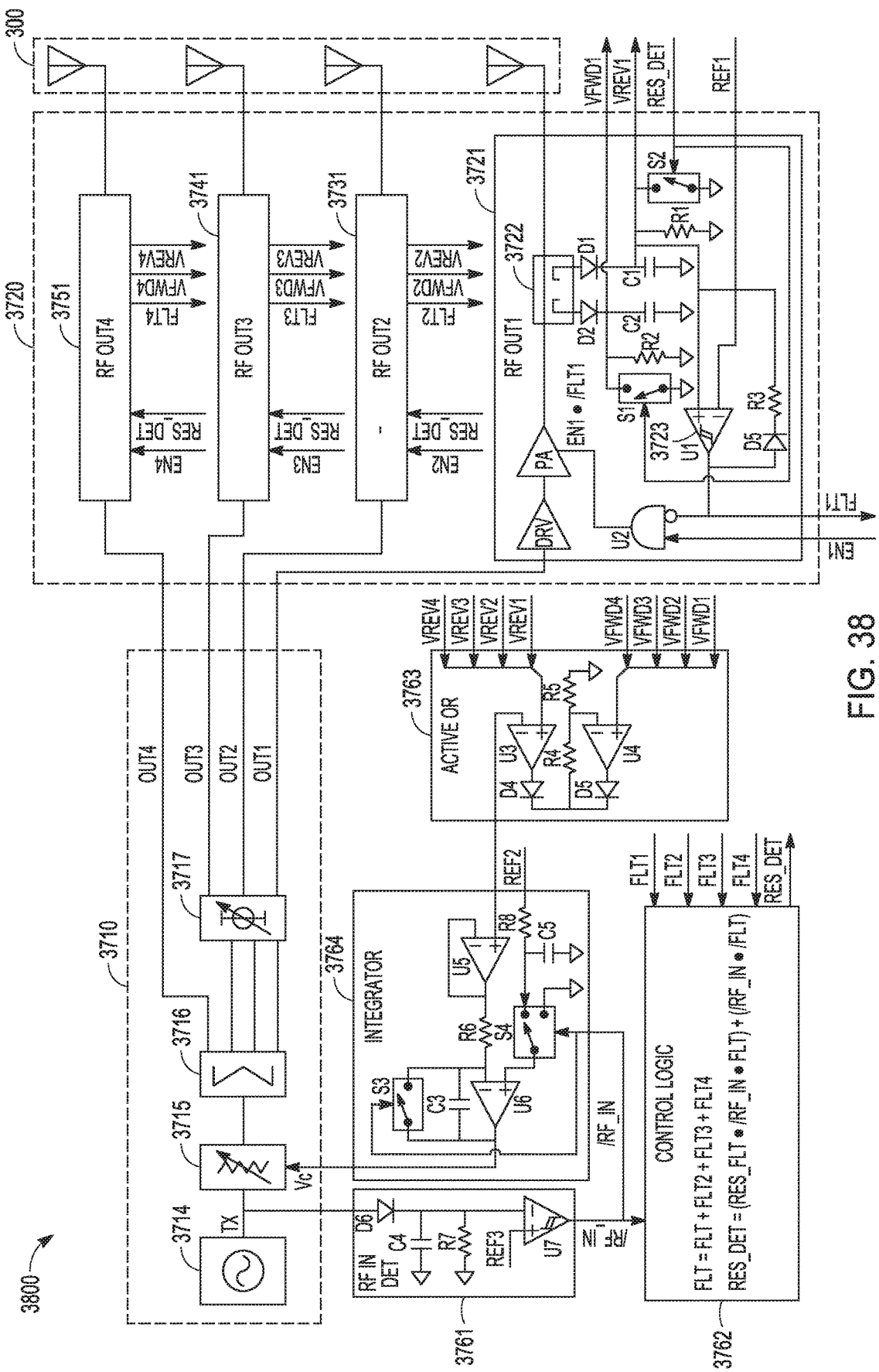
FIG. 38 illustrates generally a second example of transmitter circuitry that can be used or included in an external source.

FIG. 38 illustrates generally an example of second transmitter circuitry 3800. The example of FIG. 38 includes substantially the same drive and splitter circuit 3710 and first protection circuit 3720 from the example of FIG. 37. The example of the second transmitter circuitry 3800, however, includes example implementation details for various portions of the second protection circuit 3760. For example, the second protection circuit 3760 can include an RF detector circuit 3761, a control logic circuit 3762, a feedback circuit 3763, and an integrator circuit 3764.

The RF detector circuit 3761 can be configured to receive information about a drive signal TX that is generated in or carried by the drive and splitter circuit 3710. In an example, the RF detector circuit 3761 includes a comparator circuit that provides information about a relationship between the drive signal TX and a reference value REF3. When the drive signal TX is present, and optionally when the drive signal TX exceeds the reference value REF3 by at least a specified threshold amount, then the comparator can provide a binary signal to the control logic circuit 3762 indicating that the drive signal TX is present.

The integrator circuit 3764 can be configured to adjust or tune a response characteristic of the second protection circuit 3760, and can be used to maintain an output power level at or near a target level. In an example, the integrator circuit 3764 receives an indication from the feedback circuit 3763 about a relationship between the forward and reverse voltage signal characteristics from the various forward and reverse nodes Vfwd1-Vfwd4 and Vrev1-Vrev4. The relationship information can be compared with a threshold value (e.g., REF2) and a result of the comparison can be used to adjust a value of the control signal Vc provided to the gain circuit 3715. In an example, a response time characteristic can be adjusted to determine how quickly or slowly a value of Vc is changed in response to the information from the feedback circuit 3763. In an example, the integrator circuit 3764 is further configured with a reset switch that can receive a signal LOOP_RST, such as from the control logic circuit 3762. When the LOOP_RST signal is high, for example, then the integrator circuit 3764 can provide the control signal Vc with a signal level that indicates the gain circuit 3715 should apply maximum attenuation to effectively reduce an output of the transmitter.

In an example, the integrator circuit 3764 comprises a dual time constant integrator configured to provide independent control of initial RF output ramp-up characteristics and dynamic closed loop response characteristics. In other examples, RF ramp-up and closed loop dynamic response times can be defined by a single time constant. However, the dual time constant approach provides, for example, for a relatively slow RF output ramp-up to minimize overshoot and out-of-band emissions, and provides quicker dynamic loop response to thereby provide better amplifier protection for sudden load mismatches.

In the example of FIG. 38, the integrator circuit 3764 includes components configured to provide various characteristics of a dynamic response, including a PA RF output power ramp for the various channel drivers and RF output levels to account for output load mismatches or other changes, such as due to supply voltage or temperature changes, such as can indicate a gain adjustment to maintain or achieve a target output power. In the example, the integrator circuit 3764 includes U6, R6, C3, R8 and C5, which together provide two time constants. A first one of the time constants is primarily responsible for the RF output ramp-up under initial conditions, and the second time constant defines the dynamic response after ramp-up. That is, the first time constant T1 is defined as R8\*C5, the second time constant T2 is defined as R6\*C3, and generally T1>T2. The two time constant approach enables controlled RF output ramp up at a relatively slow $T_{RAMP}$ rate to minimize potentially damaging RF output overshoot and to minimize emissions outside the communications channel, further while enabling rapid adjustments to the RF output power to protect the PAs in the presence of sudden output load mismatch events.

In the example of FIG. 38, U6 receives inputs REF2 via R8 (e.g., corresponding to the PA RF output power target), and the Vfwd and Vrev Active OR output via buffer U5 and R6. The output of U6 is Vc, which thereby adjusts to minimize an error between REF2 and the PA RF output levels as indicated by the Active OR output. This can be achieved by varying the gain setting of the VVA (voltage variable attenuator, or gain circuit 3715).

In an example, the integrator circuit 3764 is active when the RF input to the PAs in the channel drivers is present, for example as determined by the /RF_IN logic low state. In this case, S3 is open and S4 connects the reference REF2 to U6. When the RF input to the PAs is not present (e.g., when /RF_IN is in a logic high state), then S3 is closed and S4 is switched to ground. This places the output of U6 close to zero, maximizes the attenuation of the gain circuit 3715, and thereby minimizes the amplitude of the drive signals on channels OUT1-OUT4. This configuration helps provide optimal RF output ramp up conditions at an onset of an RF input.

The control logic circuit 3762 can receive various input signals from elsewhere in the transmitter, process such signals, and then instruct the transmitter to take some responsive action. In an example, the control logic circuit 3762 includes failsafe logic for the transmitter configured to prevent the transmitter from inadvertently disabling one or more of its protection mechanisms. For example, the logic can allow assertion of a reset condition only if an amplifier fault is present and an RF input signal is not present.

The control logic circuit 3762 can be configured to establish conditions for resetting the RF detectors or managing PA load faults in the transmitter, for example by discharging the detector capacitors to ground via S1 and S2. In an example, the detectors are reset in the absence of an RF input as indicated by a logic high /RF_IN state, or via the control logic circuit 3762 following a detected load mismatch fault (FLT) event. The control logic circuit 3762 can be configured to ensure that PA faults cannot be reset by /RF_IN if one or more PA faults are present, or if an RF input is present and no faults are present. This can help prevent /RF_IN from clearing faults before they have been processed by the controller, and helps prevent the controller from holding the detectors in a reset state (RES_DET=logic high) after a fault is cleared. Reduced RF output under control of the second protection circuit 3760 can continue for the duration of the transmit interval following the occurrence of up to (3) PA faults, and the FLT1-FLT4 status lines provide interrupt signals to ensure that faults are not missed or inadvertently cleared.

In an unillustrated example, the control logic circuit 3762 can provide a reset signal, LOOP_RST, to the integrator circuit 3764 based on detected RF input signal conditions and/or based on a fault condition at any one or more of the first, second, third, and fourth channel drivers 3721, 3731, 3741, and 3751. That is, a fault detected in any one or more of the channel drivers can provide a fault condition that terminates the provision of RF signals to the output or antenna ports. The transmitter circuitry can be differently configured to tolerate one or more channel faults, for example by adjusting the parameters of the control logic circuit 3762. For example, the statement LOOP_RST=/RF_IN+FLT can be changed to LOOP_RST=/RF_IN with the rest of the circuitry substantially unchanged. That is, the integrator circuit 3764 can directly receive and respond to a detected presence or absence of the RF input. In an example, the control logic circuit 3762 is further configured to determine a control signal RES_DET to indicate a fault condition that will shut down or inhibit the channel drivers. That is, the RES_DET signal can be generated by the control logic circuit 3762 and used by the channel driver circuits to inhibit a forward signal path to the antenna ports.

The feedback circuit 3763 includes various processing circuitry to receive signals from the forward and reverse nodes Vfwd1-Vfwd4 and Vrev1-Vrev4 of the channel drivers and, in response, provide a feedback signal to the integrator circuit 3764. In an example, the feedback circuit 3763 is configured to monitor signals from the various nodes (e.g., the processor circuit can monitor the signals together, such as using an "active or" configuration to monitor the nodes concurrently) and determine whether an antenna mismatch or loading issue exists. The monitored signals can optionally be scaled by the feedback circuit 3763 to provide greater or lesser sensitivity to forward path and reverse path signal changes in the various channel drivers. In an example, the output power reference signal REF2 includes an analog reference voltage signal that can be used to set an output power level for the external source 102 under normal or nominal loading conditions, that is, under conditions when the antenna is sufficiently matched or loaded by tissue. Under mismatched or poor loading conditions, a signal on one or more of the forward nodes Vfwd1-Vfwd4 and the reverse nodes Vrev1-Vrev4 can deviate from the output power reference signal REF2 and the feedback circuit 3763 can adjust its output or feedback signal accordingly.

In an example, the feedback circuit 3763 is further configured to handle or accept a specified amount of modulation in signals at the forward and reverse nodes Vfwd1-Vfwd4 and Vrev1-Vrev4. That is, the feedback circuit 3763 can be configured to respond only to forward or reverse node signal magnitude changes that exceed a specified threshold magnitude change, such as within a specified duration.

In the example of FIG. 38, the feedback circuit 3763 includes U3, U4, D4, D5, R4, and R5. The feedback circuit 3763 receives the forward and reverse detector outputs from RF OUT1-RF OUT4 and consolidates them into a single analog input, and the highest voltage signal from among Vfwd1-Vfwd4 and Vrev1-Vrev4 can drive a response. In the example of FIG. 38, the Vrev inputs are scaled up via R4 and R5 such that the OR'd Vrev output at U4–D5 is equal to the Vfwd OR output U3–D4 at the maximum allowable PA forward and reverse power levels. That is, Vrev=Vfwd/(U4 gain)=Vfwd/(1+R4/R5). The ratio R4/R5 is then: R4/R5= (Vfwd/Vrev)−1.

In an example, U4 gain (and thus R4 and R5) is selected to limit a maximum load VSWR at a maximum allowable PA RF output such that the VSWR at PA RFout_max=(1+ Vrev_max/Vfwd_max)/(1−Vrev_max/Vfwd_max). By substitution, R4/R5=[(VSWR at PA RFout_max+1)/(VSWR at PA RFout_max−1)]−1. For example if the maximum PA safe load VSWR at maximum output power is 3, then R4/R5= [(3+1)/(3−1)]−1=1 for a U4 gain of 2.

Various other benefits and features are provided according to the example transmitter circuitry 3800. For example, the transmitter circuitry supports envelope-modulated RF signals through use of longer forward and reverse detector and Integrator time constants. Long time constants relative to an envelope frequency can cause the control circuitry to limit peak RF output power while ignoring envelope values below the peaks, thus ensuring integrity of the modulated RF output.

Figure 39:
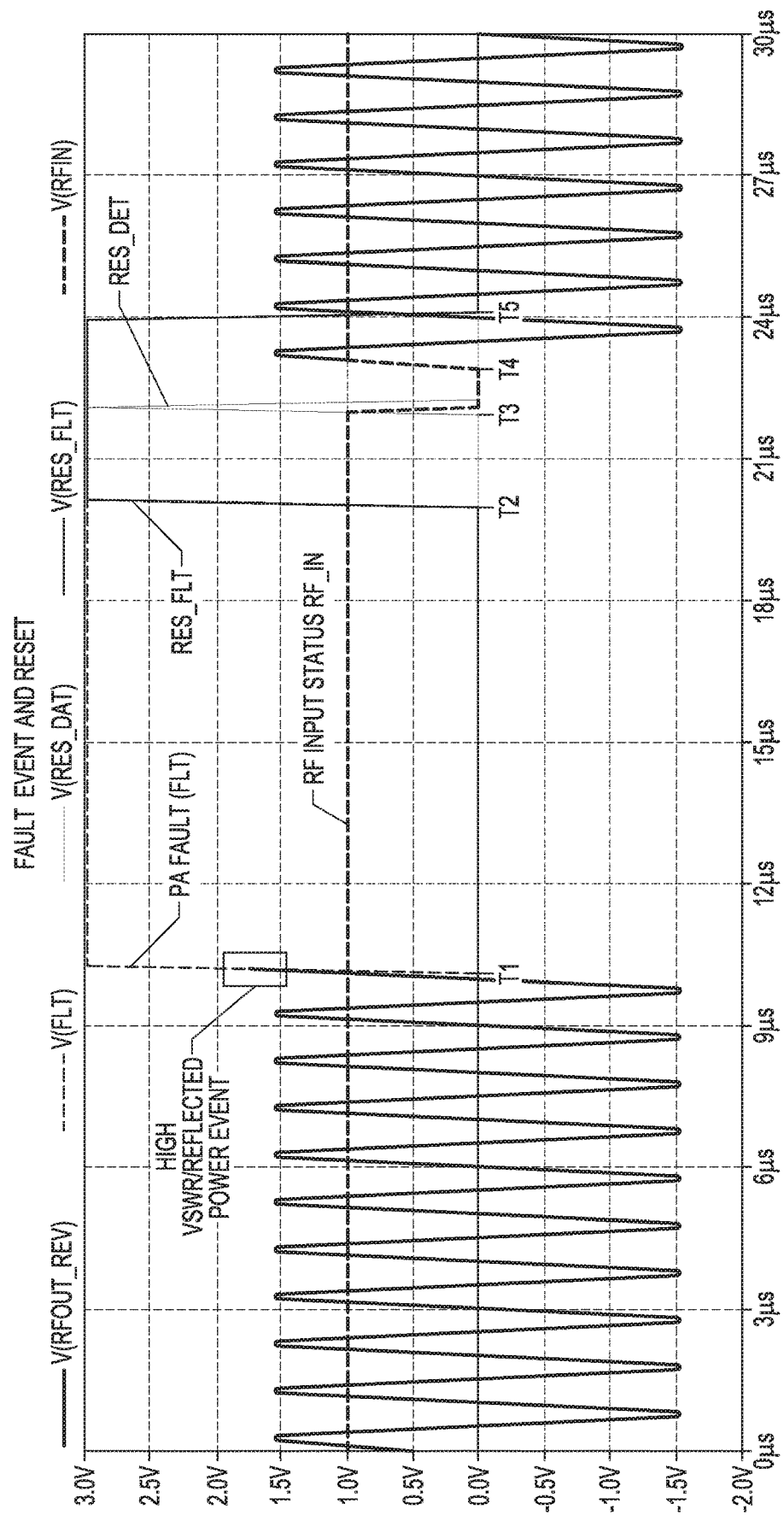
FIG. 39 illustrates generally an example of transmitter protection circuitry behavior during a fault event and reset.

Operating examples of the various transmitter and protection circuitry are discussed next. FIG. 39 illustrates generally a first example that includes PA protection (e.g., PA protection inside one or more of the first, second, third, and fourth channel drivers 3721, 3731, 3741, and 3751) following a high VSWR or load mismatch event. The example includes a resetting of the fault condition and continued operation of the PA following the reset. V(rfout_rev) is the reflected power at the PA directional coupler output corresponding to the DC output into D1 (see, e.g., FIG. 38), and equates to a 3:1 VSWR at 30 dBm RF output power for a 10 dB coupling factor. In the first example, from time 0-10 uS, the PA provides an RF output into a 3:1 VSWR load mismatch with V(rfout_rev) below the fault threshold as determined by REFL. At T1=10.2 uS a high VSWR/reflected RF output power event occurs and causes the FLT line to transition high, thereby shutting down the PA and minimizing its corresponding RF output. The RF input to the PA persists as indicated by the high state of RF_IN (the positive logic complement to /RF_IN, used here for clarity). In the first example, the FLT output remains in a latched high state through an attempted fault reset by the control logic via RES_FLT at T2=20 uS because the RF input is still present. At T3=22 uS, the control logic turns off the RF input, RF_IN transitions low, and the fault is reset as indicated by the RES_DET pulse generated by the control logic and by the transition of FLT from high to low. RES_DET remains high briefly because the control logic forces the logic signal low when the fault is cleared. This prevents the control loop from inadvertently being held in a reset or inactive state by the control logic, which would defeat the protection circuit. In the first example, at time T4=23 uS, the RF input is resumed (RF_IN goes high) and the PA RF output is restored at the same level and under the same load mismatch conditions (e.g., high VSWR event not present) as existed during the example's initial 0-10 uS interval. The control logic-generated RES_FLT line can transition back to a low state at T5, with no effect on the operation as the controller renders this input inactive once the fault is cleared. In an example if RES_FLT remained high following T5, then the operation would not be adversely affected.

Figure 40:
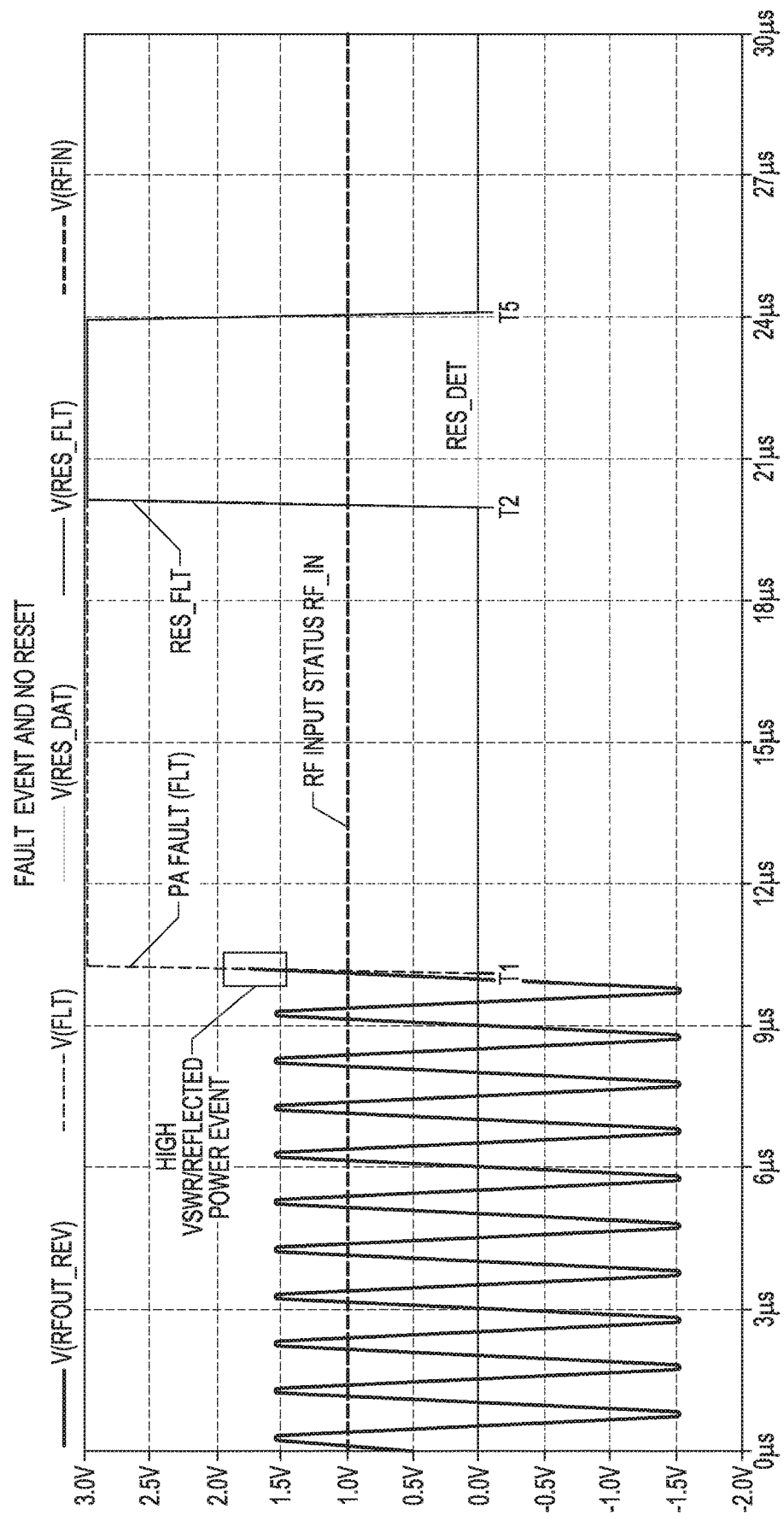
FIG. 40 illustrates generally an example of transmitter protection circuitry behavior during a fault event and without a reset.
Figure 41:
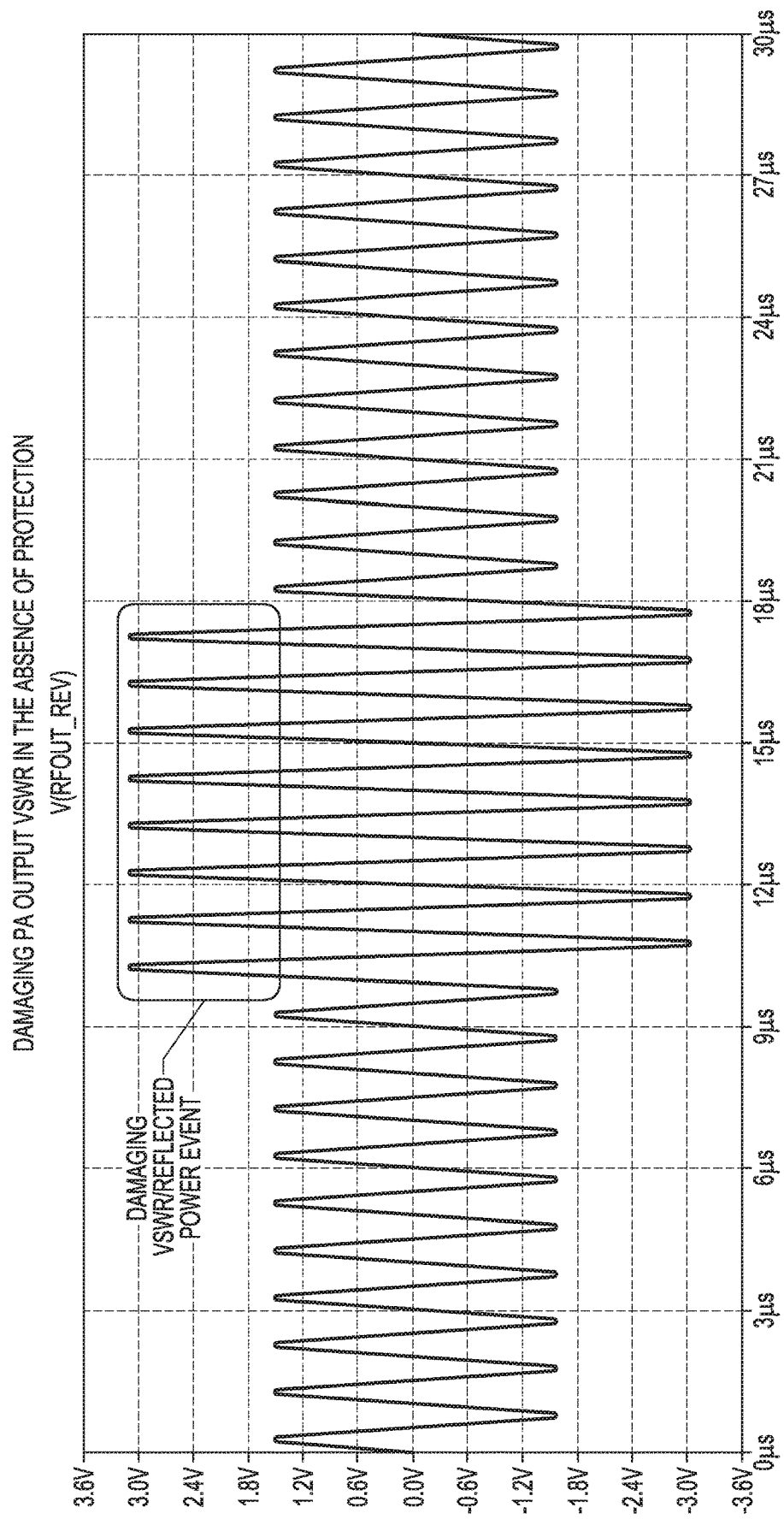
FIG. 41 illustrates generally an example of a reflected power signal in the absence of a protection circuit.

FIG. 40 illustrates generally a second example with substantially the same sequence of events discussed above regarding FIG. 39. However, in FIG. 40, the RF input remains constant. Therefore the control circuit prevents assertion of RES_DET in response to the attempted fault reset via RES_FLT. In this second example, U1 remains latched in a logic high fault state and the PA remains shut down. FIG. 41 illustrates generally the same high VSWR/ reflected power event from the second example of FIG. 40, however, without protection circuitry, such as can lead to probable damage to the PA.

Figure 42:
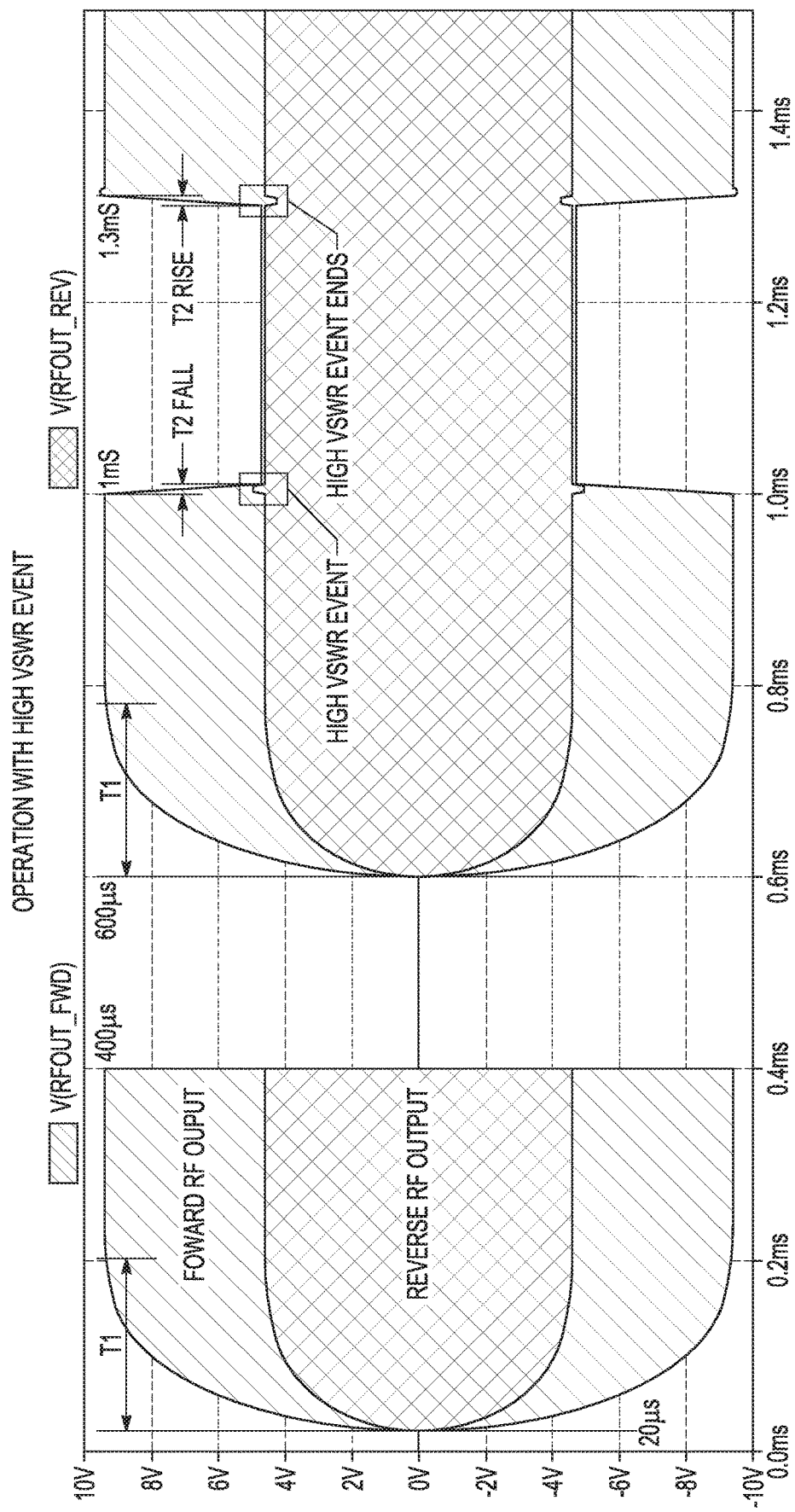
FIG. 42 illustrates generally an example of transmitter protection circuitry behavior during a high VSWR event.
Figure 43:
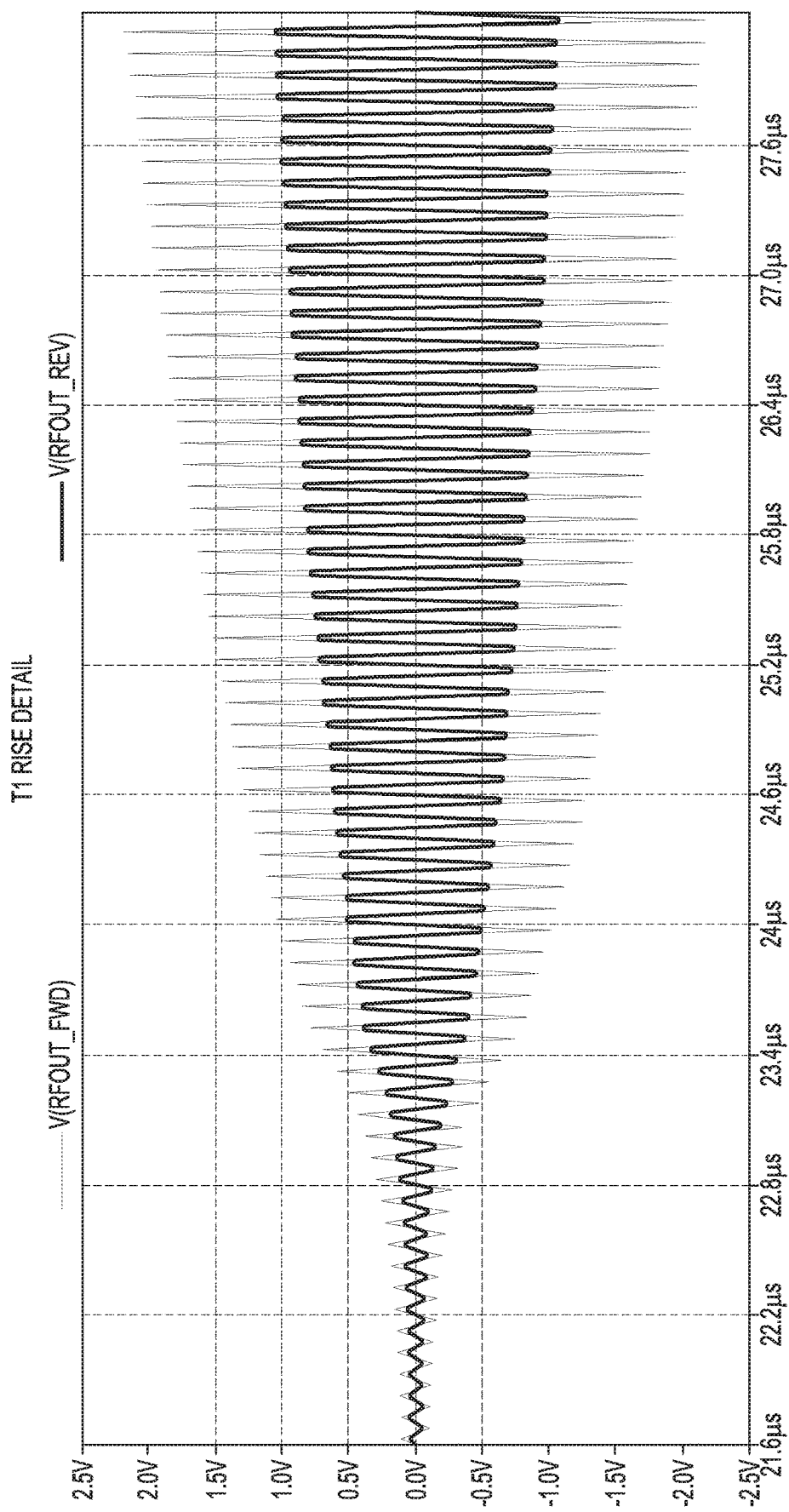
FIG. 43 illustrates generally an example of rise time behavior for a portion of a transmitter protection circuit.
Figure 44:
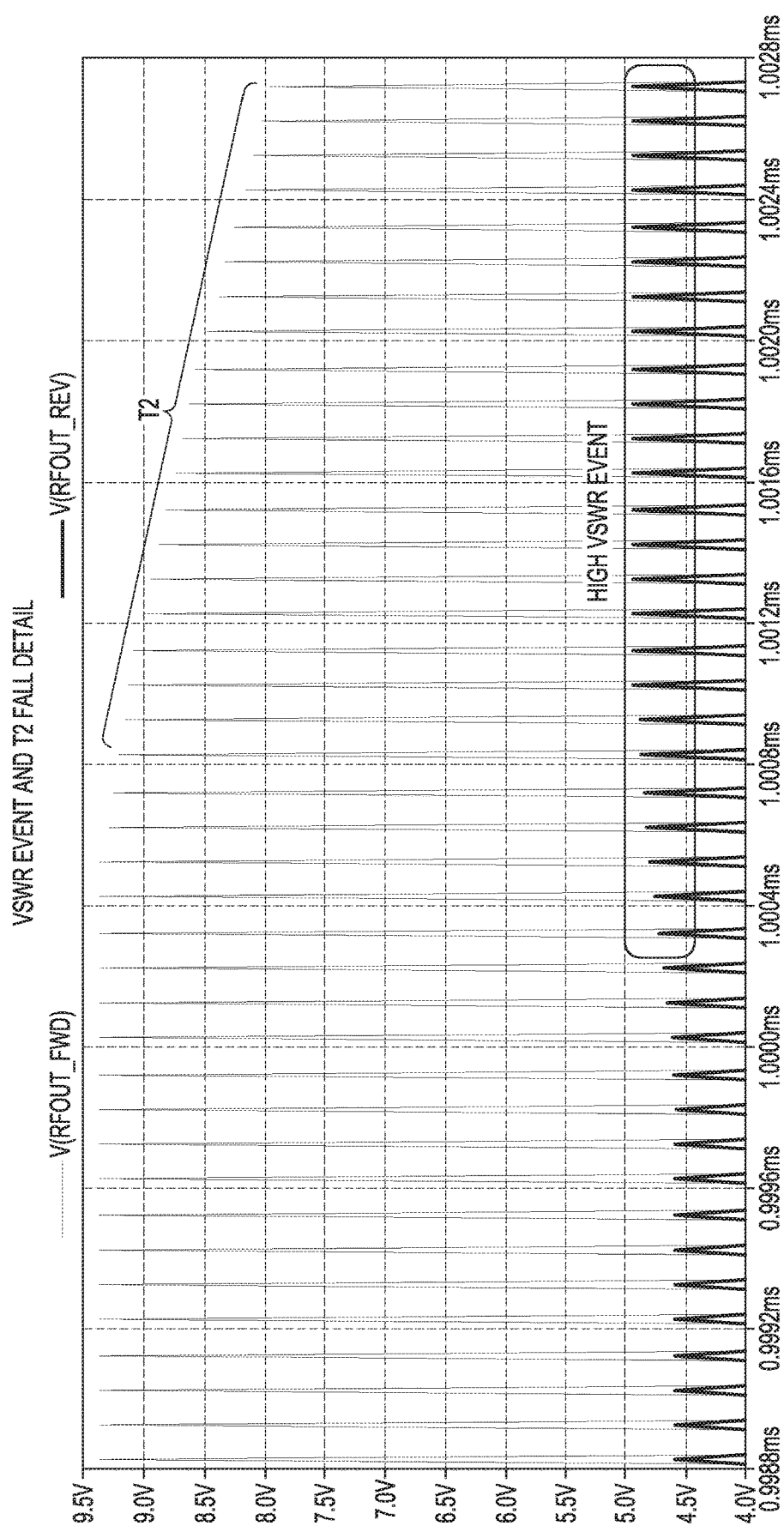
FIG. 44 illustrates generally an example of fall time behavior for a portion of a transmitter protection circuit.
Figure 45:
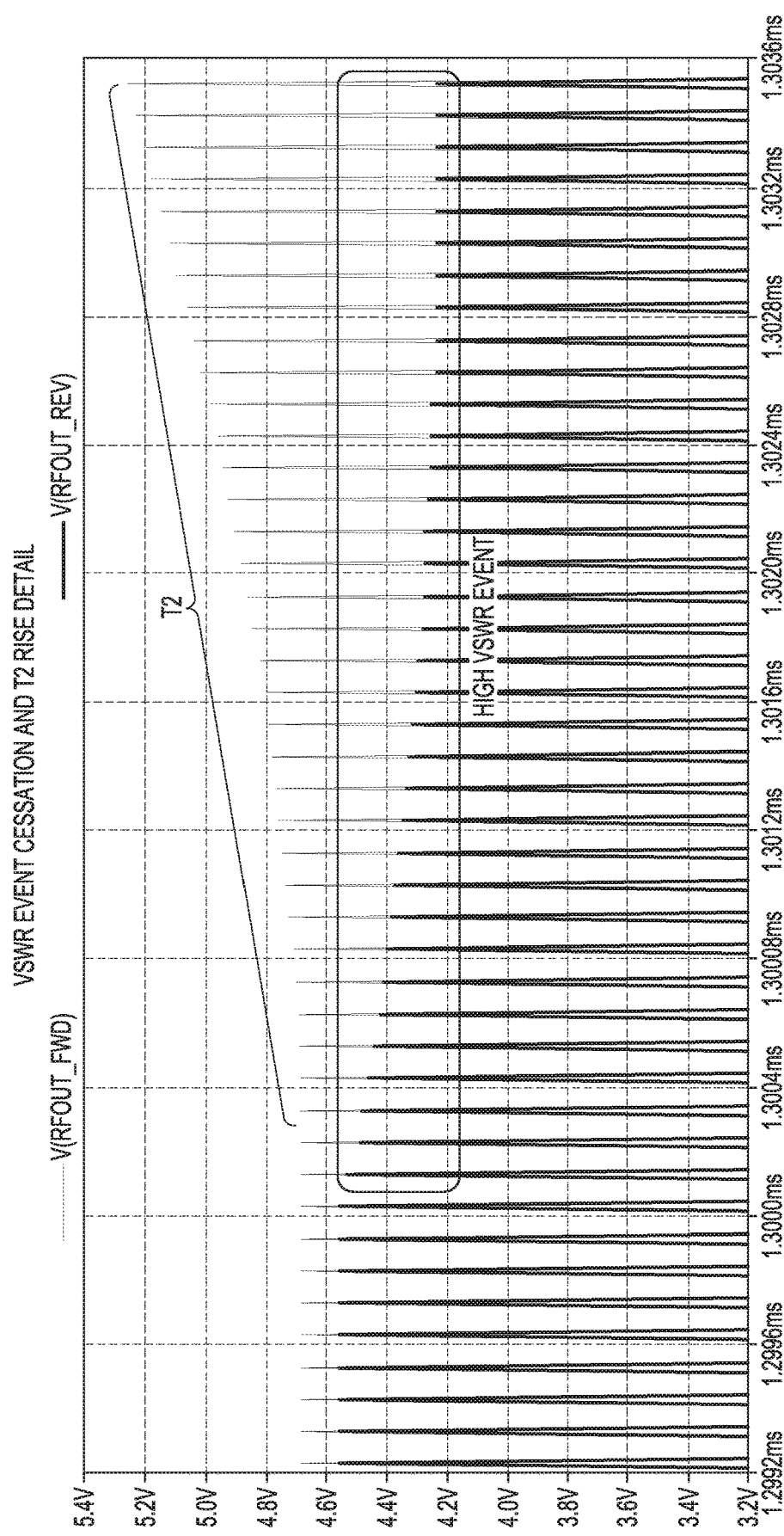
FIG. 45 illustrates generally an example of transmitter protection circuitry behavior following a VSWR event.
Figure 46:
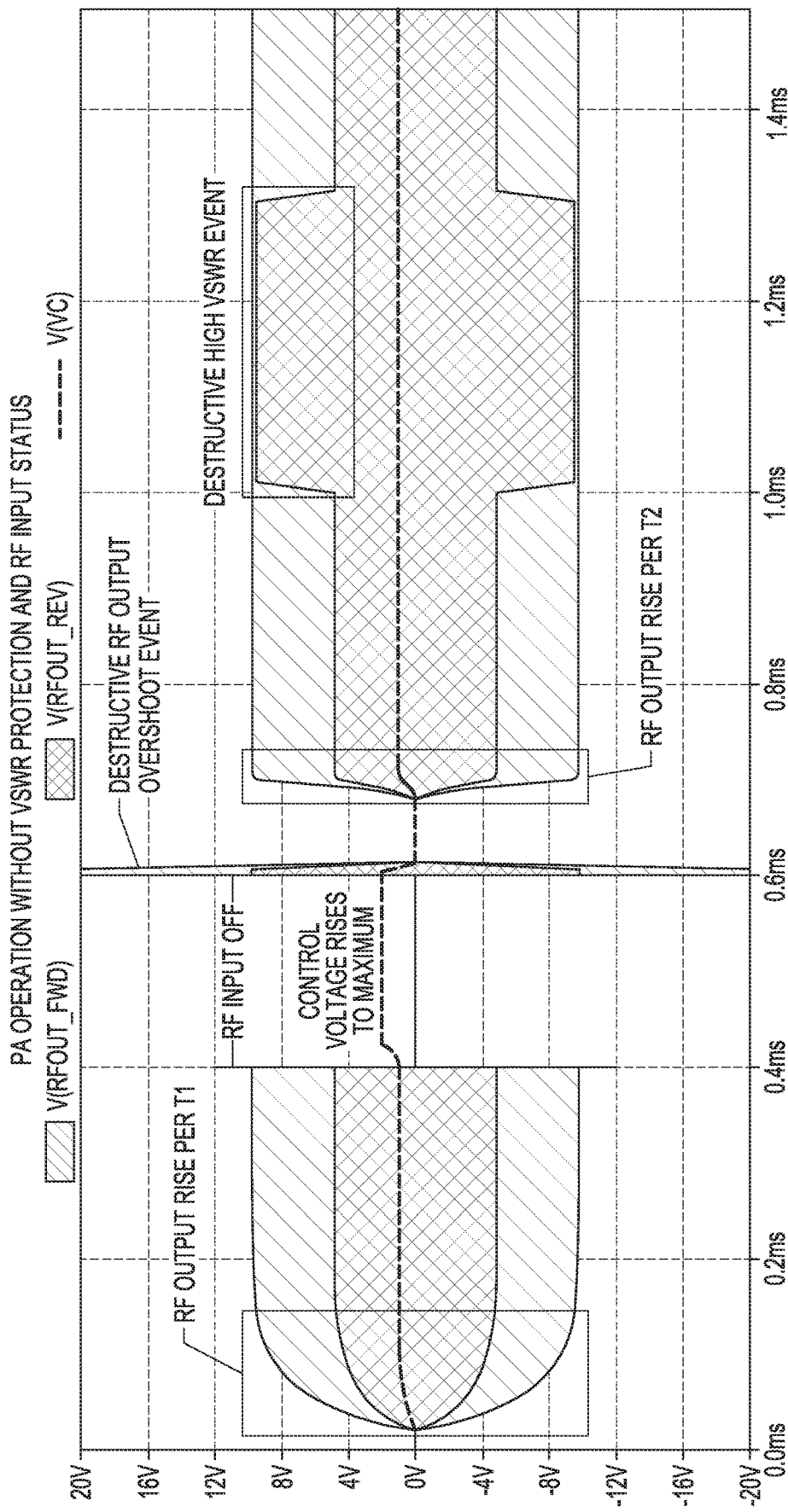
FIG. 46 illustrates generally an example of transmitter behavior without a VSWR protection circuit.

Referring now to the examples of FIGS. 42-46, a PA forward output power can be governed by a specified target output power and can be reduced to maintain a safe reflected power level. In the examples, FIGS. 42 and 46 illustrate generally forward and reverse RF outputs V(rfout_fwd) and V(rfout_rev) as envelopes rather than sinusoidal waveforms as is necessary to capture the event timing, such as occurs over many RF cycles. FIGS. 43-45 represent zoomed-in plots showing details of the events in FIG. 42. In an example, the second protection circuit 3760 operates more slowly than the first protection circuit 3720, but is capable of dynamically reducing PA output power for slower, high VSWR events to maintain safe operation and maintain a target RF output power for load VSWRs within the full output power capabilities of the PA. For very rapid high VSWR events such as may occur if the transmitter antenna is suddenly disconnected or shorted, the first protection circuit 3720 takes control to protect the PAs.

The example of FIG. 42 shows an initial RF ramp up followed by cessation of the RF input, followed by a second ramp up after RF input is reintroduced. The example further includes an RF output power reduction following a high VSWR event, and finally shows resumption of full RF output power after the high VSWR event ends. In the example, the RF output power setting via REF2 is 30 dBm, corresponding to 10 Vp-p RF output voltage into a 50 ohm system impedance. The actual forward RF output power V(rfout_fwd) is slightly below this as the PA is operating into a 3:1 VSWR, and the second protection circuit 3760 is set to begin limiting the PA RF output power for VSWRs≥3: 1. The reverse power V(rfout_rev) at the 30 dBm forward power setting is ½ the forward power, corresponding to a 3:1 VSWR. As V(rfout_rev) increases, the loop reduces V(rfout_fwd) to maintain a constant V(rfout_rev) to maintain operation within the PA safe operating range. From time 0 to 20 uS, the RF input as indicated by the /RF_IN status line is not present and the loop remains in a high attenuation state. At 20 uS, RF input is initiated and the PA RF output ramps up in accordance with the RF output ramp up time constant T1=R8*C5. The RF input ceases at 400 uS, at which point the loop is reset, placing it in a maximum attenuation state via switches S3 and S4. The RF detectors are also reset via RES_DET. These actions ensure that the subsequent RF ramp up, such as following resumption of RF input at 600 uS, occurs without overshoot and in accordance with time constant T1. Full RF output is resumed at 600 uS+T1 and continues until the high VSWR event at 1 mS. At time 1 mS, the integrator circuit 3764 rapidly increases RF attenuation by reducing the control voltage to the gain circuit 3715, thereby reducing the PA forward output power to maintain a constant reverse power. The T2 fall output power reduction rate is determined by the overall loop dynamics, and is dominated by the time constant T2=R6*C3, such as can be less than the ramp up time constant T1. In the example of FIG. 42, at time 1.3 mS, the high VSWR event subsides and RF output power is rapidly increased over the T2 rise interval back to the target value. In an example, T2 rise can be slightly longer than T2 fall due to the loop dynamics which include the natural asymmetry from the RF detector fast attack/slow decay characteristics. This can be desirable, for example, for rapidly responding to a high VSWR event to protect the PA. Resumption of full output power following a high VSWR event can be slower to thereby minimize RF output overshoot. FIGS. 43-45 illustrate generally detailed or zoomed-in views of RF ramp up T1, T2 fall during the high VSWR event, and T2 rise following the high VSWR event, respectively.

FIG. 46 illustrates generally an example of second protection circuit 3760 operation with high VSWR output power reduction and RF input status control eliminated. The event timing in the example of FIG. 46 is the same as the event timing in the example of FIG. 42. In FIG. 46, the second protection circuit 3760 controls only the initial RF output ramp-up and forward output power without monitoring reverse power. The events and features preceding time 600 uS is the same as for the fully functional loop (described above with respect to FIG. 42), but the second RF ramp up after 600 uS when RF input is resumed results in a large and potentially destructive overshoot. The overshoot can be due to the gain circuit 3715 control signal from the integrator circuit 3764, which saturates to its maximum value during the RF input off interval from time 400 uS to 600 uS. In the absence of an RF input status, the loop continues to increase RF gain in an attempt to deliver the target RF output power. Consequently, when RF input is resumed, the RF output will jump to the maximum possible level from the PA, which can damage the PA. Following this likely-destructive RF output overshoot event, the output quickly drops back to zero due to overcorrection by the loop, followed by a third ramp up at the T2 rate rather than at the T1 rate due to the absence of an /RF_IN driven loop reset. Finally, the high VSWR event starting at 1 mS is unsuppressed, also therefore also is likely to damage the PA. In an example, similar VSWR events can have negative consequences if the forward power is controlled but reverse power is not.

Receiver and Rectifier Circuitry for Use in Implantable Devices

Figure 47:
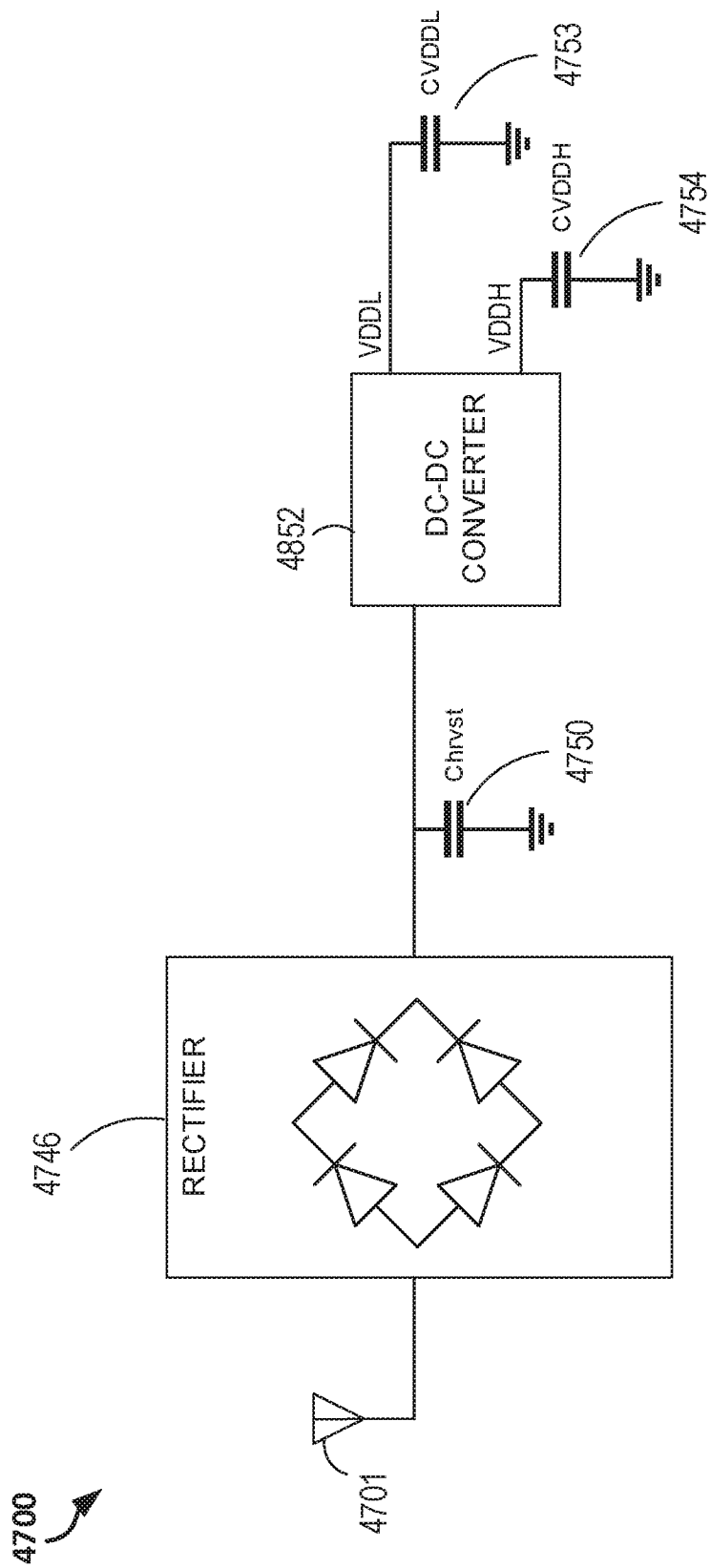
FIG. 47 illustrates generally an example that can include a portion of a receiver circuit for an implantable midfield receiver device.

FIG. 47 illustrates generally an example that can include a portion of a receiver circuit 4700 for the implantable device 110, for a target device, or for another midfield receiver device. In an example, the receiver circuit 4700 can be included or used in an elongated device consistent with this disclosure, and can optionally be deployed inside a patient tissue, such as including inside of a blood vessel. The receiver circuit 4700 can include, in an example, components corresponding to those described herein at FIG. 5, including the rectifier 546, the charge pump 552, or the stimulation driver circuit 556.

In an example, the receiver circuit 4700 includes an antenna 4701 that is configured to receive a midfield power signal or data signal. In an example, the antenna 4701 comprises the antenna 108. The received signal can comprise a portion of a propagating signal inside of tissue, and can originate from an external midfield transmitter, such as can be configured to manipulate evanescent fields at a tissue interface to generate the propagating signal inside the tissue. The receiver circuit 4700 can further include a rectifier circuit 4746 configured to rectify a received AC power signal from the antenna 4701. Other circuitry in a signal path following the rectifier circuit 4746 can include power storage, level conversion, and stimulation control circuitry, among other things. For example, a first capacitor 4750, illustrated in FIG. 47 as Chrvst, can include a capacitor configured to store harvested energy that is received using the antenna 4701.

In an example, the receiver circuit 4700 includes a DC-DC converter circuit 4752. The converter circuit 4752 can be configured to increase a voltage of a received signal from the rectifier circuit 4746, or from the first capacitor 4750, to provide another signal that is configured for electrostimulation or for operation of other circuitry inside the implantable device 110. The converter circuit 4752 can have multiple outputs, such as to serve first and second power domains. In an example, the first power domain is served by a low voltage capacitor 4753, or CVDDL, and the second power domain is served by a high voltage capacitor 4754, or CVDDH.

In an example, the high voltage capacitor 4754 drives a stimulation circuit, such as the stimulation driver circuit 556 from the example of FIG. 5. The stimulation driver circuitry can provide programmable stimulation through one or more outputs to an electrode array.

The example receiver circuit 4700 can have various drawbacks, including potential opportunities for power losses to occur. For example, a power loss can occur due to conversion or regulation of power signals, such as at the rectifier circuit 4746 or in the converter circuit 4752. Leakage-related losses can accrue due to one or more of the first capacitor 4750, the low voltage capacitor 4753, and/or the high voltage capacitor 4754. In an example, energy stored in the low voltage capacitor 4753 can be used by various circuitry or other controller components to regulate electrostimulation, and the electrostimulation can use energy stored by the high voltage capacitor 4754. Although the low voltage capacitor 4753 and high voltage capacitor 4754 are represented as discrete capacitors, these capacitors can include multiple respective capacitors or banks or arrays of capacitors.

The present inventors have recognized that a problem to be solved includes increasing an efficiency of wireless power signal receipt, conversion, and use in electrostimulation. The present inventors have further recognized that a solution to the problem can include bypassing the first capacitor 4750 to avoid losses that accrue following the rectifier circuit 4746. The present inventors have further recognized that a solution to the problem can include using a multiple-stage rectifier circuit. In an example, the multiple-stage rectifier can include respective outputs for each stage, and the outputs can be coupled to a multiplexer and used for electrostimulation or used to supply power signals to other components or devices in, for example, a midfield device. Different outputs or branches of the multiplexer can be selected depending on a desired electrostimulation level.

Figure 48:
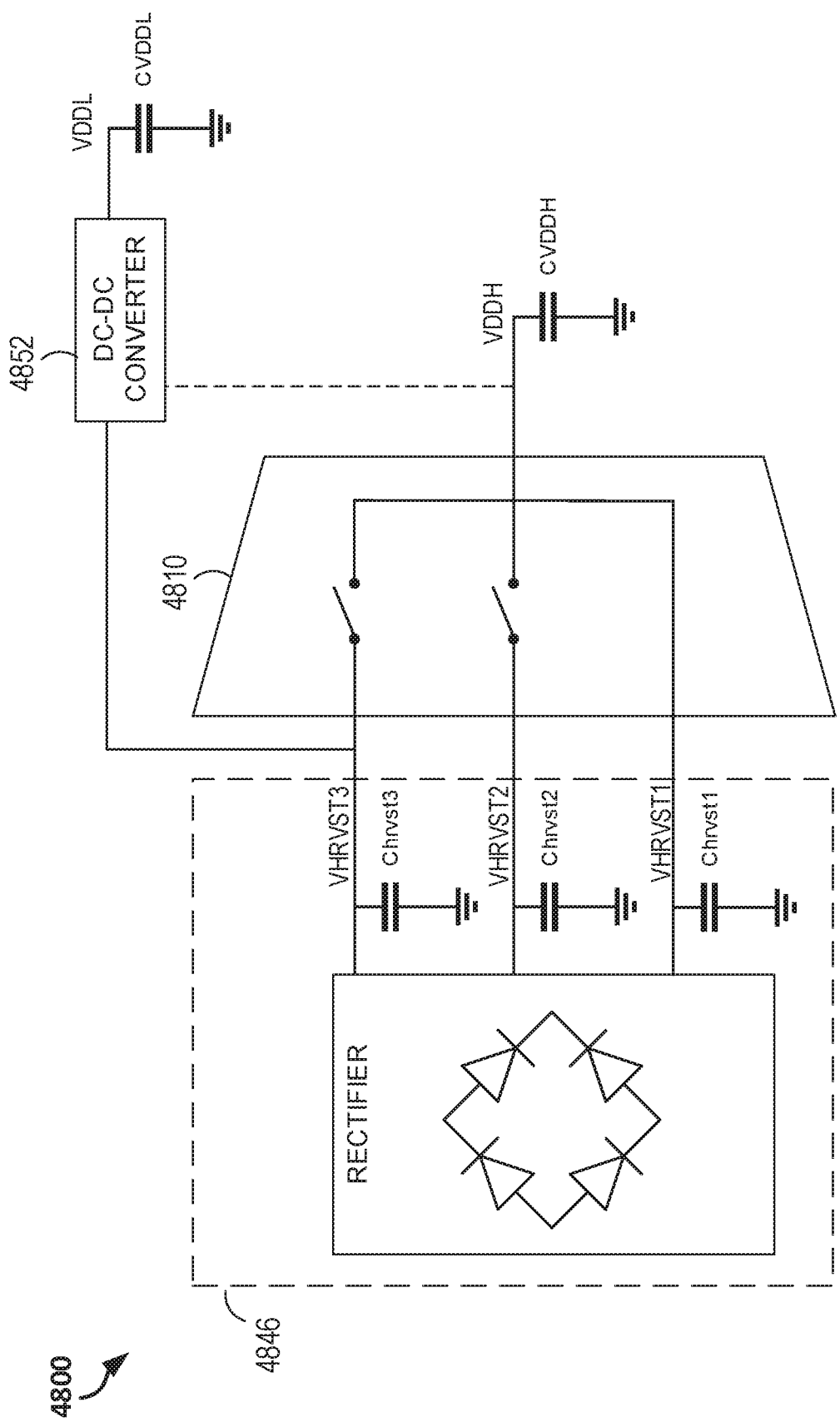
FIG. 48 illustrates generally an example that includes a multiple-stage rectifier circuit and a multiplexer circuit.

FIG. 48 illustrates generally an example that includes a multiple-stage rectifier circuit 4846 and a multiplexer circuit 4810. The multiple-stage rectifier circuit 4846 includes multiple taps or outputs at different levels or power domains, such as corresponding to a harvested first power domain (e.g., designated VHRVST1 in the example of FIG. 48), a harvested second power domain (e.g., designated VHRVST2), and a harvested third power domain (e.g., designated VHRVST3). Taps from the multiple-stage rectifier circuit 4846 can be coupled to inputs of the multiplexer circuit 4810, and an output from the multiplexer circuit 4810 can feed a stimulation power domain (e.g., at a power or signal level designated VDDH).

In the example of FIG. 48, the harvested third power domain can be coupled to a DC-DC converter circuit 4852, such as can be used to provide a low voltage power domain (at VDDL). Signals from the DC-DC converter circuit 4852, or from control circuitry coupled to the DC-DC converter circuit 4852, can be used to modulate electrostimulation using signals in the stimulation power domain. This is represented schematically in the example of FIG. 48 by the dashed line coupling the DC-DC converter circuit 4852 to the stimulation power domain VDDH. One or more switches or other control circuits can be provided in the stimulation power domain to modulate or control delivery of electrostimulation signals, such as to one or more electrodes of the implanted device.

Figure 49:
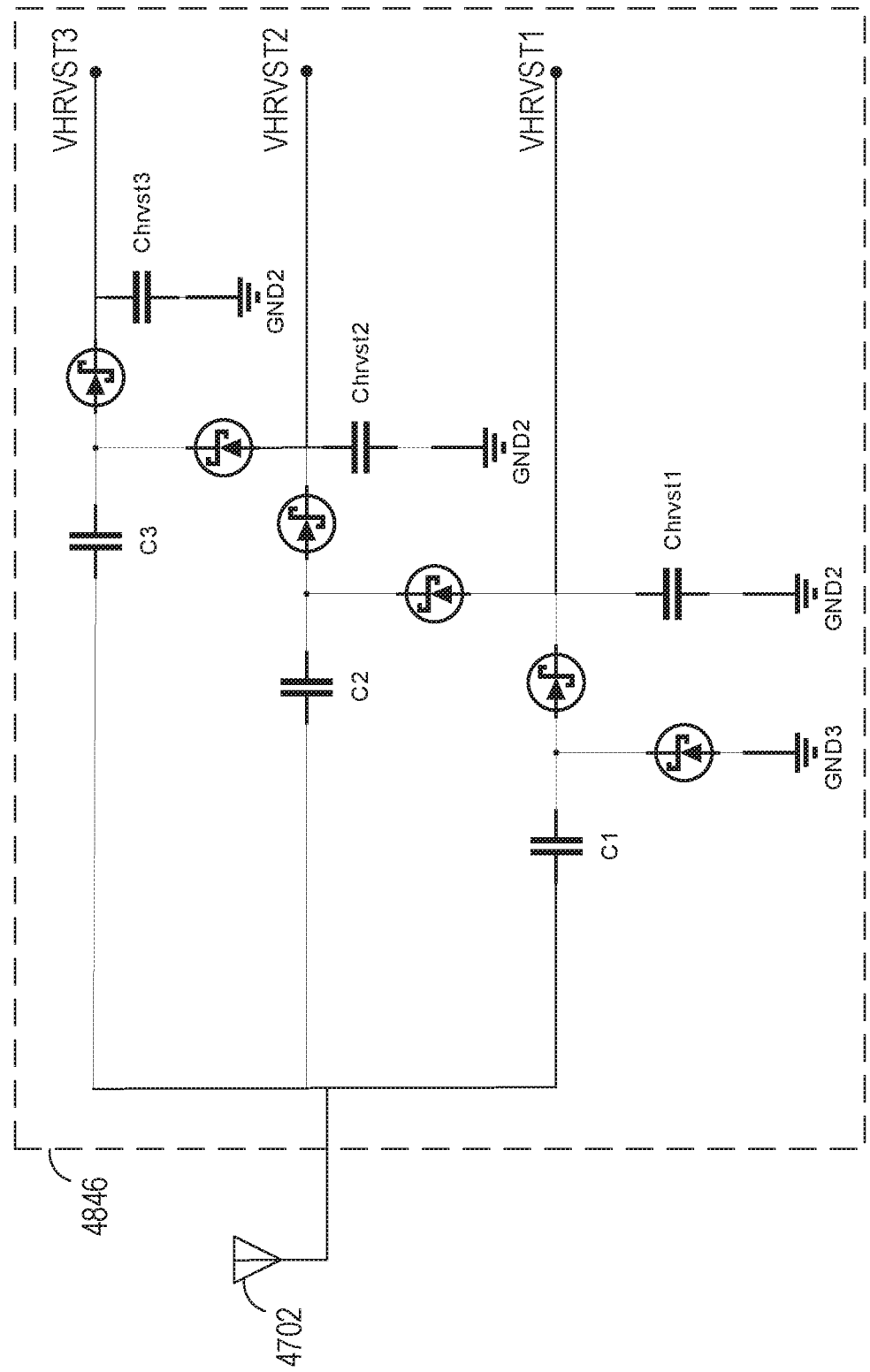
FIG. 49 illustrates generally a schematic showing an example of a multiple-stage rectifier circuit.

FIG. 49 illustrates generally a schematic showing an example of the multiple-stage rectifier circuit 4846. In the example, energy or power signals harvested from an antenna 4702 (e.g., comprising the antenna 108) can be coupled to one or several different legs or stages inside the rectifier, and processed to yield voltage signals for different power domains at each of a first stage capacitor Chrvst1, such as at VHRVST1 (e.g., up to about 1.4 volts), a second stage capacitor Chrvst2, such as at VHRVST2 (e.g., up to about 3.0 volts), and a third stage capacitor Chrvst3, such as at VHRVST3 (e.g., up to about 5.0 volts).

In the example of FIG. 49, the multiple-stage rectifier circuit 4846 comprises discrete stages, with each stage capacitively coupled to the antenna 4702. For example, the capacitors C1, C2, and C3 can be coupled between the antenna 4702 and respective ones of the power domains. Each of the capacitors can be configured to block transmission of DC signal components and pass RF or AC signals. In the example of FIG. 49, inputs to the different power domains are capacitively coupled to the antenna 4702. Following the inputs, each stage is coupled to at least one common node between a series-coupled pair of diodes. A first one of the diodes is coupled between the common node and a reference node, and a second one of the diodes is coupled between the common node and a rectifier output. In an example, the reference node for a first or lowest rectifier stage can be a ground level. The reference node for, for example, a second rectifier stage can be a voltage level corresponding to the first stage. The reference node for a third rectifier stage can be a voltage level corresponding to the second stage, and so on, for each of multiple stages.

Referring again to FIG. 48, a first stage of the rectifier circuit 4846 is selected by the multiplexer circuit 4810 to couple the first power domain at VHRVST1 to the output. Thus a maximum voltage signal available at the output can be VHRVST1 at VDDH.

Figure 50:
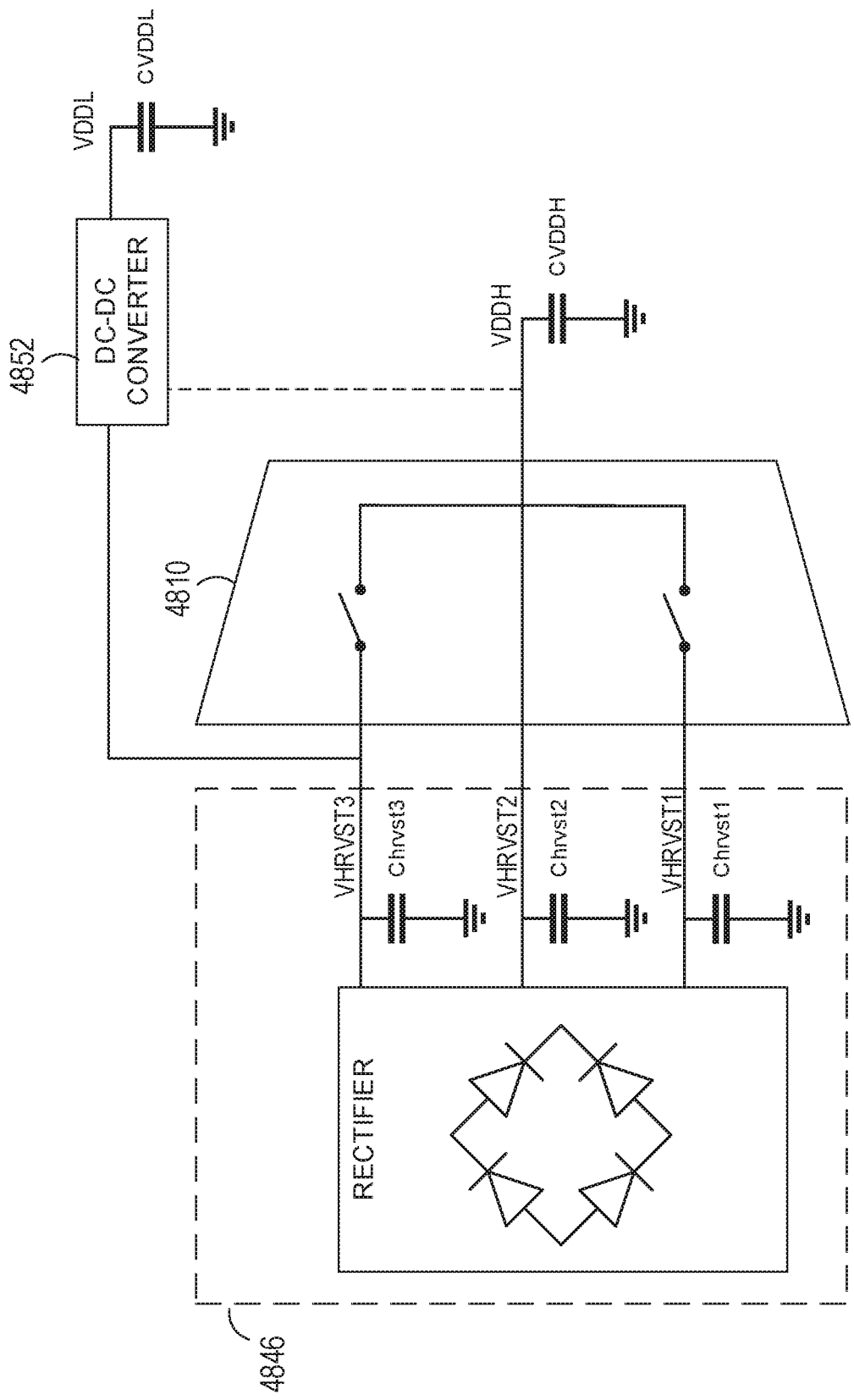
FIG. 50 illustrates generally an example that includes the multiple-stage rectifier circuit from the example of FIG. 48 with its second stage selected for output.
Figure 51:
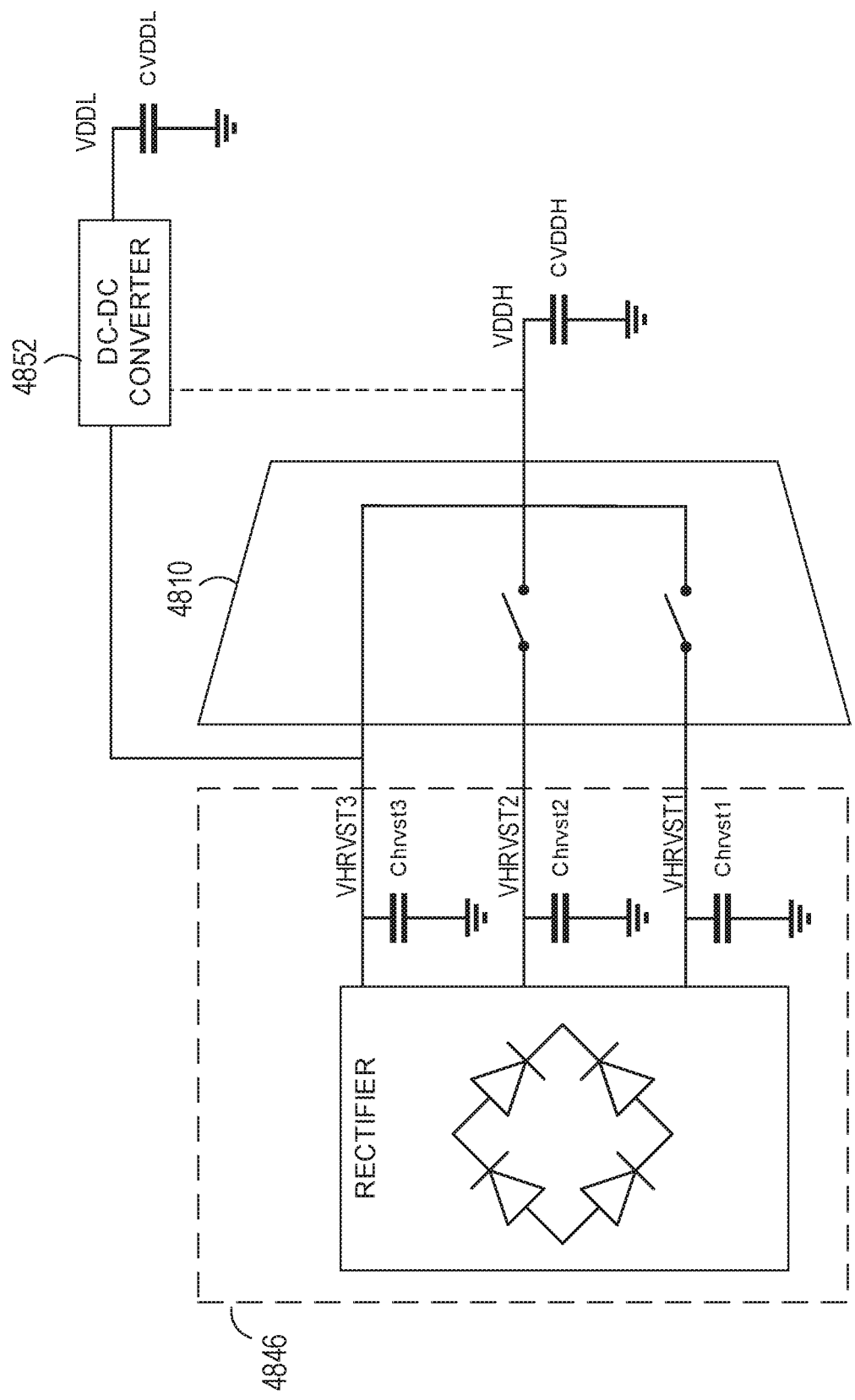
FIG. 51 illustrates generally an example that includes the multiple-stage rectifier circuit from the example of FIG. 48 with its third stage selected for output.

FIG. 50 illustrates generally an example that includes the multiple-stage rectifier circuit 4846 from the example of FIG. 48, with its second stage selected for output at VDDH. In the illustrated configuration, a maximum voltage signal available at the output can be VHRVST2 at VDDH. FIG. 51 illustrates generally an example that includes the multiple-stage rectifier circuit 4846 from the example of FIG. 48 with its third stage selected for output at VDDH. In the illustrated configuration, a maximum voltage signal available at the output can be VHRVST3 at VDDH.

In an example, power signals from the harvested third power domain (e.g., at signal level VHRVST3, such as between about 3.2 and 5.0 VDC) can be used to power startup circuitry on-board the implantable device 110. That is, signals from the third power domain can be used to initiate or power one or more other processor circuits, memory circuits, oscillator circuits, switching circuits, or other circuits that provide one or more functions of the implantable device 110, such as when the implantable device 110 first receives a power signal from a remote (e.g., external) midfield transmitter or when the implantable device 110 is configured to wake from a sleep state or other low power state.

In an example, increasing a number of rectifier stages (e.g., beyond the three stages or power domains shown in the examples) can correspondingly increase a maximum voltage that can be made available for a given RF power received by the antenna. However, increasing an operating voltage or number of stages also corresponds to a decrease in power conversion efficiency through the rectifier, such as due to increases in ohmic or other losses through the various stages of the rectifier.

In the example of FIGS. 48-51, an output from the multiple-stage rectifier circuit 4846 to the third power domain signal level VHRVST3 can be used to "wake up" or initialize other circuitry in the implantable device 110 under low-power conditions. In such a low-power consumption state, the implantable device 110 can be configured to establish communication with, and optionally provide feedback to, the remote midfield transmitter, such as to establish better or more efficient coupling and thereby enhance power transmission to the implantable device 110. After enhanced coupling and better power conversion efficiency is achieved, then a lower level signal from the multiple-stage rectifier circuit 4846 (e.g., at the first or second power domain signal levels VHRVST1 or VHRVST2) can be used by the implantable device 110 to perform one or more other device functions, or can be used for electrostimulation.

For example, a stimulation signal can be prepared using signals from any one or more of the different available power domains. That is, a choice of output from the multiple-stage rectifier circuit 4846 for stimulation can be based on a desired stimulation voltage level or current level. In an example, the stages of the multiple-stage rectifier circuit 4846 can be used as a digital to analog converter (DAC) circuit. In this example, a selected one of the outputs or stages from the rectifier circuit 4846 can be used as a coarse output voltage. The selection of a particular stage to use can be based on feedback from the external transmitter device and/or an RF transmission power level. In an example, parameters such as a specified target stimulation voltage level, a specified RF transmission level of the external transmitter device, a specified duty cycle of the external transmitter device, and a selected stage or output from the multiple-stage rectifier circuit 4846 can be tuned together or optimized, such as in a closed-loop manner, to maximize a transmitted RF power-to-stimulation signal conversion efficiency. Finer adjustment of a stimulation voltage magnitude or waveform can be controlled or provided using a regulator circuit.

In an example, a stimulation signal can include or use a current signal. In this example, a current limiter can be used, such as together with a feedback circuit, to ensure that an available voltage from the rectifier circuit 4846 is sufficiently high to drive the programmed current through an output impedance that can include the stimulation electrodes.

In an example, the implantable device 110 can be configured to communicate with the external source 102 using backscatter communications, such as using the backscatter signal 112. In an example, the implantable device 110 can be configured to receive and load power at particular times and can be configured to reflect power at different times. A digital signal can be derived from the power loading and reflecting times and, in an example, the implantable device 110 can encode in the digital signal various information for communication to the external source 102 or to another receiver. In an example, a modulation depth of the backscatter signal 112 can be changed or enhanced. The modulation depth can be enhanced using a dedicated circuit or using a portion of a multiple-stage rectifier circuit that is configured to provide stimulation or power based on a received midfield signal from the source 102.

Figure 52:
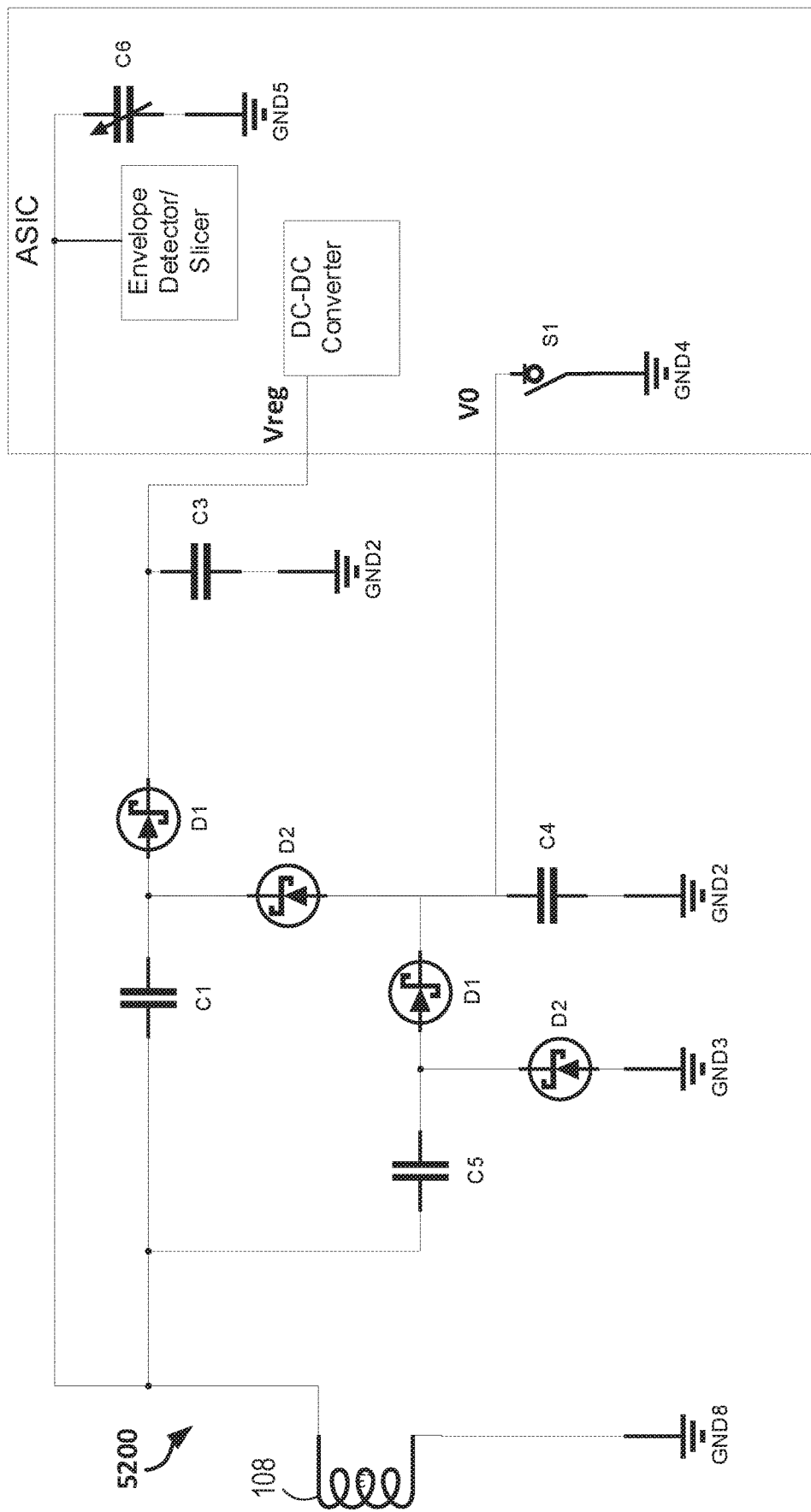
FIG. 52 illustrates generally an example of a first rectifier circuit.

FIG. 52 illustrates generally an example of a first rectifier circuit 5200. The first rectifier circuit 5200 can include a topology or components that are similar to those in the multiple-stage rectifier circuit 4846 illustrated in the example of FIG. 49. In the example of FIG. 52, energy or power signals harvested from the antenna 108 can be coupled to one or several different legs or stages inside the rectifier, and can be processed to provide voltage signals for different power domains at each of multiple different legs or stages. For example, the first rectifier circuit 5200 can include a first stage with a first stage capacitor C4, such as can be charged to V0 (e.g., up to about 1.4 volts), and can include a second stage with a second stage capacitor C3, such as can be charged to Vreg (e.g., up to about 3.0 volts). The first rectifier circuit 5200 can further include an adjustable output capacitor C6.

In an example, the first rectifier circuit 5200 can be configured to increase backscatter modulation depth for both high power and low power modes of the circuit while minimizing parasitic losses such as due to loading on the antenna 108. At low levels of received or harvested power from the antenna 108, for example before Vreg is achieved, a Q-factor of the circuit can be relatively high with high frequency selectivity.

In an example, a capacitance value of the output capacitor C6 can be changed to correspondingly change a tuning or operating frequency of the circuit. Changes in the circuit tuning can lead to corresponding changes in loading and reflected power. When the capacitance value of C6 is changed such that the circuit is detuned, then relatively more power can be reflected (e.g., to the external source 102) and used as the backscatter signal 112. Accordingly, a relatively high degree of modulation depth can be achieved by modulating or changing a value of C6, which in turn changes or shifts a resonant frequency of the first rectifier circuit 5200.

In an example, the first rectifier circuit 5200 is a substantially non-linear circuit, and a voltage magnitude of Vreg is desired to be held steady or fixed. Therefore if a resonant frequency of the first rectifier circuit 5200 changes, then a current at the DC-DC converter input node can correspondingly change to keep Vreg steady. In an example, if a capacitance value of C6 is changed to achieve modulation, such as for use in backscatter communication, then a depth of the modulation signal can be small. For example, when Vreg is achieved, the RF voltage swing can be limited to approximately a center peak voltage of the diode D1, such as can be about Vdiode+(Vreg/4), where Vdiode is the forward voltage threshold of the diode. At higher powers or signal levels, the current increases to maintain Vreg at a steady value. Therefore the Q factor of the receiver decreases or an equivalent series resistance, Rs of the complex impedance, increases. Generally, one cannot simply increase a size of the swing in available capacitance values at the output capacitor C6 because of corresponding parasitic losses and a fixed non-zero baseline capacitance that is proportional to the tunable range of capacitance.

The present inventors have recognized that adding switch S1 at the first power domain can help increase modulation depth. S1 is configured to short the first power domain or first stage of the rectifier. By shorting the first stage of the rectifier, such as to ground or a reference node, an RF swing of the circuit can be reduced to approximately the Vc-p of Vdiode. The switch S1 may not be similarly effective at lower powers since the Vc-p of the RF swing can already be close to Vdiode. In an example, the implantable device 110 can include logic or processor circuitry that is configured to substantially concurrently change C6 and switch the switch S1 to increase modulation depth. In an example, to ease implementation, the first rectifier circuit 5200 can apply its capacitance updates to the output capacitor C6 and can switch the switch S1 all of the time such as without differentiating between low and high power modes even though the modulation depth enhancement is more pronounced in a high power mode.

Figure 53:
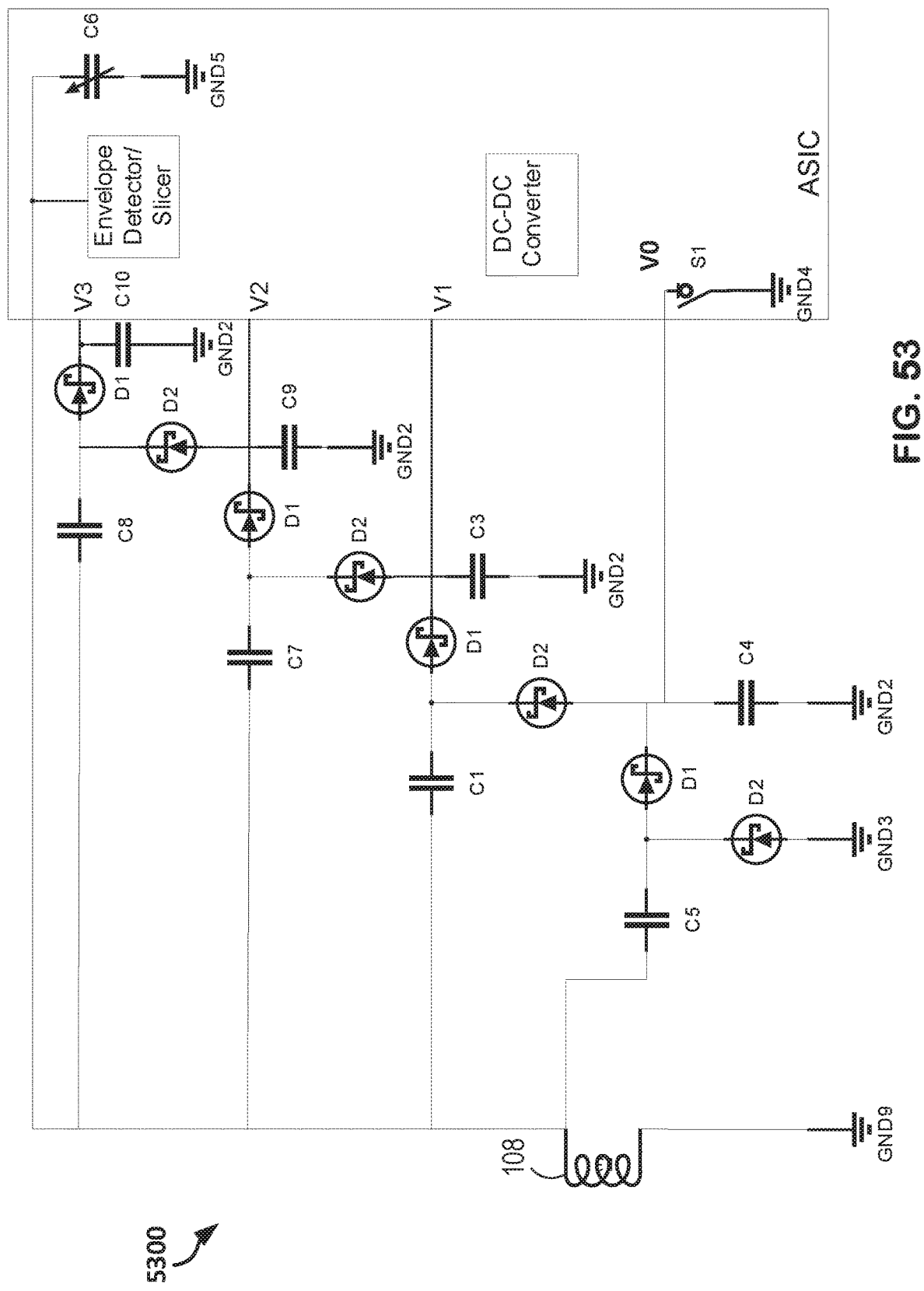
FIG. 53 illustrates generally an example of a second rectifier circuit.

FIG. 53 illustrates generally an example of a second rectifier circuit 5300. The second rectifier circuit 5300 can include a topology or components that are similar to those in the multiple-stage rectifier circuit 4846 illustrated in the example of FIG. 49 however with four stages. In the example of FIG. 53, energy or power signals harvested from the antenna 108 can be coupled to one or several different legs or stages inside the rectifier, and can be processed to provide voltage signals for respective different power domains at each of a first stage capacitor C4, such as at V0, a second stage capacitor C3, such as at V1, a third stage capacitor C9, such as at V2, and a fourth stage capacitor C10, such as at V3. The second rectifier circuit 5300 can include an adjustable output capacitor C6.

The example of FIG. 53 does not include a Vreg leg. Instead, a Q-factor for the circuit can be reduced when any one of the voltage sources V1, V2, or V3, is used for stimulation and current is sunk from that leg or source. The switch S1 can be coupled to the V0 leg of the rectifier and used to shunt power and enhance a modulation depth, such as for use in backscatter communication.

Figure 54:
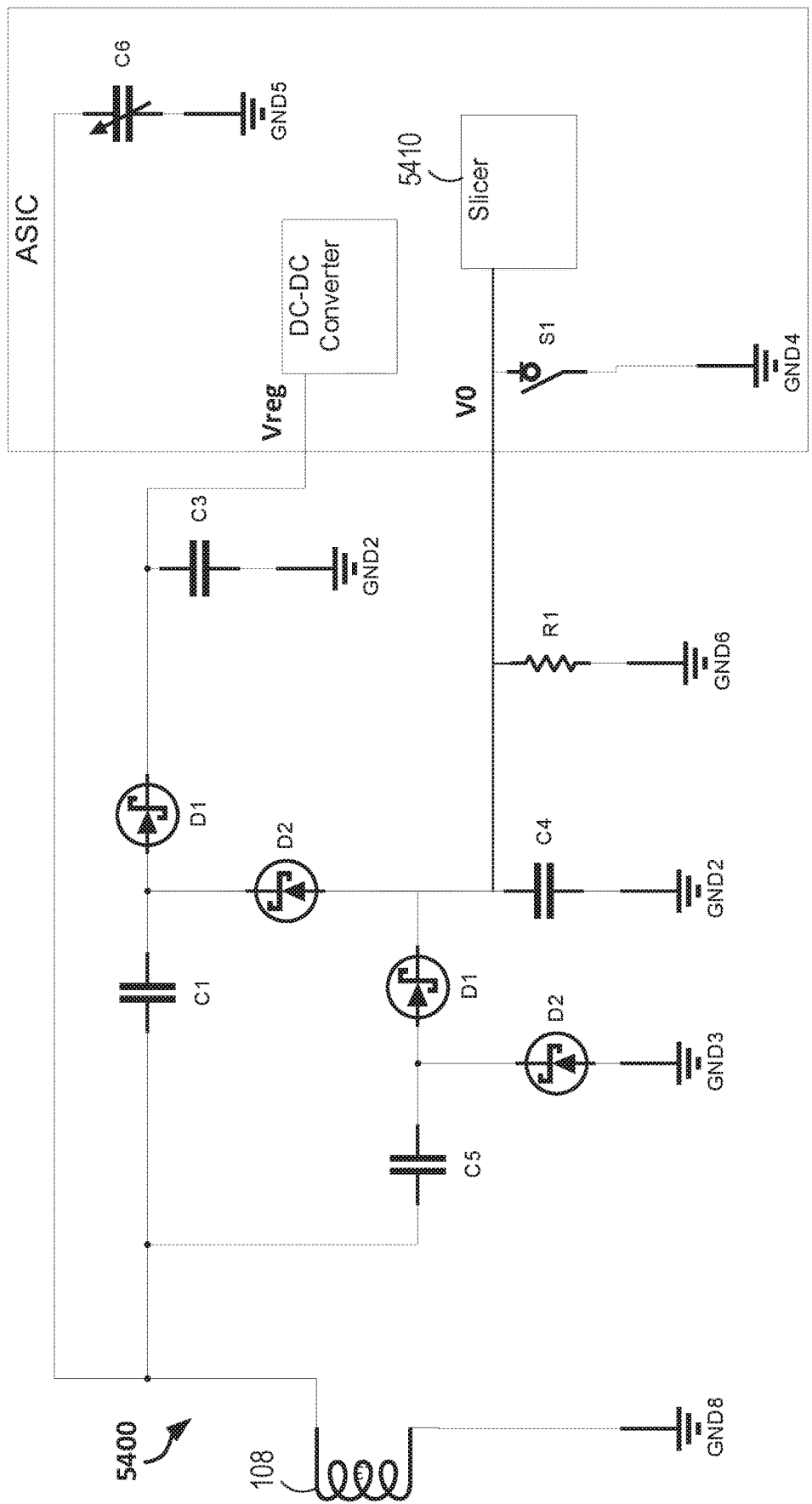
FIG. 54 illustrates generally an example of a third rectifier circuit.

FIG. 54 illustrates generally an example of a third rectifier circuit 5400. The third rectifier circuit 5400 can correspond generally to the example of the first rectifier circuit 5200 from the example of FIG. 52. In the example of FIG. 54, the third rectifier circuit 5400 includes a resistor R1 provided in parallel with the switch S1, and the V0 leg of the rectifier is coupled to a slicer circuit 5410.

In an example, the addition of parallel resistor R1 enables the ASIC input for S1 to be used as a slicer circuit input such as for decoding modulation data (e.g., OOK data) transmitted to the implantable device 110. In the example of FIG. 54, a connection from the antenna 108 to the adjustable capacitor C6 provides an RF input to the ASIC and can be optional since backscatter modulation and data decoding can be performed with an analog RF input. Without this feature, an envelope detector may need to be implemented on-chip, which can compound losses and detract from a capacitance budget to achieve a desired resonant frequency.

In the example of FIG. 54, the resistor R1 and capacitor C4 can be tuned for a particular time constant to allow for data decoding. For example, with a modulation rate of 500 KHz, a time constant of 1 us can be desirable with a C4 value of 5 pF and a R1 value of 200K ohms. In an example, increasing the resistance of the resistor R1 and decreasing a capacitance of the capacitor C4 can help reduce losses in the circuit. However, limitations of reduction of stray capacitances inherent to the electro-mechanical structure and the input impedance of the slicer circuit 5410 can limit an amount by which the values of the resistor R1 and the capacitor C4 can be tuned.

Midfield Receiver Implantation Systems and Methods

Figure 55:
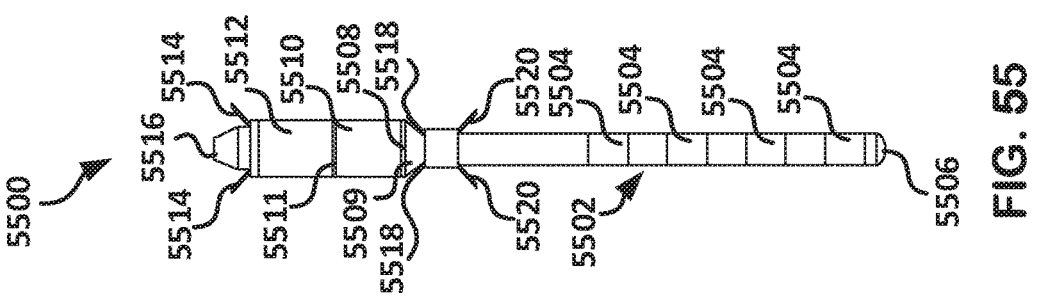
FIG. 55 illustrates generally an example of a side view of an implantable device.

Various systems, devices, and methods can be provided for implantable device insertion, affixation, and removal. FIG. 55 illustrates generally an example of a side view of an implantable device 5500. The implantable device 5500 can comprise all or a portion of the implantable device 110 or one or more other devices discussed herein. The implantable device 5500, as illustrated, includes an elongated, distal body portion 5502. In an example, the body portion 5502 includes or comprises a body portion of the implantable device 110. The body portion 5502 includes a plurality of electrodes 5504 embedded at least partially therein or affixed thereto. The body portion 5502 includes a distal end 5506 and a proximal end 5508. The proximal end 5508 is affixed to a circuitry housing 5510. The circuitry housing 5510 is affixed to an antenna housing 5512. The antenna housing 5512, as illustrated, includes first tines 5514 affixed thereto. In an example, the antenna housing 5512 comprises the antenna housing 610 discussed herein, and the circuitry housing 5510 comprises the circuitry housing 606 discussed herein. In an example, the implantable device 5500 can include other tines affixed thereto such as near the proximal end 5508.

The body portion 5502, electrodes 5504, circuitry housing 5510, and antenna housing 5512 are illustrated, only by way of example, as being generally cylindrical. The implantable device 5500 is configured to be powered wirelessly (e.g., through electromagnetic waves incident on the implantable device 5500 from external to the tissue in which the implantable device 5500 is implanted). The implantable device 5500 is configured to provide electrical stimulation to a therapy site within a patient (e.g., a human or other animal patient). The implantable device 5500 can be situated within a patient using the method discussed regarding FIGS. 56-68.

The body portion 5502 can include a flexible material. The flexible material can include polyurethane, silicone, or epoxy. The flexible material can provide the ability to shape the body portion 5502, such as while the body portion is internal to the patient.

The electrodes 5504 illustrated include an electrode array of four stimulation electrodes 5504 along the body portion 5502. The electrodes 5504, in one or more embodiments, include platinum, iridium, stainless steel, titanium, titanium nitride, or other biocompatible, conductive material. In one or more embodiments, the electrodes include a platinum and iridium alloy, such as a combination that is 90% platinum and 10% iridium. In one or more embodiments, the electrodes 5504 are electrically separated from one another, such as by one or more electrical switches. The electrodes 5504 are respectively, electrically connected to a circuit hermetically enclosed in the circuitry housing 5510.

The circuitry housing 5510 can provide a hermetic enclosure for the circuitry therein. The circuitry housing 5510 can include titanium (e.g., commercially pure, 6Al/4V or another alloy), stainless steel, or a ceramic material (such as zirconia or alumina, for example), or other hermetic, biocompatible material. The circuitry housing 5510 provides an airtight space for the circuitry. If a metallic material is used for the circuitry housing 5510, the circuitry housing 5510 can be used as part of the electrode array, effectively increasing the number of selectable electrodes 5504 for stimulation. FIGS. 89 and 90 illustrate a method of forming a hermetic circuitry housing 5510.

The antenna housing 5512 can be attached at a proximal end 5511 of the circuitry housing 5510. An antenna within the antenna housing 5512 can be used for powering and communication to and/or from the implantable device 5500, such as from a device external to the medium in which the implantable device 5500 is situated. Portions of an embodiment of the antenna housing 5512 are illustrated in further detail in FIGS. 20-25, FIGS. 85-87, and FIG. 93, among others.

Tines 5514 can be attached at a proximal portion of the antenna housing 5512 (e.g., a portion of the antenna housing 5512 that faces a surface of the tissue 5728 (see FIG. 57) after implantation). The first tines 5514 can provide the ability to affix the implantable device 5500 at a specific location within the tissue. The first tines 5514 can be configured to affix the implantable device 5500 to or near a specific anatomical structure. The first tines 5514 can be made of a polymer or other flexible or semi-flexible material, such as can include silicone, polyurethane, epoxy, or like materials. The first tines 5514 can flare away from a central or longitudinal axis of the antenna housing 5512 such that a distal portion of a given one of the first tines 5514 can be closer to the central axis than a more proximal portion of the same tine, such as is shown in FIG. 55, among other FIGS. An end of the first tines 5514 that is not attached to the antenna housing 5512 (e.g., a free end of a tine) can be closer to a tissue surface (e.g., after implantation) than an end of the first tines 5514 that is attached to the antenna housing 5512. Such a configuration can help ensure that the implantable device 5500 does not migrate or wander toward the tissue surface such as when a patient moves or progresses through various regular activities.

Second tines 5518 and third tines 5520 can be attached near a proximal end of the body portion 5502. The second and third tines 5518 and 5520 can be similar to the first tines 5514 but can be attached to the implantable device 5500 at a different location along the longitudinal axis of the device. The second and third tines 5518 and 5520 can be attached to the device 5500 near the proximal end 5508. An end of the second tines 5518 that is not attached to the body portion 5502 (e.g., a free end of the second tines 5518) can be closer to a tissue surface than an end of the second tines 5518 that is attached to the body portion 5502. Such a configuration can help ensure that the implantable device 5500 does not wander or migrate after implantation. An end of the third tines 5520 that is not attached to the body portion 5502 (e.g., a free end of the third tines 5520) can be further from a tissue surface than an end of the third tines 5520 attached to the body portion 5502. Such a configuration can help ensure that the implantable device 5500 does not wander or migrate after implantation.

A push rod interface 5516 can be situated on a proximal end of the implantable device 5500. The push rod interface 5516 can be sized and shaped to mate with a push rod (see FIGS. 26-30, among others). More details regarding embodiments of some of the components of the implantable device 5500 are provided regarding other FIGS. and elsewhere herein.

Figure 56:
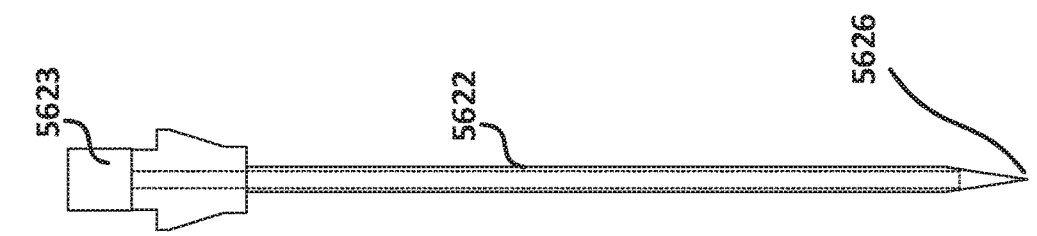

FIGS. 56-68 illustrate generally side view diagrams of portions of a process for implanting a device in tissue. FIG. 56 illustrates, by way of example, a side view diagram of an embodiment of a needle 5622 and stylet 5623. The needle 5622 includes a hollow point 5626 to pierce through tissue and allow a guidewire 5624 to slide therethrough. The needle 5622 can be made of metal, such as can include a biocompatible metal, such as platinum, titanium, iridium, nitinol, or the like. The needle 5622 includes a lumen (e.g., a tubular structure) through which the guidewire 5624 can be situated.

The stylet 5623 is a structure that fills a lumen of the needle 5622. The stylet 5623, when inserted in the needle 5622, can help prevent material from getting into the lumen of the needle 5622 as the needle 5622 is advanced through tissue.

Figure 57:
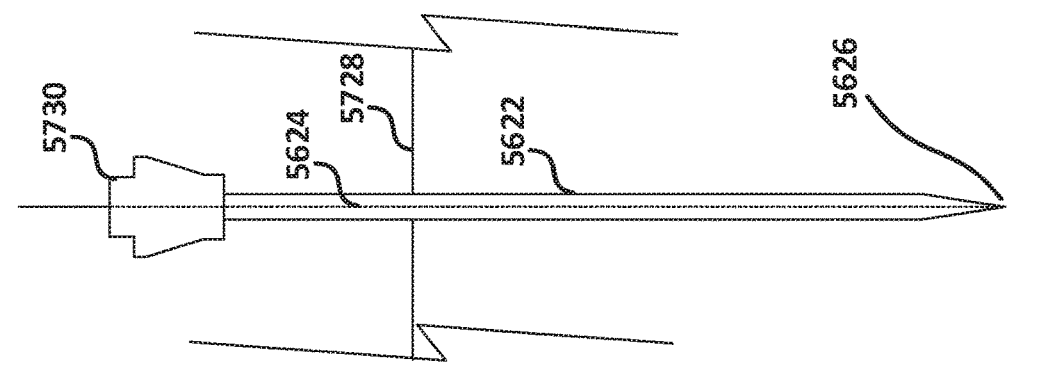

FIG. 57 illustrates, by way of example, a side view diagram of the needle 5622 and the guidewire 5624 partially situated in tissue 5728 after the stylet 5623 is removed. The needle 5622 can pierce the surface of the tissue 5728 and tissue 5728 below the surface thereof. The needle 5622 can be pushed, generally by a handle 5730, until the point 5626 is near an implant site for the implantable device 5500. The needle 5622 can be situated in a desired location and orientation in the tissue 5728. The guidewire 5624 can be pushed through the needle 5622 until it is at or near the point 5626.

The guidewire 5624 provides a structure over or around which other tools can be inserted into an implant site. The guidewire 5624 can be inserted, using the needle 5622, to a location near which the implantable device 5500 is to be implanted. The guidewire 5624 can be made of a biocompatible metal material, such as can include platinum, titanium, iridium, nitinol, or the like.

Figure 59:
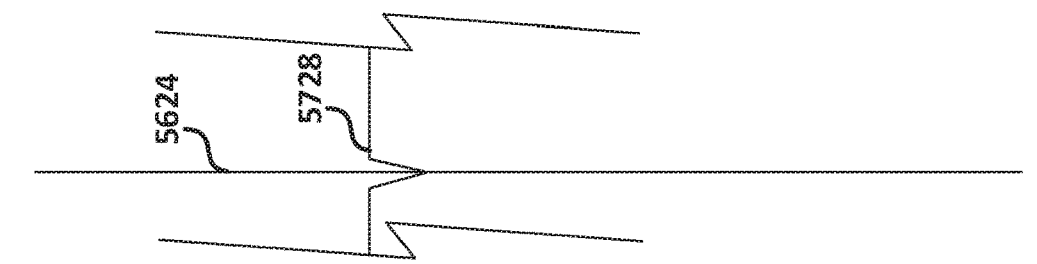
Figure 58:
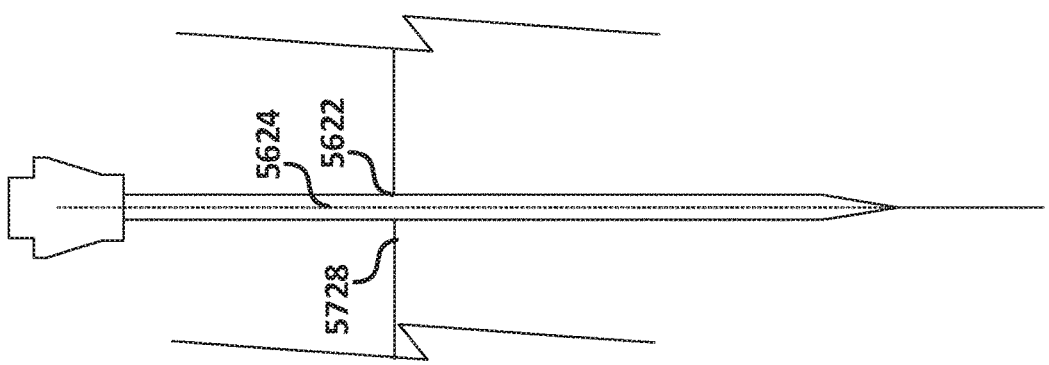

FIG. 58 illustrates, by way of example, a side view diagram of an embodiment of the needle 5622 partially removed from the tissue 5728. The guidewire 5624 can be left in the tissue 5728 after removal of the needle 5622, as illustrated in FIG. 59. The guidewire 5624 can provide a path to the implant site for other implantation tools or the implantable device 5500.

Figure 60:
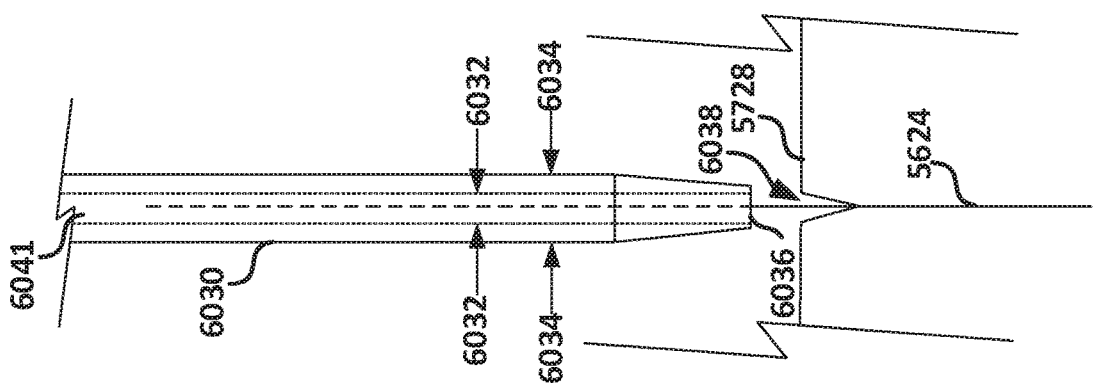

FIG. 60 illustrates, by way of example, a side view diagram of an embodiment of a dilator 6030 situated over a portion of the guidewire 5624. The dilator 6030 includes a lumen 6041 through which the guidewire 5624 can travel. The lumen 6041 includes a diameter (indicated by arrows 6032) sufficient to accommodate the guidewire 5624. The dilator 6030 can be tapered at a distal end 6036. The taper can make it easier to insert the dilator 6030 in a hole 6038 in the tissue 5728, as compared to dilators without the taper. The taper can make it easier to widen the hole 6038, as compared to dilators without the taper. The dilator 6030 can be pushed into the hole 6038 in the tissue 5728 formed by the needle 5622. The dilator 6030 can widen the hole 6038 to the outer diameter (indicated by arrows 6034). The dilator 6030 can include a metal or other rigid structure. The rigid material can prevent kinking, crushing, and buckling of the dilator 6030 due to force from the fascia or bone.

Figure 61:
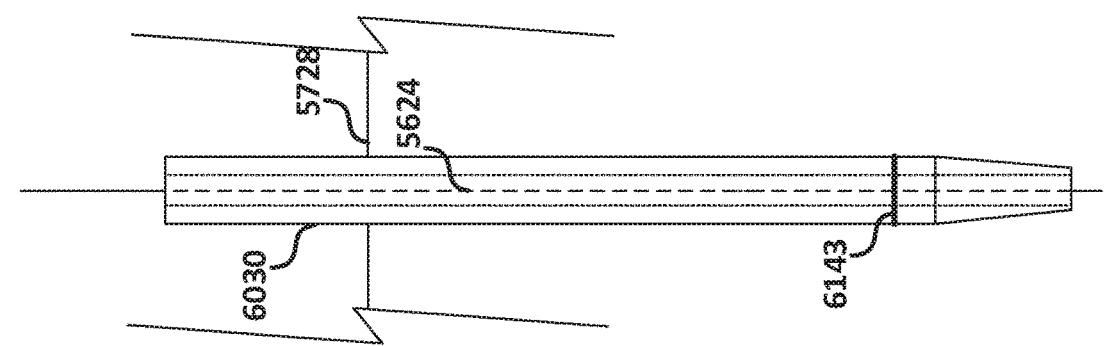

FIG. 61 illustrates, by way of example, a side view diagram of an embodiment of the dilator 6030 pushed through the surface of the tissue 5728 and into the hole 6038. The end 6036 can be situated near the implant site. The dilator 6030 can include a radiopaque marker 6143. The radiopaque marker 6143, such as under fluoroscopy, can help guide the dilator 6030 to the implant site. The radiopaque marker 6143 can be near the end 6036 of the dilator 6030, such as to be located near the tapered portion of the dilator 6030.

Figure 62:
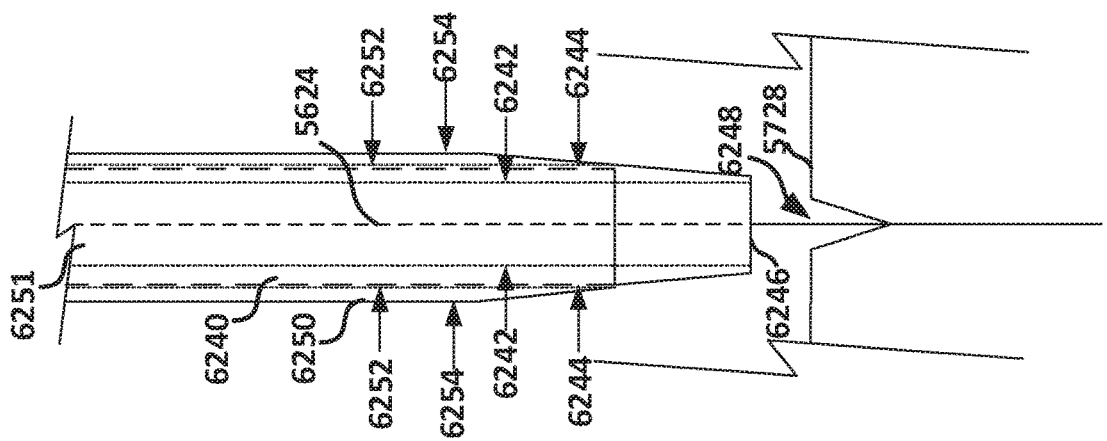

FIG. 62 illustrates, by way of example, a side view diagram of an embodiment of the dilator 6030 removed from the tissue, and another dilator 6240 situated in a catheter 6250 and directed toward the surface of the tissue 5728. The dilator 6240 includes a lumen 6251 through which the guidewire 5624 can travel. The lumen 6251 includes a diameter (indicated by arrows 6242) sufficient to accommodate the guidewire 5624. The dilator 6240 can be tapered at a distal end 6246. The taper can make it easier to insert the dilator 6240 in the widened hole 6248 produced by the dilator 6030, as compared to dilators without the taper.

The dilator 6240 can be pushed into the hole 6248 in the tissue 5728 formed by the dilator 6030. The dilator 6240 can widen the hole 6248 to the outer diameter (indicated by arrows 6244). The dilator 6240 can include a metal or other rigid material. The rigid material can prevent kinking, crushing, and buckling of the dilator 6240 due to force from the fascia or bone.

The dilator 6240 can widen the hole 6248 produced by pushing the dilator 6030 through the tissue 5728. For example, the dilator 6030 can widen the hole to about 5 French (e.g., about 1.6667 mm) and the dilator 6240 can widen the hole further, to about 7 French (e.g., about 2.3333 mm). These dimensions are merely examples and can be varied for the application.

The catheter 6250 can include a lumen through which the dilator 6240 can pass. The inner diameter of the catheter 6250 can be sufficient to accommodate a maximum width of the implantable device 5500. The maximum width of the implantable device 5500 is the greatest length perpendicular to the length (the longest dimension) of the implantable device 5500. In the example of the implantable device 5500 of FIG. 55, a maximum width is the width of the circuitry housing 5510 or the antenna housing 5512. Since the tines 5514, 5518, and 5520 are flexible, they do not need to be considered in the width determination. The catheter 6250 can include an inner diameter (indicated by arrows 6252) and an outer diameter (indicated by arrows 6254). The catheter 6250 with the dilator 6240 inserted therein, can be pushed (e.g., manually) toward and into the hole 6248. The catheter 6250 can include a metal or other rigid material. The rigid material can prevent kinking, crushing, and buckling of the catheter 6250 due to force from the fascia or bone.

The catheter 6250 can include a radiopaque marker 6257 situated near a distal end thereof. The radiopaque marker 6257, under fluoroscopy, can help an entity visualize a location or the radiopaque marker 6257. In embodiments in which the implantable device 5500 is to be situated near a sacral nerve, the radiopaque marker 6257 can be located in an opening in bone known as the S3 foramen.

Figure 63:
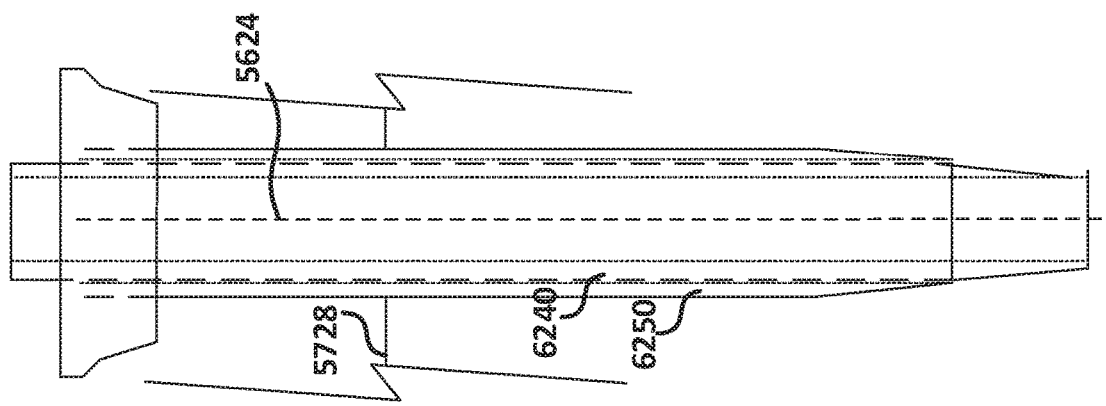
Figure 64:
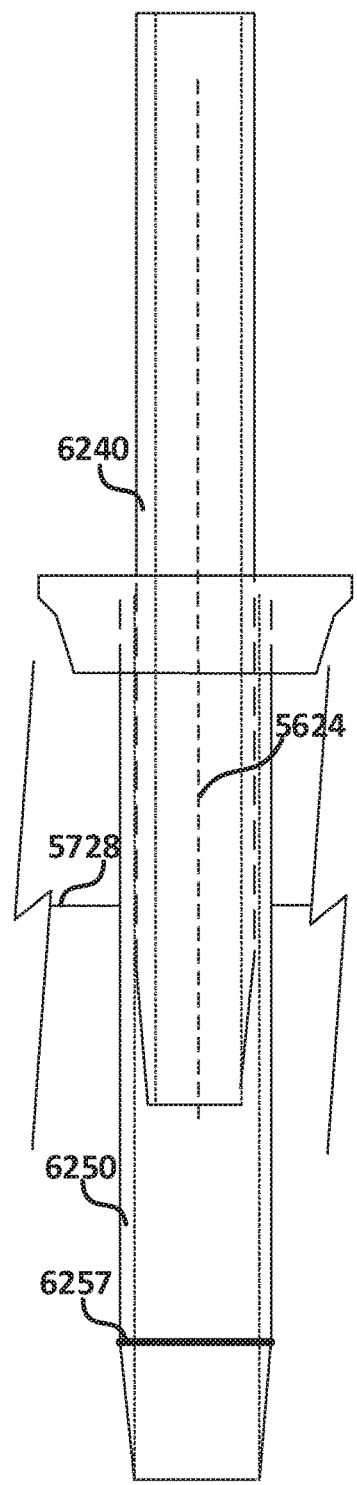

FIG. 63 illustrates, by way of example, a side view diagram of an embodiment of the dilator 6240 and catheter 6250 inserted into position in the tissue. FIG. 64 illustrates, by way of example, a side view diagram of an embodiment of the dilator 6240 and guidewire 5624 being removed, leaving the catheter 6250 in the tissue. In some embodiments, the guidewire 5624 may be removed before or after the dilator 6240 or the guidewire 5624 may be removed simultaneously with the dilator 6240.

Figure 65A:
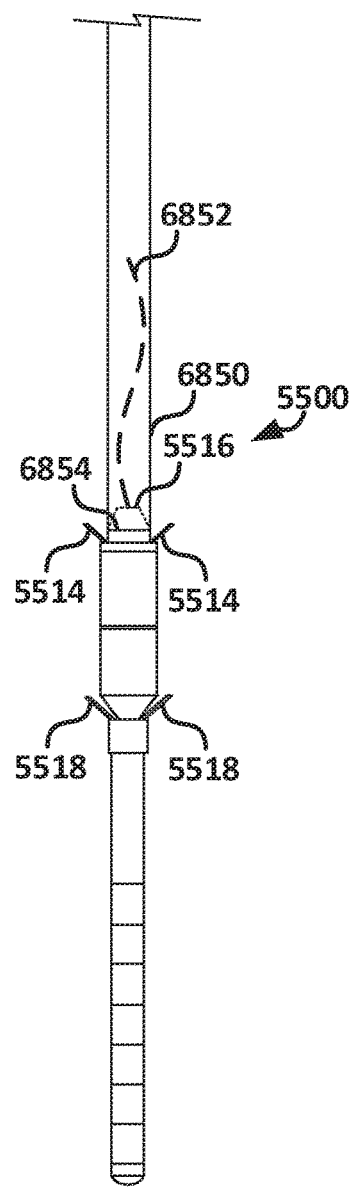

FIG. 65A illustrates, by way of example, a diagram of an example of the implantable device 5500 mated with a push rod 6850. In the example of FIG. 65A, the implantable device 5500 includes a proximal portion that can include or use tine structures, such as can be configured to help prevent migration of the implantable device 5500 when the device is implanted in tissue. In the example of FIG. 65A, the implantable device 5500 includes first tines 5514 and second tines 118. The first or second tines 114 and 118 can be configured to extend radially away from a longitudinal axis of the implantable device 5500, and the first and second tines 114 and 118 can be similarly or differently dimensioned. In an example, the first or second tines 114 or 118 can be angled such as to extend radially away from and in a longitudinal direction of the implantable device 5500. In the example of FIG. 65A, the first tines 5514 and the second tines 118 extend or are angled in substantially the same direction, that is, radially away from the longitudinal axis and toward the proximal portion.

Figure 65B:
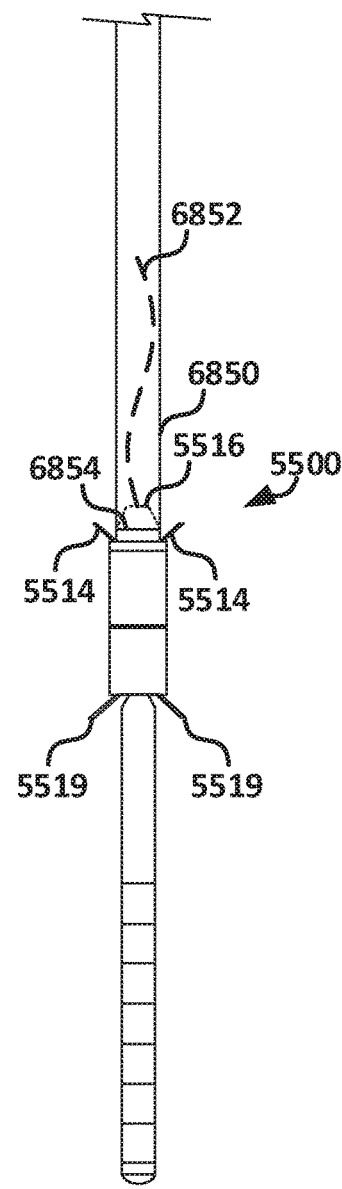

FIG. 65B illustrates, by way of example, a diagram of an example of the implantable device 5500 mated with a push rod 6850 and including other tine structures. The example of FIG. 65B includes the first tines 5514 and includes fourth tines 5519. The fourth tines 5519 can be configured to extend radially away from a longitudinal axis of the implantable device 5500 and can be configured to extend in a direction opposite from the first tines 5514. That is, the fourth tines 5519 can be configured to extend or to be angled toward a distal portion of the implantable device 5500. In an example, the implantable device 5500 and/or a delivery device coupled thereto can be configured to retain the fourth tines 5519 in an undeployed configuration during implantation and the fourth tines 5519 can be released and expanded when the implantable device 5500 is positioned at a target tissue site. The oppositely oriented first tines 5514 and fourth tines 5519 can help prevent migration of the implantable device 5500 away from the target tissue site.

The implantable device 5500 can include a suture 6852 extending from a proximal end thereof. The suture 6852 may extend beyond the surface of the tissue 5728 (after implantation), to be external to the entity in which the implantable device 5500 is situated after the implantation. The suture 6852 may provide a structure that may be pulled, such as to extract the implantable device 5500 from the tissue.

The push rod 6850 can include a distal interface 6854 configured to mate with the push rod interface 5516 of the implantable device 5500. The push rod 6850 is described in more detail for example at FIGS. 26-30, among others.

Figure 66:
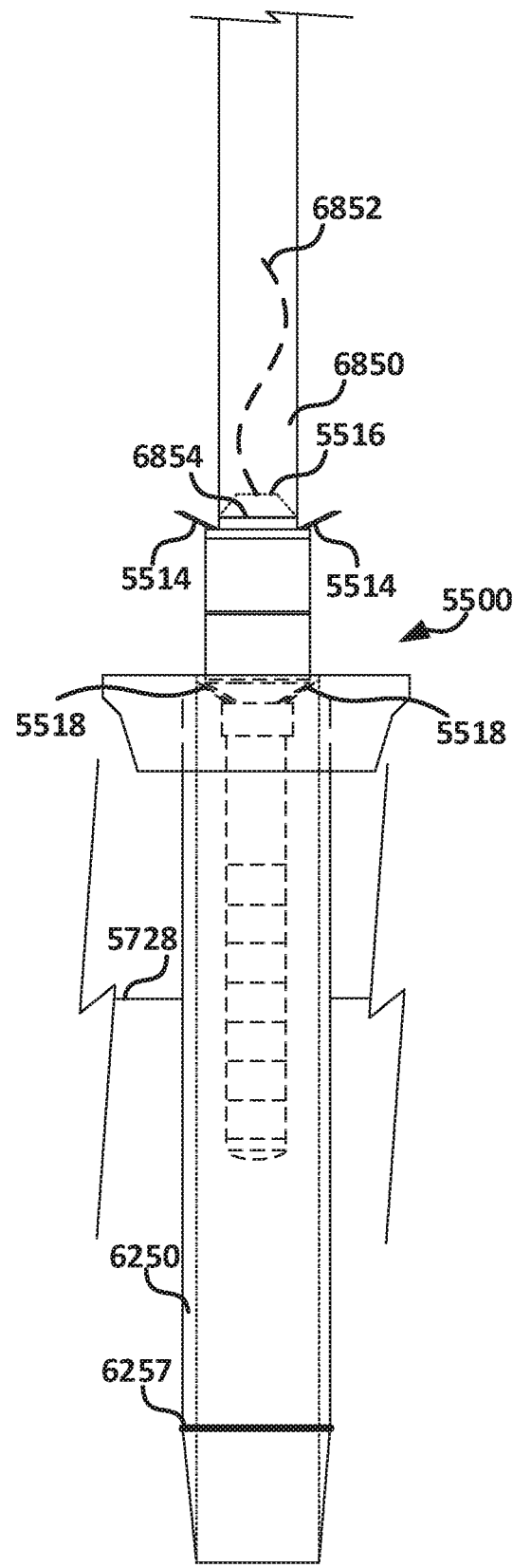

FIG. 66 illustrates, by way of example, a diagram of an embodiment of the implantable device 5500 being pushed into the catheter 6250 by the push rod 6850. The tines 5514 and 5518 (or other tines) can be collapsed against the inner wall of the catheter 6250 as they are inserted into the catheter 6250. Note that other tines, such as the tines 5520, are not illustrated, but can be included in the implantable device 5500.

FIG. 67 illustrates, by way of example, a diagram of an embodiment of the implantable device 5500 pushed into position in the tissue 5728 and through the catheter 6250, and the catheter 6250 pulled out to deploy the tines 5514 and 5518. The implantable device 5500 may be situated such that the suture 6852 is partially internal to the tissue 5728 and partially external to the tissue 5728 in which the implantable device 5500 is situated.

The push rod 6850 can include a marker 6760 indicating how far to push the push rod 6850 into the tissue 5728. An entity performing the implantation can know that the implantable device 5500 is in the proper location when the marker 6760 is at or near a proximal end 6770 of the catheter 6250 or a surface of the tissue 5728.

The marker 6760 on the pushrod 6850 can be situated such that the electrodes 5504 are at the right positions when the marker 6760 is aligned with the proximal end of the catheter 6250. The marker 6760 is visible to the naked eye. At this point, the tines 5514 and 5518 (or other tines) are still within the catheter 6250 and not yet deployed. After the entity performing the implantation is confident of the electrode placement (e.g., through x-ray (fluoroscope)), the entity can pull the catheter 6250 toward the surface of the tissue 5728, releasing the tines 5514 and 5518. Confirmation with fluoroscopy can be done to confirm that the implantable device 5500 remains properly situated.

FIG. 68 illustrates, by way of example, a diagram of an embodiment that includes the push rod 6850 and catheter 6250 removed from the tissue, leaving the implantable device 5500 implanted in the tissue.

An example implant procedure consistent with FIGS. 56-68 is provided herein regarding implanting the implantable device 5500 near a sacral nerve through an S3 foramen. An entity or operator can palpate the sciatic notches to landmark S3 and S4. A sterile surgical marker can be used to identify the boney landmarks. A fluoroscopy device can be maneuvered into position to provide fluoroscopic imaging or mapping of the S3 sacral region to allow for location of a midline of sacrum, sacroiliac (SI) joints, sciatic notches, medial foraminal borders or the sacral foramena. In an example, C-Arm fluoroscopy can be used during device insertion.

The foramen needle 5622 can be situated approximately 2 cm cephalad to the sacroiliac joints and 2 cm lateral to a sacral midline, feeling for foraminal margins until the S3 foramen is identified and penetrated. If necessary, an operator can adjust positioning by removing the needle 5622 and reinserting. Using fluoroscopy, an operator can ensure the insulated foramen needle 5622 is inserted into the foramen with an approximate angle (e.g., a 60-degree insertion angle) relative to the skin (e.g., surface of the tissue 5728). The needle 5622 can enter the foraminal canal perpendicular to the bony surface. This can position the needle 5622 substantially parallel to the sacral nerve. An operator can confirm the location, orientation, and depth of the needle 5622 fluoroscopically and, if necessary, adjust positioning by removing the needle and reinserting. Images can be saved throughout the implantation process for later reference or comparison.

The stylet 5623 can be removed from the needle 5622 and discarded. The guidewire 5624 can be provided through the needle until a mark (not illustrated) on the guidewire 5624 reaches the top of the needle 5622. The foramen needle 5622 can be withdrawn over the guidewire 5624 while holding the guidewire 5624 stable. The needle 5622 can be discarded.

A stab incision can be made along the guidewire 5624 prior to inserting dilator 6030. The dilator 6030 can be provided over the guidewire 5624 and advanced into the tissue 5728 such as until the distal tip 6036 of the dilator 6030 is provided at an anterior surface of the sacrum. If required, an operator can rotate the dilator 6030 to help advance it into the tissue. The dilator 6030 can be withdrawn while keeping the guidewire 5624 stable. The dilator 6030 can be discarded.

The combined dilator 6240 and catheter 6250 can be advanced over the guidewire 5624 into the tissue 5728 such as until the radiopaque marker 6257 is midway between the anterior and posterior surfaces of the sacrum. If required, an operator can rotate the dilator 6240 and catheter 6250 to help advance it into the tissue 5728. An operator can remove the guidewire 5624 while leaving the dilator 6240 and catheter 6250 in position. The guidewire 5624 can then be discarded.

In an example, the dilator 6240 can be removed, leaving the catheter 6250 in position, and the dilator 6240 can be discarded. The implantable device 5500 and the push rod 6850 can be connected, such as by mating the push rod interface 5516 with an implantable device interface 8022, to create a push rod assembly. The push rod assembly can be advanced into the catheter 6250, distal tip of the implantable device 5500 first. The assembly can be advanced until the marker 6760 on the push rod 6850 reaches the top of the catheter 6250. The push rod 6850 can be rotated to position the implantable device 5500.

Using fluoroscopy, an operator can confirm that the implantable device 5500 is in the proper position. A most proximal electrode 5504 from the distal tip 5506 can be aligned with the radiopaque marker 6257 on the sheath. An image of the implantable device 5500 under fluoroscopy can be saved. The position of the implantable device 5500 can be adjusted if required (and confirmed with fluoroscopy).

Firmly keeping the push rod 6850 in place with one hand, an operator can use a different hand to partially withdraw the catheter 6250 until it meets a handle of the push rod 6850 and cannot withdraw further. This can expose the tines on the implantable device 5500. The length of the push rod 6850 can generally be sufficient to insert the implantable device 5500 into the catheter 6250 and allow the catheter 6250 to be withdrawn to expose the tines.

Using fluoroscopy, an operator can verify a location of the implantable device 5500 such as to determine whether the device has or has not moved. A position of the implantable device 5500 can then be adjusted by the operator, if necessary. A luer cap (see, e.g., FIG. 82) can be removed from the push rod 6850. The push rod 6850 can be removed about a quarter to about half way out of the catheter 6250. Using fluoroscopy, it can again be confirmed by an operator whether the implantable device 5500 remains in the same or target position. If the implantable device 5500 has not moved, then the push rod 6850 can be removed over the suture 6852 attached to the proximal end of the implantable device 5500. The radial tines (e.g., tines 5514, 5518, 5519, or 5520) on the implantable device 5500 can generally maintain the implantable device 5500 in its desired axial position. The push rod 6850 can be discarded.

If the implantable device 5500 has moved, then while holding the suture 6852 taut, an operator can re-insert the push rod 6850 to properly position the implantable device. Push rod 6850 removal steps can be repeated after the implantable device 5500 is in a target or correct position. Using fluoroscopy, an operator can determine whether the implantable device 5500 has migrated or moved. The catheter 6250 can then be at least partially removed. Using fluoroscopy, an operator can confirm the implantable device 5500 has still not moved. If the implantable device 5500 has not moved, then the operator can continue to remove the catheter 6250 and discard the catheter 6250. The operator can then use fluoroscopy to visualize a position of the implantable device 5500 such as relative to a target tissue site. If necessary, the operator can adjust a position of the implantable device 5500 by, for example, pulling on the suture 6852.

Figure 69:
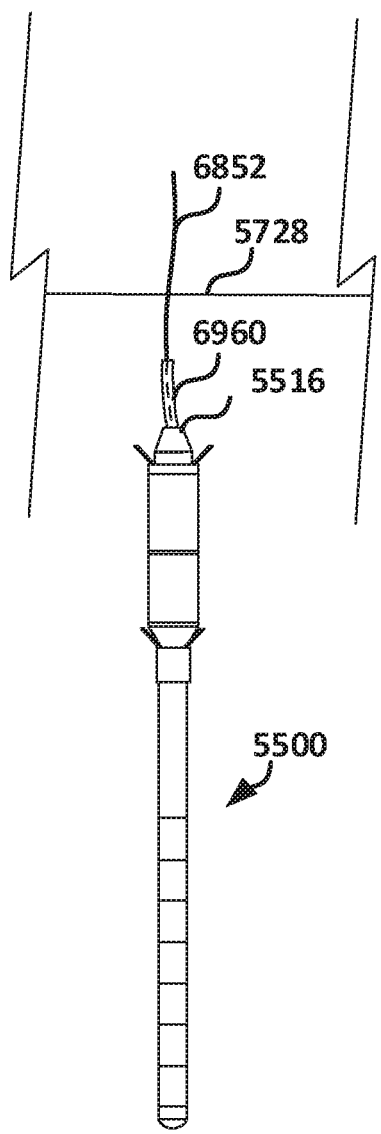
FIG. 69 illustrates, by way of example, a diagram of another embodiment of the implantable device left implanted after a catheter and push rod are fully removed.

FIG. 69 illustrates, by way of example, a diagram of another embodiment of the implantable device 5500 left implanted after the catheter 6250 and the push rod 6850 are fully removed. To extract the implantable device 5500, the suture 6852 can be pulled away from the surface of the tissue 5728. The push rod interface 5516 can be tapered, such as to help make extracting the implantable device 5500 easier (require less force) or cause less damage to the tissue in which the implantable device 5500 was implanted.

Extraction by pulling on the suture 6852 can be difficult. To help with the extraction, a sheath 6960 can be situated around a distal portion of the suture 6852 (the portion of the suture 6852 attached to the implantable device 5500). The sheath 6960 can include a flexible polymer material, such as can include pebax, polyurethane, nylon, polyethylene, polypropylene, or the like. The sheath 6960 may help protect the proximal portion of the suture 6852 from becoming affixed to tissue. The tissue may heal on and around the suture 6852, such as to make extraction of the implantable device 5500 more difficult. The sheath 6960 may protect the suture 6852 from such healing and provide a larger space between the suture 6852 and the surrounding tissue than is realized without the sheath 6960.

Figure 70:
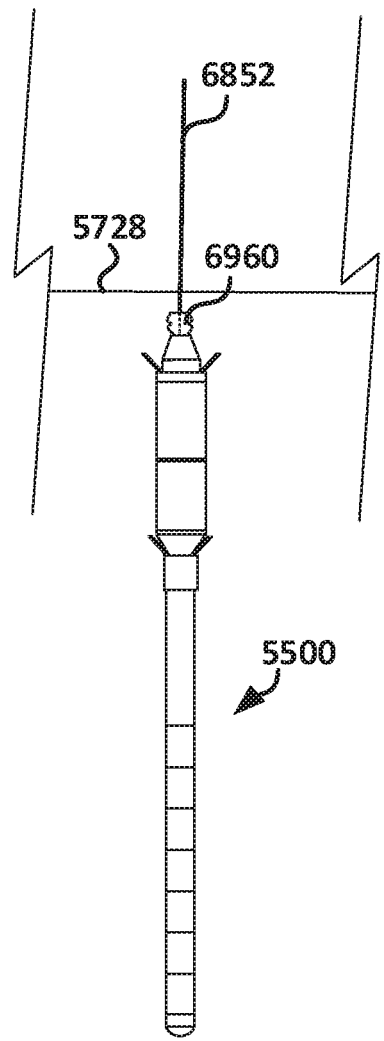
FIG. 70 illustrates, by way of example, a diagram of an embodiment of the implantable device after the suture is pulled and the implantable device begins travelling toward the surface of the tissue.

FIG. 70 illustrates, by way of example, a diagram of an embodiment of the implantable device 5500 after the suture 6852 is pulled and the implantable device 5500 begins travelling toward the surface of the tissue 5728. The sheath 6960 may collapse in response to movement through the tissue 5728. Collapse of the sheath 6960 may help form a path for extraction of the implantable device 5500.

Midfield Receiver Components, Assembly, and Tuning

Figure 71:
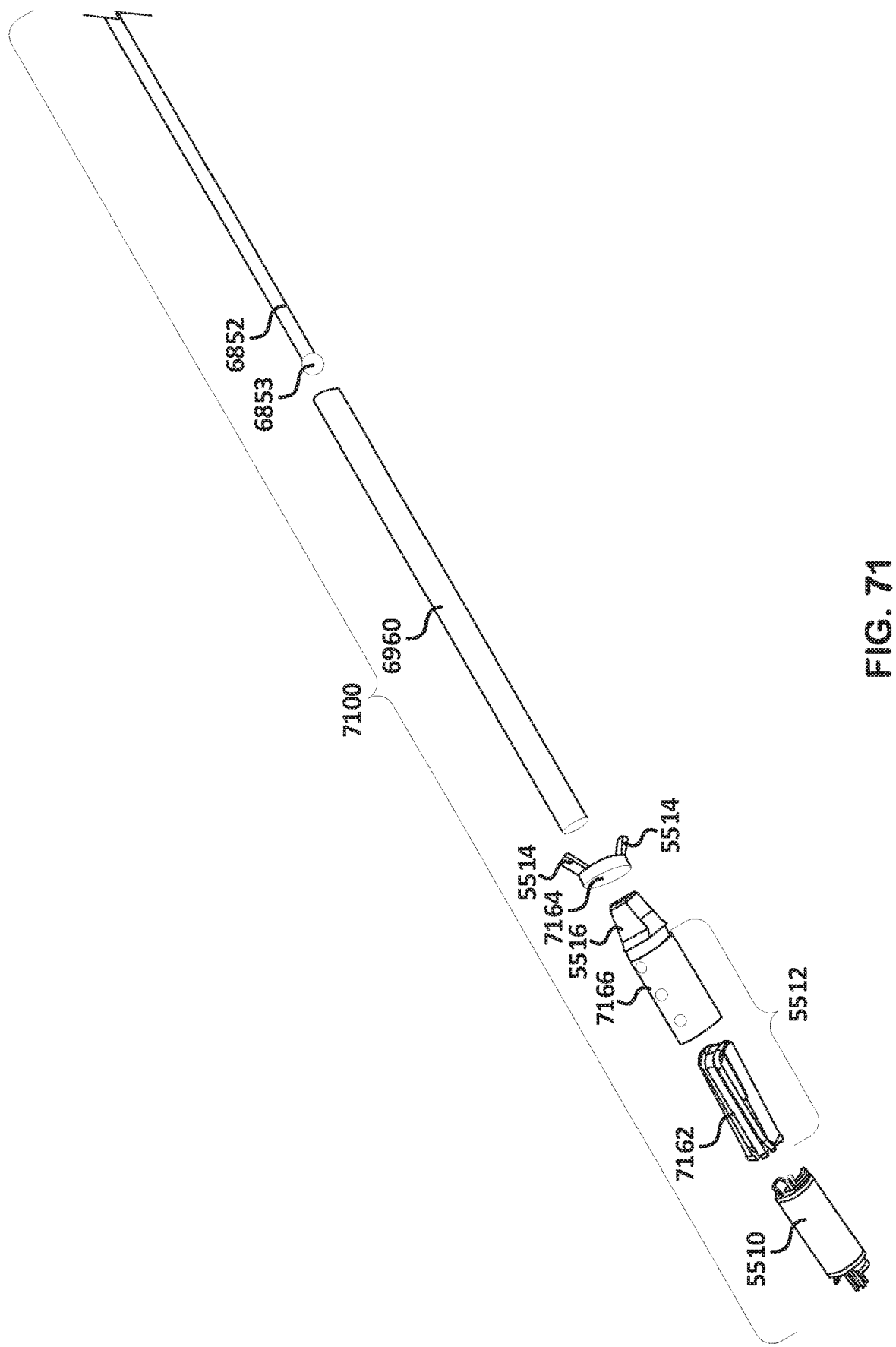
FIG. 71 illustrates, by way of example, an exploded view diagram of a portion of an implantable device.

FIG. 71 illustrates, by way of example, an exploded view diagram of a portion 7100 of an implantable device, such as the implantable device 5500. The portion 7100 illustrated includes the suture 6852, the sheath 6960, tines 5514 on a retainer 7164, the push rod interface 5516, the antenna housing 5512 and the circuitry housing 5510.

In assembling the implantable device, the suture 6852 may be attached to the push rod interface 5516. The sheath 6960 may be situated around the suture 6852, such as before or after the suture 6852 is attached to the push rod interface 5516. The retainer 7164 can be fitted around the push rod interface 5516. The retainer 7164 The retainer 7164 may be situated so that it abuts a proximal end of the antenna housing 5512. The antenna housing 5512 can include an antenna core 7162 and a core housing 7166. In an example, the antenna core 7162 comprises a dielectric member, such as the first dielectric core 7488 discussed herein. The core housing 7166 can be situated around the antenna core 7162, such that the antenna core 7162 is surrounded by the core housing 7166. A distal end of the antenna core 7162 can be attached to the circuitry housing 5510. The core housing 7166 can surround a proximal portion of the circuitry housing 5510 (e.g., proximal winged flanges 7270A and 7270B, see FIGS. 18 and 19, among others). The antenna core 7162 can be attached to the circuitry housing 5510. Some embodiments of the components of FIG. 71 are described in more detail regarding FIGS. 72-83, and elsewhere herein. In an example, the core housing 7166 comprises a dielectric material such as can include polyether ether ketone (PEEK), liquid crystal polymer (LCP), or other material. In an example, the core housing 7166 is configured to provide a solid and robust mechanical joint between the antenna core 7162 and, for example, the circuitry housing 5510.

Figure 73:
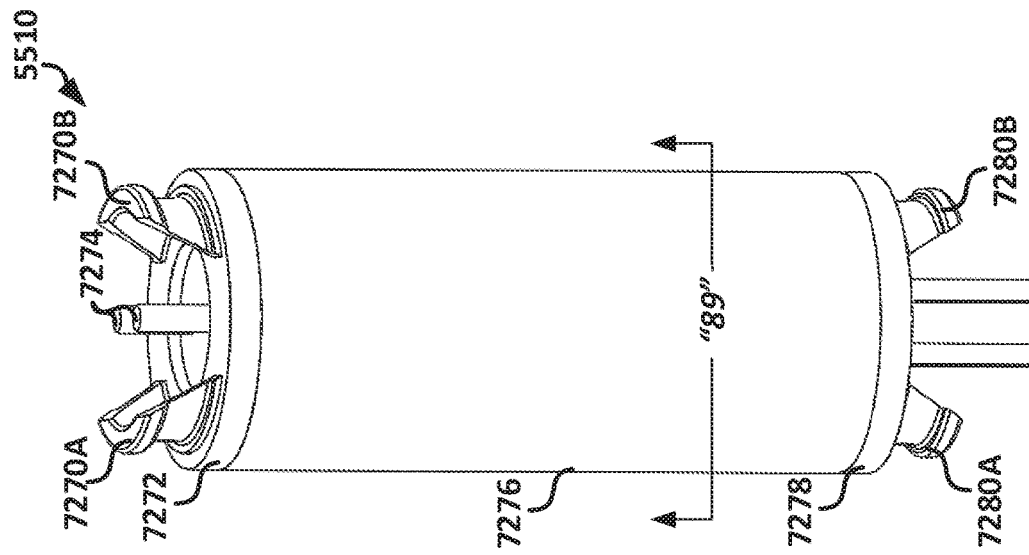
FIGS. 72-73 illustrate, by way of example, respective diagrams of an embodiment of the circuitry housing.
Figure 72:
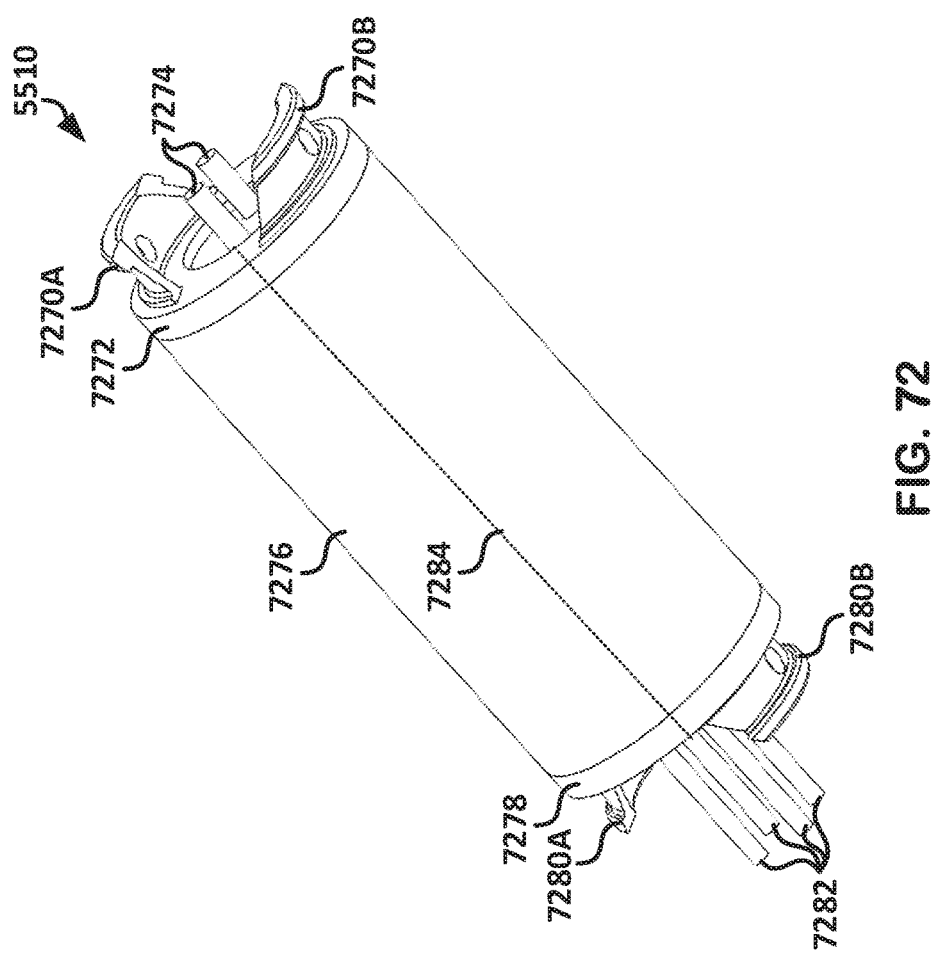

FIGS. 72 and 73 illustrate, by way of example, respective diagrams of an embodiment of the circuitry housing 5510. The circuitry housing 5510 as illustrated includes proximal winged flanges 7270A, 7270B, a first housing plate 7272, proximal conductive feedthroughs 7274, a hollow container 7276, a second housing plate 7278, distal winged flanges 7280A, 7280B, and distal conductive feedthroughs 7282. The winged flanges 7270A-7270B and 7280A-7280B can be situated within a footprint of the container 7276.

Figure 76:
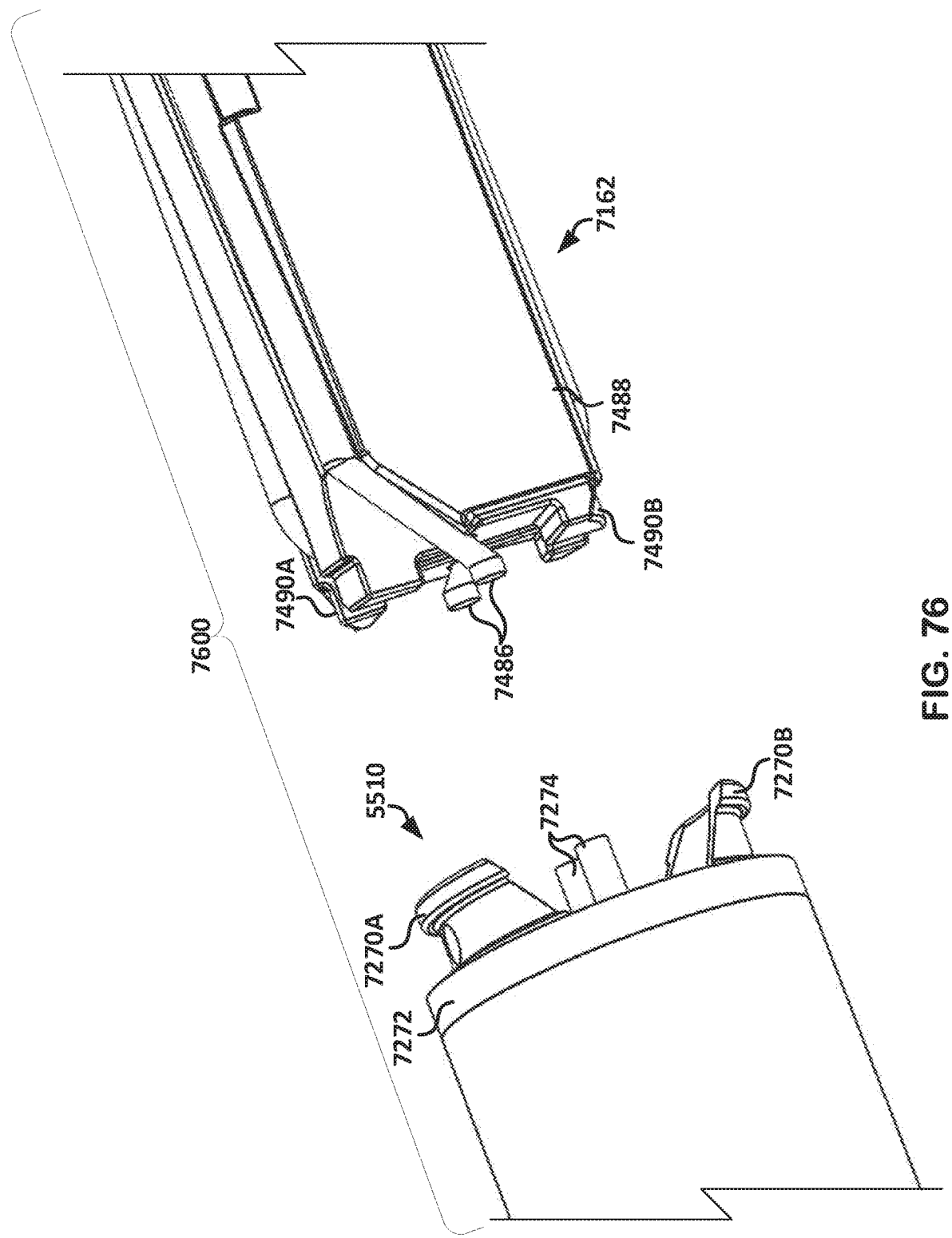
FIG. 76 illustrates, by way of example, a diagram of an embodiment of a coupling between a circuitry housing and an antenna core of an implantable device.

The winged flanges 7270A-7270B can be configured to engage corresponding features of the antenna core 7162 (see FIG. 76, among others). The winged flanges 7280A-7280B can be configured to engage corresponding features at or near the proximal end 5508 of the body portion 5502. The winged flanges 7270A-7270B and 7280A-7280B can include an arcuate or curved wall and a track running between ends of the curved wall. On each side of the track, the winged flanges 7270A-7270B and 7280A-7280B can include a lip or protrusion extending outward from a longitudinal axis (indicated by dashed line 7284) of the circuitry housing 5510.

Figure 74:
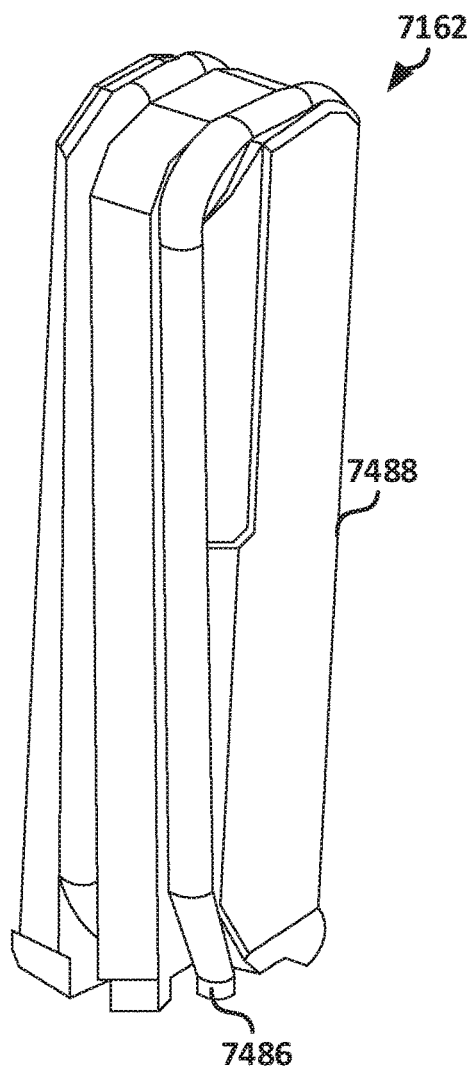
FIGS. 74-75 illustrate, by way of example, respective diagrams of an embodiment of the antenna core.
Figure 75:
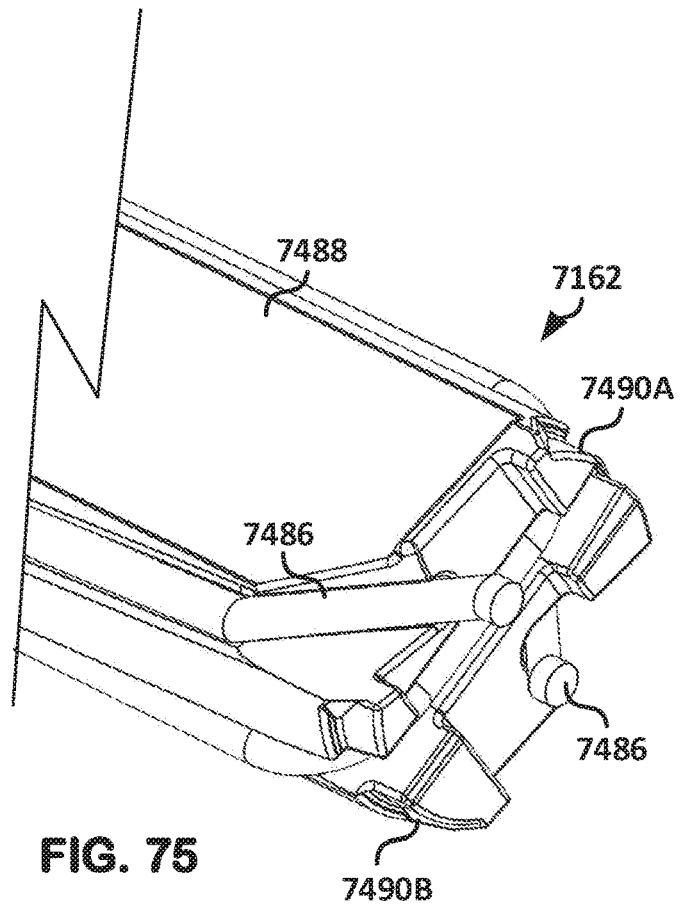

The conductive feedthroughs 7274 can be configured to engage mating conductors of the antenna core 7162 (see FIGS. 74-76, among others). The conductive feedthroughs 7274 can provide a path through which electrical signals can travel to an antenna 7486. In an example, the antenna 7486 comprises an example of the antenna 108 such as can be provided in the implantable device 110. The antenna 7486 can be provided or wound around a first dielectric core 7488 (see FIGS. 74-76, among others). The antenna 7486 can be coupled to circuitry in the circuitry housing 5510. The conductive feedthroughs 7274 can extend through the first housing plate 7272.

The first housing plate 7272 and second housing plate 7278 can be brazed, welded, or otherwise attached to opposing ends of the container 7276. The attachment of the first housing plate 7272 and second housing plate 7278 to the container 7276 can hermetically seal the circuitry housing 5510, such as to protect the circuitry in the circuitry housing 5510. An embodiment of the circuitry housing 5510 is described regarding FIGS. 90 and 91.

The conductive feedthroughs 7282 can be configured to engage mating conductors of the body portion 5502 that are electrically coupled or connected to respective electrodes 5504. The conductive feedthroughs 7282 can provide a path through which electrical signals from the circuitry in the circuitry housing 5510 are provided to the electrodes 5504. The conductive feedthroughs 7282 can extend through the second housing plate 7278.

FIGS. 74 and 75 illustrate, by way of example, a diagram of an embodiment of the antenna core 7162. The antenna core 7162 may include a first dielectric core 7488 and an antenna 7486. The first dielectric core 7488 may be made of a non-conductive material, such as a dielectric material. The dielectric material can include polyether ether ketone (PEEK), liquid crystal polymer (LCP), (plastics like PEEK can retain moisture and shift dielectric constant, whereas LCPs have less dielectric shift with moisture saturation), epoxy mold, or the like. The antenna 7486 can include a conductive material, such as copper, silver, gold, platinum, tin, aluminum, brass, nickel, titanium, a combination thereof, or the like. The antenna 7486 can be wound around the first dielectric core 7488. The first dielectric core 7488 can provide a mechanical support for the antenna 7486, such as to help prevent the antenna 7486 from collapsing in after it is situated around the first dielectric core 7488.

The first dielectric core 7488 can include arcuate or curved walls 7490A and 7490B that are curved to mate with the arcuate or curved walls of the winged flanges 7270A-7270B. The winged flanges 7270A-7270B can be situated outside the curved walls 7490A-7490B when the circuitry housing 5510 is mated with the antenna core 7162.

FIG. 76 illustrates, by way of example, a diagram of an embodiment of the coupling between the circuitry housing 5510 and the antenna core 7162. The feedthroughs 7274 can be electrically connected to the antenna 7486. The feedthroughs 7274 can be soldered, welded, brazed, or otherwise electrically to respective antenna 7486 conductors. More details regarding connecting the conductive feedthroughs 7274 to the antenna 7486 are described regarding FIGS. 86 and 87.

Figure 78:
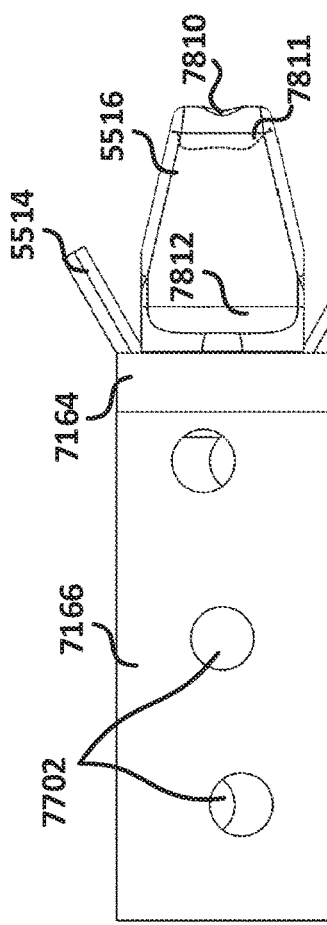
FIGS. 77-79 illustrate, by way of example, respective diagrams of a core housing and a push rod interface.
Figure 77:
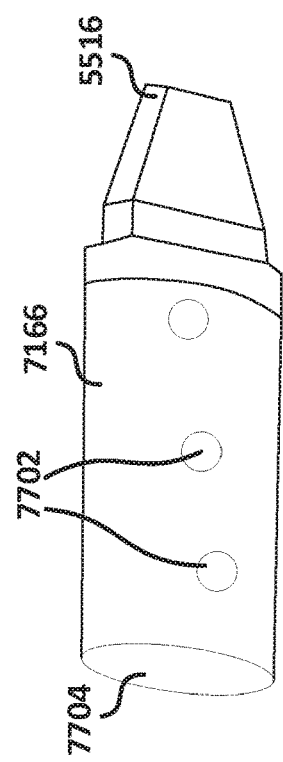
Figure 79:
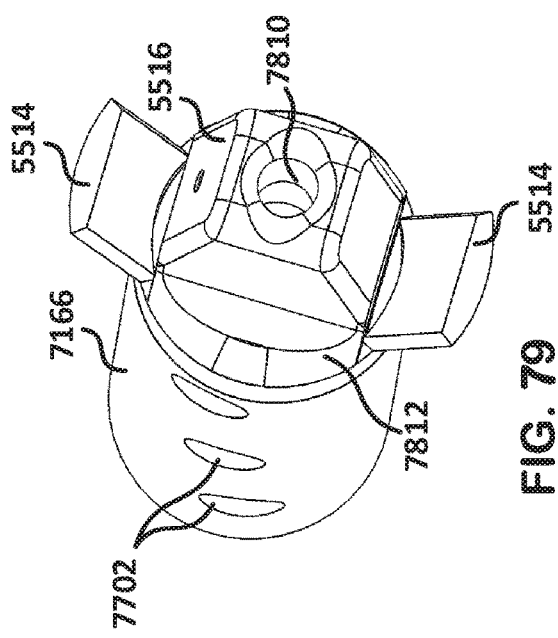

FIGS. 77-79 illustrate, by way of example, respective diagrams of the core housing 7166 and push rod interface 5516. The core housing 7166 can include engagement holes 7702 therethrough. The engagement holes 7702 can engage surrounding tissue when implanted. The engagement holes 7702 can help retain the implantable device 5500 in the implanted location. The core housing 7166 can include an opening 7704 in a distal end thereof. The antenna core 7162 can be situated in the opening 7704. The core housing 7166 can surround the antenna core 7162.

The push rod interface 5516 as illustrated includes a trapezoidal shape, such as a trapezoidal prism with exposed rounded edges. A shorter base of the trapezoidal shape is more proximal than a longer base of the trapezoidal shape. The sides of the push rod interface 5516 can be tapered from the longer base to the shorter base. Such a configuration can help make it easier to explant the implantable device 5500 while still providing an interface to engage the distal end of the push rod 6850.

The push rod interface 5516 can include a socket opening 7810 to engage a suture retainer 6853 (e.g., a ball or knot or the like) on a distal end of the suture 6852 (see FIG. 71). The suture 6852 can be pushed through the socket opening 7810 starting with a proximal end of the suture 6852. The suture can be pulled through the socket opening 7810 until the retainer 6853 is situated in the socket opening 7810. The retainer 6853 can include a structure with bounds or a radius that is greater than a radius of the exposed portion of the socket opening 7810, such as to ensure that the suture 6852 remains coupled to the push rod interface 5516 and can be pulled to extract the implantable device 5500.

The push rod interface 5516 can further include a base 7812 that caps the core housing 7166. The base 7812 can be attached to the core housing 7166, such as by an adhesive, force produced by elastic retraction of the core housing 7166, or the like. The base 7812 can include a lip that extends beyond the retainer 7164 and helps ensure that the retainer 7164 does not travel toward the socket opening 7810.

The antenna core 7162 can be situated in the core housing 7166. The antenna core 7162 can be fixed to the core housing 7166, such as by using an epoxy or other dielectric adhesive. The dielectric adhesive can be introduced through one or more of the holes 7702, such as while the antenna core 7162 is in the core housing 7166 and after the antenna 7486 is electrically connected to the feedthroughs 7274.

A connective material 7811 can be situated in the push rod interface 5516. The connective material 7811 can help retain a retainer 6853 or knot in an end of the suture 6852. The connective material 7811 can be cured while the retainer 6853 is in contact with the connective material 7811. The connective material 7811 can help ensure that the retainer 6853 does not slide through the opening 7810 or toward the core housing 7166.

FIG. 80 illustrates, by way of example, a perspective view diagram of an embodiment of the push rod 6850. The push rod 6850 can include an elongated body portion 8024. The elongated body portion 8024 can be hollow in a distal portion thereof, such as to allow the suture 6852 or sheath 6960 to pass therethrough. The elongated body portion 8024 can include a metal, plastic, stainless steel, polyvinyl chloride (PVC), polytetrafluoroethylene (PTFE) or the like.

The push rod 6850 can include the marker 6760 that indicates the position of the marker 6760 relative to the catheter 6250. In use, an entity performing the implant procedure can push the push rod 6850 until the marker 6760 is at or near a most proximal end of the catheter 6250. The push rod 6850 can include an implantable device interface 8022. The implantable device interface 8022 is configured to mate with the push rod interface 5516.

FIG. 81 illustrates, by way of example, an exploded view diagram of an embodiment of the implantable device interface 8022 of the push rod 6850. The implantable device interface 8022 includes opposing legs 8130A, 8130B extending from the elongated body portion 8024. The opposing legs 8130A, 8130B can be partial cylinders, partial ellipsoids, partial hypercubes, other polygonal shape, or the like. The legs 8130A, 8130B can include respective opposing faces 8136A, 8136B facing each other. The opposing faces 8136A, 8136B can be generally flat, or otherwise complement a shape of the push rod interface 5516. The opposing faces 8136A, 8136B can include a divot 8132 therein, such as to accommodate the shape of the suture 6852 or the sheath 6960. The divot 8132 can be arcuate. The elongated body portion 8024 can be hollow such as to include a lumen 8134 (e.g., a tubular structure) extending therethrough. The lumen 8134 can include a shape that allows the suture 6852 or the sheath 6960 to pass therethrough. Such a configuration can allow the implantable device interface 8022 to engage the push rod interface 5516 with the suture 6852 or sheath 6960 at least partially in the lumen 8134.

FIG. 82 illustrates, by way of example, a diagram of an embodiment of a proximal portion of the push rod 6850. The pushrod 6850 as illustrated includes a hollow rod elongated body portion 8024, a handle 8280, detents 8282, a luer cap 8284, and a suture 6852. The pushrod 6850 can be used as described elsewhere herein. The luer cap 8284 can be removably attached to the handle 8280 by a mating luer thread (not shown as it is occluded by the luer cap 8284). As the luer cap 8284 is screwed onto the luer thread a tapered opening of the luer thread puts pressure on the suture 6852 to retain it in place. To remove the push rod 6850 from the suture 6852, the luer cap 8284 can be unthreaded from the luer thread and advanced along the suture 6852. After the suture 6852 is no longer in the luer cap 8284, the push rod 6850 can be advanced over the suture 6852 and removed from the implantable device 5500.

FIG. 83 illustrates, by way of example, a perspective view diagram of an embodiment of the push rod 6850 with the suture 6852 situated partially in the lumen 8134. FIG. 84 illustrates, by way of example, a perspective view diagram of an embodiment of the push rod interface 5516 engaged with the implantable device interface 8022. The sheath 6960 and the suture 6852 are situated in the lumen 8134 of the push rod 6850. The faces 8136A, 8136B are engaged with corresponding faces of the push rod interface 5516.

To help ensure that the electrical connection between the feedthroughs 7274 and the antenna 7486 are not compromised, such as by the implantation process or otherwise, an epoxy, resin, polymer, molding material, or other dielectric material, can be injected around the first dielectric core 7488. The dielectric material, indicated by dashed line 9213, may be injected through one or more of the holes 7702. The dielectric material may further couple the core housing 7166 to the first dielectric core 7488 and the winged flanges 7270A-7270B or other items protruding from the plate 7272 of the circuitry housing 5510.

Figure 85:
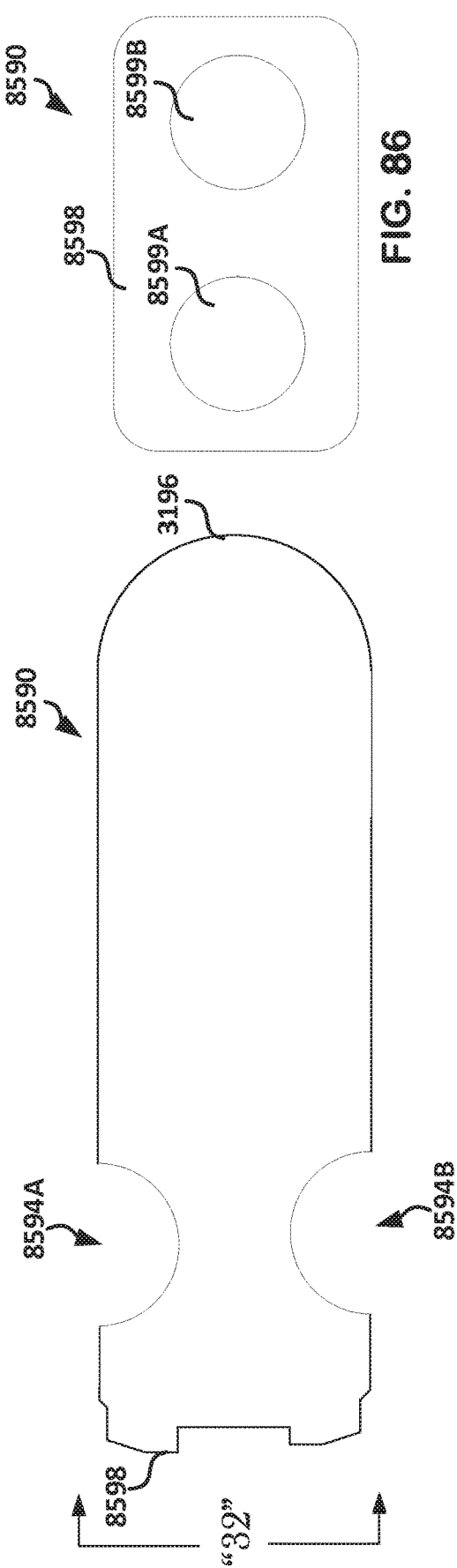
FIG. 85 illustrates, by way of example, a side view diagram of an embodiment of a dielectric core.

FIG. 85 illustrates, by way of example, a diagram of an embodiment of a second dielectric core 8590. To electrically connect the antenna 7486 to the feedthroughs 7274, the antenna core 7162 can be situated near the circuitry housing 5510, such that the winged flanges 7270A-7270B abut the curved walls 7490A-7490B. The antenna core 7162 and the circuitry housing 5510 can be held in this position while the feedthroughs 7274 and antenna 7486 are laser welded or otherwise electrically connected to each other.

Executing such a laser weld is difficult. This difficulty can be partially from the chemistry of joining the conductive surfaces of the feedthroughs 7274 and antenna 7486 and partially from the difficulty of retaining the feedthroughs 7274 sufficiently close to the antenna 7486 to form the weld. The second dielectric core 8590 can help retain the antenna 7486 sufficiently close to feedthroughs 7274, such as to aid in the process of electrically connecting them together.

The second dielectric core 8590 as illustrated includes a second dielectric core 8590 with a proximal end 3196 and a distal end 8598. Distal and proximal, as used herein, are relative to one another. A distal part is one that is closer to an implant site than a proximal part when the distal and proximal parts are fully implanted. The second dielectric core 8590 as illustrated includes two depressions 8594A, 8594B in sides thereof. The depressions 8594A, 8594B may be near the distal end 8598 of the second dielectric core 8590. The second dielectric core 8590 may include a same material as the first dielectric core 7488.

Figure 86:
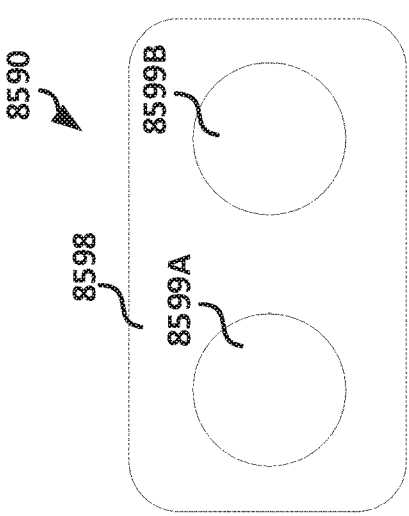
FIG. 86 illustrates, by way of example, an end view diagram of the example of the dielectric core of FIG. 85.
Figure 87:
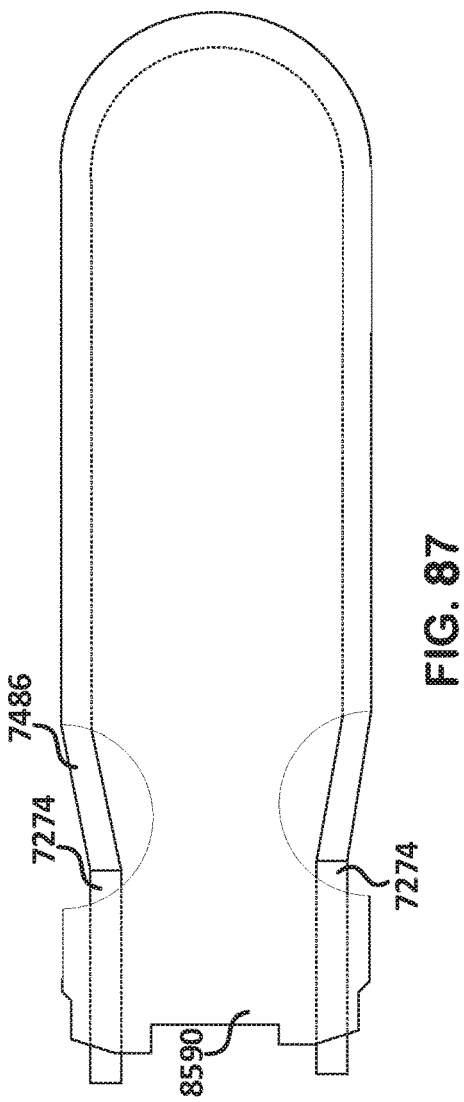
FIG. 87 illustrates, by way of example, a side view diagram of an embodiment of a portion of an implantable device after feedthroughs are situated in depressions near an antenna.

FIG. 86 illustrates, by way of example, a diagram of the embodiment of the dielectric core of FIG. 85 as viewed from the direction of the arrows labelled "86". The distal end 8598 of the second dielectric core 8590 can include holes 8599A, 8599B therein for each feedthrough 7274. The hole 8599A-8599B can be sized and shaped to accommodate the feedthrough 7274. The feedthroughs 7274 can be pushed through the holes 8599A-8599B such that ends of the feedthroughs 7274 are situated in the depressions 8594A-8594B, respectively. The holes 8599A-8599B can be configured such that the feedthroughs 7274 are held in place when inserted therein. In some embodiments, an epoxy, resin, or other adhesive can be situated in the hole 8599A-8599B before or after the feedthroughs 7274 are inserted in the holes 8599A-8599B. In such embodiments, the feedthroughs 7274 can be retained in place by the adhesive. FIG. 87 illustrates, by way of example, a side view of an embodiment of a portion of an implantable device after the feedthroughs 7274 are situated in the depressions 8594A-8594B near the antenna 7486 and ready for laser welding.

As previously mentioned, laser welding two metals can be difficult. For example, consider a conductive (e.g., metal, such as gold, platinum, iridium, nitinol, or the like) antenna 7486 and conductive (e.g., metal, such as gold, platinum, iridium, nitinol, or the like) feedthroughs 7274. The feedthroughs 7274 may reflect the laser energy, such that the antenna 7486 may not absorb enough energy to melt and form a conductive connection with another conductor, or vice versa.

FIG. 88 illustrates, by way of example, a diagram of an embodiment 8800 of a portion of an antenna assembly for an implantable device and the antenna assembly includes a sleeve 8802 to help aid in forming a conductive connection between the feedthroughs 7274 and the antenna 7486. The sleeve 8802 can be used or applied in any of the different antenna example assemblies discussed herein. The sleeve 8802 can be made of a material such as platinum, such as can have a high absorption rate at a frequency of the energy source to be used to connect an antenna lead to one or more other conductive leads, traces, pads, or other material. The sleeve 8802 can be situated in the depression 8594A or 8594B. The sleeve 8802 can be situated around a portion of the antenna 7486. The feedthrough 7274 can be situated in the sleeve 8802. To help aid in energy absorption and ultimately a conductive connection between the feedthrough 7274 and the antenna 7486, the sleeve 8802 may be situated around an interface between feedthroughs 7274 and the antenna 7486. The sleeve 8802 can absorb energy from the laser or other energy source and transfer the energy to the feedthroughs 7274 and the antenna 7486. The transferred energy can help melt the feedthroughs 7274 and/or antenna 7486, such as to allow a conductive connection to be formed therebetween.

The sleeve 8802 can include a sight hole 8803. Through the sight hole 8803, an entity laser welding the feedthroughs 7274 and the antenna 7486 can visually verify whether the feedthroughs 7274 and the antenna 7486 are situated properly within the sleeve 8802.

FIG. 89 illustrates, by way of example, a cross-section view diagram of an embodiment of the circuitry housing 5510 from a direction indicated by the arrows labelled "89" in FIG. 73. The circuitry housing 5510 as illustrated includes the container 7276, a dielectric liner 8906, circuitry 8908, and a desiccant 8910. The container 7276 can be made of ceramic, metal, or other biocompatible material which can be hermetically sealed, such as to protect the circuitry 8908.

The dielectric liner 8906 can include a Kapton or other dielectric material. The dielectric liner 8906 can cover an inner surface of the container 7276. The dielectric liner 8906 can help prevent electrical connections from forming between the circuitry 8908 and the container 7276, such as in embodiments in which the container 7276 includes a conductive material.

The circuitry 8908 can include electrical or electronic components configured to provide electrical stimulation signals to the electrodes 5504, harvest energy from signals incident thereon, such as to provide power to the electrical or electronic components, energy storage components (e.g., a capacitor or battery), receiver circuitry (e.g., a demodulator, amplifier, oscillator, or the like) to convert signals incident on the antenna to data, transmitter circuitry (e.g., a modulator, amplifier, phase locked loop, oscillator, or the like) to convert data to be transmitted to a wave, or the like. The electrical or electronic components can include one or more transistors, resistors, capacitors, inductors, diodes, switches, surface acoustic wave devices, modulators, demodulators, amplifiers, voltage, current, or power regulators, power supplies, logic gates (e.g., AND, OR, XOR, negate, or the like), multiplexers, memory devices, analog to digital or digital to analog converters, a digital controller (e.g., a central processing unit (CPU), application specific integrated circuit (ASIC), or the like), a rectifier, or the like. The circuitry 8908 can include a routing board, such as a printed circuit board (PCB), such as can be rigid, flexible, or a combination thereof.

The desiccant 8910 can be situated on the circuitry 8908, the dielectric liner 8906, or the container 7276. The desiccant 8910 can absorb any moisture in the circuitry housing 5510, such as before or after implantation of the implantable device 5500. Common desiccants include silica, activated charcoal, calcium sulfate, calcium chloride, and zeolites.

FIGS. 90 and 91 illustrate, by way of example, diagrams of an embodiment of hermetically sealing the circuitry housing 5510. An indium or indium alloy solder 9040 can be situated near a junction of the container 7276 and the feedthrough plate 7272 and the container 7276 and the feedthrough plate 7278. The indium alloy solder 9040 can be reflowed (heated to liquefy). Reflowing the indium alloy solder 9040 can cause the solder 9040 to travel and fill the gaps between the container 7276 and the feedthrough plates 7272 and 7282. After cooling, a reliable, hermetic, conductive connection can be formed between the container 7276 and the feedthrough plates 7272 and 7282.

FIGS. 92 and 93 illustrate, by way of example, perspective view diagrams of an embodiment of situating the dielectric material (indicated by the dashed line 9213) into the antenna housing 5512. First, a portion of a needle 9222 can be cooled to reduce a temperature thereof. The temperature can be sufficient to stop the dielectric material from flowing through the needle 9222. The cooling can be performed by a cooling device 9220. Example cooling devices operate using a variety of heat transfer mechanisms including convection, conduction, thermal radiation, and evaporative cooling. In one or more embodiments a Peltier cooler (a device that operates based on the Peltier effect) can be used as the cooling device 9220.

The needle 9222 can be situated on or near the cooling device 9220 so that a portion of the needle 9222 is cooled below a temperature at which the dielectric material may flow freely. The dielectric material may then be inserted into the needle 9222. The dielectric material will flow until its temperature falls below a free flow temperature, at which point the dielectric material will stop flowing and begin pooling in the needle 9222. After sufficient dielectric material is situated in the needle 9222, the needle 9222 may be removed from the cooling device 9220. An ambient temperature around the needle 9222 (after removal from the cooling device 9220) can be greater than the free flow temperature of the dielectric material. Thus, the dielectric material may increase in temperature. The needle 9222 may be situated such that an end thereof is in the core housing 7166, such as through the hole 7702. As the dielectric material heats up (through ambient heating) it will reach the temperature at which it free flows. The dielectric material will then flow through the end of the needle 9222, into the core housing 7166, and in and around one or more of the winged flanges 7270A-7270B, the first dielectric core 7488, the feedthroughs 7274, the antenna 7486, and the sleeve 8802. By the method of FIGS. 91 and 92, an amount and location of the dielectric material can be controlled.

Figure 96:
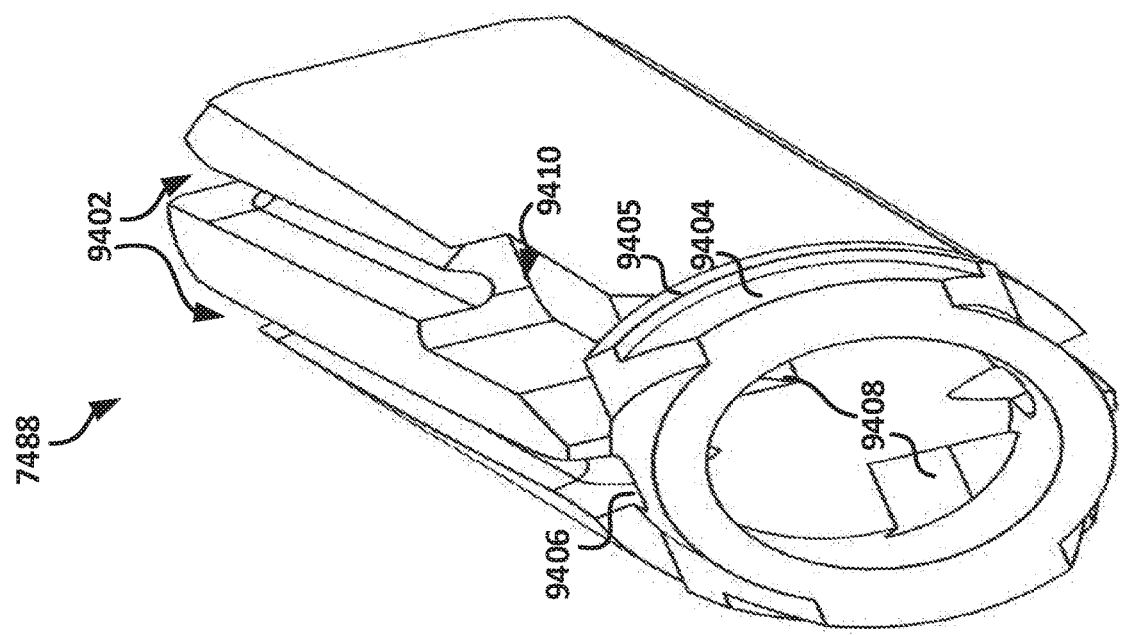
FIGS. 94-96 illustrate, by way of example, respective perspective view diagrams of an embodiment of a dielectric core.
Figure 95:
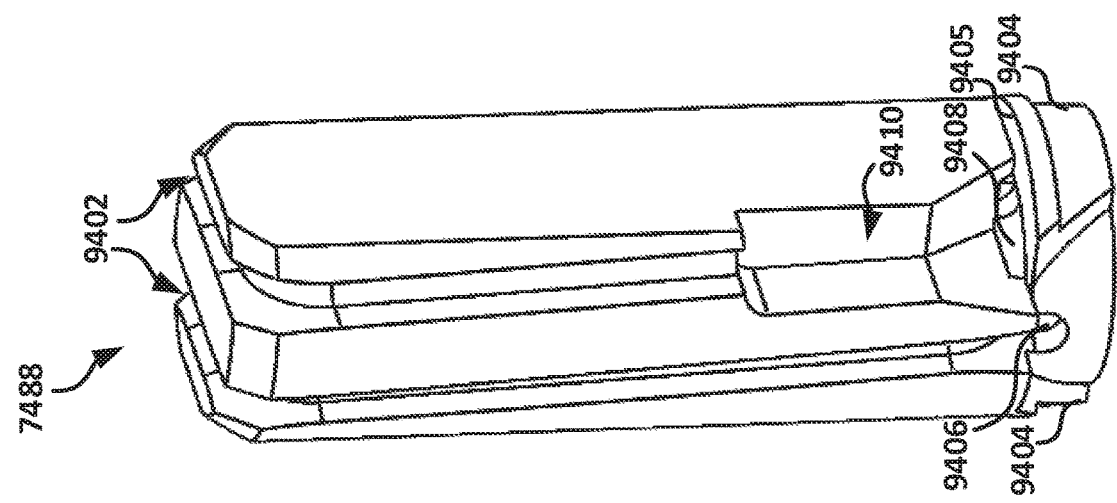
Figure 94:
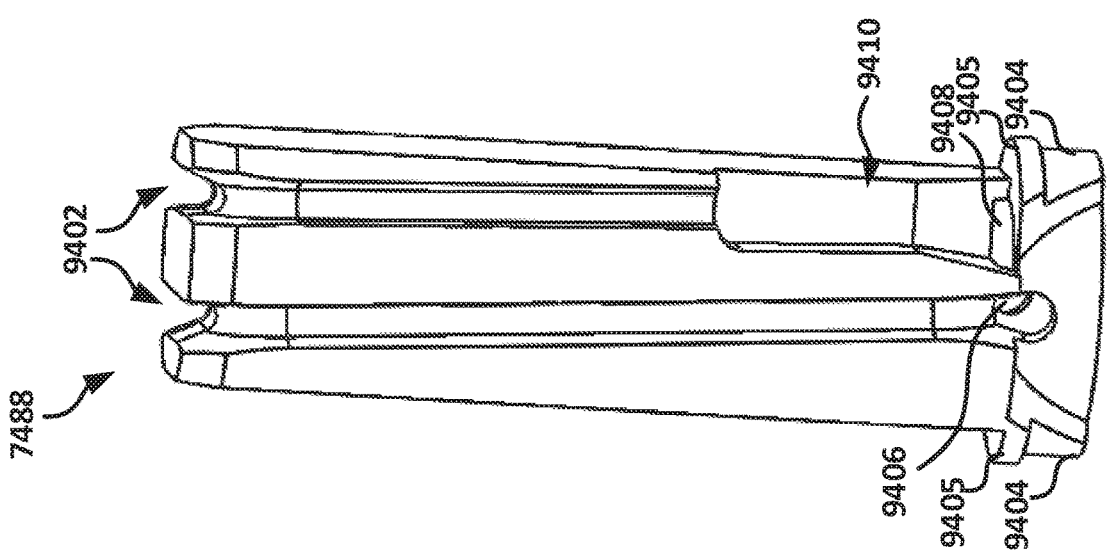

FIGS. 94-96 illustrate, by way of example, respective perspective view diagrams of an embodiment of the first dielectric core 7488. The first dielectric core 7488 can be used in place of the second dielectric core 8590 and can include the same or different materials. The second dielectric core 8590 as illustrated includes a continuous groove 9402 therein. The groove 9402 is shaped and sized, such that when the antenna 7486 is situated in the groove 9402, the antenna has a specified frequency response. When situated in the groove 9402 (see FIGS. 96-98), the antenna 7486 has nearly two full windings (e.g., between about 1.5 and about 1.75 full windings). The groove 9402 defines a desired shape of the antenna 7486, which affects the frequency response of the antenna 7486. The groove 9402 provides mechanical support for the antenna 7486. The groove 9402 helps ensure that the antenna 7486 does not move or otherwise alter shape after the antenna 7486 is situated therein. The groove 9402 can be generally semicircular with extended sidewalls, such that an antenna 7486 with a circular cross-section can be situated therein. A hole 9406 in the first dielectric core 7488 that is generally transverse to a longitudinal axis of the first dielectric core 7488 can provide a path to an opposite side of the first dielectric core 7488 for the antenna 7486 and the groove 9402. The material of the first dielectric core 7488 surrounding the hole 9406 can help retain the position of the antenna 7486.

Figure 98:
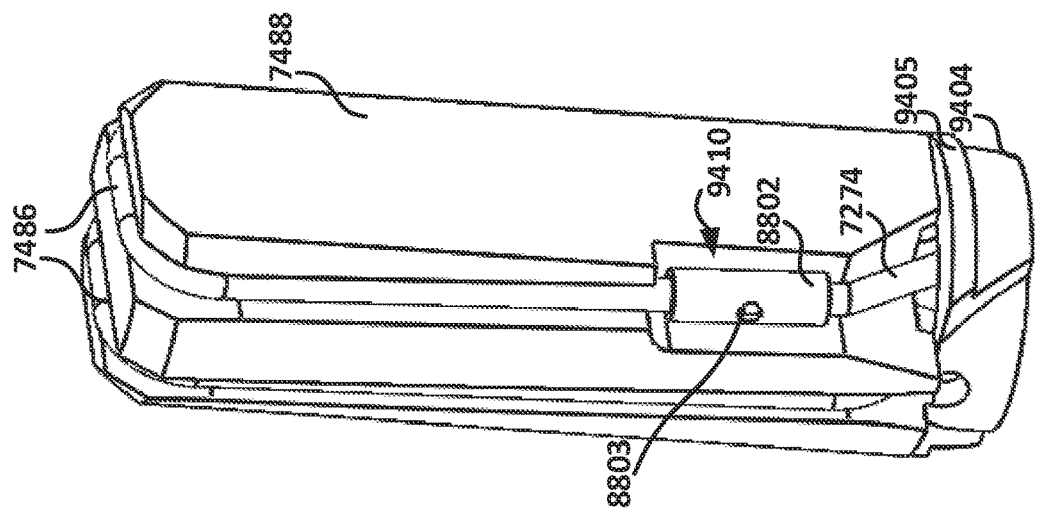
Figure 97:
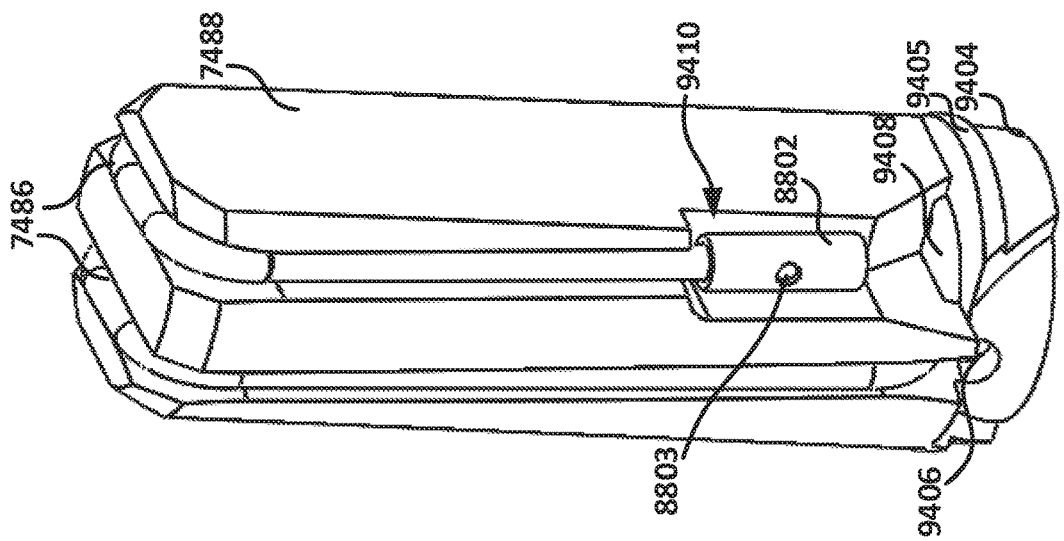

An end of the antenna 7486 can extend into a recess 9410 contiguous with the groove 9402 (see FIGS. 97 and 98). Note that there is another recess on the side of the first dielectric core 7488 that is not visible in FIGS. 94-96. Each respective end of the antenna 7486 can extend into a respective recess 9410 in the first dielectric core 7488. The recess 9410 can provide a space in which the antenna 7486 can be conductively connected to a feedthrough 7274 of the circuitry housing 5510. The feedthrough 7274 can be situated in the recess 9410, such as by pushing the feedthrough 7274 through a hole 9408 in the distal end of the first dielectric core 7488. The sleeve 8802 can be situated around an end of the antenna 7486 or the feedthrough 7274, such that the antenna 7486 or the feedthrough 7274 is visible through the sight hole 8803. The end of the feedthrough 7274 or the antenna 7486 can then be slid into the sleeve 8802 with the end of the antenna 7486 or the feedthrough 7274. The two ends in the sleeve 8802 can then be connected to each other, such as by melting the two ends (e.g., by laser excitation incident on the sleeve) and cooling the sleeve 8802, such as through ambient or other cooling.

The first dielectric core 7488 as illustrated includes a distal portion that includes curved walls 7490 sized and shaped to conform to the walls of the winged flanges 7270A-7270B of the circuitry housing 5510. When the first dielectric core 7488 is pushed on the circuitry housing 5510, the curved walls 7490 can press against the walls of the winged flanges 7270A-7270B that face the feedthroughs 7274. The first dielectric core 7488 can further include a lip 9405 extending radially outward from the curved walls 7490. The lip 9405 can sit on (be in physical contact) with an upper lip (the most proximal portion of the winged flanges 7270A-7270B) when the first dielectric core 7488 is situated on the circuitry housing 5510.

Figure 99:
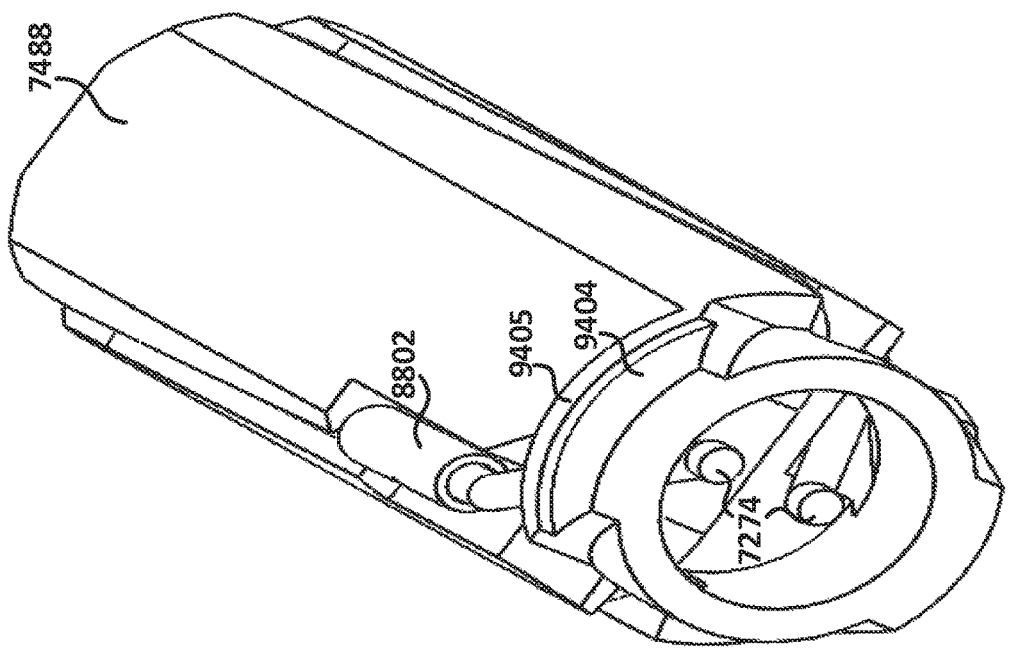
FIGS. 97-99 illustrate, by way of example, examples of a dielectric core with an antenna.

FIGS. 97-99 illustrate the first dielectric core 7488 with the antenna 7486 situated in the groove 9402 and the sleeve 8802 situated over the antenna 7486 in the recess 9410. FIGS. 98 and 99 illustrate the feedthroughs 7274 in the holes 9408 and in the recesses 9410. The feedthroughs 7274 may also be situated in the sleeve 8802, such as can be verified by looking in the sight hole 8803.

The implantable device 5500 can include a stepped simulation circuit such as described herein at, for example, FIGS. 48-54. The circuitry housing 5510 can include circuitry as described herein. The implantable device 5500 can be wirelessly coupled to a device external to the tissue in which it is implanted, such as the source 102 or another device. In an example, an external device is sometimes referred to as an external transceiver, external powering unit (EPU), midfield transmitter, transmitter, or the like. Such a combination of an implantable device and transmitter can form an implantable device system that can be used for electro-stimulation, biological monitoring, or the like.

In an example, an impedance of one or more circuits for use in an implantable device can be tuned such that the implantable device can communicate using non-overlapping frequency bands. A method of tuning the impedance of an implantable device antenna can include adjusting a capacitance across antenna terminals via changes to printed circuit patterns. The impedance of a circuit comprising the circuit patterns or traces can be changed by removing a portion of one or more of the patterns or traces based upon, for example, measurement of a printed circuit substrate or board assembly such as prior to connection of the antenna to drive circuitry. The antenna can then be attached to the implantable device, such as after the board is sealed in a circuitry housing. The implantable device can then be situated in or near a material that simulates the impedance of tissue. The implantable device can then be provided with electrical energy, such as from a midfield transmitter.

Verification of an antenna tuning for an implantable assembly can be accomplished or performed using a field-coupled measurement technique or other functional testing. For a field-coupled measurement, an excitation source can be near-field coupled to the implantable device antenna and changes to the excitation source incident voltages or currents can be measured to determine the implantable device antenna impedance. Functional testing may be accomplished in a number of ways, including by verification of reliable communications with the implantable device at the intended operating frequencies.

A method of making an implantable stimulation device can include forming electrical connections at each of two opposite ends of a circuitry housing, such as can be a hermetically sealed circuitry housing. The method can include forming electrical connections between a feedthrough assembly (e.g., a cap of a structure in which electric and/or electronic components can be situated) and pads of a circuit board. A surface of the pads of the circuit board can be generally perpendicular to a surface of an end of feedthroughs of the feedthrough assembly.

The method can be useful in, for example, forming a hermetic circuitry housing, such as can be part of an implantable stimulation device or other device that can be exposed to liquid or other environmental elements that can adversely affect electric and/or electronic components. Using techniques such as wirebonding are difficult since connections of the substrate may include a surface generally perpendicular to a feedthrough. A wirebond is generally compressed in sealing the circuitry housing. Using thin wires that can be compressed to make the connection between the electronic substrate and the board, can increase parasitic capacitance and/or inductance of the RF feedthrough and may detune an RF receiving structure. Further, manufacturing yield may be limited through such compression and/or thin wires. The compression can break a bond between a wire and a pad or the wire itself. The thickness of the wire can affect how likely the wire is to break. A thinner wire can be more likely to break, when compressed, than a thicker wire.

There is an ongoing desire to further reduce a displacement volume of implantable neuro stimulation devices. Additional miniaturization can allow for an easier and less invasive implant procedure, reduce a surface area of the implantable device which can in turn reduce a probability of a post implant infection, or provide patient comfort in a chronic ambulatory setting.

A configuration of an implantable stimulation device can be different from a conventional lead implanted with a pulse generator. The implantable stimulation device can include a lead-less design, such as can be powered from a source (e.g., a midfield source). Midfield powering technology, including transmitters, transceivers, implantable devices, circuitry, and other details are discussed herein. In an example, the implantable stimulation device can include the first implantable device 600 from the example of FIG. 6.

In operation, the first implantable device 600 can be situated in tissue. There can be some flexibility in adjusting an impedance affecting the antenna 108 in the implant environment, such as by digitally switching one or more capacitors or inductors into or out of an electrical path of the antenna 108 or by changing a digital value of a digitally controllable capacitor or other impedance-modulating device. This flexibility can allow optimization of the antenna impedance to accommodate variations in the implant environment over an operating frequency range, thereby optimizing energy transfer to the implantable device antenna or optimizing an integrity of communications between the implantable device and an external powering unit (EPU) or external device such as the source 102.

However, impedance adjustment using switchable components can have limitations. The circuitry housing 606 can have a limited physical size, and passive components including capacitors, inductors, or the like, can be relatively large and thus can occupy valuable real estate or volume inside the circuitry housing 606. Thus, to help provide that the antenna 108 operates in a desired or proper frequency range, the antenna 108 can be tuned or adjusted before implantation. Such tuning can present a new set of challenges, for example, because tuning activities, measurements, or adjustments can be performed before implantation, and the antenna tuning is likely to change or shift when the device 600 is implanted. The characteristics of the tuning change or shift due to implantation is generally not precisely known due to variations in the implant environment such as tissue type, implantation depth, proximity to other tissue types or body structures, and other variables. In an example, the unpredictability of the antenna impedance can be due, at least in part, to variations in a dielectric constant of tissue in or around the device 600 when the device 600 is implanted in the tissue. Various examples of an antenna tuning process are described herein with reference to, for example, FIGS. 106-116.

Assembly of various circuitry and the circuitry housing 606 can be performed in various ways. Some examples of such assembly are described herein at FIGS. 7 and 100-105, however, other techniques can be used.

Referring again to FIG. 7, for example, a cross-section view diagram of an example of the circuitry housing 606 can include various components (e.g., illustrated as component blocks 712A, 712B, 712C, 712D, 712E, 712F, and 712G) such as can be electrically connected to the circuit board 714. The components 712A-G and the circuit board 714 can be provided inside an enclosure 722. Additionally or alternatively to being hermetically sealed, as discussed above, the enclosure 722 can be backfilled to prevent ingress of moisture therein. The backfill material can include a non-conductive, water proof material, such as an epoxy, parylene, tecothane, or another material.

Figure 100:
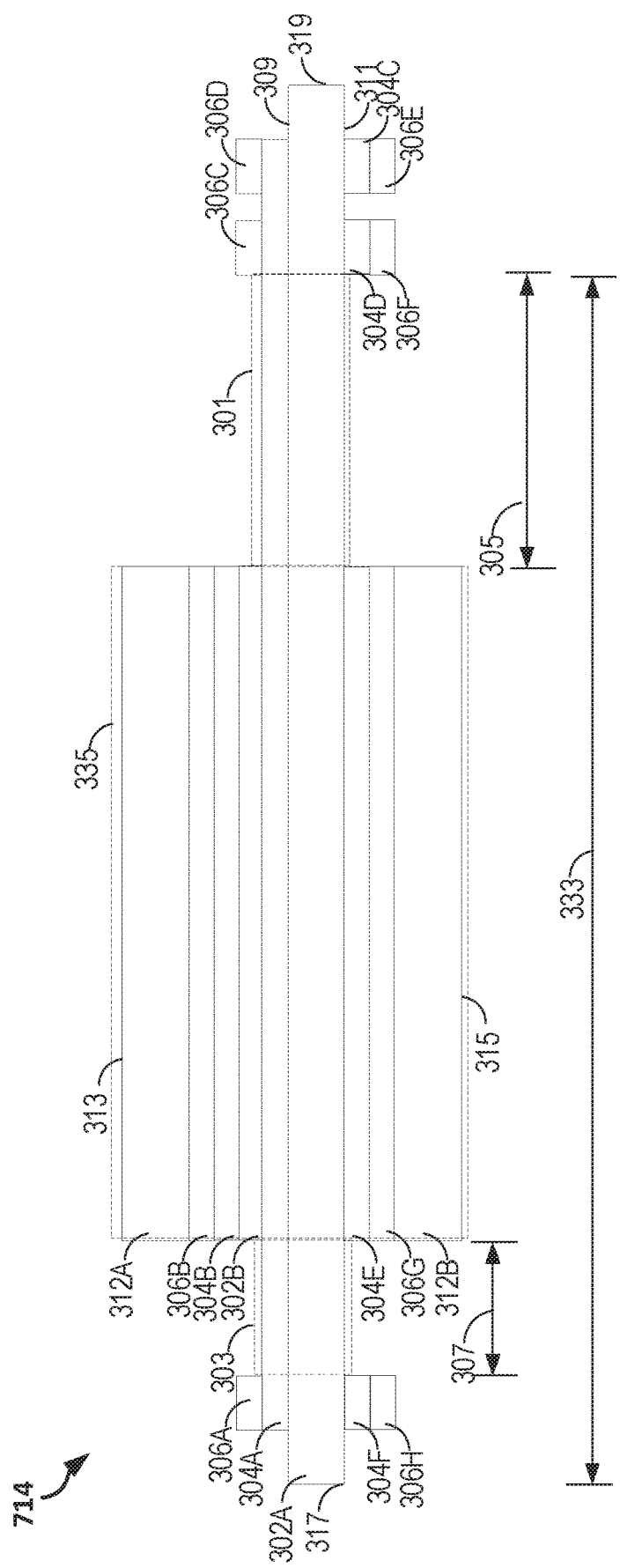
FIG. 100 illustrates, by way of example, a side view diagram of an embodiment of a circuit board.

FIG. 100 illustrates, by way of example, a side view diagram of an embodiment of the circuit board 714. FIGS. 101A and 101B illustrate, by way of example, top view diagrams of embodiments of the circuit board 714. The circuit board 714 as illustrated includes materials that can be combined or stacked to provide a circuit board with one or more portions that are flexible. In FIG. 100, for example, the portions of the circuit board 714 illustrated within the dashed line boxes 301 and 303 can include deformable or flexible portions. Other portions of the circuit board 714 can similarly be configured to be flexible or deformable or rigid.

In an example, the circuit board 714 can include a first dielectric material 302A or 302B, a first conductive material 304A, 304B, 304C, 304D, 304E, or 304F, a second conductive material 306A, 306B, 306C, 306D, 306E, 306F, 306G, or 306H, or a second dielectric material 312A and 312B. The first dielectric material 302A-B can include a polyimide, nylon, polyether ether ketone (PEEK), a combination thereof, or other flexible dielectric material. In one or more embodiments, the first conductive material 304A-F can be rolled and/or annealed. The first conductive material 304A-F can include copper, silver, nickel, gold, titanium, platinum, aluminum, steel, a combination thereof, or other conductive material. The second conductive material 306A-H can include a solderable material (e.g., a material with an ability to form a bond with molten solder), such as can include a material as discussed with regard to the first conductive material 306A-H. The second conductive material 306A-H can include a plating that includes a material that has a relatively low rate of oxidation, such as can include silver, gold, nickel, and/or tin. The second dielectric material 312A-B can include a solder mask and/or stiffener. The second dielectric material 312A-C can include a polymer, epoxy, or other dielectric solder mask and/or stiffener material.

The first dielectric material 302A can form a base layer on which one or more other materials can be stacked to form the circuit board 714. Some materials can be stacked on a first surface 309 of the first dielectric material 302A and some materials can be stacked on a second surface 311 of the first dielectric material 302A, and the first surface 309 can be opposite the second surface 311.

The first conductive material 304A can interface with the first surface 309 of the first dielectric material 302A. In an example, materials, components, or elements that interface with another material, component, or element can be coupled or can be otherwise provided in mechanical contact. In an example, the first conductive material 304A can interface with the second conductive material 306A, 306C, and 306D and the first dielectric material 302B. The first conductive material 304A can be situated between the first dielectric material 302A and the first dielectric material 302B and the second conductive material 306A, 306C, and 306D. The first conductive material 304A can extend into and through the flexible portions (e.g., the areas designated in FIG. 100 by the dashed line boxes 303 and 301).

The second conductive material 306A, 306C, 306D, 306I, 306J, or 306K can interface with the first conductive material 304A. The second conductive material 306A, 306C, 306D, 306I, 306J, or 306K can be arranged around respective openings 420A, 420B, 420C, 420D, 420E, and 420F. The openings 420A-F can extend from a surface of the second conductive material 306A, 306C, 306D, 306I, 306J, or 306K to a respective opposite surface of the second conductive material 306H, 306F, or 3056E, respectively (some of which are obscured in the views shown). The openings 420A-F can extend through the second conductive material 306A, 306C, 306D, 306I, 306J, or 306K, the first conductive material 304A, 304C, 304D, or 304F, and or first dielectric material 302A.

In an example, the first dielectric material 302B can interface with the first conductive material 304A and the first conductive material 304B. The first dielectric material 302B can be provided on the first conductive material 304A. The first dielectric material 302B can be situated between the first conductive material 304A and the first conductive material 304B. The first dielectric material 302B can be situated between the second conductive material 306A and the second conductive material 306C, such as with an open space corresponding to the flexible portions (e.g., the areas designated in FIG. 100 by the dashed line boxes 303 and 301) between the second conductive material 306A and the second conductive material 306C, respectively.

The first conductive material 304B can interface with the first dielectric material 302B and the second conductive material 306B. The first conductive material 304B can be on the first dielectric material 302B. The first conductive material 304B can be situated between the first dielectric material 302B and the second conductive material 306B. The first conductive material 304B can be situated between the second conductive material 306A and the second conductive material 306C, such as with an open space corresponding to the flexible portions (e.g., the areas designated in FIG. 100 by the dashed line boxes 303 and 301) such as between the second conductive material 306A and the second conductive material 306C, respectively.

The second conductive material 306B can interface with the first conductive material 304B and the second dielectric material 312A. The second conductive material 306B can be on the first conductive material 304B. The second conductive material 306B can be situated between the first conductive material 304B and the second dielectric material 312A. The second conductive material 306B can be situated between the second conductive material 306A and the second conductive material 306C, such as with an open space corresponding to the flexible portions (e.g., the areas designated in FIG. 100 by the dashed line boxes 303 and 301) between the second conductive material 306A and the second conductive material 306C, respectively.

The second dielectric material 312A can interface with the second conductive material 306B. The second dielectric material 312A is on the second conductive material 306B. The second dielectric material 312A can be exposed at a surface 313 facing away from the second conductive material 306B. The second dielectric material 312A can be situated between the second conductive material 306A and the second conductive material 306C, such as with an open space corresponding to the flexible portions (e.g., the areas designated in FIG. 100 by the dashed line boxes 303 and 301) between the second conductive material 306A and the second conductive material 306C, respectively.

The first conductive material 304E can interface with the second surface 311 of the first dielectric material 302A. The first conductive material 304E can interface with the second conductive material 306G and the first dielectric material 302A. The first conductive material 304E can be on the first dielectric material 302B. The first conductive material 304E can be situated between the first dielectric material 302B and the second conductive material 306G. The first conductive material 304E is situated between the first conductive material 304D and 304F, such as with an open space corresponding to the flexible portions (e.g., the areas designated in FIG. 100 by the dashed line boxes 303 and 301) between the first conductive material 304D and 304F, respectively.

The second conductive material 306G can interface with the first conductive material 304E and the second dielectric material 312B. The second conductive material 306G can be on the first conductive material 304E. The second conductive material 306G is situated between the first conductive material 304E and the second dielectric material 312B. The second conductive material 306G can be situated between the first conductive material 304D and the first conductive material 304F, such as with an open space corresponding to the flexible portions (e.g., the areas designated in FIG. 100 by the dashed line boxes 303 and 301) between the first conductive material 304D and the first conductive material 304F, respectively.

The second dielectric material 312B can interface with the second conductive material 306G. The second dielectric material 312B can be on the second conductive material 306G. The second dielectric material 312B can be exposed at a surface 315 facing away from the second conductive material 306G. The second dielectric material 312B can be situated between the first conductive material 304D and the first conductive material 304F, such as with an open space corresponding to the flexible portions (e.g., the areas designated in FIG. 100 by the dashed line boxes 303 and 301) between the first conductive material 304D and the first conductive material 304F, respectively.

The flexible portions can have different respective lengths 307 and 305. A length 307 can be less than or greater than a length 305. The second conductive material 306A, 306H, or 306K can be connected to the antenna 108 or antenna 108. The length of a flexible portion near a first end 317 of the circuit board 714 can affect a parasitic inductance and/or parasitic capacitance that can affect the antenna 108 or antenna 108. Thus, the length 307 can be configured or selected to reduce such parasitics. In an example, the length 305 can be longer than a length 723 (see FIG. 7). The length 723 can be measured from an end 625 of the second dielectric material 312A, 312B to and end of the enclosure 722. The length 305 can be configured such that the openings 420C-F can be provided outside of the enclosure 722 when the openings 420A-B are on respective feedthroughs 718A (other feedthrough obscured in the view of FIG. 7) and the cap 716A can be situated on, or at least partially in, the enclosure 722.

A length (indicated by the arrow 333) of the circuit board from an end 317 to an end of the flexible portion indicated by the dashed line box 301 can be greater than a length (indicated by the arrow 227 in FIG. 2) of the enclosure 722, such as to allow the portion of the circuit board on which the openings 420C-F or pads 1102 reside. A portion (indicated by the dashed line box 335) between the first flexible portion and the second flexible portion can be flexible or rigid. A rigidity of a portion of the circuit board 714 can be provided by solder, electric and/or electronic components, one or more of the first and second conductive materials 304 and 306 and/or one or more of the first and second dielectric materials 302 and 312.

FIGS. 101A and 101B illustrate generally examples of respective circuit boards, including a first circuit board 714A and a second circuit board 714B, such as can include different instances or examples of the circuit board 714. The first circuit board 714A can be similar to the second circuit board 714B, with the second circuit board 714B including pads 1102 instead of vias. In an example, the second circuit board 714B can be reflowed onto the pins 1110 (see, e.g., FIGS. 106-108, discussed below). In an example, the first circuit board 714A can be inserted over ends of feedthroughs 718A-C (sometimes referred to as pins) and soldered onto the feedthroughs 718A-C. Note that while the first circuit board 714A includes vias and no pads and the second circuit board 714B includes pads and no vias, a circuit board can include a combination of pads and vias and the caps 716A-B can be configured to accommodate the pads and/or vias. For example, the cap 716A can include one or more feedthroughs 718A while the cap 716B can include pads, or one cap can include feedthroughs 718A and pads 1102.

FIGS. 7 and 102-105 illustrate generally, by way of example, diagrams showing different operations of an embodiment of a method to electrically connect and enclose the circuit board 714 in the circuitry housing 606. FIG. 102 illustrates an example of a device 1020 that can include the electrical and/or electronic components 712A-G soldered or otherwise electrically connected to the circuit board 714.

FIG. 103 illustrates an embodiment of a device 1022 that can include the device 1020 after the second conductive material 306A, 306K, and/or 306H is soldered or otherwise electrically connected to respective feedthroughs of the cap 716A, such as can include the feedthrough 316A. FIG. 104 illustrates an embodiment of a device 1024 that can include the device 1022 after the circuit board 714 and the electric and/or electronic components 712A-G are situated in the enclosure 722. The cap 716A can be aligned with an opening in the enclosure 722. The cap 716A can be situated at least partially in the enclosure 722. In an example as illustrated in FIG. 104, the circuit board 714 can extend beyond an end 731 of the enclosure 722. This extension facilitate connection or soldering of the circuit board 714 to, for example, the cap 716B (see FIG. 105).

FIG. 105 illustrates an embodiment of a device 1026 that includes the device 1024 after the second conductive material 306C-D and/or 306I-J are soldered or otherwise electrically connected to respective feedthroughs of the cap 716B, such as can include the feedthrough 718B-C. Referring again to FIG. 7, the illustrated example of the circuitry housing 606 shows the device 1026 such as after the cap 716B is situated on the end 731 of the enclosure 722. The cap 716A can be situated on an end of the enclosure 722 opposite the end 731. In an example, the cap 716B can be situated at least partially in the enclosure 722. In the example of FIG. 7, the circuitry housing 606 includes a device with the caps 716A-B attached to the enclosure 722, such as can be attached by brazing, welding, or one or more other attachment processes or techniques. The weld/braze marks 720A, 720B, 720C, and 720D indicate that the caps 716A-B are attached to the enclosure 722. Variations on this example method can similarly be used for assembly. For example, the cap 716A can be welded, brazed, bonded, or otherwise attached to the enclosure 722 before the circuit board 714 is soldered to the cap 716B.

FIG. 106 illustrates, by way of example, a diagram of an example of a third circuit board 714C. The third circuit board 714C can be similar to the first and second circuit boards 714A and 714B. The third circuit board 714C can include one or more conductive tabs 1050 configured to extend from traces 304. The trace 304B can be electrically connected via antenna terminal pads 1102 to the antenna 108 or antenna 108. The one or more conductive tabs 1050 provide a conductive portion that, if trimmed, can change an electrical characteristic of a circuit that includes or uses the trace 304B. For example, an impedance of such a circuit can be changed by correspondingly changing a volume or surface area of the conductive tabs 1050. In an example, a capacitance of a circuit that comprises the traces 304B can be modified or changed by changing a volume or surface area of the conductive tabs 1050. In an example, removal of material from the conductive tabs 1050 decreases a capacitance that is seen or measured at the antenna terminal pads 1102.

In an example, the one or more conductive tabs 1050 can extend from a bus trace 1052 that extends from the trace 304B. The one or more conductive tabs 1050 can include the same or different conductive material as the trace 304B. In an example, the bus trace 1052 and the conductive tabs 1050 are electrically open and do not form a part of a complete circuit from power to ground. Thus, charge can build up on one or more of the conductive tabs 1050 and influence an impedance of the third circuit board 714C. While FIG. 106 illustrates three conductive tabs and each tab is electrically connected to one of the pads 1102, the third circuit board 714C can include additional or fewer tabs. While FIG. 106 illustrates the bus trace 1052 as including all the one or more conductive tabs 1050, separate traces can be used for each respective conductive tab, such as to provide conductive tabs that can be electrically coupled in parallel.

The one or more conductive tabs 1050 can be provided as single and discrete conductive tabs and an impedance of a circuit implemented using the third circuit board 714C can be tuned by selective removal of material at the edges of the tabs. A layout of one or more components on or coupled to the third circuit board 714C can be provided such that the components or traces coupled to the components are present in one or more layers that do not include a conductive tab, and thus removal of tab material can be performed while avoiding or limiting risk to damaging other components or traces.

FIG. 107 illustrates, by way of example, a diagram of an embodiment of a system 1070 that can be configured for measuring an impedance of the antenna 108. The system 1100 as illustrated includes an LCR meter 1154, an antenna assembly 2162, and an antenna 108 such as can be wrapped in part around a dielectric core (e.g., the first dielectric core 7488) of the antenna assembly 2162. Electrically conductive probes 1158 can provide a low impedance electrical path between the LRC meter 1154 and the terminals of the antenna 108. Effects of the probes 1158 on the measurement accuracy can be minimized by way of a de-embedding procedure, whereby short and open circuit measurements can be performed to remove effects of the probes 1158 on the measurement. The LCR meter 1154 can measure an inductance (L), resistance (R), capacitance (C), or a combination thereof, sometimes called an impedance. Through experimentation, guess and check, electrical theory, a combination thereof, or the like, a target impedance for the antenna 108 can be determined or identified.

An impedance 1156 as measured using the LCR meter 1154 can be in the form of a real, imaginary, net impedance, a combination thereof, or the like. The imaginary impedance can include a phase angle of the real impedance. The net impedance can be a measure of the real impedance after being adjusted by the imaginary impedance. A target impedance can include a specified real, imaginary, or net impedance, or a combination thereof. The impedance 1156 as measured can be compared to the target impedance. If an impedance 1156 as measured is not sufficiently close to the target (e.g., is greater than or less than the target impedance by at least a specified threshold amount), then a shape of the antenna 108 can be adjusted, such as manually by an operator or automatically using a mechanical trimming or adjusting machine.

FIG. 108 illustrates, by way of example, a diagram of an embodiment of a system 1080 that can be configured for measuring an impedance of one or more circuits on or coupled to the third circuit board 714C, such as measured from the perspective of the pads 1102. The system 1080 can include the LCR meter 1154, the electrically conductive probes 1158, and the third circuit board 714C. The electrically conductive probes 1158 can provide a low impedance electrical path between the LCR meter 1154 and the pads 1102 of the circuit board 714C. The LCR meter 1154 can measure an inductance (L), resistance (R), capacitance (C), or a combination thereof, sometimes called an impedance. Through experimentation, guess and check, electrical theory, a combination thereof, or the like, a target impedance can be determined or identified. The LCR meter 1154 can be electrically connected to the pads 1102, such as using the probes 1158, and the LCR meter 1154 can provide a measure of an impedance 1162 from the perspective of the pads 1102.

The impedance 1162 as measured can be compared to a target impedance for the third circuit board 714C. If the impedance 1162 as measured is sufficiently large (e.g., the impedance 1162 as measured is greater than a specified target impedance, such as by at least a specified threshold amount), then one or more of the conductive tabs 1050 can be trimmed to electrically isolate the one or more tabs from the bus trace 1052.

Electrically isolating one or more of the conductive tabs 1050 can include removing conductive material 1160 that can electrically couple respective ones of the conductive tabs 1050 with the bus trace 1052. In an example, the conductive material 1160 can be narrower than the bus trace 1052. Electrically isolating the conductive tabs 1050 can include removing a portion of the bus trace 1052 such as can be electrically situated between directly adjacent ones of the conductive tabs 1050 or can be electrically situated between the conductive tabs 1050 and the traces 304B. Removing the conductive material, such as including removal of at least a portion of the bus trace 1052 or the conductive material 1160, can include milling, etching, cutting, sanding or the like.

Removing one or more of the conductive tabs 1050 can reduce a capacitance of the circuit board 714C as measured from the pads 1102. The conductive tabs 1050 can be removed until the impedance 1162, or an impedance derived therefrom, is sufficiently close to a target impedance value. The conductive tabs 1050 can be sized, shaped, or can include a material, such that removing a conductive tab adjusts the impedance by (about) a pre-determined amount. In general, if a tab occupies a small area or volume, then removal or decoupling of the tab from the bus trace 1052 corresponds to a relatively small change in impedance. In an example, from experimentation it can be known that removal of a single one of the conductive tabs 1050 corresponds to an impedance reduction that corresponds to a change of about ten picofarads as measured at the pads 1102. Thus, when it is determined that an impedance of the third circuit board 714C is greater than the target impedance by about 30 picofarads, then three of the conductive tabs 1050 can be removed or decoupled from the bus trace 1052.

Figure 109:
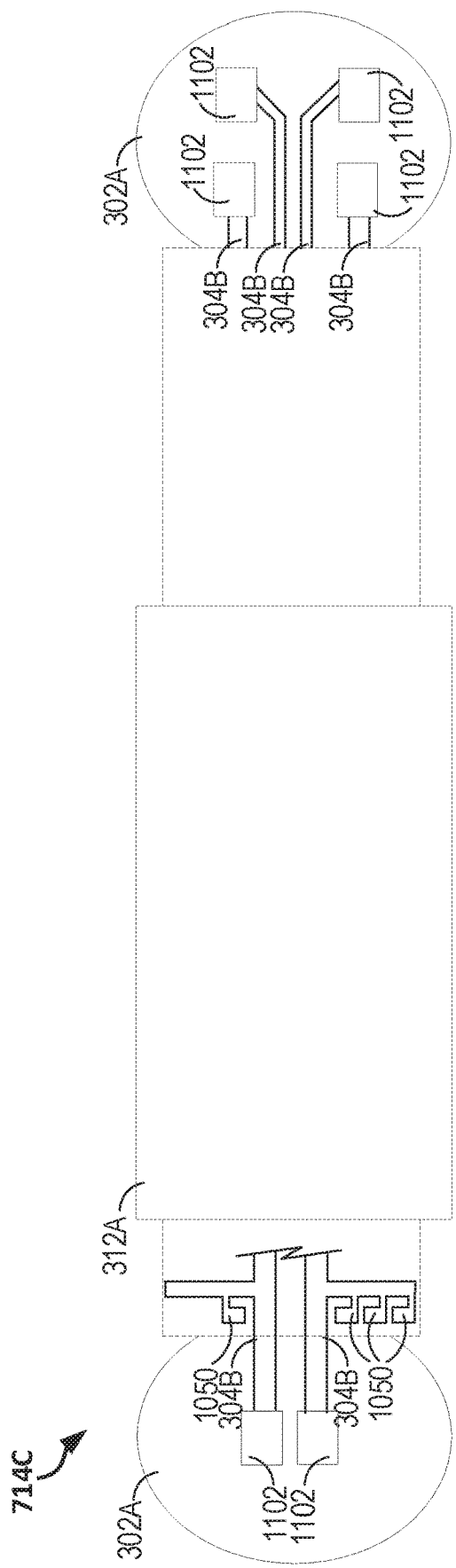
FIG. 109 illustrates, by way of example, a diagram of an embodiment of a circuit board with conductive capacitance tuning tabs removed.

FIG. 109 illustrates, by way of example, a diagram of an embodiment of the third circuit board 714C after two of the one or more conductive tabs 1050 are removed. After removal of the tabs and the third circuit board 714C impedance is measured to be sufficiently close to a target impedance, then the third circuit board 714C can be assembled into the implantable device 110, such as using one of the assembly techniques discussed herein.

In an example, the implantable device 110 can include the third circuit board 714C inside the circuitry housing 606 and electrically connected to a body portion of the device, and the antenna 108 and antenna housing can be connected to the circuitry housing 606, such as illustrated in the examples of FIG. 1 or FIG. 6. The antenna 108 can be electrically connected to the circuitry housing 606 for example after an impedance of the third circuit board 714C is determined to be at or sufficiently close to a target impedance value. That is, the antenna 108 can be connected after the circuit board impedance is verified, for example, because the one or more conductive tabs 1050 may be inaccessible after the third circuit board 714C is disposed in the circuitry housing 606.

Figure 110:
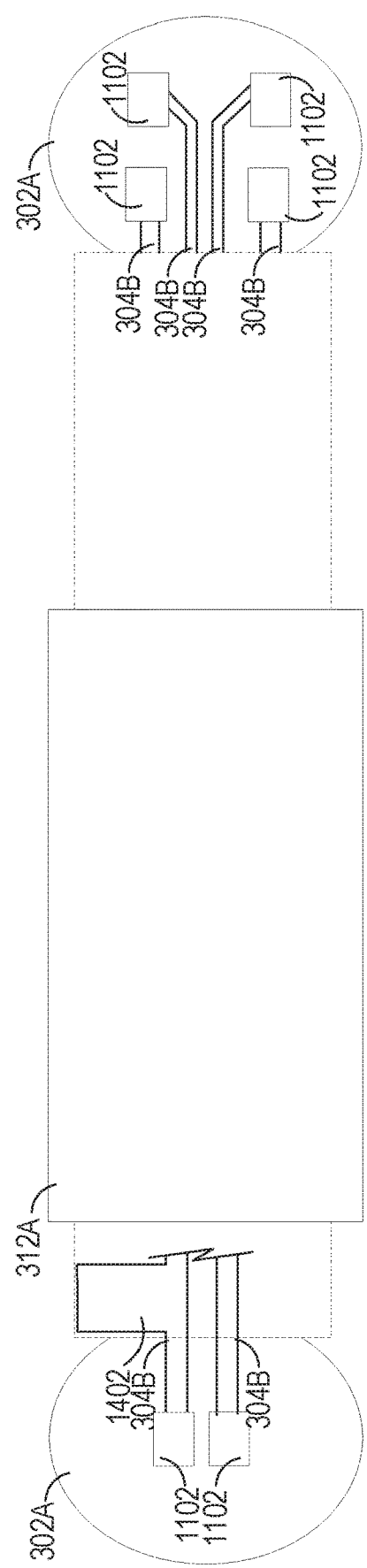
FIG. 110 illustrates, by way of example, a diagram of an embodiment of a circuit board that includes a conductive patch.

FIG. 110 illustrates, by way of example, a diagram of another embodiment of the third circuit board 714C that includes a patch of conductive material 1402 and omits the conductive tabs 1050. Any layers of the circuit board 714C under or above a footprint of the conductive material 1402 can be devoid of any conductive material or electrical or electronic components. In an example, the conductive material 1402 can be removed, such as by trimming or cutting a portion of the third circuit board 714C.

Figure 111:
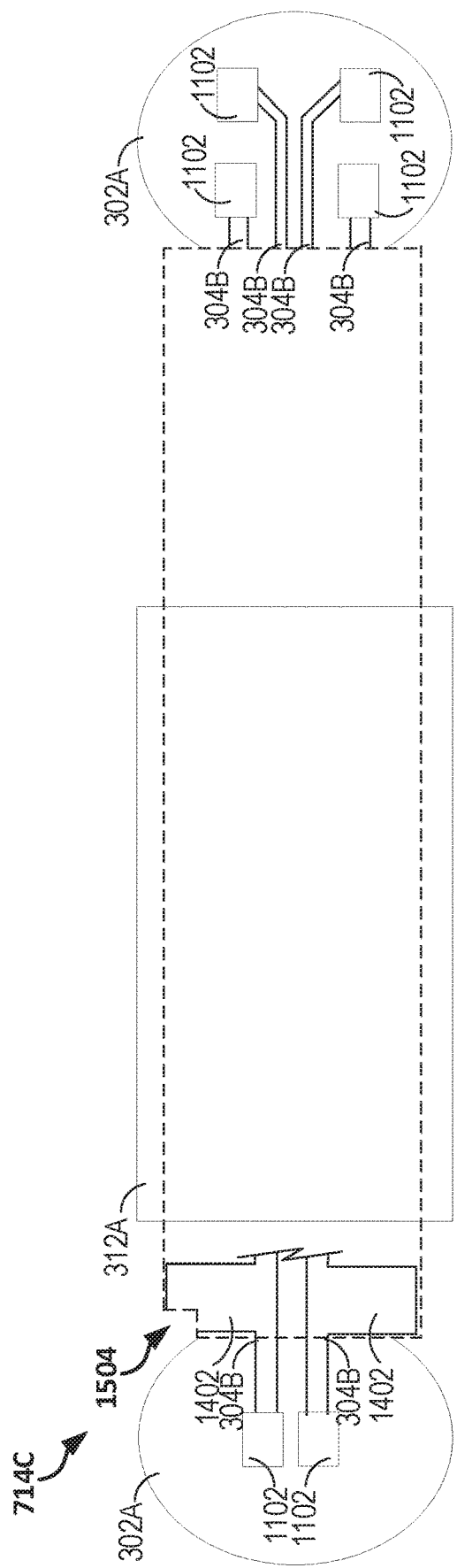
FIG. 111 illustrates, by way of example, a diagram of an embodiment of the circuit board of FIG. 100 with a portion of the conductive patch removed.

FIG. 111 illustrates, by way of example, a diagram of an embodiment of the third circuit board 714C after a portion of the conductive material 1402 is removed. In an example, removal of the conductive material 1402 includes removal of any one or more other materials of the third circuit board 714C such as can be provided on a layer that is above or below a footprint of the conductive material 1402. The portion of the third circuit board 714C that is removed is indicated by the arrow 1504.

Figure 112:
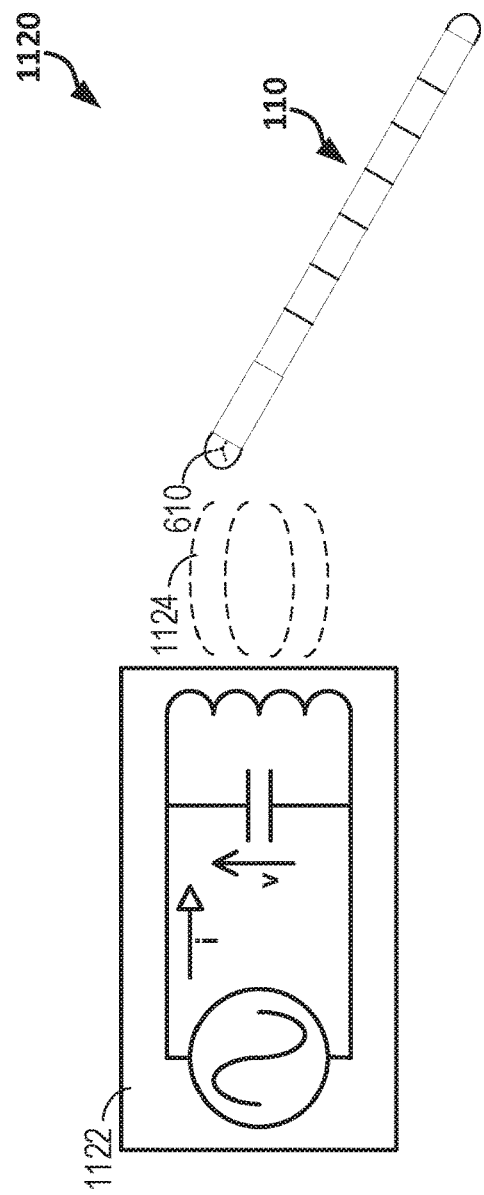
FIG. 112 illustrates, by way of example, a diagram of an embodiment of a system for field-coupled resonance testing of an implantable device.

FIG. 112 illustrates, by way of example, a diagram of an embodiment of a system 1120 for field-coupled resonance testing of the implantable device 600. A correct impedance, and hence frequency of operation, of the implantable device 600 can be tested using a coupled resonance technique. An embodiment of such a technique can include a measuring device 1122 that can include or use a tunable RF source that is configured to energize a resonant circuit adjusted to the same frequency as the RF source. The resonant circuit of the measuring device 1122 can be placed near the implantable device 600. For example, the measuring device 1122 can be provided sufficiently close to the implantable device 600 such that an electromagnetic field of the implantable device 600 is incident on the measuring device 1122. The resonant circuit of the measuring device 1122 can electromagnetically couple to the antenna 108 of the implantable device 600. The separation between the measuring device 1122 and implantable device 600 can, in an example, be no closer than is necessary to obtain an accurate measurement at the measuring device 1122, thus ensuring a coupling level (e.g., 1% or less) between the measuring device 1122 and the implantable device 600. Such a separation can prevent the measuring device 1122 from significantly influencing the impedance of the implantable device 600. When positioned in this manner, changes in the electrical current into, or the voltage across, the measuring device's resonant circuit can be used to detect an impedance and hence resonant frequency of the implantable device 600. An increase in current into, or decrease in voltage across, the measuring device resonant circuit can indicate that the implantable device 600 is tuned to the same frequency as the measuring device 1122. The frequency to which the measurement device 1122 is tuned can be known via an internal measurement circuit (e.g., a frequency counter), or an external frequency measurement device connected to the field-coupled measurement device 1122. The system 1120 thus can be used to measure an impedance and hence frequency of operation of the implantable device 600 such as without a physical electrical connection between the measuring device 1122 and implantable device 600. For example, a physical electrical connection may not be possible when the implantable device 600 is fully assembled and sealed.

Figure 113:
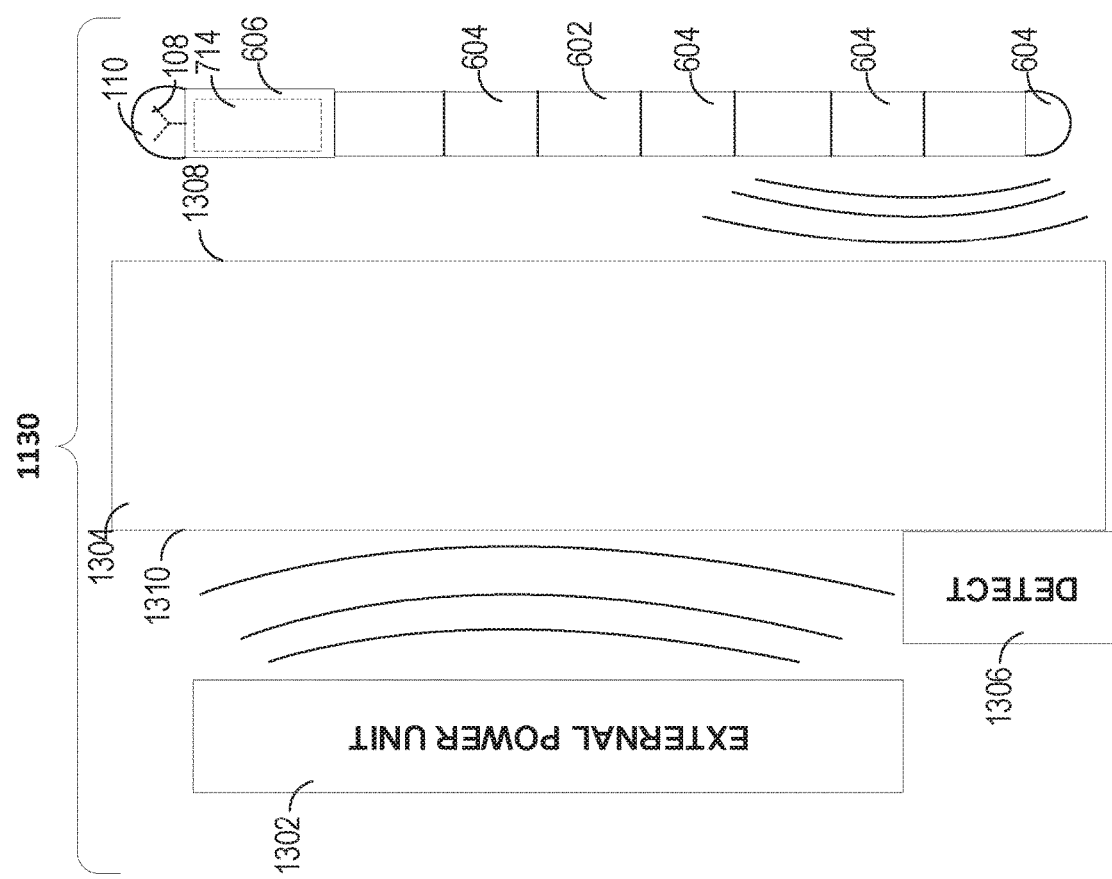
FIGS. 113-114 illustrate, by way of example, diagrams of respective systems for testing a frequency response of an antenna.
Figure 114:
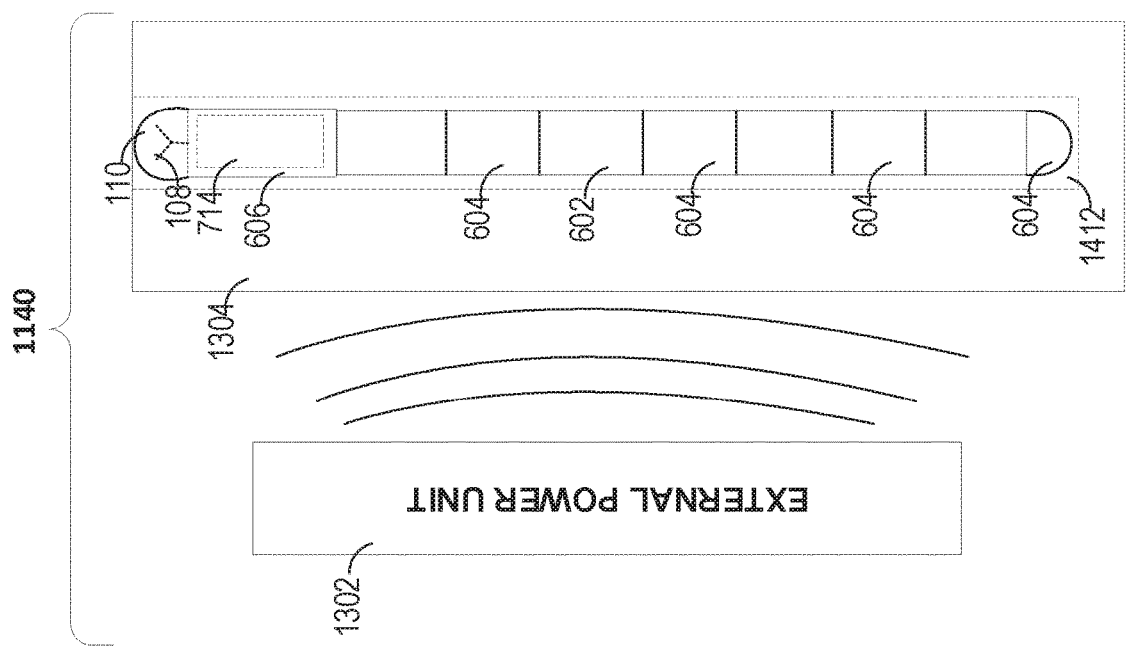

FIGS. 113 and 114 illustrate, by way of example, diagrams of respective systems 1130 and 1140 for testing a frequency response of the antenna 108 such as after the implantable device 110 is implanted. A dielectric constant of tissue into which the implantable device 110 is to be implanted can be estimated. As previously discussed, a dielectric constant of the tissue can vary. However, some tissue is known to have a greater or lesser dielectric constant. For example, muscle has a greater dielectric constant (about 55) than adipose tissue (about 5.6). In another example, blood has a greater dielectric constant (about 61.4) than a dielectric constant of connective tissue (e.g., tendon (about 45.8), cartilage (about 42.7), or the like).

An estimated dielectric constant of the tissue can be used to engineer a material 1304 with a same or similar dielectric constant (e.g., within a specified percentage of the estimated dielectric constant, such as less than 1%, 1%, 2%, 3%, 4%, 5%, 10%, 15%, 20%, 25%, etc. or some percentage therebetween). The material 1304 can include ceramic embedded hydrocarbon material or ceramic impregnated resin, among others.

In the example of FIGS. 113 and 114, an external power unit 1302 can include a midfield power device or transmitter, such as the source 102. While circuitry of the external power unit 1302 is generally described for midfield powering embodiments, a two-part proximal assembly packaging strategy (e.g., a device that includes a circuitry housing 606 and an antenna housing 610) can also be applicable to inductive near-field, far-field, capacitively coupled, and/or ultrasonically powered implantable devices as well.

In an example, the external power unit 1302 can provide an electromagnetic wave that is incident on the antenna 108. The antenna 108 can transduce the electromagnetic wave to electrical signals that provide power to the implantable device 110. The circuit board 714 can include an energy storage component that additionally, or alternatively, can be charged to provide power to circuitry of the implantable device 110. To ensure that circuitry the implantable device 110 is tuned to a proper impedance, such as to efficiently receive transmissions from the external power unit 1302, the implantable device 110 can be situated a specified distance (e.g., an implant distance) from the external power unit 1302. The material 1304 can be situated between the external power unit 1302 and the implantable device 110. The material 1304 can be situated such that transmissions from the external power unit 1302 travel through the material 1304 before being incident on or received by the implantable device 110.

FIG. 113 illustrates the implantable device 110 situated on a first side 1308 of the material 1304 and the external power unit 1302 on a second side 1310 opposing the first side 1308. FIG. 114 illustrates, by way of example, a diagram of an embodiment in which the implantable device 110 is situated in a cavity 1412 in the material 1304.

To verify that the implantable device 110 receives transmissions from the external power unit 1302, detection circuitry 1306 can be provided to detect transmissions from the implantable device 110. An amplitude of the transmissions, a time between a transmission from the external power unit 1302 and reception of a transmission at the detection circuitry 1306, or the like, can be used to determine whether a tuning of the circuitry (e.g., traces, electric or electronic components, conductive tabs, or the like) such as on the circuit board 714 is accurate or sufficient.

In some embodiments, circuitry of the circuit board 714 is digitally programmable, such as in response to communication from the external power unit 1302 to the implantable device 110. In some embodiments, the external power unit 1302 can be electrically coupled to the detection circuitry 1306 or the detection circuitry 1306 can be part of the external power unit 1302. The detection circuitry 1306 can cause the external power unit 1302 to transmit an electromagnetic wave that causes the implantable device 110 to adjust a capacitance, resistance, or inductance thereof, such as by issuing a digital or analog command to an electric or electronic component that can be used to change an impedance characteristic of a circuit in the implantable device 110.

In an example, tuning a frequency at which the implantable device operates includes selecting between two desired frequency spectrums or bands. For example, a frequency spectrum dedicated for implantable device operation in the United States is centered at 915 MHz (902 MHz to 928 MHz frequency range) and a frequency spectrum dedicated for implantable device operation in Europe is 868-870 MHz. The implantable device 110 can be tuned, such as by tuning the circuit board 714 to about a target impedance, to be most efficient when operating using electromagnetic waves at a frequency between the two spectrums (e.g., about 888 MHz if between medical device operation in the U.S. and E.U.). The implantable device 110 can thus be tuned, after deployment, to operate most efficiently at a selected one of the two spectrums, such as by adjusting or programming an impedance of the circuitry of the circuit board 714.

In an example, the external power unit 1302 can determine a location of use, such as by requesting the location from an external device, a positioning system of the external power unit 1302 (e.g., a global positioning system, a Galileo positioning system, or a different position determination technique, or the like). The external power unit 1302 can issue a communication to the implantable device 110 to alter the impedance thereof until an efficiency target is reached.

In an example, the implantable device 110 can include circuitry (e.g., a speaker, optical emission device, motor, or the like) that can be configured to indicate an efficiency of a transmission from the external power unit 1302 is received. For example, the implantable device 110 can produce a sound (e.g., by the speaker), light (e.g., by a light emitting diode or the like), or a vibration (e.g., by the motor) that indicates the impedance of the circuitry of the circuit board 714 is sufficiently matched. The emission (e.g., light, sound, physical vibration, or the like) can be adjusted to indicate a relative efficiency of the transmission reception. For example, a light can get brighter, a sound can get louder, or a vibration can be stronger with better efficiency.

Referring again to FIG. 99, an antenna assembly can include the antenna 108 situated or provided around a first dielectric core 7488. The antenna assembly can be similar to the antenna assembly 2162 from the example of FIG. 107. In an example, the first dielectric core 7488 can include a substantially non-conductive dielectric material. The dielectric material can include polyether ether ketone (PEEK), liquid crystal polymer (LCP) (plastics like PEEK can retain moisture and shift dielectric constant, whereas LCPs have less dielectric shift with moisture saturation), epoxy mold, or the like. The first dielectric core 7488 can include a continuous groove 9402 therein (see, e.g., the example of FIG. 96). The groove 9402 can be shaped and sized such that when the antenna 108 is situated in the groove 9402, the antenna 108 has a specified frequency response (e.g., a frequency response centered at a specified frequency, such as between two frequency spectrums or at or near a center frequency of a specified frequency spectrum). When situated in the groove 9402, the antenna 108 can have nearly two full windings (e.g., between about 1.5 and about 1.75 full windings). Other numbers of windings can similarly be used.

The groove 9402 can define a desired or target shape of the antenna 108, and the shape can affect a frequency response of the antenna 108. The groove 9402 can provide mechanical support for the antenna 108. The groove 9402 can be configured to retain or brace the antenna 108 such that the antenna 108 does not move or otherwise unintentionally change shape after the antenna 108 is situated therein. The groove 9402 can be generally semicircular with extended sidewalls, such that an antenna 108 with a circular cross-section can be situated therein. Other shapes can similarly be used.

In an example, an end or terminal portion of the antenna 108 can extend into a recess 9408 such as can be contiguous with the groove 9402. Each respective end or terminal of the antenna 108 can extend into a respective recess 9408 in the first dielectric core 7488. The recess 9408 can provide a space in which the antenna 108 can be conductively connected to a feedthrough 7274 of the circuitry housing 606. The feedthrough 7274 can be situated in the recess 9408, such as by pushing the feedthrough 7274 through a hole in the distal end of the first dielectric core 7488.

A conductive sleeve 8802 can be provided about a portion of the antenna 108 or the feedthrough 7274, such that the antenna 108 or the feedthrough 7274 is visible through a site hole (not illustrated in FIG. 99). An end of the feedthrough 7274 or of the antenna 108 can then be slid into the sleeve 8802. The two ends in the sleeve 8802 can then be connected to each other, such as by melting the two ends (e.g., by laser excitation incident on the sleeve) and cooling the sleeve 3302, such as using ambient or other cooling.

The first dielectric core 7488 can include a distal portion that includes curved walls 7490 sized and shaped to conform to walls of, for example, winged flanges of the circuitry housing 606. In an example, when the first dielectric core 7488 is pushed on the circuitry housing 606, the curved walls 7490 can press against the walls of the winged flanges that face the feedthroughs 7274. The first dielectric core 7488 can further include a lip 9405 extending radially outward from the curved walls 7490. In an example, the lip 9405 can sit on or be in physical contact with an upper lip at the most proximal portion of the winged flanges 7270A-7270B when the first dielectric core 7488 is situated on the circuitry housing.

In an example, a shape of the antenna 108 can be changed, such as to adjust a frequency response of the antenna 108. The antenna 108 can be deformed, such as by pulling the antenna 108 away from the groove 9402 or by denting or otherwise reshaping or reconfiguring the antenna 108. The effect of the shape change on the frequency response can be difficult to predict, but a change to the antenna shape can alter a frequency response of the antenna 108 to be sufficiently close to a target frequency response. The shape of the antenna 108 can be changed, for example, prior to situating the antenna housing 610 around the antenna 108.

FIG. 115 illustrates generally an example of a fourth circuit board 714D. In an example, a circuit board 714 can include one or more of the features illustrated in FIG. 115. The fourth circuit board 714D can include a proximal electrical connection portion 11501, slits 11502 in a proximal neck region 1709, a body portion 1703 more distal than the proximal electrical connection portion 11501, a distal neck region 1711 connecting the body portion 1703 to a distal electrical connection portion 1713, slits 1705 and 1706 in the distal neck region 1711, and a distal connection portion cover 1712.

The proximal electrical connection portion 11501 can include the conductive material 306A, 306K to be electrically connected to respective ends of the antenna 108 such as through the feedthroughs 718 on a proximal end of the circuitry housing 606. A shape of the proximal electrical connection portion 11501 can include a rectangle with rounded ends. This shape can consume less space than the circular shape illustrated in FIG. 106, for example, among others. The space savings can help aid in assembling the fourth circuit board 714D into the circuitry housing 606.

In an example, the neck region 1709 can connect the body portion 1703 and the proximal electrical connection portion 11501. The neck region 1709 can be separated from the body portion 1703 by cuts 1707 in the body portion 1703. The cuts 1707 can recess the neck region 1709 into the body portion 1703. By including the cuts 1707, the neck region 1709 can bend, without bending the body portion 1703, thus increasing flexibility of the neck region 1709. Further, by including the cuts 1707, an overall length of the fourth circuit board 714D (indicated by arrows 1704) can be reduced relative to other circuit boards 714 (e.g., 714A-714C) discussed herein. An amount of the reduction in length is indicated by arrows 1716. The arrows 1704 indicate a longitudinal axis of the fourth circuit board 714D.

The neck region 1709 can include slits 11502 cut therein. The slits 11502 can increase a flexibility of the material of the circuit board 714D. The slits 11502 can aid in assembling the fourth circuit board 714D into the circuitry housing 606, making it easier to manipulate a direction the conductive material 306A, 306K is facing.

The body portion 1703 connects the proximal neck region 1709 and the distal neck region 1711. The body portion 1703 includes the electrical and electronic components of the implantable device 110, such as tuning capacitors and tabs to be used in tuning an impedance of the implantable device 110.

The distal neck region 1711 connects the body portion 1703 with the distal electrical connection portion 1713. The distal neck region 1711 can include slits 1705, 1706 cut therein. The slits 1705, 1706, like the slits 11502, can increase a flexibility of the material in the neck region 1711. The slits 1705, 1706 can help in assembling the fourth circuit board 714D into the circuitry housing 606, making it easier to change a direction in which the conductive material 306C, 306D, 306I, and 306J faces. In an example, the slits 1706 can be wider or narrower than the slits 1705. In an example, a slit 1706 can provide a location for a tab 1714 on the cover 1712 to be inserted. When inserted in the slit 1706, the tab 1714 can retain the cover 1712 in its location over the distal electrical connection portion 1713.

The distal neck region 1711 can further include meandering traces 1708. The meandering traces 1708 can change an elasticity of a trace relative to a straight trace, can reduce a susceptibility for a trace to snap when bent, and can increase a number of times the trace can be bent and un-bent without breaking the trace.

A slit 1710 can form a portion of a region between the distal electrical connection portion 1713 and the cover 1712. The slit 1710 can allow the cover 1712 to be folded over the distal electrical connection portion 1713 more easily as compared to embodiments that do not include the slit 1710.

The cover 1712 can be folded over (as indicated by an arrow 1719) the distal electrical connection portion 1713. The cover 1712 can provide electrical or mechanical shielding for the distal electrical connection portion 1713 when it is folded over the distal electrical connection portion 1713. FIG. 116 illustrates generally an example of the fourth circuit board 714D after the cover 1712 is folder over the distal electrical connection portion 1713, and the tab 1714 is inserted in the slit 1706.

Examples of Related Computer Hardware and/or Architecture

Figure 117:
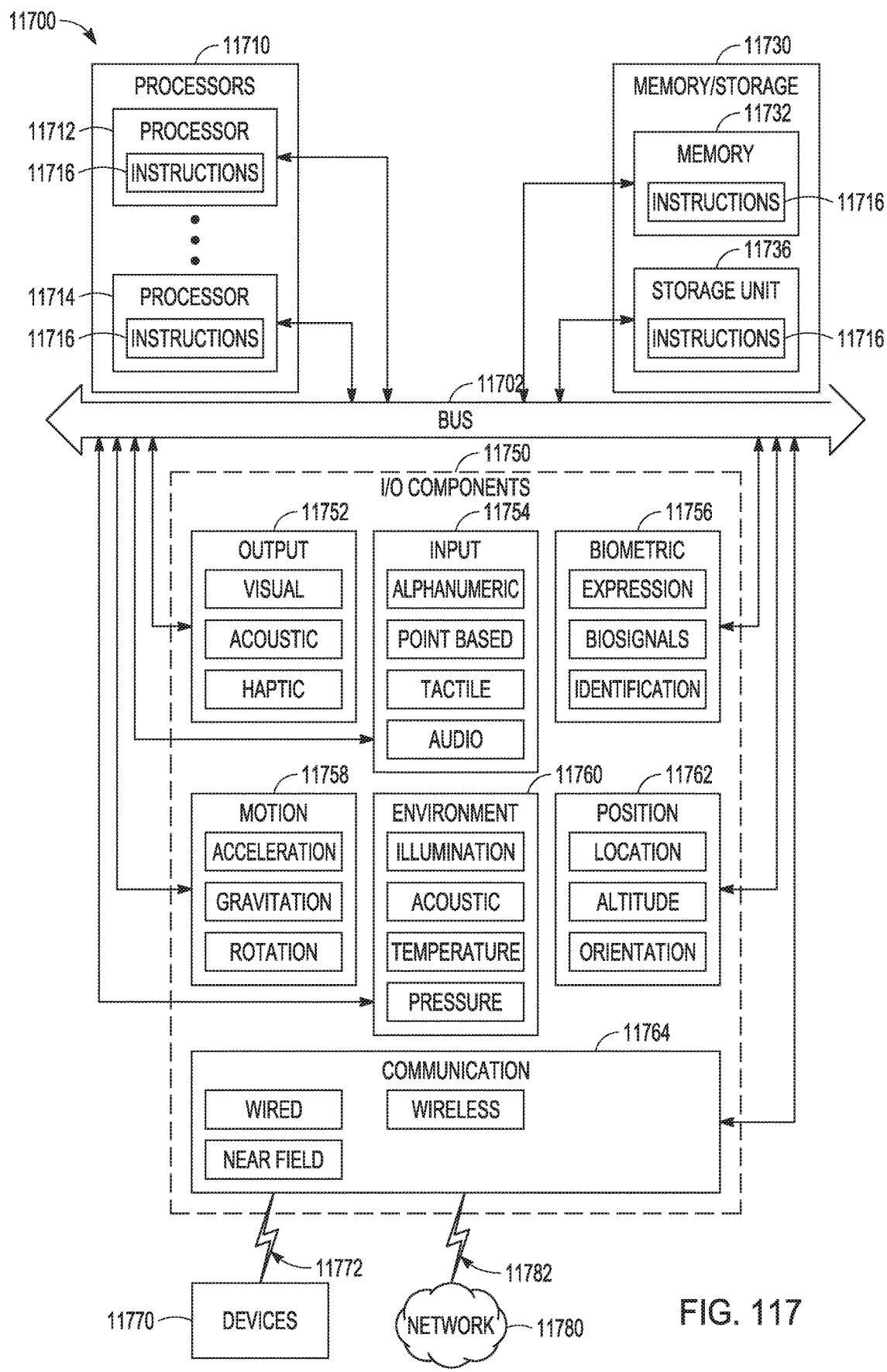
FIG. 117 illustrates a block diagram of an embodiment of a machine upon which one or more methods discussed herein can be performed or in conjunction with one or more systems or devices described herein may be used.

FIG. 117 illustrates, by way of example, a block diagram of an embodiment of a machine 11700 upon which one or more methods discussed herein can be performed or in conjunction with one or more systems or devices described herein may be used. FIG. 117 includes reference to structural components that are discussed and described in connection with several of the embodiments and figures above. In one or more examples, the implantable device 110, the source 102, the sensor 107, the processor circuitry 210, the digital controller 548, circuitry in the circuitry housing 606-606C, system control circuitry, power management circuitry, the controller, stimulation circuitry, energy harvest circuitry, synchronization circuitry, the external device, control circuitry, feedback control circuitry, the implantable device 110, location circuitry, control circuitry, other circuitry of the implantable device 110, and/or circuitry that is a part of or connected to the external source 102, can include one or more of the items of the machine 11700. The machine 11700, according to some example embodiments, is able to read instructions from a machine-readable medium (e.g., a machine-readable storage medium) and to perform any one or more of the methodologies, one or more operations of the methodologies, or one or more circuitry functions discussed herein, such as the methods described herein. For example, FIG. 117 shows a diagrammatic representation of the machine 11700 in the example form of a computer system, within which instructions 11716 (e.g., software, a program, an application, an applet, an app, or other executable code) for causing the machine 11700 to perform any one or more of the methodologies discussed herein can be executed. The instructions transform the general, non-programmed machine into a particular machine programmed to carry out the described and illustrated functions in the manner described. In alternative embodiments, the machine 11700 operates as a standalone device or can be coupled (e.g., networked) to other machines. In a networked deployment, the machine 11700 can operate in the capacity of a server machine or a client machine in a server-client network environment, or as a peer machine in a peer-to-peer (or distributed) network environment. Various portions of the machine 11700 can be included in, or used with, one or more of the external source 102 and the implantable device 110. In one or more examples, different instantiations or different physical hardware portions of the machine 11700 can be separately implanted at the external source 102 and the implantable device 110.

In one or more examples, the machine 11700 can comprise, but is not limited to, a server computer, a client computer, a personal computer (PC), a tablet computer, a laptop computer, a cellular telephone, a smart phone, a mobile device, a wearable device (e.g., a smart watch), an implantable device, a smart home device (e.g., a smart appliance), other smart devices, a web appliance, a network router, a network switch, a network bridge, or any machine capable of executing the instructions 11716, sequentially or otherwise, that specify actions to be taken by machine 11700. Further, while only a single machine 11700 is illustrated, the term "machine" shall also be taken to include a collection of machines 11700 that individually or jointly execute the instructions 11716 to perform any one or more of the methodologies discussed herein.

The machine 11700 can include processors 11710, memory 11730, or I/O components 11750, which can be configured to communicate with each other such as via a bus 11702. In one or more examples embodiment, the processors 11710 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuitry (ASIC), a Radio-Frequency Integrated Circuitry (RFIC), another processor, or any suitable combination thereof) can include, for example, processor 11712 and processor 11714 that can execute instructions 11716. The term "processor" is intended to include multi-core processors that can include two or more independent processors (sometimes referred to as "cores") that can execute instructions contemporaneously. Although FIG. 117 shows multiple processors, the machine 11700 can include a single processor with a single core, a single processor with multiple cores (e.g., a multi-core process), multiple processors with a single core, multiple processors with multiples cores, or any combination thereof.

The memory/storage 11730 can include a memory 11732, such as a main memory, or other memory storage, and a storage unit 11736, both accessible to the processors 11710 such as via the bus 11702. The storage unit 11736 and memory 11732 store the instructions 11716 embodying any one or more of the methodologies or functions described herein. The instructions 11716 can also reside, completely or partially, within the memory 11732, within the storage unit 11736, within at least one of the processors 11710 (e.g., within the processor's cache memory), or any suitable combination thereof, during execution thereof by the machine 11700. Accordingly, the memory 11732, the storage unit 11736, and the memory of processors 11710 are examples of machine-readable media.

As used herein, "machine-readable medium" means a device able to store instructions and data temporarily or permanently and can include, but is not be limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions 11716. The term "machine-readable medium" shall also be taken to include any medium, or combination of multiple media, that is capable of storing instructions (e.g., instructions 11716) for execution by a machine (e.g., machine 11700), such that the instructions, when executed by one or more processors of the machine 11700 (e.g., processors 11710), cause the machine 11700 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The I/O components 11750 can include a wide variety of components to receive input, provide output, produce output, transmit information, exchange information, capture measurements, and so on. The specific I/O components 11750 that are included in a particular machine will depend on the type of machine. For example, portable machines such as mobile phones or other external devices will likely include a touch input device or other such input mechanisms, while a headless server machine will likely not include such a touch input device. It will be appreciated that the I/O components 11750 can include many other components that are not shown in FIG. 117. The I/O components 11750 are grouped according to functionality merely for simplifying the following discussion and the grouping is in no way limiting. In various example embodiments, the I/O components 11750 can include output components 11752 and input components 11754. The output components 11752 can include visual components (e.g., a display such as a plasma display panel (PDP), a light emitting diode (LED)

display, a liquid crystal display (LCD), a projector, or a cathode ray tube (CRT)), acoustic components (e.g., speakers), haptic components (e.g., a vibratory motor, resistance mechanisms, other signal generators, and so forth. The input components 11754 can include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 11750 can include biometric components 11756, motion components 11758, environmental components 11760, or position components 11762 among a wide array of other components. For example, the biometric components 11756 can include components to detect expressions (e.g., hand expressions, facial expressions, vocal expressions, body gestures, or eye tracking), measure physiologic signals (e.g., blood pressure, heart rate, body temperature, perspiration, or brain waves, neural activity, or muscle activity), identify a person (e.g., voice identification, retinal identification, facial identification, fingerprint identification, or electroencephalogram based identification), and the like.

The motion components 11758 can include acceleration sensor components (e.g., accelerometer), gravitation sensor components, rotation sensor components (e.g., gyroscope), and so forth. In one or more examples, one or more of the motion components 11758 can be incorporated with the external source 102 or the implantable device 110, and can be configured to detect motion or a physical activity level of a patient. Information about the patient's motion can be used in various ways, for example, to adjust a signal transmission characteristic (e.g., amplitude, frequency, etc.) when a physical relationship between the external source 102 and the implantable device 110 changes or shifts.

The environmental components 11760 can include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that can provide indications, measurements, or signals corresponding to a surrounding physical environment. The position components 11762 can include location sensor components (e.g., a Global Position System (GPS) receiver component), altitude sensor components (e.g., altimeters or barometers that detect air pressure from which altitude can be derived), orientation sensor components (e.g., magnetometers), and the like. In one or more examples, the I/O component(s) 11750 can be a part of the implantable device 110 and/or the external source 102.

Communication can be implemented using a wide variety of technologies. The I/O components 11750 can include communication components 11764 operable to couple the machine 11700 to a network 11780 or devices 11770 via coupling 11782 and coupling 11772 respectively. For example, the communication components 11764 can include a network interface component or other suitable device to interface with the network 11780. In further examples, communication components 11764 can include wired communication components, wireless communication components, cellular communication components, Near Field (nearfield) Communication (NFC) components, midfield communication components, farfield communication components, and other communication components to provide communication via other modalities. The devices 11770 can be another machine or any of a wide variety of peripheral devices.

Moreover, the communication components 11764 can detect identifiers or include components operable to detect identifiers. For example, the communication components 11764 can include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information can be derived via the communication components 11764, such as, location via Internet Protocol (IP) geo-location, location via Wi-Fi signal triangulation, location via detecting a NFC beacon signal that can indicate a particular location, and so forth.

In some embodiments, the systems comprise various features that are present as single features (as opposed to multiple features). For example, in one embodiment, the system includes a single external source and a single implantable device or stimulation device with a single antenna. Multiple features or components are provided in alternate embodiments.

In some embodiments, the system comprises one or more of the following: means for tissue stimulation (e.g., an implantable stimulation device), means for powering (e.g., a midfield powering device or midfield coupler), means for receiving (e.g., a receiver), means for transmitting (e.g., a transmitter), means for controlling (e.g., a processor or control unit), etc.

To better illustrate the methods, systems, devices, and apparatuses disclosed herein, a non-limiting list of examples is provided here.

Example 1 can include or use subject matter (such as an apparatus, a system, a device, a method, a means for performing acts, or a device readable medium including instructions that, when performed by the device, can cause the device to perform acts, or an article of manufacture), such as can include or use a midfield transmitter comprising a first conductive portion provided on a first layer of the transmitter, a second conductive portion including one or more striplines provided on a second layer of the transmitter, a third conductive portion provided on a third layer of the transmitter, the third conductive portion electrically coupled to the first conductive portion using one or more vias that extend through the second layer; a first dielectric member interposed between the first and second layers; and a second dielectric member interposed between the second and third layers.

Example 2 can include or use, or can optionally be combined with the subject matter of Example 1 to include the first conductive portion including an inner disc region and an outer annular region spaced apart by a first slot.

Example 3 can include or use, or can optionally be combined with the subject matter of Example 2 to include the outer annular region of the first conductive portion is electrically coupled to the third conductive portion on the third layer using the one or more vias.

Example 4 can include or use, or can optionally be combined with the subject matter of one or any combination of Examples 1 through 3 to optionally include or use the first conductive portion including first and second discrete regions spaced apart by a slot. In Example 4, the midfield transmitter can further include a variable capacitor having a first capacitor node coupled to the first region of the first conductive portion and a second capacitor node coupled to the second region of the first conductive portion.

Example 5 can include or use, or can optionally be combined with the subject matter of Example 4 to include a control circuit configured to adjust a capacitance of the variable capacitor based on a specified target resonant frequency.

Example 6 can include or use, or can optionally be combined with the subject matter of Example 5 to include the control circuit configured to adjust the capacitance of the variable capacitor using information about a reflected portion of a power signal transmitted using the transmitter.

Example 7 can include or use, or can optionally be combined with the subject matter of Example 5 to include the control circuit configured to adjust the capacitance of the variable capacitor using information about a portion of a power signal received at a receiver device from the transmitter.

Example 8 can include or use, or can optionally be combined with the subject matter of Example 7 to include a backscatter receiver circuit configured to receive a backscatter signal from the receiver device and determine the information about the portion of the power signal received at the receiver device.

Example 9 can include or use, or can optionally be combined with the subject matter of one or a combination of Examples 7 and 8 to optionally include a data receiver circuit configured to receive a data signal from the receiver device and determine the information about the portion of the power signal received at the receiver device.

Example 10 can include or use, or can optionally be combined with the subject matter of one or any combination of Examples 5-9 to optionally include or use a processor circuit, wherein the control circuit is configured control excitation of the midfield transmitter at each of multiple different capacitance values for the variable capacitor and monitor respective power transfer characteristics for each of the different capacitance values, and wherein the processor circuit is configured to determine whether the midfield transmitter is or is likely to be near body tissue based on the power transfer characteristics.

Example 11 can include or use, or can optionally be combined with the subject matter of one or any combination of Examples 5-9 to optionally include or use a processor circuit, wherein the control circuit is configured control excitation of the midfield transmitter at each of multiple different capacitance values for the variable capacitor and monitor respective VSWR characteristics for each of the different capacitance values, and wherein the processor circuit is configured to determine whether the midfield transmitter is or is likely to be near body tissue based on the VSWR characteristics.

Example 12 can include or use, or can optionally be combined with the subject matter of one or any combination of Examples 1-11 to optionally include or use at least one of the striplines has an undulating or wavy side edge profile.

Example 13 can include or use, or can optionally be combined with the subject matter of one or any combination of Examples 1-12 to optionally include or use a bidirectional coupler configured to receive a drive signal at a first coupler port and provide portions of the drive signal to a transmitted port and to a terminated port, wherein the transmitted port is coupled to at least one of the striplines provided on the second layer of the transmitter, and wherein the terminated port is coupled to a load circuit.

Example 14 can include or use, or can optionally be combined with the subject matter of Example 13 to include a feedback signal processing circuit, wherein the bidirectional coupler includes an isolated port coupled to the feedback signal processing circuit, and wherein the feedback signal processing circuit is configured to receive information at the isolated port about a reflected power signal, and wherein the feedback signal processing circuit is configured to determine an efficiency of a transmitted power signal using the information about the reflected power signal.

Example 15 can include or use, or can optionally be combined with the subject matter of Example 13 to include the load circuit, wherein the load circuit comprises one or more variable capacitors configured to provide an adjustable impedance load at the terminated port of the bidirectional coupler.

Example 16 can include or use, or can optionally be combined with the subject matter of one or any combination of Examples 1-15 to optionally include the first and second dielectric members with different permittivity characteristics.

Example 17 can include or use, or can optionally be combined with the subject matter of Example 16 to include a thickness of the second dielectric member is greater than a thickness of the first dielectric member.

Example 18 can include or use, or can optionally be combined with the subject matter of one or any combination of Examples 1-17 to optionally include the first conductive portion having an annular outer region electrically coupled to the third conductive portion, and the first conductive portion further includes an inner region that is spaced apart from the annular outer region by a first slot.

Example 19 can include or use, or can optionally be combined with the subject matter of Example 18 to include slot extension arms that extend from the first slot toward a central axis of the first conductive portion.

Example 20 can include or use, or can optionally be combined with the subject matter of Example 19 to include four slot extension arms spaced about 90 degrees apart and extending at least half of a distance from the first slot to the central axis of the first conductive portion.

Example 21 can include or use, or can optionally be combined with the subject matter of Example 19 or 20 to include the slot extension arms have a slot width that is substantially the same as a width of the first slot.

Example 22 can include or use, or can optionally be combined with the subject matter of one or any combination of Examples 18-21 to optionally include or use a capacitor having an anode coupled to the inner region of the first conductive portion and a cathode coupled to the annular region of the first conductive portion.

Example 23 can include or use, or can optionally be combined with the subject matter of one or any combination of Examples 1-22 to optionally include or use the first conductive portion including an etched copper layer comprising a grounded first region and a separate second region electrically isolated from the grounded first region.

Example 24 can include or use, or can optionally be combined with the subject matter of Example 23 to include the one or more striplines extending from a peripheral portion of the transmitter toward a central portion of the transmitter and the one or more striplines are disposed over at least a portion of the second region of the first conductive portion.

Example 25 can include or use, or can optionally be combined with the subject matter of one or any combination of Examples 23 or 24 to optionally include the separate second region including etched features or vias that divide the second region into quadrants.

Example 26 can include or use, or can optionally be combined with the subject matter of one or any combination of Examples 1-25 to optionally include or use a signal generator circuit configured to provide respective excitation signals to each of the one or more striplines, wherein the signal generator circuit is configured to adjust phase or amplitude characteristics of at least one of the excitation signals to adjust a current distribution about the first conductive portion.

Example 27 can include or use, or can optionally be combined with the subject matter of Example 26 to include the signal generator disposed on a first side of the third conductive plane and an opposite second side of the third conductive plane faces the first conductive portion.

Example 28 can include or use, or can optionally be combined with the subject matter of one or any combination of Examples 1-27 to optionally include a surface area of the third conductive portion is the same or greater than a surface area of the first conductive plane.

Example 29 can include or use, or can optionally be combined with the subject matter of one or any combination of Examples 1-28 to optionally include the first and third conductive portions comprise substantially circular and coaxial conductive members.

Example 30 can include or use, or can optionally be combined with the subject matter of one or any combination of Examples 1-29 to optionally include at least one of the first conductive portion and the third conductive portion is coupled to a reference voltage or ground.

Example 31 can include or use, or can optionally be combined with the subject matter of one or any combination of Examples 1-30 to optionally include the first or second dielectric member has a dielectric constant Dk of about 3-13.

Example 32 can include or use, or can optionally be combined with the subject matter of one or any combination of Examples 1-30 to optionally include the first or second dielectric member has a dielectric constant Dk of about 6-10.

Example 33 can include or use, or can optionally be combined with the subject matter of one or any combination of Examples 1-32 to optionally include or use a plurality of vias that extend between the first and third conductive portions and are isolated from the second layer, wherein an arrangement of the plurality of vias divides the first conductive portion into substantially separately-excitable quadrants.

Example 34 can include or use, or can optionally be combined with the subject matter of Example 33 to include each of the separately-excitable quadrants including a grounded peripheral region and an inner conductive region, and wherein the first conductive portion is etched with one or more features to isolate at least a portion of the peripheral region from the inner conductive region.

Example 35 can include or use subject matter (such as an apparatus, a system, a device, a method, a means for performing acts, or a device readable medium including instructions that, when performed by the device, can cause the device to perform acts, or an article of manufacture), such as can include or use a tunable midfield transmitter comprising a first substrate, a first emitter provided on a first surface of the first substrate, and a variable capacitor coupled to the first emitter, the variable capacitor being configured to adjust a capacitance characteristic of the first emitter to tune a resonant frequency of the midfield transmitter based on at least one of a reflection coefficient or feedback information from a receiver device.

Example 36 can include or use, or can optionally be combined with the subject matter of Example 35 to include a control circuit configured to provide an indication about whether the transmitter is or is likely to be near body tissue based on information about the reflection coefficient.

Example 37 can include or use, or can optionally be combined with the subject matter of one or any combination of Examples 35 or 36 to optionally include or use a stripline provided on a second surface adjacent and parallel to the first substrate, the stripline extending at least partially over the first emitter.

Example 38 can include or use, or can optionally be combined with the subject matter of Example 37 to include the first emitter including an inner disc region and an outer annular region, and wherein the stripline extends at least partially over the inner disc region of the first emitter.

Example 39 can include or use, or can optionally be combined with the subject matter of Example 38 to include the inner disc region divided by non-conductive slots into multiple discrete conductive regions.

Example 40 can include or use, or can optionally be combined with the subject matter of Example 39 to include each of the conductive regions has substantially the same surface area.

Example 41 can include or use, or can optionally be combined with the subject matter of one or any combination of Examples 35-40 to optionally include or use a ground plane, and a second substrate, wherein the second substrate is provided between the ground plane and the stripline.

Example 42 can include or use, or can optionally be combined with the subject matter of one or any combination of Examples 35-41 to optionally include or use the midfield transmitter configured to generate an adaptive steering field in tissue, wherein the adaptive steering field has a frequency between about 300 MHz and 3000 MHz.

Example 43 can include or use, or can optionally be combined with the subject matter of one or any combination of Examples 35-42 to optionally include or use an excitation circuit configured to provide an excitation signal to the stripline, the excitation signal having a frequency between about 300 MHz and 3000 MHz.

Example 44 can include or use, or can optionally be combined with the subject matter of one or any combination of Examples 35-43 to optionally include or use a capacitance value of the variable capacitor selected or configured to be updated based on a detected reflection coefficient or based on feedback from an implanted midfield receiver device.

Example 45 can include or use subject matter (such as an apparatus, a system, a device, a method, a means for performing acts, or a device readable medium including instructions that, when performed by the device, can cause the device to perform acts, or an article of manufacture), such as can include or use a method of tuning a midfield transmitter to adjust a power transfer efficiency between the midfield transmitter and an implanted receiver, the midfield transmitter including a conductive plate excitable by a stripline. In Example 45, the method can include providing a pilot signal to the stripline, the pilot signal having a pilot frequency, monitoring a received power signal from the midfield transmitter at the implanted receiver, and adjusting an electrical coupling characteristic between the conductive plate and a reference node based on the monitored gain/received power signal.

Example 46 can include or use, or can optionally be combined with the subject matter of Example 45 to include adjusting the electrical coupling characteristic, including changing a capacitance of a variable capacitor that is coupled to the conductive plate and the reference node.

Example 47 can include or use subject matter (such as an apparatus, a system, a device, a method, a means for performing acts, or a device readable medium including instructions that, when performed by the device, can cause the device to perform acts, or an article of manufacture), such as can include or use a method of tuning a midfield transmitter to adjust a power transfer efficiency between the midfield transmitter and an implanted receiver, the midfield transmitter including a conductive plate excitable by a stripline. In Example 47, the method can include providing a pilot signal to the stripline, the pilot signal having a pilot frequency, monitoring a coupling characteristic between the midfield transmitter and the implanted receiver, and adjusting an electrical coupling characteristic between the conductive plate and a reference node based on the monitored gain/received power signal.

Example 48 can include or use, or can optionally be combined with the subject matter of Example 47 to include adjusting the electrical coupling characteristic, including changing a capacitance of a variable capacitor that is coupled to the conductive plate and the reference node.

Example 49 can include or use subject matter (such as an apparatus, a system, a device, a method, a means for performing acts, or a device readable medium including instructions that, when performed by the device, can cause the device to perform acts, or an article of manufacture), such as can include or use a midfield transmitter comprising first and second substantially planar, circular, conductive members that are substantially coaxial and parallel to each other and spaced apart by a first dielectric member, wherein the second conductive member serves as an electrical reference plane of the transmitter, and a first pair of excitation members interposed on an intermediate layer between the conductive members, and an excitation patch coplanar with or offset in the coaxial direction from the first conductive member.

Example 50 can include or use, or can optionally be combined with the subject matter of Example 49 to include the excitation members being electrically isolated from the first and second conductive members and each other, and wherein the first pair of excitation members are provided at opposite sides of the transmitter.

Example 51 can include or use, or can optionally be combined with the subject matter of one or any combination of Examples 49 or 50 to optionally include or use the excitation members being electrically coupled to the excitation patch using respective vias.

Example 52 can include or use, or can optionally be combined with the subject matter of one or any combination of Examples 49-51 to optionally include or use the excitation patch including a portion of the first conductive member.

Example 53 can include or use, or can optionally be combined with the subject matter of one or any combination of Examples 49-52 to optionally include or use the excitation patch being a passive member that is electrically isolated from the first and second conductive members.

Example 54 can include or use, or can optionally be combined with the subject matter of one or any combination of Examples 49-53 to optionally include or use the excitation members being striplines.

Example 55 can include or use, or can optionally be combined with the subject matter of Example 54 to include respective vias that couple the striplines to respective portions of the passive excitation patch.

Example 56 can include or use subject matter (such as an apparatus, a system, a device, a method, a means for performing acts, or a device readable medium including instructions that, when performed by the device, can cause the device to perform acts, or an article of manufacture), such as can include or use a midfield transmitter comprising a first conductive plane provided on a first layer of the transmitter, the first conductive plane comprising an outer annular region spaced apart from an inner disc region, a second conductive plane provided on a second layer of the transmitter, the second conductive plane electrically coupled to the outer annular region of the first conductive plane using one or more vias, a first dielectric member interposed between the first and second conductive planes, and multiple signal input ports coupled to the inner disc region of the first conductive plane and coupled to vias that extend through and are electrically isolated from the second conductive plane and the first dielectric member.

Example 57 can include or use, or can optionally be combined with the subject matter of Example 56 to include transmitter excitation circuitry disposed on a first side of the second layer opposite the first layer, wherein the transmitter excitation circuitry is configured to provide drive signals to the inner disc region using the multiple signal input ports.

Example 58 can include or use, or can optionally be combined with the subject matter of Example 57 to include the transmitter excitation circuitry configured to be coupled to the first side of the second conductive plane using solder bumps.

Example 59 can include or use, or can optionally be combined with the subject matter of one or any combination of Examples 56-58 to optionally include or use a capacitor having an anode coupled to the annular region of the first conductive plane and a cathode coupled to the disc region of the first conductive plane.

Example 60 can include or use, or can optionally be combined with the subject matter of one or any combination of Examples 56-59 to optionally include or use the first conductive plane including multiple linear slots that extend at least part way from a perimeter of the disc region to a center of the disc region.

Example 61 can include or use, or can optionally be combined with the subject matter of Example 60 to include a length of the multiple linear slots is selected or configured to tune a resonance characteristic of the transmitter.

Example 62 can include or use, or can optionally be combined with the subject matter of one or any combination of Examples 56-61 to optionally include or use a signal generator circuit configured to provide respective excitation signals to the multiple signal input ports.

Example 63 can include or use, or can optionally be combined with the subject matter of Example 62 to include the signal generator circuit is configured to adjust phase or amplitude characteristics of at least one of the excitation signals to adjust a current distribution over the first conductive plane.

Example 64 can include or use subject matter (such as an apparatus, a system, a device, a method, a means for performing acts, or a device readable medium including instructions that, when performed by the device, can cause the device to perform acts, or an article of manufacture), such as can include or use a signal processor for use in a wireless transmitter device, the signal processor comprising a first control circuit configured to receive an RF drive signal and conditionally provide an output signal to an antenna or to another device, a second control circuit configured to generate a control signal based on information about the antenna output signal and/or information about the RF drive signal, and a gain circuit configured to provide the RF drive signal to the first control circuit, wherein the gain circuit is configured to change an amplitude of the RF drive signal based on the control signal from the second control circuit.

Example 65 can include or use, or can optionally be combined with the subject matter of Example 64 to include the first control circuit configured to receive a reflected voltage signal that indicates a loading condition of the antenna, and change a phase or amplitude of the antenna output signal based on the reflected voltage signal.

Example 66 can include or use, or can optionally be combined with the subject matter of Example 65 to include the first control circuit is configured to attenuate the antenna output signal when the reflected voltage signal exceeds a specified reflection signal magnitude or threshold value.

Example 67 can include or use, or can optionally be combined with the subject matter of one or any combination of Examples 64-66 to optionally include or use an amplifier circuit configured to conditionally amplify the RF drive signal and provide the antenna output signal when information received from the antenna indicates the antenna is or is likely to be loaded by body tissue.

Example 68 can include or use, or can optionally be combined with the subject matter of one or any combination of Examples 64-67 to optionally include or use the first control circuit including a bidirectional coupler circuit that includes an input port coupled to the gain circuit and configured to receive the RF drive signal, a transmitted port coupled to the antenna and configured to provide the antenna output signal, and a coupled port coupled to the second control circuit, and an isolated port coupled to the second control circuit.

Example 69 can include or use, or can optionally be combined with the subject matter of Example 68 to include an RF diode detector circuit coupled to the isolated port of the bidirectional coupler.

Example 70 can include or use, or can optionally be combined with the subject matter of one or any combination of Examples 68 or 69 to optionally include or use a backscatter receiver circuit coupled to the isolated port of the bidirectional coupler, wherein the backscatter receiver circuit is configured to receive a backscatter data communication from an implanted device.

Example 71 can include or use, or can optionally be combined with the subject matter of one or any combination of Examples 64-70 to optionally include or use the first control circuit configured to generate a fault signal when information received from the antenna about a reflected power signal exceeds a specified threshold amount of reflected power.

Example 72 can include or use, or can optionally be combined with the subject matter of Example 71 to include the first control circuit configured to inhibit providing the output signal when the fault signal is generated.

Example 73 can include or use, or can optionally be combined with the subject matter of Example 72 to include the first control circuit configured to persist in a fault state until the first control circuit receives a reset signal.

Example 74 can include or use, or can optionally be combined with the subject matter of one or any combination of Examples 64-73 to optionally include or use the first control circuit configured to respond, at a first response rate, to a detected fault condition by inhibiting provision of the output signal, and wherein the second control circuit is configured to respond, at a lesser second response rate, to the same or different fault condition by generating the control signal.

Example 75 can include or use, or can optionally be combined with the subject matter of one or any combination of Examples 64-74 to optionally include or use the first control circuit configured to conditionally provide the output signal based on a detected envelope characteristic of the RF drive signal.

Example 76 can include or use, or can optionally be combined with the subject matter of one or any combination of Examples 64-75 to optionally include or use the second control circuit configured to generate the control signal based on a detected envelope characteristic of the RF drive signal.

Example 77 can include or use, or can optionally be combined with the subject matter of one or any combination of Examples 64-76 to optionally include or use the gain circuit configured to provide the RF drive signal based on an RF input signal, and wherein the second control circuit is configured to generate the control signal based on an amplitude characteristic of the RF input signal.

Example 78 can include or use, or can optionally be combined with the subject matter of one or any combination of Examples 64-77 to optionally include or use the second control circuit configured to generate the control signal having a first control signal value when either (1) the information about the antenna output signal indicates a sub-optimal loading condition of the antenna and (2) the information about the RF drive signal indicates an amplitude of the RF drive signal exceeds a specified drive signal amplitude threshold, and wherein the gain circuit attenuates the RF drive signal when the control signal has the first control signal value.

Example 79 can include or use, or can optionally be combined with the subject matter of one or any combination of Examples 64-77 to optionally include or use the second control circuit configured to generate the control signal having a second control signal value when either (1) the information about the antenna output signal indicates a known-good loading condition of the antenna and (2) the information about the RF drive signal indicates an amplitude of the RF drive signal is less than a specified drive signal amplitude threshold, and wherein the gain circuit does not attenuate the RF drive signal when the control signal has the second control signal value.

Example 80 can include or use, or can optionally be combined with the subject matter of one or any combination of Examples 64-79 to optionally include or use the second control circuit configured to generate the control signal for the gain circuit to ramp-up the RF drive signal provided to the first control circuit under initial device conditions or device reset conditions.

Example 81 can include or use, or can optionally be combined with the subject matter of one or any combination of Examples 64-80 to optionally include or the second control circuit configured to generate the control signal for the gain circuit to attenuate the RF drive signal provided to the first control circuit under antenna mismatch conditions.

Example 82 can include or use, or can optionally be combined with the subject matter of one or any combination of Examples 64-81 to optionally include, following a detected fault condition, the second control circuit being configured to generate the control signal for the gain circuit to cause a magnitude of the RF drive signal to revert to a magnitude level corresponding to a magnitude of the RF drive signal preceding the detected fault condition.

Example 83 can include or use, or can optionally be combined with the subject matter of one or any combination of Examples 64-82 to optionally include or use the second control circuit configured to generate the control signal for the gain circuit based on information from a feedback circuit, wherein the feedback circuit provides information about an antenna mismatch condition and wherein the feedback circuit provides information about an actual output power of the device relative to a specified nominal output power.

Example 84 can include or use, or can optionally be combined with the subject matter of Example 83 to include the second control circuit configured to generate the control signal to cause the gain circuit to ramp-up the RF drive signal provided to the first control circuit under initial device conditions or device reset conditions.

Example 85 can include or use, or can optionally be combined with the subject matter of one or any combination of Examples 83 or 84 to optionally include or use the second control circuit configured to generate the control signal to cause the gain circuit to rapidly attenuate the RF drive signal provided to the first control circuit under antenna mismatch conditions.

Example 86 can include or use, or can optionally be combined with the subject matter of Example 85 to include the first control circuit configured to provide information to the first control circuit about an antenna mismatch status, the information about the antenna mismatch status based on a reflected power from the antenna.

Example 87 can include or use, or can optionally be combined with the subject matter of one or any combination of Examples 83-86 to optionally include or use a scaling circuit configured to adjust a sensitivity of the feedback circuit to changes in a reflected power from the antenna.

Example 88 can include or use, or can optionally be combined with the subject matter of one or any combination of Examples 83-87 to optionally include or use the feedback circuit configured to normalize changes in a forward power of the output signal based on a specified maximum VSWR.

Example 89 can include or use, or can optionally be combined with the subject matter of one or any combination of Examples 83-88 to optionally include or use the feedback circuit configured to provide information about a relationship between a forward power signal to the antenna relative to a specified reference power level when the antenna is well-matched to a receiver, and wherein the feedback circuit is configured to provide information about a relationship between a reverse power signal from the antenna relative to the specified reference power level when the antenna is not well-matched to the receiver.

Example 90 can include or use, or can optionally be combined with the subject matter of one or any combination of Examples 64-89 to optionally include or use the first control circuit configured to provide the antenna output signal using a signal having a frequency between about 850 MHz and 950 MHz.

Example 91 can include or use subject matter (such as an apparatus, a system, a device, a method, a means for performing acts, or a device readable medium including instructions that, when performed by the device, can cause the device to perform acts, or an article of manufacture), such as can include or use a method for configuring a wireless power transmitter, the wireless power transmitter including a signal generator coupled to an antenna, and a tuner circuit configured to influence a resonant frequency of the antenna, the method comprising energizing an antenna with a first drive signal having a first frequency, the first drive signal provided by the signal generator, and sweeping parameter values of the tuner circuit to tune the antenna to multiple different resonant frequencies at respective multiple instances. Example 91 can include, for each of the multiple different resonant frequencies, detecting respective amounts of power reflected by the antenna when the antenna is energized by the first drive signal, identifying a particular parameter value (e.g., a particular component value, such as a capacitance value) of the tuner circuit corresponding to a detected minimum amount of power reflected to the antenna, and programming the wireless power transmitter to use the particular parameter value of the tuner circuit to communicate power and/or data to an implanted device using a wireless propagating wave inside body tissue.

Example 92 can include or use, or can optionally be combined with the subject matter of Example 91 to include, based on a priori information about the tuner circuit, providing a likelihood that the wireless power transmitter is positioned within a specified distance range of a body tissue interface based on the identified particular parameter value of the tuner circuit.

Example 93 can include or use, or can optionally be combined with the subject matter of Example 92 to include, when the likelihood indicates the wireless power transmitter is within the specified distance range of the body tissue interface, then communicating power and/or data with an implantable device using the wireless power transmitter and the tuner circuit tuned to the particular parameter value.

Example 94 can include or use, or can optionally be combined with the subject matter of one or any combination of Examples 91-93 to optionally include energizing the antenna with the first drive signal using a signal having a frequency between about 850 MHz and 950 MHz.

Example 95 can include or use, or can optionally be combined with the subject matter of one or any combination of Examples 91-94 to optionally include or use sweeping parameter values of the tuner circuit to tune the antenna to multiple different resonant frequencies including adjusting a capacitance value of a capacitor.

Example 96 can include or use subject matter (such as an apparatus, a system, a device, a method, a means for performing acts, or a device readable medium including instructions that, when performed by the device, can cause the device to perform acts, or an article of manufacture), such as can include or use a method for configuring a wireless transmitter, the wireless transmitter including a tuning circuit configured to tune an antenna of the wireless transmitter to multiple different resonant frequencies, the method comprising energizing the antenna of the wireless transmitter with a first frequency sweep drive signal when the tuning circuit tunes the antenna to a first resonant frequency, and, for each of multiple frequencies of the first frequency sweep drive signal, detecting respective amounts of power reflected to the antenna. Example 96 can include determining whether the wireless transmitter is or is likely to be near body tissue based on the detected respective amounts of power reflected to the antenna.

Example 97 can include or use, or can optionally be combined with the subject matter of Example 96 to include, when the wireless transmitter is determined to be or likely to be near body tissue based on the detected respective amounts of power reflected to the antenna, energizing the antenna of the wireless transmitter with a second drive signal, and sweeping parameter values of the tuner circuit to tune the antenna to multiple different resonant frequencies at respective multiple instances while the antenna is energized by the second drive signal. In Example 97, for each of the multiple different resonant frequencies, the example can include detecting respective amounts of power reflected to the antenna and identifying a particular parameter value of the tuner circuit corresponding to a detected minimum amount of power reflected to the antenna, and confirming whether the wireless transmitter is near body tissue based on the identified particular parameter value.

Example 98 can include or use, or can optionally be combined with the subject matter of Example 97 to include attempting to communicate power and/or data to an implanted device when the wireless transmitter is confirmed to be near body tissue, wherein the attempting to communicate includes tuning the tuner circuit using the particular parameter value.

Example 99 can include or use, or can optionally be combined with the subject matter of one or any combination of Examples 96-98 to optionally include energizing the antenna including energizing a first one of multiple antenna ports distributed about a surface of the antenna, and wherein the detecting the respective amounts of power reflected to the antenna includes receiving a reflected signal using a second one of the multiple antenna ports.

Example 100 can include or use, or can optionally be combined with the subject matter of Example 99 to include the antenna is substantially symmetrical about an axis extending through the first and second antenna ports.

Example 101 can include or use subject matter (such as an apparatus, a system, a device, a method, a means for performing acts, or a device readable medium including instructions that, when performed by the device, can cause the device to perform acts, or an article of manufacture), such as can include or use a method for tuning a midfield transmitter, the midfield transmitter including an antenna with one or more excitable structures and a transmitter tuner circuit configured to change a resonant frequency characteristic of the antenna based on a tuner parameter, the method comprising energizing the antenna with a first test signal when the tuner circuit is tuned using a reference capacitance value, measuring a magnitude of power reflected by the antenna in response to the energizing the antenna with the first test signal and, when the magnitude of power reflected to the antenna exceeds a specified minimum power reflection magnitude, then adjusting the tuner circuit to use a lesser capacitance value, and when the magnitude of power reflected to the antenna does not exceed the specified minimum power reflection magnitude, then adjusting the tuner circuit to use a greater capacitance value.

Example 102 can include or use subject matter (such as an apparatus, a system, a device, a method, a means for performing acts, or a device readable medium including instructions that, when performed by the device, can cause the device to perform acts, or an article of manufacture), such as can include or use a method for tuning a midfield transmitter, the midfield transmitter including an antenna with one or more excitable structures and a transmitter tuner circuit configured to change a resonant frequency characteristic of the antenna based on a tuner parameter, the method comprising energizing the antenna with a first test signal when the tuner circuit is tuned using a reference capacitance value and, at an implanted device, measuring a magnitude of power received from the antenna in response to the energizing the antenna with the first test signal. Example 102 can include communicating information about the magnitude of power received from the implanted device to the midfield transmitter, wherein when the magnitude of the power received is less than a specified minimum power magnitude, then the example can include adjusting the tuner circuit to use a lesser capacitance value, and when the magnitude of power received is greater than the specified minimum power magnitude, then the example can include adjusting the tuner circuit to use a greater capacitance value.

Example 103 can include or use subject matter (such as an apparatus, a system, a device, a method, a means for performing acts, or a device readable medium including instructions that, when performed by the device, can cause the device to perform acts, or an article of manufacture), such as can include or use a midfield transmitter comprising an antenna surface including at least an inner central region and an outer region, multiple excitation features provided near or adjacent to the antenna surface, and a signal generator configured to provide different signals to respective ones of the multiple excitation features, wherein in response to the different signals from the signal generator, the antenna surface conducts a first surface current substantially in a first direction across the inner central region of the antenna surface and the antenna surface conducts a second surface current at least partially in an opposite second direction across the outer region of the antenna surface. In Example 103, when the signal generator provides the different signals to the respective ones of the multiple excitation features, the midfield transmitter influences an evanescent field adjacent to the antenna surface such that the evanescent field includes multiple adjacent field lobes.

Example 104 can include or use, or can optionally be combined with the subject matter of Example 103 to include the inner central region and the outer region of the antenna surface are coplanar and coaxial.

Example 105 can include or use, or can optionally be combined with the subject matter of Example 104 to include the inner central region and the outer region of the antenna surface are separated by a dielectric material or airgap.

Example 106 can include or use, or can optionally be combined with the subject matter of one or any combination of Examples 103-105 to optionally include, when the signal generator provides the different signals to the respective ones of the multiple excitation features, the midfield transmitter influences the evanescent field adjacent to the antenna surface such that the evanescent field includes multiple oppositely-oriented field lobes.

Example 107 can include or use, or can optionally be combined with the subject matter of one or any combination of Examples 103-106 to optionally include, when the midfield transmitter is positioned against body tissue and the signal generator provides the different signals to the respective ones of the multiple excitation features, the midfield transmitter influences the evanescent field adjacent to the antenna surface such that a propagating field is induced in the body tissue.

Example 108 can include or use subject matter (such as an apparatus, a system, a device, a method, a means for performing acts, or a device readable medium including instructions that, when performed by the device, can cause the device to perform acts, or an article of manufacture), such as can include or use a midfield receiver device comprising a first antenna configured to receive a propagating wireless power signal originated at a remote midfield transmitter, a rectifier circuit coupled to the first antenna and configured to provide at least first and second harvested power signals having respective first and second voltage levels, and a multiplexer circuit coupled to the rectifier circuit and configured to route a selected one of the first and second harvested power signals to an electrostimulation output circuit.

Example 109 can include or use, or can optionally be combined with the subject matter of Example 108 to include or use a DC-DC converter circuit configured to receive one or the other of the first and second harvested power signals and provide a converted DC signal.

Example 110 can include or use, or can optionally be combined with the subject matter of Example 109 to include the electrostimulation output circuit, wherein the DC-DC converter circuit provides the converted DC signal to the electrostimulation output circuit.

Example 111 can include or use, or can optionally be combined with the subject matter of one or any combination of Examples 108-110 to optionally include or use a feedback circuit configured to receive at least one of the first and second harvested power signals and provide information to the remote midfield transmitter about the received propagating wireless power signal.

Example 112 can include or use, or can optionally be combined with the subject matter of one or any combination of Examples 108-111 to optionally include the rectifier circuit configured to provide the first harvested power signal at a voltage level of about 1 volt to 1.4 volts, and wherein the rectifier circuit is configured to provide the second harvested power signal at a voltage level of about 1.6 volts to 3.0 volts.

Example 113 can include or use, or can optionally be combined with the subject matter of Example 112 to include the rectifier circuit configured to provide a third harvest power signal at a voltage level greater than 3.0 volts, and wherein the multiplexer circuit is configured to route a selected one of the first, second, and third power signals to the output circuit.

Example 114 can include or use, or can optionally be combined with the subject matter of one or any combination of Examples 108-113 to optionally include or use the rectifier circuit comprising a first input coupled to the first antenna and to a first common node, wherein the first common node is coupled to (a) a cathode of a first diode, (b) an anode of a second diode, and (c) an anode of a third diode, wherein a cathode of the second diode is coupled to a first rectifier output that provides the first harvested power signal at the first voltage level, and the rectifier circuit further comprising a second input coupled to the first antenna and to a second common node, wherein the second common node is coupled to (a) a cathode of the third diode, and (b) an anode of a fourth diode, wherein a cathode of the fourth diode is coupled to a second rectifier output that provides the second harvested power signal at the second voltage level.

Example 115 can include or use, or can optionally be combined with the subject matter of Example 114 to include the second voltage level being greater than the first voltage level.

Example 116 can include or use, or can optionally be combined with the subject matter of Example 115 to include the first and second inputs are capacitively coupled to the first antenna using respective capacitors.

Example 117 can include or use, or can optionally be combined with the subject matter of one or any combination of Examples 108-116 to optionally include or use a backscatter modulation depth adjustment circuit.

Example 118 can include or use, or can optionally be combined with the subject matter of Example 117 to include the backscatter modulation depth adjustment circuit includes a switch provided in a shunt path between a reference node and one of multiple taps from the rectifier circuit.

Example 119 can include or use, or can optionally be combined with the subject matter of one or any combination of Examples 108-116 to optionally include or use an adjustable capacitor coupled to the first antenna and configured to modulate a tuning characteristic of the first antenna.

Example 120 can include or use, or can optionally be combined with the subject matter of Example 119 to include a backscatter modulation depth adjustment circuit and a control circuit, wherein the control circuit is configured to adjust, substantially concurrently, a capacitance value of the adjustable capacitor and a shunt path between a reference node and one of multiple taps from the rectifier circuit.

Example 121 can include or use, or can optionally be combined with the subject matter of one or any combination of Examples 108-120 to optionally include or use a dielectric antenna core around which the first antenna is wound, and an antenna housing substantially surrounding the antenna and the dielectric antenna core, and a circuitry housing substantially surrounding the rectifier circuit and multiplexer circuit, wherein the antenna housing and the circuitry housing can be electrically and/or mechanically coupled together.

Example 122 can include or use subject matter (such as an apparatus, a system, a device, a method, a means for performing acts, or a device readable medium including instructions that, when performed by the device, can cause the device to perform acts, or an article of manufacture), such as can include or use a multiple-stage rectifier circuit comprising a first input configured to receive a first harvested energy signal and coupled to a first common node, wherein the first common node is coupled to (a) a cathode of a first diode, (b) an anode of a second diode, and (c) an anode of a third diode, wherein a cathode of the second diode is coupled to a first rectifier output that provides a first harvested power signal at a first voltage level, and comprising a second input configured to receive the first harvested energy signal and coupled to a second common node, wherein the second common node is coupled to (a) a cathode of the third diode, and (b) an anode of a fourth diode, wherein a cathode of the fourth diode is coupled to a second rectifier output that provides a second harvested power signal at a second voltage level. In Example 122, the second voltage level can be greater than the first voltage level.

Example 123 can include or use subject matter (such as an apparatus, a system, a device, a method, a means for performing acts, or a device readable medium including instructions that, when performed by the device, can cause the device to perform acts, or an article of manufacture), such as can include or use an electrostimulation circuit for an implantable midfield device, the electrostimulation circuit comprising a power harvesting circuit that comprises a first antenna configured to receive a wireless power signal from a midfield transmitter, a rectifier circuit coupled to the first antenna and configured to provide at least first and second harvested power signals having respective first and second voltage levels, and a multiplexer circuit coupled to the rectifier circuit and configured to route a selected one of the first and second harvested power signals to a multiplexer output node. In Example 123, the electrostimulation circuit can further comprise at least two electrostimulation electrodes and switching circuitry configured to route a signal from the multiplexer output node to the at least two electrostimulation electrodes to provide an electrostimulation therapy using a portion of the wireless power signal received from the midfield transmitter.

Example 124 can include or use, or can optionally be combined with the subject matter of Example 123 to include or use the first antenna configured to receive a propagating wireless power signal originated from a midfield transmitter external to a patient body.

Example 125 can include or use subject matter (such as an apparatus, a system, a device, a method, a means for performing acts, or a device readable medium including instructions that, when performed by the device, can cause the device to perform acts, or an article of manufacture), such as can include or use a method that can be performed by an operator, such as a human or mechanical operator, for implanting a wireless implantable device in body tissue, the method comprising at least (1) piercing tissue with a foramen needle that includes a guidewire therein, (2) removing the foramen needle, leaving the guidewire at least partially in the tissue, (3) situating a dilator and catheter over an exposed portion of the guidewire to at least partially situate the guidewire in the dilator, (4) pushing the dilator and catheter along the guidewire and into the tissue, (5) removing the guidewire and dilator from the tissue, (6) inserting an implantable device into a lumen in the catheter, (7) pushing, using a push rod, the implantable device into the tissue through the catheter, and (8) removing the catheter, leaving the implantable device in the tissue.

Example 126 can include or use, or can optionally be combined with the subject matter of Example 125 to include the dilator being a second dilator, and the method can further include situating a first dilator over the guidewire, pushing the first dilator along the guidewire and into the tissue, and removing the first dilator from the tissue.

Example 127 can include or use, or can optionally be combined with the subject matter of one or any combination of Examples 125 or 126 to optionally include situating a suture attached to a distal end of the implantable device at least partially in a lumen of the push rod prior to pushing the implantable device into the tissue.

Example 128 can include or use, or can optionally be combined with the subject matter of Example 127 to include the step of pushing, using the push rod, the implantable device into the tissue through the catheter, including pushing the push rod to leave at least portion of the suture out of the tissue.

Example 129 can include or use, or can optionally be combined with the subject matter of one or any combination of Examples 127 or 128 to optionally include situating a sheath that is around the suture into the lumen of the push rod prior to pushing the implantable device into the tissue.

Example 130 can include or use, or can optionally be combined with the subject matter of Example 129 to include extracting the implantable device from the tissue by pulling on the suture.

Example 131 can include or use, or can optionally be combined with the subject matter of one or any combination of Examples 125-130 to optionally include the dilator comprises a radiopaque marker, and wherein the step of pushing the dilator into the tissue includes locating the dilator at a target tissue site using information about a location of the radiopaque marker as determined using fluoroscopy or other radio imaging.

Example 132 can include or use, or can optionally be combined with the subject matter of one or any combination of Examples 125-131 to optionally include or use the catheter having a radiopaque marker, and wherein pushing the catheter into the tissue includes locating the catheter at a target tissue site using information about a location of the radiopaque marker as determined using fluoroscopy or other radio imaging.

Example 133 can include or use subject matter (such as an apparatus, a system, a device, a method, a means for performing acts, or a device readable medium including instructions that, when performed by the device, can cause the device to perform acts, or an article of manufacture), such as can include or use an implantable device comprising an elongated body portion including a plurality of electrodes exposed thereon, a circuitry housing including circuitry electrically coupled to provide electrical signals to the electrodes, a connector, such as can have a frustoconical body profile, provided between the circuitry housing and the elongated body portion, the connector attached to the body portion at a distal end thereof and the circuitry housing at a proximal end thereof, an antenna housing including an antenna therein and connected to the circuitry housing at a proximal end of the circuitry housing, and a push rod interface connected to the antenna housing at a proximal end of the antenna housing.

Example 134 can include or use, or can optionally be combined with the subject matter of Example 133 to include the push rod interface having a substantially trapezoidal shape with a shorter or smaller base portion facing away from the antenna housing and a longer or larger base portion facing the antenna housing.

Example 135 can include or use, or can optionally be combined with the subject matter of one or any combination of Examples 133 or 134 to optionally include or use a first tine collar including a first set of tines coupled to a proximal end of the antenna housing.

Example 136 can include or use, or can optionally be combined with the subject matter of Example 135 to include a second tine collar including a second set of tines coupled to the body portion by the connector.

Example 137 can include or use, or can optionally be combined with the subject matter of Example 136 to include the second set of tines extending from the second tine collar toward the distal end of the body portion.

Example 138 can include or use, or can optionally be combined with the subject matter of Example 137 to include the first set of tines extending from the first tine collar toward a proximal end of the push rod interface.

Example 139 can include or use, or can optionally be combined with the subject matter of one or any combination of Examples 136-138 to optionally include or use the second tine collar including a third set of tines extending therefrom from the proximal end of the body portion toward the circuitry housing.

Example 140 can include or use, or can optionally be combined with the subject matter of one or any combination of Examples 133-139 to optionally include or use the circuitry housing including first winged flanges extending from a distal housing plate toward the body portion.

Example 141 can include or use, or can optionally be combined with the subject matter of Example 140 to include the proximal end of the connector is configured to engage the first winged flanges.

Example 142 can include or use, or can optionally be combined with the subject matter of one or any combination of Examples 140 or 141 to optionally include or use the circuitry housing including second winged flanges extending from a proximal housing plate toward the antenna housing.

Example 143 can include or use, or can optionally be combined with the subject matter of Example 142 to include the antenna housing including a dielectric core in a core housing, the dielectric core including a dielectric material and the antenna wound around the dielectric core.

Example 144 can include or use, or can optionally be combined with the subject matter of Example 143 to include the core housing including one or more holes therethrough.

Example 145 can include or use, or can optionally be combined with the subject matter of Example 144 to include or use a second dielectric material provided or situated on or around conductive feedthroughs and the antenna in the core housing.

Example 146 can include or use, or can optionally be combined with the subject matter of one or any combination of Examples 143-145 to optionally include or use a conductive sleeve provided substantially around the antenna and the feedthroughs.

Example 147 can include or use, or can optionally be combined with the subject matter of one or any combination of Examples 143-146 to optionally include or use the dielectric housing including holes through a distal portion thereof and further including divots in opposing sides thereof, and wherein the feedthroughs and ends of the antenna are situated in the divots of the dielectric core.

Example 148 can include or use, or can optionally be combined with the subject matter of one or any combination of Examples 133-147 to optionally include or use the push rod interface including an opening in a proximal end thereof, and the implantable device further comprises a suture with a retaining device situated on a distal end of the suture, wherein the suture extends through the opening and the retaining device includes a dimension greater than a corresponding dimension of the opening.

Example 149 can include or use, or can optionally be combined with the subject matter of Example 148 to include a flexible sheath situated over the suture.

Example 150 can include or use, or can optionally be combined with the subject matter of one or any combination of Examples 133-149 to optionally include or use a dielectric liner in the circuitry housing, the dielectric liner provided between a container of the circuitry housing and the circuitry in the circuitry housing.

Example 151 can include or use, or can optionally be combined with the subject matter of one or any combination of Examples 133-150 to optionally include or use a desiccant in the circuitry housing.

Example 152 can include or use, or can optionally be combined with the subject matter of one or any combination of Examples 133-151 to optionally include or use the circuitry housing including indium or an indium alloy between a container and feedthrough plates thereof.

Example 153 can include or use subject matter (such as an apparatus, a system, a device, a method, a means for performing acts, or a device readable medium including instructions that, when performed by the device, can cause the device to perform acts, or an article of manufacture), such as can include or use a method comprising cooling a portion of a hollow needle below a free flow temperature of a dielectric material by situating the needle on or near a cooling device, flowing the dielectric material into the needle to the cooled portion of the hollow needle, situating the hollow needle in a hole in a core housing of an implantable device, warming the hollow needle to the free flow temperature of the dielectric material or a greater temperature, and retaining the hollow needle in the hole to allow the dielectric material to free flow through the needle.

Example 154 can include or use, or can optionally be combined with the subject matter of Example 153 to include warming the hollow needle including moving the needle away from the cooling device and allowing ambient air to warm the needle.

Example 155 can include or use, or can optionally be combined with the subject matter of Example 154 to include the dielectric material including an epoxy.

Example 156 can include or use, or can optionally be combined with the subject matter of one or any combination of Examples 153 and 154 to optionally include or use the cooling device including a Peltier cooling device.

Example 157 can include or use, or can optionally be combined with the subject matter of one or any combination of Examples 153-156 to optionally include or use material with a free flow temperature that is between about −40 degrees Celsius and about 0 degrees Celsius.

Example 158 can include or use subject matter (such as an apparatus, a system, a device, a method, a means for performing acts, or a device readable medium including instructions that, when performed by the device, can cause the device to perform acts, or an article of manufacture), such as can include or use a method comprising situating an indium solder on a container of a circuitry housing near a junction between a feedthrough plate and the container, and reflowing the indium solder to join the feedthrough plate with the container.

Example 159 can include or use, or can optionally be combined with the subject matter of Example 158 to include reflowing the indium solder to form a hermetic seal between the feedthrough plate and the container.

Example 160 can include or use subject matter (such as an apparatus, a system, a device, a method, a means for performing acts, or a device readable medium including instructions that, when performed by the device, can cause the device to perform acts, or an article of manufacture), such as can include or use a method comprising determining an impedance of a circuit board of an implantable device from the perspective of conductive contact pads to which an antenna assembly is to be attached, and in response to determining the impedance is not within a target range of impedance values, removing conductive material from other circuitry of the circuit board, and in response to determining the impedance is within the target range of impedance values, electrically connecting the antenna assembly to the contact pads to create a circuit board assembly, and sealing the circuit board in a hermetic enclosure. Example 160 can further include situating the circuit board assembly near or at least partially in a material such that transmissions from an external power unit travel through the material to be incident on an antenna of the antenna assembly, wherein the material includes a dielectric constant about that of tissue in which the implantable device is to be implanted, receiving the transmissions from the external power unit, and producing a response indicative of a power of the received transmissions.

Example 161 can include or use, or can optionally be combined with the subject matter of Example 160 to include, before situating the circuit board assembly near or at least partially in the material, assembling the circuit board into a circuitry housing such that the circuit board is contained within the circuitry housing.

Example 162 can include or use, or can optionally be combined with the subject matter of Example 161 to include hermetically sealing the circuitry housing prior to electrically connecting the antenna to the contact pads, and electrically connecting the antenna to the contact pads can include electrically connecting the antenna to feedthroughs of the circuitry housing that are electrically connected to the contact pads.

Example 163 can include or use, or can optionally be combined with the subject matter of one or any combination of Examples 161 or 162 to optionally include or use the antenna electrically connected to a proximal end of the circuitry housing. Example 163 can include attaching a distal end of the circuitry housing to an elongated implantable assembly such that the other circuitry of the circuit board is electrically connected to one or more electrodes of the elongated implantable assembly.

Example 164 can include or use, or can optionally be combined with the subject matter of one or any combination of Examples 160-163 to optionally include electrically isolating one or more conductive tabs from other circuitry of the circuit board such as by removing conductive material so that the one or more conductive tabs is not electrically connected to a trace that is electrically connected to a contact pad.

Example 165 can include or use, or can optionally be combined with the subject matter of one or any combination of Examples 160-164 to optionally include the contact pads situated on a proximal portion of the circuit board and the circuit board further includes second contact pads situated on a distal portion of the circuit board.

Example 166 can include or use, or can optionally be combined with the subject matter of Example 165 to include the circuit board further including a first flexible portion, a second flexible portion, and a body portion situated between the first and second flexible portions, the first contact pads are coupled to the circuit portion through the first flexible portion and the second contact pads are coupled to the circuit portion through the second flexible portion.

Example 167 can include or use, or can optionally be combined with the subject matter of Example 166 to include the first flexible portion having a length that is shorter than a length of the second flexible portion.

Example 168 can include or use, or can optionally be combined with the subject matter of one or any combination of Examples 166 and 167 to optionally include the first flexible portion includes cuts therein that are generally perpendicular to a longitudinal axis of the circuit board.

Example 169 can include or use, or can optionally be combined with the subject matter of one or any combination of Examples 166-168 to optionally include folding a cover integral with the circuit board over a contiguous distal electrical connection portion of the circuit board.

Example 170 can include or use, or can optionally be combined with the subject matter of one or any combination of Examples 160-169 to optionally include situating the circuit board assembly near or at least partially in a material including situating the circuit board assembly in a cavity in the material.

Example 171 can include or use, or can optionally be combined with the subject matter of one or any combination of Examples 160-170 to optionally include or use the material including a dielectric constant between about 5 and about 70.

Example 172 can include or use, or can optionally be combined with the subject matter of one or any combination of Examples 160-171 to optionally include producing a response indicative of a power of the received transmissions including generating an optical transmission, a sound, a vibration, or an electromagnetic wave.

Example 173 can include or use, or can optionally be combined with the subject matter of one or any combination of Examples 160-172 to optionally include determining, based on the produced response, the impedance of the circuit board is not within the specified range of target values and generating a communication that causes the other circuitry of the circuit board to digitally adjust an impedance of a component thereof.

Example 174 can include or use, or can optionally be combined with the subject matter of one or any combination of Examples 160-173 to optionally include determining an impedance of the antenna assembly before electrically connecting the antenna to the contact pads, and electrically connecting the antenna to the contact pads in response to determining that both the impedance of the circuit board is within the target range of impedance values and the impedance of the antenna is with a different target range of impedance values.

Example 175 can include or use subject matter (such as an apparatus, a system, a device, a method, a means for performing acts, or a device readable medium including instructions that, when performed by the device, can cause the device to perform acts, or an article of manufacture), such as can include or use a method for tuning an impedance of an implantable device, the method including removing conductive material from a circuit board of an implantable device to adjust an impedance of the circuit board, hermetically sealing the circuit board in a circuitry housing of the implantable device after verifying an impedance of the circuit board is within a specified range of frequencies and after removing the conductive material, and attaching an antenna to a feedthrough of the circuitry housing after hermetically sealing the circuit board in the circuitry housing.

Example 176 can include or use, or can optionally be combined with the subject matter of Example 175 to include, after attaching the antenna, verifying an operational frequency of the implantable device is within a specified range of frequencies using a field-coupled resonance test.

Each of these Examples can be used alone or combined in various combinations and permutations.

Although various general and specific embodiments are described herein, it will be evident that various modifications and changes can be made to these embodiments without departing from the broader spirit and scope of the present disclosure. Accordingly, the specification and drawings are to be regarded in an illustrative rather than a restrictive sense. The accompanying drawings that form a part of this application show, by way of illustration, and not of limitation, specific embodiments in which the subject matter can be practiced. The embodiments illustrated are described in sufficient detail to enable those skilled in the art to practice the teachings disclosed herein. Other embodiments can be used or derived therefrom, such that structural and logical substitutions and changes can be made without departing from the scope of this disclosure. This Detailed Description, therefore, is not to be taken in a limiting sense, and the scope of various embodiments is defined only by the appended claims, along with the full range of equivalents to which such claims are entitled. Specific embodiments or examples are illustrated and described herein, however, it should be appreciated that any arrangement calculated to achieve the same purpose can be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 kHz" includes "10 kHz." Terms or phrases preceded by a term such as "substantially" or "generally" include the recited term or phrase. For example, "substantially parallel" includes "parallel" and "generally cylindrical" includes cylindrical.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention(s) and embodiments should be determined with reference to the appended claims, along with the full scope of equivalents to which such claims are entitled.

What is claimed is:

1. A tunable transmitter comprising:
    an excitation structure configured to receive an excitation signal;
    a first substrate;
    a first emitter comprising first and second conductive regions excitable by the excitation structure in response to the excitation structure receiving the excitation signal, wherein the first and second conductive regions are provided on a first surface of the first substrate and the first and second conductive regions are spaced apart from the excitation structure and the first and second conductive regions are electrically decoupled from each other on the first surface of the first substrate and from the excitation structure, and wherein an insulator electrically separates the first and second conductive regions; and
    a variable capacitor coupling the first and second conductive regions of the first emitter, the variable capacitor being configured to adjust a capacitance characteristic of the first emitter to tune a resonant frequency of the tunable transmitter based on at least one of a reflection coefficient or feedback information from a receiver device.

2. The tunable transmitter of claim 1, further comprising a control circuit configured to provide an indication about whether the tunable transmitter is or is likely to be near body tissue based on information about the reflection coefficient.

3. The tunable transmitter of claim 1, wherein the excitation structure comprises a stripline provided on a second surface adjacent and parallel to the first substrate, the stripline extending at least partially over the first emitter.

4. The tunable transmitter of claim 3, wherein the first conductive region of the first emitter comprises an inner disc region and the second conductive region of the first emitter comprises an outer annular region, and wherein the stripline extends at least partially over the inner disc region of the first emitter.

5. The tunable transmitter of claim 4, wherein the inner disc region and the outer annular region have substantially the same surface area.

6. The tunable transmitter of claim 1, further comprising:
    a ground plane; and
    a second substrate, wherein the second substrate is provided between the ground plane and the excitation structure.

7. The tunable transmitter of claim 1, wherein the tunable transmitter is configured to generate an adaptive steering field in tissue, wherein the adaptive steering field has a frequency between about 300 MHz and 3000 MHz.

8. The tunable transmitter of claim 1, further comprising an excitation circuit configured to provide the excitation signal to the excitation structure, the excitation signal having a frequency between about 300 MHz and 3000 MHz.

9. The tunable transmitter of claim 1, wherein a capacitance value of the variable capacitor is configured to be updated based on the reflection coefficient or based on the feedback from the receiver device.

10. The tunable transmitter of claim 1, further comprising:
    a signal generator coupled to the excitation structure; and
    processing circuitry configured to:
    cause the signal generator to energize the excitation structure with a first drive signal having a first frequency; and
    sweep parameter values of the variable capacitor to change a capacitive coupling between the first and second conductive regions of the first emitter to thereby tune the first emitter to multiple different resonant frequencies at respective multiple instances.

11. The tunable transmitter of claim 10, wherein the processing circuitry is further configured to:
    for each of the multiple different resonant frequencies, detect respective amounts of power reflected by the first emitter when the first emitter is energized by the first drive signal;
    identify a particular parameter value, among the swept parameter values, of the variable capacitor corresponding to a detected minimum amount of power reflected by the first emitter; and programming the variable capacitor to the particular parameter value to communicate power and/or data to an implanted device using a wireless propagating wave inside body tissue.

12. The tunable transmitter of claim 11, wherein the processing circuitry is further configured to:
based on information about capacitance value states of the variable capacitor and the identified particular parameter value, provide a likelihood indication that the tunable transmitter is positioned within a specified distance range of a body tissue interface.

13. The tunable transmitter of claim 12, wherein the processing circuitry is further configured to:
when the likelihood indication indicates the tunable transmitter is within the specified distance range of the body tissue interface, communicate power and/or data with an implantable device using the excitation structure and the variable capacitor tuned to the particular parameter value.

14. The tunable transmitter of claim 11, wherein the excitation structure is configured to energize a first one of the first and second conductive regions distributed about the first emitter; and
wherein the detecting the respective amounts of power reflected by the first emitter includes receiving a reflected signal using a second one of the first and second conductive regions.

15. The tunable transmitter of claim 10, wherein the first drive signal includes a frequency between about 850 MHz and 950 MHz.

16. The tunable transmitter of claim 10, wherein the first emitter is substantially symmetrical about an axis extending through the first and second conductive regions.

17. The tunable transmitter of claim 1, wherein the excitation structure is a subwavelength conductive member.

18. A transmitter comprising:
an excitation structure configured to receive an excitation signal;
a signal generator coupled to the excitation structure;
a first substrate;
a first emitter comprising first and second conductive regions provided on a first surface of the first substrate and spaced apart from the excitation structure;
a variable capacitor coupling the first and second conductive regions of the first emitter, the variable capacitor configured to tune a resonant frequency of the transmitter; and
processing circuitry configured to:
cause the signal generator to energize the excitation structure with a first drive signal having a first frequency; and
sweep capacitance values of the variable capacitor to change a capacitive coupling between the first and second conductive regions of the first emitter to tune the first emitter to multiple different resonant frequencies at respective multiple instances;
wherein the processing circuitry is further configured to:
for each of the multiple different resonant frequencies, detect respective amounts of power reflected by the first emitter when the first emitter is energized by the first drive signal;
identify a particular capacitance value, of the swept capacitance values, corresponding to a detected minimum amount of power reflected by the first emitter; and
adjusting the variable capacitor to the particular capacitance value.

19. The transmitter of claim 18, wherein the processing circuitry is further configured to:
based on both capacitance value states of the variable capacitor and the identified particular capacitance value, provide a likelihood indication that the transmitter is positioned within a specified distance range of a body tissue interface; and
communicate power and/or data with an implantable device using the excitation structure and the variable capacitor tuned to the particular capacitance value when the likelihood indication indicates the transmitter is within the specified distance range of the body tissue interface.

20. The transmitter of claim 18, wherein the first conductive region of the first emitter comprises an inner disc region and the second conductive region of the first emitter comprises an outer annular region, and wherein the excitation structure extends at least partially over the inner disc region.

21. The transmitter of claim 18, wherein the first drive signal has a frequency between 850 MHz and 950 MHz.

* * * * *